United States Patent
Liu et al.

(10) Patent No.: US 12,064,430 B2
(45) Date of Patent: Aug. 20, 2024

(54) KINASE INHIBITOR SALTS AND COMPOSITIONS THEREOF

(71) Applicant: Handa Oncology, LLC, San Jose, CA (US)

(72) Inventors: Fang-Yu Liu, San Jose, CA (US); K. C. Sung, Tainan (TW); Chin-Yao Yang, Tainan (TW); Chi-Cheng Lin, Tainan (TW); Yi-Hsin Lin, Tainan (TW); Li Qiao, San Jose, CA (US)

(73) Assignee: Handa Oncology, LLC, San Jose, CA (US)

( * ) Notice: Subject to any disclaimer, the term of this patent is extended or adjusted under 35 U.S.C. 154(b) by 0 days.

(21) Appl. No.: 18/096,598

(22) Filed: Jan. 13, 2023

(65) Prior Publication Data

US 2023/0142737 A1   May 11, 2023

Related U.S. Application Data

(63) Continuation of application No. 17/321,864, filed on May 17, 2021, which is a continuation of application No. 17/167,719, filed on Feb. 4, 2021, now Pat. No. 11,052,088, which is a continuation of application No. 16/701,941, filed on Dec. 3, 2019, now Pat. No. 11,007,195, which is a continuation of application No. PCT/US2019/036947, filed on Jun. 13, 2019.

(60) Provisional application No. 62/811,368, filed on Feb. 27, 2019, provisional application No. 62/791,356, filed on Jan. 11, 2019, provisional application No. 62/685,411, filed on Jun. 15, 2018.

(51) Int. Cl.
| | | |
|---|---|---|
| *A61K 31/506* | (2006.01) | |
| *A61K 9/00* | (2006.01) | |
| *A61K 9/20* | (2006.01) | |
| *A61K 9/48* | (2006.01) | |
| *A61P 35/02* | (2006.01) | |

(52) U.S. Cl.
CPC .......... *A61K 31/506* (2013.01); *A61K 9/0053* (2013.01); *A61K 9/20* (2013.01); *A61K 9/48* (2013.01); *A61P 35/02* (2018.01)

(58) Field of Classification Search
CPC ...... A61K 31/506; A61K 9/0053; A61K 9/20; A61K 9/48; A61P 35/02
See application file for complete search history.

(56) References Cited

U.S. PATENT DOCUMENTS

| | | | |
|---|---|---|---|
| 6,596,746 B1 | 7/2003 | Das et al. | |
| 6,762,180 B1 | 7/2004 | Roth et al. | |
| 7,087,614 B2 | 8/2006 | Guo et al. | |
| 7,105,530 B2 | 9/2006 | Boloor et al. | |
| 7,119,093 B2 | 10/2006 | Roth et al. | |
| 7,125,875 B2 | 10/2006 | Das et al. | |
| 7,153,856 B2 | 12/2006 | Barrish et al. | |
| 7,169,771 B2 | 1/2007 | Hynes et al. | |
| 7,169,791 B2 | 1/2007 | Breitenstein et al. | |
| 7,189,854 B2 | 3/2007 | Das et al. | |
| 7,262,203 B2 | 8/2007 | Boloor et al. | |
| 7,265,134 B2 | 9/2007 | Hartman | |
| 7,323,482 B2 | 1/2008 | Hynes et al. | |
| 7,408,069 B2 | 8/2008 | Schaefer et al. | |
| 7,491,725 B2 | 2/2009 | Lajeunesse et al. | |
| 7,575,473 B2 | 8/2009 | Bannen et al. | |
| 7,622,472 B2 | 11/2009 | Lee | |
| 7,622,473 B2 | 11/2009 | Arora et al. | |
| 7,645,778 B2 | 1/2010 | Sutton et al. | |
| 7,652,146 B2 | 1/2010 | Chen et al. | |
| 7,666,874 B2 | 2/2010 | Manley et al. | |
| 7,709,657 B2 | 5/2010 | Acemoglu et al. | |
| 7,767,688 B2 | 8/2010 | Alland et al. | |
| 7,781,597 B2 | 8/2010 | Abel et al. | |
| 7,798,475 B2 | 9/2010 | Demirbüker | |
| 7,932,386 B2 | 4/2011 | Schaefer et al. | |
| 7,973,045 B2 | 7/2011 | Simo et al. | |
| 7,977,345 B2 | 7/2011 | Bannen et al. | |
| 7,989,474 B2 | 8/2011 | Roth et al. | |
| 8,007,995 B2 | 8/2011 | Finn et al. | |
| 8,008,504 B2 | 8/2011 | Abel et al. | |
| 8,017,621 B2 | 9/2011 | Buchdunger et al. | |
| 8,067,423 B2 | 11/2011 | Simo et al. | |
| 8,067,436 B2 | 11/2011 | Bannen et al. | |
| 8,093,259 B2 | 1/2012 | Manley et al. | |
| 8,114,885 B2 | 2/2012 | Boloor et al. | |
| 8,124,611 B2 | 2/2012 | Buchdunger et al. | |
| 8,124,763 B2 | 2/2012 | Shieh et al. | |
| 8,163,904 B2 | 4/2012 | Manley et al. | |
| 8,227,477 B2 | 7/2012 | Sterimbaum et al. | |
| 8,242,270 B2 | 8/2012 | Lajeunesse et al. | |
| 8,247,419 B2 | 8/2012 | Lee et al. | |

(Continued)

FOREIGN PATENT DOCUMENTS

| | | |
|---|---|---|
| CN | 102453024 | 5/2012 |
| CN | 103038227 | 4/2013 |

(Continued)

OTHER PUBLICATIONS

Kasashima et al., "Oral Sustained Release of a Hydrophilic Drug Using the Lauryl Sulfate Salt/Complex," Chem. Pharm. Bull. 64, 1304-1309 (2016). (Year: 2016).*
Kasashima et al., "Oral sustained-release based on a lauryl-sulfate salt/complex," International Journal of Pharmaceutics 515 (2016) 677-683. (Year: 2016).*
U.S. Appl. No. 16/701,941 now U.S. Pat. No. 11,007,195, filed Dec. 3, 2019, Kinase Inhibitor Salts and Compositions Thereof.
U.S. Appl. No. 16/798,935 now U.S. Pat. No. 11,160,805, filed Feb. 24, 2020, Kinase Inhibitor Salts and Compositions Thereof.
U.S. Appl. No. 17/084,971 now U.S. Pat. No. 10,940,149, filed Oct. 30, 2020, Kinase Inhibitor Salts and Compositions Thereof.
U.S. Appl. No. 17/167,719 now U.S. Pat. No. 11,052,088, filed Feb. 24, 2020, Kinase Inhibitor Salts and Compositions Thereof.

(Continued)

*Primary Examiner* — Jared Barsky
(74) *Attorney, Agent, or Firm* — FLOREK & ENDRES PLLC

(57) ABSTRACT

The present invention relates to cabozantinib lauryl sulfate salt and methods of use.

19 Claims, 21 Drawing Sheets

(56) References Cited

U.S. PATENT DOCUMENTS

| | | |
|---|---|---|
| 8,293,756 B2 | 10/2012 | Bruneau |
| 8,343,984 B2 | 1/2013 | Manley et al. |
| 8,389,537 B2 | 3/2013 | Manley et al. |
| 8,415,363 B2 | 4/2013 | Manley et al. |
| 8,426,418 B2 | 4/2013 | Coopersmith et al. |
| 8,497,284 B2 | 7/2013 | Bannen et al. |
| 8,501,760 B2 | 8/2013 | Bruneau |
| 8,580,806 B2 | 11/2013 | Manley et al. |
| 8,585,942 B2 | 11/2013 | Demirbüker |
| 8,585,943 B2 | 11/2013 | Demirbüker |
| 8,592,442 B2 | 11/2013 | Sterimbaum et al. |
| 8,604,045 B2 | 12/2013 | Manley |
| 8,653,093 B2 | 2/2014 | Alland et al. |
| 8,673,912 B2 | 3/2014 | Cannon et al. |
| 8,673,930 B2 | 3/2014 | Alland et al. |
| 8,680,103 B2 | 3/2014 | Lajeunesse et al. |
| 8,703,788 B2 | 4/2014 | Reddy et al. |
| 8,753,674 B2 | 6/2014 | Helson |
| 8,815,260 B1 | 8/2014 | Wu et al. |
| 8,816,077 B2 | 8/2014 | Riggs-Sauthier et al. |
| 8,829,015 B2 | 9/2014 | Manley |
| 8,877,776 B2 | 11/2014 | Brown et al. |
| 8,884,013 B2 | 11/2014 | Yan et al. |
| 8,937,082 B2 | 1/2015 | Piran et al. |
| 8,946,416 B2 | 2/2015 | Shieh et al. |
| 9,061,028 B2 | 6/2015 | Kompella et al. |
| 9,061,029 B2 | 6/2015 | Gallagher et al. |
| 9,084,828 B2 | 7/2015 | Riggs-Sauthier et al. |
| 9,090,598 B2 | 7/2015 | Piran et al. |
| 9,108,954 B2 | 8/2015 | Yan et al. |
| 9,115,124 B1 | 8/2015 | Baruto et al. |
| 9,145,406 B2 | 9/2015 | Purohit et al. |
| 9,163,005 B2 | 10/2015 | Manley et al. |
| 9,168,226 B1 | 10/2015 | Wong et al. |
| 9,174,947 B2 | 11/2015 | Bannen et al. |
| 9,187,452 B1 | 11/2015 | Hung et al. |
| 9,249,134 B2 | 2/2016 | Dwivedi et al. |
| 9,301,957 B2 | 4/2016 | Bhardwaj et al. |
| 9,340,536 B2 | 5/2016 | Chiodo et al. |
| 9,365,516 B2 | 6/2016 | Wilson et al. |
| 9,365,526 B2 | 6/2016 | Jaryal et al. |
| 9,376,419 B2 | 6/2016 | Datta et al. |
| 9,402,918 B2 | 8/2016 | Koyakutty et al. |
| 9,440,959 B2 | 9/2016 | Kompella et al. |
| 9,456,992 B2 | 10/2016 | Brisander et al. |
| 9,556,164 B2 | 1/2017 | Hafner et al. |
| 9,566,344 B2 | 2/2017 | Wang et al. |
| 9,567,317 B2 | 2/2017 | Chiodo et al. |
| 9,623,025 B2 | 4/2017 | Supuran et al. |
| 9,682,041 B2 | 6/2017 | Helson |
| 9,682,081 B2 | 6/2017 | Fanda et al. |
| 9,707,265 B2 | 7/2017 | Winder |
| 9,717,720 B2 | 8/2017 | Wilson et al. |
| 9,724,342 B2 | 8/2017 | Wilson et al. |
| 9,751,861 B2 | 9/2017 | Buchstaller |
| 9,809,549 B2 | 11/2017 | Brown et al. |
| 9,815,789 B2 | 11/2017 | Jetti et al. |
| 9,827,230 B2 | 11/2017 | Brisander et al. |
| 9,833,442 B2 | 12/2017 | Brisander et al. |
| 9,833,443 B2 | 12/2017 | Brisander et al. |
| 9,861,624 B2 | 1/2018 | Aftab |
| 9,884,857 B2 | 2/2018 | Hafner et al. |
| 9,907,756 B2 | 3/2018 | Messerschmid et al. |
| 9,926,296 B2 | 3/2018 | Tummala et al. |
| 9,969,692 B2 | 5/2018 | Wilson et al. |
| 9,981,947 B2 | 5/2018 | Peddy et al. |
| 10,000,470 B1 | 6/2018 | Hong et al. |
| 10,016,423 B2 | 7/2018 | Pompili et al. |
| 10,023,566 B2 | 7/2018 | Marvanyos et al. |
| 10,034,873 B2 | 7/2018 | Wilson et al. |
| 10,039,757 B2 | 8/2018 | Wilson et al. |
| 10,052,307 B2 | 8/2018 | Kurisawa et al. |
| 10,053,427 B2 | 8/2018 | Stefinovic et al. |
| 10,076,520 B2 | 9/2018 | Reyland et al. |
| 10,080,723 B2 | 9/2018 | Figueiredo et al. |
| 10,105,323 B2 | 10/2018 | Messerschmid et al. |
| 10,117,881 B2 | 11/2018 | Helson |
| 10,123,999 B2 | 11/2018 | Wilson |
| 10,138,221 B2 | 11/2018 | Thennati et al. |
| 10,143,683 B2 | 12/2018 | Brisander et al. |
| 10,150,733 B2 | 12/2018 | Chokshi et al. |
| 10,154,990 B2 | 12/2018 | Park et al. |
| 10,159,666 B2 | 12/2018 | Aftab et al. |
| 10,166,225 B2 | 1/2019 | Aftab et al. |
| 10,206,916 B2 | 2/2019 | Stefinovic et al. |
| 10,238,602 B2 | 3/2019 | Helson et al. |
| 10,253,371 B2 | 4/2019 | Boudjelal et al. |
| 10,258,691 B2 | 4/2019 | Helson et al. |
| 10,260,097 B2 | 4/2019 | Harkin et al. |
| 10,272,102 B2 | 4/2019 | Westphal et al. |
| 10,273,211 B2 | 4/2019 | Aftab et al. |
| 10,280,153 B2 | 5/2019 | Shi et al. |
| 10,301,282 B2 | 5/2019 | Rao et al. |
| 10,301,302 B2 | 5/2019 | Rao et al. |
| 10,314,830 B2 | 6/2019 | Brisander et al. |
| 10,349,884 B2 | 7/2019 | Helson et al. |
| 10,357,458 B2 | 7/2019 | Helson |
| 10,392,351 B2 | 8/2019 | Xu et al. |
| 10,449,193 B2 | 10/2019 | Helson et al. |
| 10,501,418 B2 | 12/2019 | Aftab et al. |
| 10,532,045 B2 | 1/2020 | Helson et al. |
| 10,543,206 B2 | 1/2020 | Wilson et al. |
| 10,548,888 B2 | 2/2020 | Wilson et al. |
| 10,736,886 B2 | 8/2020 | Aftab et al. |
| 10,940,149 B1 | 3/2021 | Liu et al. |
| 11,007,195 B2 | 5/2021 | Liu et al. |
| 11,052,088 B2 | 7/2021 | Liu et al. |
| 11,065,240 B2 | 7/2021 | Aftab et al. |
| 11,091,439 B2 | 8/2021 | Brown et al. |
| 11,091,440 B2 | 8/2021 | Brown et al. |
| 11,098,015 B2 | 8/2021 | Brown et al. |
| 11,124,481 B2 | 9/2021 | Xu et al. |
| 11,124,482 B2 | 9/2021 | Bannen et al. |
| 11,141,413 B2 | 10/2021 | Aftab et al. |
| 11,160,805 B2 | 11/2021 | Liu et al. |
| 11,261,160 B2 | 3/2022 | Srinivasan et al. |
| 11,498,902 B2 | 11/2022 | Amala et al. |
| 2008/0275009 A1 | 11/2008 | Chidambaram et al. |
| 2009/0118297 A1 | 5/2009 | Simo et al. |
| 2009/0274693 A1 | 11/2009 | Gilmer et al. |
| 2010/0016590 A1 | 1/2010 | Wang et al. |
| 2010/0143459 A1 | 6/2010 | Leipold et al. |
| 2010/0256158 A1 | 10/2010 | Simo et al. |
| 2012/0070368 A1 | 3/2012 | Bannen et al. |
| 2012/0252840 A1 | 10/2012 | Aftab et al. |
| 2012/0270872 A1 | 10/2012 | Cannon et al. |
| 2012/0282179 A1 | 11/2012 | Aftab et al. |
| 2012/0309968 A1 | 12/2012 | Yan et al. |
| 2013/0030172 A1 | 1/2013 | Wilson et al. |
| 2013/0093111 A1 | 4/2013 | Demirbüker et al. |
| 2013/0122093 A1 | 5/2013 | Gao et al. |
| 2013/0143881 A1 | 6/2013 | Cannon et al. |
| 2013/0197230 A1 | 8/2013 | Wilson et al. |
| 2013/0330377 A1 | 12/2013 | Wilson |
| 2013/0337015 A1 | 12/2013 | Wilson |
| 2014/0044819 A1 | 2/2014 | Demirbüker |
| 2014/0057908 A1 | 2/2014 | Smith et al. |
| 2014/0057943 A1 | 2/2014 | Smith et al. |
| 2014/0066444 A1 | 3/2014 | Smith et al. |
| 2014/0121239 A1 | 5/2014 | Aftab |
| 2014/0154328 A1 | 6/2014 | Sovic Brkicic et al. |
| 2014/0179736 A1 | 6/2014 | Schwab et al. |
| 2014/0200242 A1 | 7/2014 | Wilson |
| 2014/0221372 A1 | 8/2014 | Kulkarni et al. |
| 2014/0228401 A1 | 8/2014 | Aftab et al. |
| 2014/0235631 A1 | 8/2014 | Bunt et al. |
| 2014/0242156 A1 | 8/2014 | Helson |
| 2014/0256938 A1 | 9/2014 | Wilson et al. |
| 2014/0323522 A1 | 10/2014 | Aftab et al. |
| 2014/0330170 A1 | 11/2014 | Holland |
| 2014/0342924 A1 | 11/2014 | Harkin et al. |
| 2014/0343073 A1 | 11/2014 | Dwivedi et al. |
| 2014/0378454 A1 | 12/2014 | Brisander et al. |
| 2015/0057446 A1 | 2/2015 | Purohit et al. |

(56) References Cited

U.S. PATENT DOCUMENTS

| | | |
|---|---|---|
| 2015/0133494 A1 | 5/2015 | Aftab |
| 2015/0164878 A1 | 6/2015 | Helson et al. |
| 2015/0183762 A1 | 7/2015 | Kompella et al. |
| 2015/0246901 A1 | 9/2015 | Chiodo et al. |
| 2015/0259337 A1 | 9/2015 | Baruto et al. |
| 2015/0273070 A1 | 10/2015 | Li et al. |
| 2015/0336913 A1 | 11/2015 | Jaryal et al. |
| 2015/0343012 A1 | 12/2015 | Winder |
| 2015/0343063 A1 | 12/2015 | Helson et al. |
| 2016/0022662 A1 | 1/2016 | DeCillis |
| 2016/0031818 A1 | 2/2016 | Aftab |
| 2016/0082019 A1 | 3/2016 | Sweeney et al. |
| 2016/0130252 A1 | 5/2016 | Peddy et al. |
| 2016/0136133 A1 | 5/2016 | Park et al. |
| 2016/0168142 A1 | 6/2016 | Hafner et al. |
| 2016/0168143 A1 | 6/2016 | Hafner et al. |
| 2016/0175341 A1 | 6/2016 | Westphal et al. |
| 2016/0193149 A1 | 7/2016 | Helson |
| 2016/0228436 A1 | 8/2016 | Reyland et al. |
| 2016/0250153 A1 | 9/2016 | Brisander et al. |
| 2016/0264565 A1 | 9/2016 | Rampalli et al. |
| 2016/0311777 A1 | 10/2016 | Xu et al. |
| 2016/0311798 A1 | 10/2016 | Buchstaller |
| 2016/0324791 A1 | 11/2016 | Messerschmid et al. |
| 2016/0346200 A1 | 12/2016 | Sommer et al. |
| 2016/0361313 A1 | 12/2016 | Brisander et al. |
| 2017/0035887 A1 | 2/2017 | Helson et al. |
| 2017/0042828 A1 | 2/2017 | Figueiredo et al. |
| 2017/0044106 A1 | 2/2017 | Aftab et al. |
| 2017/0087143 A1 | 3/2017 | Aftab et al. |
| 2017/0095489 A1 | 4/2017 | Helson |
| 2017/0119802 A1 | 5/2017 | Helson et al. |
| 2017/0143689 A1 | 5/2017 | Wilson et al. |
| 2017/0183334 A1 | 6/2017 | Marvanyos et al. |
| 2017/0197962 A1 | 7/2017 | Huang et al. |
| 2017/0209372 A1 | 7/2017 | Temtem et al. |
| 2017/0217896 A1 | 8/2017 | Xu et al. |
| 2017/0224672 A1 | 8/2017 | Aftab et al. |
| 2017/0239191 A1 | 8/2017 | Messerschmid et al. |
| 2017/0246110 A1 | 8/2017 | Helson |
| 2017/0253594 A1 | 9/2017 | Huang et al. |
| 2017/0260162 A1 | 9/2017 | Peddy et al. |
| 2017/0266178 A1 | 9/2017 | Wilson et al. |
| 2017/0281559 A1 | 10/2017 | Chaudhary |
| 2018/0042906 A1 | 2/2018 | Brisander et al. |
| 2018/0055770 A1 | 3/2018 | Helson et al. |
| 2018/0111915 A1 | 4/2018 | Rao et al. |
| 2018/0127372 A1 | 5/2018 | Chokshi et al. |
| 2018/0326078 A1 | 11/2018 | Yang et al. |
| 2018/0334449 A1 | 11/2018 | Shi et al. |
| 2019/0071426 A1 | 3/2019 | Ceric et al. |
| 2019/0133935 A1 | 5/2019 | Sommer et al. |
| 2019/0167585 A1 | 6/2019 | Helson et al. |
| 2019/0167630 A1 | 6/2019 | Bunt et al. |
| 2019/0209547 A1 * | 7/2019 | Aftab .................... A61K 31/47 |
| 2019/0262330 A1 | 8/2019 | Schwab et al. |
| 2019/0320975 A1 | 10/2019 | Helson et al. |
| 2019/0321293 A1 | 10/2019 | Helson |
| 2019/0352403 A1 | 11/2019 | Schwab et al. |
| 2019/0388422 A1 | 12/2019 | Helson et al. |
| 2020/0113903 A1 | 4/2020 | Liu et al. |
| 2020/0188400 A1 | 6/2020 | Liu et al. |
| 2020/0255382 A1 | 8/2020 | Schwab et al. |
| 2020/0268737 A1 | 8/2020 | Shah et al. |
| 2020/0330451 A1 | 10/2020 | Aftab et al. |
| 2021/0030737 A1 | 2/2021 | Tolaney et al. |
| 2021/0046077 A1 | 2/2021 | Liu et al. |
| 2021/0161885 A1 | 6/2021 | Wilson et al. |
| 2021/0161895 A1 | 6/2021 | Liu et al. |
| 2021/0188776 A1 | 6/2021 | Amala et al. |
| 2021/0261509 A1 | 8/2021 | Shah |
| 2021/0275515 A1 | 9/2021 | Apolo |
| 2021/0283133 A1 | 9/2021 | Liu et al. |
| 2021/0315815 A1 | 10/2021 | Ni et al. |
| 2021/0332014 A1 | 10/2021 | Chen et al. |
| 2022/0265633 A1 | 8/2022 | Dube et al. |
| 2022/0280500 A1 | 9/2022 | Dube et al. |
| 2022/0362235 A1 | 11/2022 | Dube et al. |
| 2022/0387418 A1 | 12/2022 | Dube et al. |

FOREIGN PATENT DOCUMENTS

| | | | |
|---|---|---|---|
| CN | 103845332 | 6/2014 | |
| CN | 104274837 | 1/2015 | |
| CN | 105055327 | 11/2015 | |
| CN | 105055367 | 11/2015 | |
| CN | 105055372 | 11/2015 | |
| CN | 107157941 | 9/2017 | |
| EP | 0275312 | 7/1988 | |
| EP | 0928790 | 12/1998 | |
| EP | 1711481 | 12/2009 | |
| EP | 2308833 | 4/2011 | |
| EP | 1821432 | 7/2011 | |
| EP | 2359813 | 8/2011 | |
| EP | 1169038 | 8/2012 | |
| EP | 3181122 | 6/2017 | |
| EP | 3181127 | 6/2017 | |
| EP | 3181128 | 6/2017 | |
| EP | 3222619 | 9/2017 | |
| EP | 2219771 | 6/2019 | |
| EP | 2229233 | 10/2019 | |
| JP | 2019123703 | 7/2019 | |
| JP | 2019147798 | 9/2019 | |
| WO | 199921845 | 5/1999 | |
| WO | 2004005281 | 1/2004 | |
| WO | 2005041925 | 5/2005 | |
| WO | 2005041927 | 5/2005 | |
| WO | 2005061090 | 7/2005 | |
| WO | 2005077945 | 8/2005 | |
| WO | 2007035874 | 3/2007 | |
| WO | 2008055966 | 5/2008 | |
| WO | WO-2008055966 A1 * | 5/2008 | ............. A61K 9/146 |
| WO | 2009072950 | 6/2009 | |
| WO | 2009072953 | 6/2009 | |
| WO | 2010067374 | 6/2010 | |
| WO | 2010139979 | 12/2010 | |
| WO | 2010139980 | 12/2010 | |
| WO | 2010139981 | 12/2010 | |
| WO | 2011033307 | 3/2011 | |
| WO | 2011159218 | 12/2011 | |
| WO | 2013055996 | 4/2013 | |
| WO | 2013105894 | 7/2013 | |
| WO | 2013105895 | 7/2013 | |
| WO | 2014043618 | 3/2014 | |
| WO | 2014086326 | 6/2014 | |
| WO | 2015049645 | 4/2015 | |
| WO | 2015090259 | 6/2015 | |
| WO | 2015092624 | 6/2015 | |
| WO | 2015171079 | 11/2015 | |
| WO | 2015181573 | 12/2015 | |
| WO | 2016004280 | 1/2016 | |
| WO | 201601665 | 2/2016 | |
| WO | 2016020697 | 2/2016 | |
| WO | 2016020891 | 2/2016 | |
| WO | 2016024289 | 2/2016 | |
| WO | 2016058081 | 4/2016 | |
| WO | 2016097011 | 6/2016 | |
| WO | 2016151304 | 9/2016 | |
| WO | 2016187824 | 12/2016 | |
| WO | 2017002131 | 1/2017 | |
| WO | 2017054741 | 4/2017 | |
| WO | 2017103057 | 6/2017 | |
| WO | 2017108605 | 6/2017 | |
| WO | 2017129694 | 8/2017 | |
| WO | 2017134615 | 8/2017 | |
| WO | 2017134617 | 8/2017 | |
| WO | 2017144109 | 8/2017 | |
| WO | 201715862 | 9/2017 | |
| WO | 2017160703 | 9/2017 | |
| WO | 2017191562 | 11/2017 | |
| WO | 2018078392 | 5/2018 | |
| WO | 2018100585 | 6/2018 | |
| WO | 2018134189 | 7/2018 | |
| WO | 2018134190 | 7/2018 | |

(56) References Cited

FOREIGN PATENT DOCUMENTS

| WO | 2020172120 | 8/2020 |
|---|---|---|
| WO | 2022040446 | 2/2022 |
| WO | 2022115464 | 6/2022 |
| WO | 2022177983 | 8/2022 |

OTHER PUBLICATIONS

U.S. Appl. No. 17/321,864, filed May 17, 2021, Kinase Inhibitor Salts and Compositions Thereof.
SELLECKCHEM.com, Dasatinib Anhydrous Datasheet, downloaded Apr. 1, 2020.
SELLECKCHEM.com Dasatinib Hydrochloride Datasheet, downloaded Mar. 30, 2020.
SELLECKCHEM.com Dasatinib Monohydrate Datasheet, downloaded Apr. 1, 2020.
Declaration Pursuant to 37 C.F.R. 1.132 of Julia (Zhihui) Gao, dated Jan. 30, 2009, submitted to USPTO during prosecution of U.S. Appl. No. 12/168,366 (U.S. Patent Application Publication No. 2008/0275009).
Declaration Pursuant to 37 C.F.R. 1.132 of George M. Derbin, dated Feb. 2, 2009, submitted to USPTO during prosecution of U.S. Appl. No. 12/168,366 (U.S. Patent Application Publication No. 2008/0275009).
Chandani et al., "Atypical Pharmacokinetic Profiles Observed With Dasatinib Reference Listed Drug Product in Bioequivalence Studies," Poster M6107 presented at the Nov. 2017 American Association of Pharmaceutical Scientists (AAPS), San Diego CA.
Eley et al., "Phase I Study of teh Effect of Gastric Acid pH Modulators on the Bioavailability of Oral Dasatinib in Healthy Subjects," Journal of Clinical Pharmacology, Jun. 2009; 49; 700-709.
Johnson et al., "Phase I Pharmacokinetic and Drug-Interaction Study of Dasatinib in Patients with Advanced Solid Tumors," Cancer Mar. 15, 2010, 1582-1591.
Lombardo et al., "Discovery of N-(2-Chloro-6-Methyl-Phenyl)-2-(6-(4-(2-Hydroxyethyl)-Piperazine-1-yl)-2-Methylpyrmidin-4-ylamino) Thiazole-5-Carboxamide (BMS-354825), a Dual Src/abl Kinase Inhibitor with Potent Antitumor Activity in Preclinical Assays," J. Med. Chem. 2004, 47, 6658-6661.
Public Assessment Report Scientific Discussion, Dasatinib CF, 20 mg, 50 mg, 70 mg, 80 mg, 100 mg, 140 mg Film Coated Tablets, College Ter Beoordeling Van Geneesmiddelen, Dec. 6, 2018.
Office Action and Search Report from Taiwan Patent Application No. 109134123 dated Dec. 30, 2021.
Office Action and Search Report from Taiwan Patent Application No. 109122037 dated Dec. 30, 2021.
European Patent Application No. 19820082.6—Supplemental Search Report, Feb. 9, 2022.
Morcos et al., "Effects of the Wetting Agent Sodium Lauryl Sulfate on the Pharmacokinetics of Alectinib: Results from a Bioequivalence Study in Healthy Subjects" Clinical Pharmacology in Drug Development, vol. 6, No. 3, May 1, 2017, pp. 266-279.
Mallikarjun et al., "In-Vitro and Kinetic Studies of Immediate Release Sorafenib Tosylate Film Coated Tablets," World Journal of Pharmaceutical Research, vol. 7, May 1, 2018, pp. 931-944.
Taiwan Patent Application No. 108120545—Allowance Notification and Search Report, Sep. 22, 2022.
PCT/US2019/036947 International Search Report Sep. 12, 2019.
PCT/US2019/036947 Written Opinion of International Searching Authority Sep. 12, 2019.
Tasigna Package Insert Feb. 2017.
Sprycel Package Insert Nov. 2017.
Votrient Package Insert May 2017.
Ofev Package Insert Dec. 2017.
Cabometyx Package Insert Dec. 2017.
Cometriq Package Insert Oct. 2017.
Liu et al., "Improving Oral Bioavailability of Sorafenib by Optimizing the "Spring" and "Parachute" Based on Molecular Interaction Mechanism," Mol. Pharm.Feb. 1, 2016;13(2): 599-608.
Sharma et al., "The Concomitant Use of Tyrosinr Kinase Inhibitors and Proton Pump Inhibitors: Prevalence, Predictors, and Impact on Survival and Discontinuation of Therapy in Older Adults with cancer," Jan. 2019.
Lv et al., FAK Inhibitors in Cancer, a Patent Review, Expert Opinion on Therapeutic Patents. 28(2), 139-145 Dec. 13, 2017.
Brockman et al., "tyrosine Kinase Inhibitors: Multi-Targeted or Single-Targeted?" World Journal of Clinical Oncology, Feb. 10, 2011, 2(2):80-93.
BASF Brochure Solubility Enhancement with BASF Pharma Polymers, Oct. 2011.
Capmul Technical Data Sheet Feb. 14, 2014.
BASF Brochure Pharma Solution Product Overview 2018 Dec. 2017.
Capmul Brochure Dec. 2015.
Sharma, M., et al. "The Prevalence and Predictors of Concomitant use of Tyrosine Kinase Inhibitors and Proton Pump Inhibitors in Older Adults with Cancer: An Observational Study Using Seer-Medicare Data." Value in Health 21 (2018): S19.
FDA Approval Package for Tysigna—Clinical Pharmacology and Biopharmaceutics Review(s), Oct. 2007.
Abitec Personal Care Products Brochure, downloaded Jun. 25, 2020.
Abitec Food, Flavor & Nutrition Brochure, downloaded Jun. 25, 2020.
K.C. Panigrahi, et al., "Gelucire: A Versatile Polymer for Modified Release Drug Delivery System," Future Journal of Pharmaceutical Sciences (Nov. 2017), https://doi.org/10.1016/j.fjps.2017.11.001.
DRUGBANK.com, Nilotinib Hydrochloride Datasheet, downloaded Jul. 16, 2020 (https://www.drugbank.ca/salts/DBSALT001325).
SELLECKCHEM.com, Nilotinib Hydorchloride Datasheet, downloaded Jul. 16, 2020 (https://www.selleckchem.com/products/nilotinib-hydrochloride.html).
Druker BJ, Talpaz M, Resta DJ, et al. Efficacy and safety of a specific inhibitor of the BCR-ABL tyrosine kinase in chronic myeloid leukemia. N Engl J Med. Apr. 2001;344(14): 1031-1037.
Rohrbacher M, Hasford J. Epidemiology of chronic myeloid leukemia (CML). Best Pract Res Clinic Haematol. 2009;22(3):295-302.
Gambacorti-Passerini C, Antolini L, Mahon F-X, et al. Multicenter independent assessment of outcomes in chronic myeloid leukemia patients treated with imatinib. J Natl Cancer Inst. Mar. 2011;103(7):553-561.
Haynes, R., Sackett, D. & Gibson, E. Improvements of medication compliance in uncontrolled hypertension. Lancet, Jun. 1976; 1256-1268.
Algra A, Tijssen JG, Roelandt JR, Pool J, Lubsen J. QTc prolongation measured by standard 12-lead electrocardiogram independent risk factor for sudden death due to cardiac arrest. Circulation. Jan. 1991;83:1888-1894.
Straus SM, Kors JA, De Bruin ML, van der Hooft CS, Hofman A, Heeringa J, Deckers JW, Kingma JH, Sturkenboom MC, Stricker BH, Witteman JC. Prolonged QTc interval and risk of sudden cardiac death in a population of older adults. J Am Coll Cardiol. 2006; 47:362-367. doi: 10.1016/j.jacc.2005.08.067.
Soliman EZ, Prineas RJ, Case LD, Russell G, Rosamond W, Rea T, Sotoodehnia N, Post WS, Siscovick D, Psaty BM, Burke GL. Electrocardiogramd clinical predictors separating atherosclerotic sudden cardiac death from incident coronary heart disease.Heart. Jan. Oct. 2011; 97:1597-1601. doi: 10.1136/hrt.2010.215871.
Daublain P, Feng K-I, Altman MD, Martin I, Mukherjee S, Nofsinger R, et al. Analyzing the Potential Root Causes of Variability of Pharmacokinetics in Preclinical Species. Mol Pharm. Mar. 2017;14:1634-45. doi:10.1021/acs.molpharmaceut.6b01118.
Fleisher D, Li C, Zhou Y, Pao LH, Karim A. Drug, meal and formulation interactions influencing drug absorption after oral administration. Clin Pharmacokinet. Mar. 1999;36:233-54.

(56) References Cited

OTHER PUBLICATIONS

Charman WN, Porter C, Methani S, Dressman JB. Physicochemical and physiological mechanisms for the effects of food on drug absorption: the role of pH and lipids. J Pharm Sci. Mar. 1997;86:269-82.

Chen, Mei-Ling (2008): Lipid excipients and delivery systems for pharmaceutical development: a regulatory perspective. In Advanced drug delivery reviews, Nov. 2017, 60 (6), pp. 768-777. DOI: 10.1016/j.addr.2007.09.010.

Porter, Christopher J. H.; Trevaskis, Natalie L.; Charman, William N. (2007): Lipids and lipid-based formulations: optimizing the oral delivery of lipophilic drugs. In Nature reviews. Drug discovery, Mar. 2007, 6 (3), pp. 231-248. DOI: 10.1038/nrd2197.

Tanaka et al., Clinical Pharmacokinetics of the BCR-ABL Tyrosine Kinase Inhibitor Nilotinib; Clinical Pharmacology & Therapeutics, vol. 87, No. 2, Feb. 2010, pp. 197-203.

FDA medical review for Tricor tablets. https://www.accessdata.fda.gov/drugsatfda_docs/nda/2004/021656s000_Tricor_MedR.pdf, Nov. 2004.

FDA medical review for tofacitinib XR. https://www.accessdata.fda.gov/drugsatfda_docs/nda/2016/208246Orig1s000MedR.pdf, Feb. 2016.

Guidance for Industry Food-Effect Bioavailability and Fed Bioequivalence Studies. https://www.fda.gov/downloads/Drugs/GuidanceComplianceRegulatoryInformation/Guidances/UCM070241.pdf, Dec. 2002.

Draft Guidance on Nilotinib Hydrochloride Monohydrate https://www.fda.gov/downloads/Drugs/GuidanceComplianceRegulatoryInformation/Guidances/UCM209248.pdf, Jul. 2014.

Tasigna (nilotinib) Risk Evaluation & Mitigation Strategy (REMS), Mar. 1, 2010.

Kasashima et al. "Oral Sustained-Release Suspension Based on a Lauryl Sulfate Salt/Complex," International Journal pf Pharmaceutics, 2016, pp. 677-683 (available online Oct. 17, 2016).

Kasashima et al., "Oral Sustained Release of a Hydrophilic Drug Using the Lauryl Sulfate Salt/Complex," Chem. Pharm. Bull. May 2016; 64(9); pp. 1304-1309 (Abstract).

Kasashima et al., "Oral Sustained Release of a Hydrophilic Drug Using the Lauryl Sulfate Salt/Complex," Chem. Pharm. Bull. May 2016; 64(9); pp. 1304-1309.

O'Brien "Small Molecule Kinase Inhibitors Approved by the FDA From 2000 to 2011: A Systematic Review of Preclinical ADME Data," Expert Opinion on Drug Metabolism & Toxicology, 9:12, 1597-1612, Aug. 31, 2013.

Sprycel Package Insert, Dec. 2018.

FDA Approval Package for Sprycel—Clinical Pharmacology and Biopharmaceutics Review(s), Jun. 2006.

FDA Approval Package for Sprycel—Chemistry Review(s), Jun. 2006.

MedChemExpress.com, Dasatinib Datasheet, downloaded Mar. 30, 2020.

MedChemExpress.com, Dasatinib Hydrochloride Datasheet, downloaded Mar. 30, 2020.

Sun, Yu, and Jesper Østergaard. "Application of UV Imaging in Formulation Dvelopment." Pharmaceutical Research 34 (2017): 929-940.

Search Report for Chinese Patent Application No. CN 202110468009.5 dated Apr. 21, 2023.

Office Action for Chinese Patent Application No. CN 202110468009.5 dated Apr. 22, 2023.

Search Report for Chinese Patent Application No. CN 202210717009.9 dated May 29, 2023.

Office Action for Chinese Patent Application No. CN 202210717009.9 dated May 31, 2023.

Office Action for Taiwan Patent Application No. 111123355 dated May 31, 2023.

Office Action for Japanese Patent Application No. 2021-518863 dated May 16, 2023.

Office Action for Chinese Patent Application No. CN 202211172792.1 dated Jun. 13, 2023.

Search Report for Chinese Patent Application No. CN 202211172792.1 dated Jun. 13, 2023.

Office Action and Search Report for Taiwan Patent Application No. 111136440 dated Jul. 3, 2023.

Search Report for Chinese Patent Application No. CN 202110466538.1 dated Aug. 10, 2023.

Office Action for Chinese Patent Application No. CN 202110466538.1 dated Aug. 28, 2023.

\* cited by examiner

| 2-Theta | Intensity | 2-Theta | Intensity |
|---|---|---|---|
| 5.62 | 2452 | 21.5 | 693 |
| 8.461 | 1841 | 22.003 | 701 |
| 9.44 | 387 | 22.832 | 548 |
| 13.021 | 418 | 24.781 | 859 |
| 13.641 | 469 | 25.778 | 697 |
| 17.082 | 812 | 26.12 | 796 |
| 19.12 | 1137 | 26.598 | 706 |
| 20.16 | 825 | | |

| 2-Theta | Intensity | 2-Theta | Intensity |
|---|---|---|---|
| 5.602 | 2246 | 20.184 | 816 |
| 8.48 | 1682 | 21.497 | 745 |
| 9.156 | 272 | 21.982 | 690 |
| 9.442 | 358 | 24.898 | 778 |
| 13.06 | 473 | 25.842 | 694 |
| 13.699 | 463 | 26.458 | 657 |
| 17.139 | 763 | 27.674 | 527 |
| 17.763 | 512 | 28.995 | 360 |
| 19.14 | 1052 | | |

| 2-Theta | Intensity | 2-Theta | Intensity | 2-Theta | Intensity |
|---|---|---|---|---|---|
| 5.621 | 2148 | 18.438 | 763 | 27.674 | 482 |
| 8.461 | 1526 | 19.082 | 992 | 29.04 | 392 |
| 9.121 | 671 | 19.62 | 1038 | 30.016 | 332 |
| 9.557 | 337 | 20.919 | 889 | 30.681 | 315 |
| 13.062 | 849 | 21.323 | 963 | 33.815 | 255 |
| 13.88 | 697 | 22.953 | 562 | 34.64 | 277 |
| 16.702 | 769 | 24.116 | 607 | 38.711 | 220 |
| 17.199 | 723 | 24.74 | 845 | | |
| 17.859 | 1073 | 25.781 | 907 | | |

| 2-Theta | Intensity | 2-Theta | Intensity | 2-Theta | Intensity |
|---|---|---|---|---|---|
| 6.857 | 441 | 17.439 | 475 | 26.942 | 295 |
| 8.28 | 136 | 18.381 | 557 | 27.421 | 255 |
| 9.877 | 307 | 19.379 | 945 | 27.812 | 253 |
| 10.5 | 389 | 20.061 | 393 | 28.722 | 303 |
| 12.579 | 310 | 21.499 | 1109 | 29.101 | 358 |
| 13.078 | 517 | 22.561 | 953 | 30.4 | 191 |
| 14.681 | 261 | 23.536 | 442 | 31.641 | 236 |
| 15.767 | 183 | 24.38 | 549 | 34.596 | 186 |
| 16.332 | 249 | 25.002 | 551 | 37.526 | 190 |
| 17.119 | 373 | 26.036 | 243 | 39.196 | 179 |
| 17.22 | 376 | 26.466 | 238 | | |

| 2-Theta | Intensity | 2-Theta | Intensity | 2-Theta | Intensity |
|---|---|---|---|---|---|
| 6.62 | 704 | 18.18 | 713 | 26.679 | 367 |
| 8.066 | 156 | 19 | 1235 | 27.222 | 325 |
| 9.641 | 220 | 19.766 | 479 | 27.541 | 296 |
| 10.22 | 384 | 20.502 | 297 | 28.359 | 321 |
| 10.661 | 246 | 21.26 | 1536 | 28.8 | 354 |
| 12.358 | 483 | 22.299 | 1154 | 30.802 | 203 |
| 12.802 | 369 | 23.221 | 516 | 31.437 | 232 |
| 14.442 | 316 | 24.101 | 706 | 32.545 | 166 |
| 15.501 | 245 | 24.762 | 606 | 33.321 | 181 |
| 15.999 | 260 | 25.823 | 294 | 34.095 | 176 |
| 17.138 | 743 | 26.115 | 266 | 34.374 | 183 |
|  |  |  |  | 39.476 | 188 |

| 2-Theta | Intensity | 2-Theta | Intensity | 2-Theta | Intensity |
|---|---|---|---|---|---|
| 5.901 | 342 | 18.078 | 577 | 28.541 | 325 |
| 6.5 | 343 | 19.08 | 920 | 28.916 | 265 |
| 7.929 | 155 | 19.777 | 298 | 30.015 | 192 |
| 9.501 | 375 | 21.141 | 909 | 30.842 | 196 |
| 10.18 | 443 | 22.22 | 787 | 31.258 | 273 |
| 12.281 | 335 | 23.181 | 388 | 34.199 | 188 |
| 12.739 | 641 | 24.058 | 490 | 35.442 | 161 |
| 14.359 | 278 | 24.681 | 610 | 37.221 | 206 |
| 14.898 | 298 | 25.641 | 239 | 38.936 | 188 |
| 15.982 | 268 | 26.598 | 272 | | |
| 16.76 | 371 | 27.575 | 253 | | |
| 17.099 | 355 | 28.065 | 247 | | |

| 2-Theta | Intensity | 2-Theta | Intensity | 2-Theta | Intensity |
|---|---|---|---|---|---|
| 6.58 | 777 | 15.98 | 263 | 25.72 | 294 |
| 8.002 | 172 | 17.059 | 831 | 26.614 | 343 |
| 9.536 | 199 | 18.1 | 697 | 27.118 | 324 |
| 10.236 | 351 | 18.94 | 1237 | 28.379 | 332 |
| 10.637 | 251 | 19.722 | 491 | 28.717 | 321 |
| 12.3 | 440 | 21.18 | 1428 | 30.877 | 184 |
| 12.817 | 292 | 22.24 | 1128 | 31.3 | 198 |
| 13.161 | 208 | 23.139 | 460 | 32.442 | 164 |
| 14.38 | 284 | 23.983 | 628 | 37.238 | 189 |
| 15.479 | 261 | 24.681 | 536 | 39.243 | 187 |

| 2-Theta | Intensity | 2-Theta | Intensity | 2-Theta | Intensity |
|---|---|---|---|---|---|
| 6.281 | 380 | 17.02 | 299 | 25.598 | 221 |
| 9.479 | 556 | 18.021 | 378 | 27.457 | 198 |
| 10.119 | 340 | 19.021 | 795 | 28.461 | 255 |
| 12.202 | 291 | 21.022 | 656 | 28.739 | 308 |
| 12.697 | 936 | 22.239 | 711 | 31.16 | 267 |
| 14.36 | 192 | 23.118 | 313 | 34.214 | 161 |
| 15.898 | 285 | 23.922 | 355 | 37.201 | 178 |
| 16.718 | 272 | 24.6 | 452 | 38.741 | 217 |

KINASE INHIBITOR SALTS AND COMPOSITIONS THEREOF

This application is a continuation of U.S. patent application Ser. No. 17/321,864 filed May 17, 2021, which is a continuation of U.S. patent application Ser. No. 17/167,719 filed Feb. 4, 2021, now U.S. Pat. No. 11,052,088, which is a continuation of U.S. patent application Ser. No. 16/701,941 filed Dec. 3, 2019, now U.S. Pat. No. 11,007,195, which is a continuation of International Patent Application Number PCT/US2019/036947, filed on Jun. 13, 2019, which claims the benefits of U.S. Provisional Patent Application Ser. No. 62/685,411, filed Jun. 15, 2018, U.S. Provisional Patent Application Ser. No. 62/791,356 filed Jan. 11, 2019 and U.S. Provisional Patent Application Ser. No. 62/811,368 filed Feb. 27, 2019; each of which is herein incorporated by reference in its entirety.

FIELD OF THE INVENTION

The present invention relates to kinase inhibitor salts formed by reacting the kinase inhibitor with a $C_8$-$C_{16}$ aliphatic sulfate. The kinase inhibitor salts may be orally administered to subjects in combination with at least one pharmaceutically acceptable excipient.

The present invention also relates to pharmaceutically acceptable compositions and dosage forms comprising the kinase inhibitor $C_8$-$C_{16}$ aliphatic sulfate salts, methods for preparing the compositions and dosage forms and methods of treating various conditions such as cancer comprising the oral administration of the compositions and dosage forms.

BACKGROUND

Kinase inhibitors (KIs) are compounds that inhibit kinase enzymes and thereby interfere with the activation of proteins. KIs are commonly used to treat cancers but are also being used to treat inflammatory and autoimmune diseases such as rheumatoid arthritis and Crohn's disease.

KIs often exhibit pH dependent solubility and thus erratic bioavailability following oral administration.

KIs are also known to exhibit large absorption fluctuations when administered under fasting conditions compared to administration in the presence of a high fat meal or when administered with other drugs such as gastric acid reducing agents, i.e., antacids, $H_2$ antagonists and proton pump inhibitors. For example, some of the KIs are known to exhibit a significant increase in pharmacokinetics values such as $C_{max}$ (maximum plasma concentration) and AUC (area under the plasma concentration curve) when the compound is orally administered in the presence of a high fat meal compared to the administration under fasting conditions. Similarly, the co-administration of KIs with gastric acid reducing agents or agents that increase gastric pH is known to reduce absorption of KIs. As a result of the large potential fluctuations, restrictions on the time and conditions of KI administration may be required resulting in unwanted inconvenience to the patient, unwanted side effects if not administered correctly or loss of efficacy.

Accordingly, it is an object of the present invention to provide novel KI salts and compositions comprising the KI salts which will improve KI absorption following oral administration, reduce the absorption variation when the KI is orally administered with or without food and or reduce the absorption variation when co-administered with other drugs such as gastric acid reducing agents.

SUMMARY OF THE INVENTION

The present invention obtains the above objectives and others.

The present invention encompasses KI salts wherein the salt is formed by reacting the KI with a $C_8$-$C_{16}$ aliphatic sulfate. In one embodiment, the KI salt is formed by reacting the KI with an alkaline or alkaline earth metal lauryl sulfate or an alkaline or alkaline earth metal tetradecyl sulfate.

The present invention also encompasses compositions and dosage forms comprising the KI $C_8$-$C_{16}$ aliphatic sulfate salts and at least one pharmaceutically acceptable excipient, preferably for oral administration to a subject.

The present invention further encompasses methods for reducing or eliminating food effects that result from the oral administration of KIs. More specifically, the present invention encompasses the oral administration of compositions and/or dosage forms of the present invention to a subject, wherein the subject may be either in a fed state or a fasted state. Upon oral administration of the compositions or dosage forms of the present invention, a KI plasma profile is obtained wherein at least one pharmacokinetic parameter differs by less than about 40% under fed and fasted conditions. In various embodiments, the pharmacokinetic parameter may vary by less than about 35%, 30%, 25%, 20%, 15%, 10%, or 5% under fed and fasted conditions. The pharmacokinetic parameter that is independent of food may be, but is not limited to, $C_{max}$, AUC, $T_{max}$, or combinations thereof. In certain embodiments, one or more dosage forms comprising the KI $C_8$-$C_{16}$ aliphatic sulfate salts and at least one pharmaceutically acceptable excipient are orally administered to cancer patients with or without food wherein the dose of the KI $C_8$-$C_{16}$ aliphatic sulfate salts administered with or without food does not require an adjustment in dose or a change in time of administration.

The present invention also further encompasses methods for reducing or eliminating drug interactions that result from the oral administration of KIs and the co-administration of other drugs such as gastric acid reducing agents or drugs that raise gastric pH. More specifically, the present invention encompasses the oral administration of compositions and/or dosage forms of the present invention to a subject, wherein the subject may also be receiving drugs that reduce gastric acid secretion or that raise gastric acid pH. Upon oral administration of the compositions or dosage forms of the present invention, a KI plasma profile is obtained wherein at least one pharmacokinetic parameter differs by less than about 40% when the compositions or dosage forms of the present invention are administered with or without a drug that reduces gastric acid secretion or that raise gastric acid pH. In various embodiments, the pharmacokinetic parameter may vary by less than about 35%, 30%, 25%, 20%, 15%, 10%, or 5% when the compositions or dosage forms of the present invention are administered with or without a drug that reduces gastric acid secretion or that raise gastric acid pH. The pharmacokinetic parameter that is independent of co-administration with a drug that reduces gastric acid secretion or that raises gastric acid pH maybe $C_{max}$, AUC, $T_{max}$, or combinations thereof. In certain embodiments, one or more dosage forms comprising the KI $C_8$-$C_{16}$ aliphatic sulfate salts and at least one pharmaceutically acceptable excipient are orally administered to cancer patients that are being co-administered gastric acid reducing agents wherein the dose of the KI $C_8$-$C_{16}$ aliphatic sulfate salts does not require an adjustment in dose or a change in time of administration.

The present invention also encompasses methods for reducing the total oral daily dose of the KI. More specifically, the present invention encompasses the oral administration of compositions and/or dosage forms prepared in accordance with the present invention wherein the total daily amount of the KI administered is at least 10%, 15%, 20%, 25%, 30%, 35%, 40%, 45% or 50% lower than the currently U.S. Food and Drug Administration approved total daily amount of the KI free base or non $C_8$-$C_{16}$ aliphatic sulfate salt.

In one embodiment of the present invention, the composition or dosage form for oral administration is a hard or soft capsule or a tablet, comprising a KI $C_8$-$C_{16}$ aliphatic sulfate salt and a pharmaceutically acceptable carrier, preferably in an intimate mixture. In certain aspects of this embodiment, the hard or soft capsule can be gelatin-based or non gelatin-based capsule. In certain aspects of this embodiment, the pharmaceutically acceptable carrier is a liquid at ambient conditions, i.e., 25° C. and standard atmospheric pressure or the pharmaceutically acceptable carrier is a solid at ambient conditions but has a melting point above 25° C. but less than 120° C., preferably less than 100° C. and most preferably less than 80° C. If the pharmaceutically acceptable carrier is a liquid at ambient conditions, the KI $C_8$-$C_{16}$ aliphatic sulfate salt and liquid carrier are mixed and the resulting mixture is filled or formed into the hard or soft capsule. The liquid mixture may further comprise one or more pharmaceutically acceptable excipients such as a stabilizer which are described in greater detail below. If the carrier is a solid at ambient temperature, the carrier may be heated to melt the carrier and the melted carrier and KI $C_8$-$C_{16}$ aliphatic sulfate salt are mixed prior to filling or forming into the hard or soft capsule or formed into a tablet. Alternatively, the carrier maybe dissolved or dispersed in a solvent and combined with the KI $C_8$-$C_{16}$ aliphatic sulfate salt alone or combined with the KI $C_8$-$C_{16}$ aliphatic sulfate salt and at least one additional pharmaceutical acceptable excipient to create an intimate admixture of the carrier and KI $C_8$-$C_{16}$ aliphatic sulfate salt. Once the intimate admixture of the KI $C_8$-$C_{16}$ aliphatic sulfate salt and carrier is created, it may be dried and filled or formed into a hard or soft capsule or the intimate admixture can be combined with at least one or more pharmaceutically acceptable excipients and the resulting combination filled or formed into a hard or soft capsule or formed into a tablet.

In another embodiment of the present invention, the compositions and/or dosage forms comprise the KI $C_8$-$C_{16}$ aliphatic sulfate salts and a carrier with an HLB value of 10 or greater wherein the carrier with an HLB value of 10 or greater is selected from the group consisting of a wetting agent, an emulsifying agent, a solubilizing agent, a surfactant or combinations thereof. In preferred embodiments, the KI $C_8$-$C_{16}$ aliphatic sulfate salt and carrier with an HLB value of 10 or greater are intimately mixed. In further embodiments, the composition is a liquid composition that may be orally administered to a subject or the liquid composition may be filled into a hard or soft capsule for oral administration to a subject. The liquid mixture may further comprise one or more pharmaceutically acceptable excipients such as a stabilizer which are described in greater detail below. Alternatively, the composition may be a solid or semi-solid composition such as a powder or granulate that may be orally administered to a subject or the solid or semi-solid composition may be formed into a tablet or filled into a capsule for oral administration to a subject.

The present invention further encompasses methods for preparing, forming and manufacturing the compositions and dosage forms comprising the KI $C_8$-$C_{16}$ aliphatic sulfate salts and at least one pharmaceutically acceptable excipient, preferably for oral administration to a subject.

The present invention also further encompasses methods of treating patients comprising orally administering the compositions and dosage forms comprising therapeutic amounts of the KI $C_8$-$C_{16}$ aliphatic sulfate salt and at least one pharmaceutically acceptable excipient.

The present invention also encompasses novel polymorphic forms of the KI $C_8$-$C_{16}$ aliphatic sulfate salts, methods for making the novel polymorphic forms, compositions and dosage forms comprising the novel polymorphic forms and methods of treating patients with the novel polymorphic forms.

DETAILED DESCRIPTION OF THE INVENTION

Figure 1:
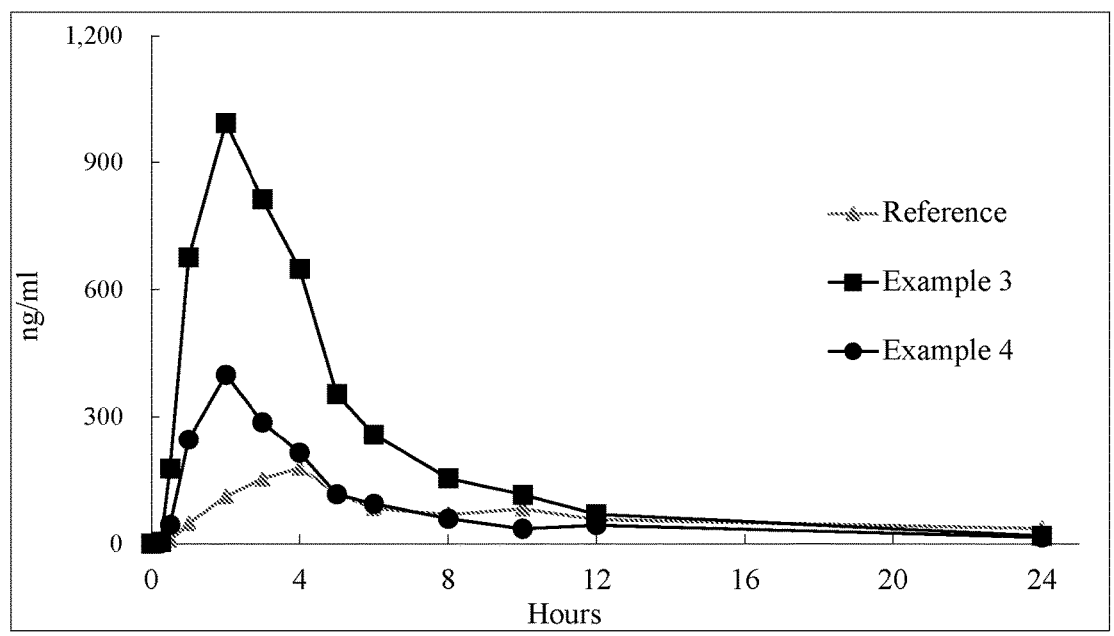
FIG. 1 is a graph of the mean in vivo plasma data provided in Example 5.

Before the present invention is further described, it is to be understood that this invention is not limited to the particular embodiments described. It is also to be understood that the terminology used herein is for the purpose of describing particular embodiments only, and is not intended to be limiting.

It should be noted that as used herein, the singular forms "a," "an," and "the" include plural referents unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the term "normal storage conditions" refers to storage at room temperature, approximately 25° C. and approximately 60% relative humidity for at least three months, preferably at least six months, and most preferably at least one year. The dosage form in accordance with the present invention should be stored in pharmaceutically acceptable containers such as glass bottles, plastic bottles, metal foil pouch, or blister packaging with or without a desiccant.

As used herein, the term "accelerated storage conditions" refers to storage at approximately 40° C. and approximately 75% relative humidity for at least two weeks or longer, one month or longer, two months or longer, three months or longer, four months or longer, five months or longer, or six months or longer. The dosage form in accordance with the present invention should be stored in pharmaceutically acceptable containers such as glass bottles, plastic bottles, metal foil pouch, or blister packaging with or without a desiccant.

The term "HLB" refers to the "hydrophilic-lipophilic balance" of a surfactant or emulsifier and is a measure of the degree to which it is hydrophilic or lipophilic and is determined by calculating values for the different regions of the molecule, as described by Griffin W C, "Calculation of HLB Values of Non-Ionic Surfactants," Journal of the Society of Cosmetic Chemists, 5:259 (1954). HLB values range from 0 to 20, with an HLB value of 0 corresponding to a completely lipophilic molecule, and a value of 20 corresponding to a completely hydrophilic molecule. HLB values are generally known and reported in the literature such as the manufacturer's technical brochures.

The term "$C_{max}$" denotes the maximum plasma concentration obtained during the dosing interval.

The term "$T_{max}$" denotes the time to maximum plasma concentration ($C_{max}$).

The term "AUC" means an area under the drug concentration-time curve (AUC) calculated using linear trapezoidal summation for a specified interval of time, for example, $AUC_{0-12}$ refers to the area under the drug concentration-time curve from the time immediately preceding administration to 12 hours after administration, $AUC_{0-24}$ refers to the area under the drug concentration-time curve from the time immediately preceding administration to 24 hours after administration, $AUC_{0-\infty}$ refers to the area under the drug concentration-time curve from the time immediately preceding administration to infinity and $AUC_{0-t}$ refers to the area under the drug concentration-time curve from the time immediately preceding administration to the designated time point such a 2 hours, 8 hours, 18 hours etc after administration. In some embodiments, the designated time point is the last time point of blood sampling.

The pharmacokinetic values described herein are generally determined according to methods known and understood by those in the art and are generally described in publications such as the United States Food and Drug Administration's (U.S. FDA) Guidance for Industry: Bioavailability and Bioequivalence Studies for Orally Administered Drug Products—General Considerations (March 2003); U.S. FDA's Guidance for Industry: Statistical Approaches to Establishing Bioequivalence (January 2001); and U.S. FDA's Guidance for Industry: Food-Effect Bioavailability and Fed Bioequivalence Studies (December 2002), which are incorporated herein by reference.

As used herein, and unless otherwise defined, the term "subject" refers to a mammal such as a human, monkey, cow, horse, sheep, pig, chicken, turkey, quail, cat, dog, mouse, rat, rabbit, or guinea pig, preferably humans and includes healthy mammals and mammals affected with a disease that may be treated with the KI. A subject that is affected with a disease that may be treated with the KI is sometimes referred to as "patient".

As used herein, and unless otherwise defined, the phrase "therapeutically effective amount" when used in connection with a pharmaceutical composition or dosage form comprising the KI salt means an amount of KI or salt thereof effective for treating a disease or disorder disclosed herein, such as cancer.

As used herein, and unless otherwise defined, the phrases "intimately mixed," "intimate mixture" and the like refer to a combination of the KI salt of the present invention and at least one pharmaceutically acceptable excipient, preferably a carrier with an HLB value of about 10 or greater, preferably about 11 or greater and most preferably about 12 or greater such as a wetting agent, emulsifying agent, solubilizing agent, surfactant or combinations thereof wherein the KI salt and at least one pharmaceutically acceptable excipient are in intimate contact or close association with each other. The intimate mixture may be prepared by any procedure that enables through blending of the KI salt of the invention and the at least one pharmaceutically acceptable excipient, preferably a carrier with an HLB value of about 10 or greater. An example of a suitable process for achieving the intimate mixture includes dissolving, suspending or dispersing the KI salt in a solution or suspension containing the at least one pharmaceutically acceptable excipient, preferably a carrier with an HLB value of about 10 or greater and optionally at least one additional pharmaceutically acceptable excipient such as a pharmaceutically acceptable solvent. The pharmaceutically solvent may or may not be removed. Another example of a suitable process for achieving the intimate mixture includes employing a liquid excipient wherein the liquid comprises at least one pharmaceutically acceptable excipient with an HLB value of about 10 or greater or melting one or more solid excipients wherein the melt comprises at least one pharmaceutically acceptable excipient with an HLB value of about 10 or greater, to create a melted or liquid excipient composition comprising at least one excipient with an HLB value of about 10 or greater, and dissolving, suspending or dispersing the KI salt in the melted or liquid excipient composition. The liquid excipient composition comprising at least one excipient with an HLB value of about 10 or greater, may also comprise one or more pharmaceutically acceptable excipients and described in greater detail below. Other processes that may be used to achieve the intimate mixture of the KI salt and at least one pharmaceutically acceptable excipient preferably with an HLB value of about 10 or greater, include co-blending, co-screening, co-compacting, co-compressing or a combination thereof. Once the intimate mixture of the KI salt and at least one pharmaceutically acceptable excipient, preferably with an HLB value of about 10 or greater, is prepared, the intimately mixed composition may be combined with at least one additional pharmaceutical excipient or carrier. The intimate mixture may preferably comprise the KI salt and one, two or three excipients prior to being combined with any additional excipients.

As used herein, and unless otherwise defined, the term "gastric acid reducing agent" refers to excipients and/or drugs that increase gastric pH or neutralize stomach acid such as antacids or compounds that reduce gastric acid secretion such as $H_2$ antagonists or proton pump inhibitors. Examples of common antacids include but are not limited to sodium bicarbonate, sodium citrate, magnesium trisilicate, aluminum trisilicate, calcium carbonate and over the counter products such as TUMS and ALKA-SELTZER. Examples of $H_2$ antagonists include but are not limited to antihistamines, cimetidine, ranitidine, famotidine, nizatidine, roxatidine and lafutidine. Examples of proton pump inhibitors include but are not limited to omeprazole, lansoprazole, pantoprazole, rabeprazole, esomeprazole and dexlansoprazole.

As used herein, and unless otherwise defined, the terms "co-administration, "co-administered," and "co-administer" refers to a subject receiving one or more non-KI drug or therapeutic agent during the course of the KI therapy. The one or more non-KI drugs or therapeutic agents may be administered concurrently or sequentially with the KI composition or dosage form of the present invention. The concurrent administration as used herein means the non-KI drug or therapeutic agent is administered within 2 hours before or after administration of the KI composition or dosage form of the present invention, preferably within 1 hour before or after administration of the KI composition or dosage form of the present invention and more preferably within 30 minute before or after administration of the KI composition or dosage form of the present invention. The sequential administration as used herein means administration of the non-KI drug or therapeutic agent at any time before or after the administration of the KI composition or dosage form of the present invention and may include administration of the non-KI drug such as 4, 6, 8, 12, or 14 hours before or after the administration of the KI composition or dosage form.

As used herein, and unless otherwise defined, the term "KI" or "KIs" refers to any compound or compounds that are pharmaceutically active and that inhibits a kinase enzyme, preferably a tyrosine kinase enzyme. Preferably, the KIs are small molecules that generally employ the "nib" suffix in the name and include the tyrosine kinase inhibitors (TKIs) which generally employ the suffix "tinib" in the name, angiogenesis inhibitors which generally employ the suffix "anib" in the name and rapidly accelerated fibrosarcoma kinase inhibitors which generally employ the suffix "rafinib" in the name. Also included are focal adhesion kinase (FAK) inhibitors.

Examples of KIs that may be employed in the present invention include, but are not limited to acalabrutinib (commercially available under the tradename CALQUENCE), afatinib (commercially available under the tradename GILOTRIF), alectinib (commercially available under the tradename ALECENSA), apatinib, axitinib (commercially available under the tradename INLYTA), bafetinib, baricitinib, bosutinib (commercially available under the tradename BOSULIF), brigatinib (commercially available under the tradename ALUNBRIG), cabozantinib (commercially available under the tradename COMETRIQ), canertinib, cediranib, ceritinib (commercially available under the tradename ZYKADIA), cobimetinib (commercially available under the tradename COTELLIC), crenolanib, crizotinib (commercially available under the tradename XALKORI), dabrafenib (commercially available under the tradename TAFINLAR), dasatinib (commercially available under the tradename SPRYCEL), defactinib (commercially available from Verastem Oncology) enasidenib (commercially available under the tradename IDHIFA), entrectinib, erlotinib (commercially available under the tradename TARCEVA), filgotinib, foretinib, fostamatinib (commercially available under the tradename TAVALISSE), gefitinib (commercially available under the tradename IRESSA), glesatinib, ibrutinib (commercially available under the tradename IMBRUVICA), icotinib, imatinib (commercially available under the tradename GLEEVEC), lapatinib (commercially available under the tradename TYKERB), lestaurtinib, lenvatinib (commercially available under the tradename LENVIMA), linifanib, lucitanib, momelotinib, motesanib, mubritinib, neratinib (commercially available under the tradename NERLYNX), nilotinib (commercially available under the tradename TASIGNA), nintedanib (commercially available under the tradename OFEV), oclacitinib (commercially available under the tradename APOQUEL), olmutinib, osimertinib (commercially available under the tradename TAGRISSO), pacritinib, pazopanib (commercially available under the tradename VOTRIENT), ponatinib (commercially available under the tradename ICLUSIG), quizartinib, radotinib, regorafenib (commercially available under the tradename STIVARGA), rociletinib, ruxolitinib (commercially available under the tradename JAKAFI), saracatinib, savolitinib, semaxanib, sitravtinib, sorafenib (commercially available under the tradename NEXAVAR), sunitinib (commercially available under the tradename SUTENT), taselisib, tesevatinib, tivozanib, toceranib, tofacitinib (commercially available under the tradename XELJANZ), trametinib (commercially available under the tradename MEKINIST), upadacitinib, vatalanib, vandetanib (commercially available under the tradename CAPRELSA) and vemurafenib (commercially available under the tradename ZELBORAF).

Some of the more preferred KIs that are useful in the present invention include but are not limited to acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, oclacitinib, osimertinib, pazopanib, ponatinib, regorafenib, ruxolitinib, sorafenib, sunitinib, trametinib, vandetanib, and vemurafenib.

Additional examples of KIs that are useful in the present invention are KIs that contain
(i) a phenyl carboxamide moiety with the following structure:

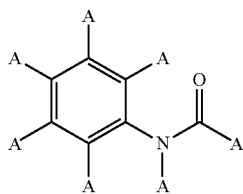

(ii) an amino pyrimidine moiety with the following structure:

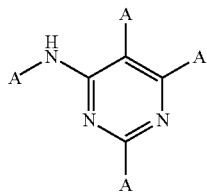

(iii) an amino pyrimidine moiety with the following structure:

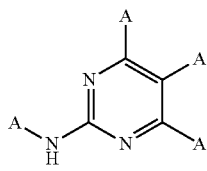

or
(iv) a combination of the moieties described in (i), (ii) or (iii)
wherein A is H, C, N, O, S, P, halogen (F, Cl, Br, I) and/or A may be part of a larger moiety such as a straight, branched or cyclic moiety for example an alkyl, aryl, alkoxy, etc. In certain embodiments, the A substituent on the nitrogen of the phenyl carboxamide moiety (i) is preferably H or $C_1$-$C_4$ alkyl Examples of KIs that contain the phenyl carboxamide moiety (i) include but are not limited to afatinib, cabozantinib, dasatinib, lenvatinib, neratinib, nilotinib, nintedanib, osimertinib, ponatinib, regorafenib, and trametinib.

Examples of KIs that contain one of the amino pyrimidine moieties (ii) or (iii) include but are not limited to afatinib, brigatinib, ceritinib, dabrafenib, dasatinib, defactinib, erlotinib, fostamatinib, gefitinib, ibrutinib, imatinib, lapatinib, nilotinib, osimertinib, pazopanib, ruxolitinib, tofacitinib and vandetanib.

In certain preferred embodiments, the KIs used in the present invention will contain: (a) a phenyl carboxamide moiety (i) and an amino pyrimidine moiety (ii) or (b) a phenyl carboxamide moiety (i) and an amino pyrimidine moiety (iii) as described above. Examples of KIs that contain both the phenyl carboxamide moiety (i) and one of the amino pyrimidine moieties (ii) or (iii) include but are not limited to afatinib, dasatinib, imatinib, nilotinib and osimertinib.

The KI $C_8$-$C_{16}$ aliphatic sulfate salts of the present invention may be formed by reacting the KI molecule with a $C_8$-$C_{16}$ aliphatic sulfate. In one embodiment, the KI $C_8$-$C_{16}$ aliphatic sulfate salt is formed by reacting the KI with an alkaline or alkaline earth metal lauryl sulfate or an alkaline or alkaline earth metal tetradecyl sulfate. Examples of preferred alkaline or alkaline earth metal lauryl sulfate or an alkaline or alkaline earth metal tetradecyl sulfate include but are not limited to sodium or potassium lauryl sulfate and sodium or potassium tetradecyl sulfate. The most preferred anionic compounds used to prepare the KI salts of the present invention are sodium lauryl sulfate or potassium lauryl sulfate.

The KI $C_8$-$C_{16}$ aliphatic sulfate salts of the present invention may be formed by dissolving a KI compound (either in a free base or salt form such as the KI HCl salt, KI citrate salt, KI phosphate salt, KI mesylate salt, KI maleate salt, or KI tosylate salt) in a suitable solvent such as water, an organic solvent such as $C_1$-$C_6$ branched or straight chain alcohols, ethers, esters or ketones or mixtures thereof, an organic solvent such as a $C_3$-$C_{12}$ branched or straight chain alkane or mixtures thereof, or a mixture of water and an organic solvent, adding a $C_8$-$C_{16}$ aliphatic sulfate to the KI solution and mixing the resulting reaction mass. Alternatively, the $C_8$-$C_{16}$ aliphatic sulfate may be dissolved in a suitable solvent, adding the KI compound (either in a free base or salt form) to the $C_8$-$C_{16}$ aliphatic sulfate solution and mixing the resulting reaction mass. The KI $C_8$-$C_{16}$ aliphatic sulfate salt of the present invention may also be formed by dissolving the KI compound (either in a free base or salt form) in a suitable solvent, dissolving the $C_8$-$C_{16}$ aliphatic sulfate in a suitable solvent, combing the KI compound solution and the $C_8$-$C_{16}$ aliphatic sulfate solution and mixing the resulting reaction mass. The solvent is removed from the resulting reaction mass by conventional techniques such as evaporation or filtration to isolate the KI $C_8$-$C_{16}$ aliphatic sulfate salt. The isolated KI $C_8$-$C_{16}$ aliphatic sulfate salt of the present invention may be used in the compositions and dosage forms described herein.

In some embodiments of the present invention the dissolved KI compound may be reacted with an acid, preferably a strong acid and most preferably an inorganic acid to protonate one or more of the nitrogen atoms. Once the KI is protonated it is combined with the $C_8$-$C_{16}$ aliphatic sulfate for form the KI $C_8$-$C_{16}$ aliphatic sulfate salt.

The molar ratio of $C_8$-$C_{16}$ aliphatic sulfate to KI compound in the reaction mass could range from about 0.5 moles of $C_8$-$C_{16}$ aliphatic sulfate to about 6 moles of $C_8$-$C_{16}$ aliphatic sulfate for each mole of KI base present in the reaction mass, preferably about 0.75 moles of $C_8$-$C_{16}$ aliphatic sulfate to about 5 moles of $C_8$-$C_{16}$ aliphatic sulfate for each mole of KI base present in the reaction mass and most preferably about 0.85 moles of $C_8$-$C_{16}$ aliphatic sulfate to about 4 moles of $C_8$-$C_{16}$ aliphatic sulfate for each mole of KI base present in the reaction mass. The KI $C_8$-$C_{16}$ aliphatic sulfate salt may also be formed during or as part of the manufacturing of the compositions or dosage forms of the present invention. In some embodiments of KI mono $C_8$-$C_{16}$ aliphatic sulfate salt, the molar ratio of $C_8$-$C_{16}$ aliphatic sulfate to KI compound in the reaction mass could range from about 0.8 moles of $C_8$-$C_{16}$ aliphatic sulfate to about 1.3 moles of $C_8$-$C_{16}$ aliphatic sulfate for each mole of KI base present in the reaction mass. In some embodiments of KI di $C_8$-$C_{16}$ aliphatic sulfate salt, the molar ratio of $C_8$-$C_{16}$ aliphatic sulfate to KI compound in the reaction mass could range from about 1.6 moles of $C_8$-$C_{16}$ aliphatic sulfate to about 2.5 moles of $C_8$-$C_{16}$ aliphatic sulfate for each mole of KI base present in the reaction mass. The KI $C_8$-$C_{16}$ aliphatic sulfate salts of the present invention may be a KI mono $C_8$-$C_{16}$ aliphatic sulfate salt or a KI multi $C_8$-$C_{16}$ aliphatic sulfate salt such as KI di $C_8$-$C_{16}$ aliphatic sulfate salt, a KI tri $C_8$-$C_{16}$ aliphatic sulfate salt, a KI tetra $C_8$-$C_{16}$ aliphatic sulfate salt or a KI penta $C_8$-$C_{16}$ aliphatic sulfate salt. Unless otherwise indicated, the term KI $C_8$-$C_{16}$ aliphatic sulfate salts as used herein encompasses the mono and multiple aliphatic sulfate salts and similarly the term KI lauryl sulfate salts encompasses the mono and multiple lauryl sulfate salts.

The present invention also encompasses compositions and dosage forms comprising the KI $C_8$-$C_{16}$ aliphatic sulfate salts and at least one pharmaceutically acceptable excipient, preferably for oral administration to a subject. The compositions and dosage forms may be a solid, semi-solid or liquid, wherein the KI $C_8$-$C_{16}$ aliphatic sulfate salt is combined with pharmaceutically acceptable excipients such as fillers, diluents, binders, stabilizing agents, lubricants, disintegrants, wetting/solubilizing/emulsifying agents or mixtures thereof. The pharmaceutically acceptable excipients are well known in the art and are described in Remington, The Science and Practice of Pharmacy, 21$^{st}$ ed. (2006), pp. 1058-1092, and Handbook of Pharmaceutical Excipients, 6$^{th}$ ed. (2009). Representative examples of the various pharmaceutically acceptable excipients employed in the embodiments of the present invention are provided below.

The solid and semi-solid compositions and dosage forms include powders, granules, pellets, mini-tablets, tablets, or capsules and may be made by methods known in the art such as direct compression, wet or dry granulation, and extrusion spheronization.

The liquid compositions and dosage forms include solutions, suspensions, or dispersions and these may also be made by methods known in the art.

In one embodiment of the present invention, the composition or dosage form for oral administration is a tablet or a hard or soft gelatin capsule comprising a KI $C_8$-$C_{16}$ aliphatic sulfate salt and a pharmaceutically acceptable carrier, preferably in an intimate mixture. In certain aspects of this embodiment, the pharmaceutically acceptable carrier is a liquid at ambient conditions, i.e., 25° C. and standard atmospheric pressure, or the pharmaceutically acceptable carrier is a solid at ambient conditions but has a melting point above 25° C. but less than 120° C., preferably less than 100° C., more preferably less than 80° C. and most preferably less than 60° C. If the pharmaceutically acceptable carrier is a liquid at ambient conditions, the KI $C_8$-$C_{16}$ aliphatic sulfate salt and liquid carrier are mixed and the resulting mixture is filled or formed into the hard or soft gelatin capsule. The liquid mixture may also comprise one or more additional pharmaceutically acceptable excipients such as a stabilizer described in greater detail below.

If the carrier is a solid or semi-solid at ambient temperature, the carrier may be mixed or granulated with the KI $C_8$-$C_{16}$ aliphatic sulfate salt and optionally one or more additional pharmaceutically acceptable excipients prior to forming into a tablet or filling or forming into a hard or soft gelatin capsule. Alternatively, if the carrier is a solid or semi-solid at ambient temperature the carrier may be heated to melt the carrier and the melted carrier, KI $C_8$-$C_{16}$ aliphatic sulfate salt and optionally one or more additional pharmaceutically acceptable excipients are mixed prior to forming into a tablet or filling or forming into a hard or soft gelatin capsule.

In certain embodiments, the KI $C_8$-$C_{16}$ aliphatic sulfate salt is dissolved in the liquid carrier or dissolved in the melted carrier. Alternatively, the KI $C_8$-$C_{16}$ aliphatic sulfate salt is dispersed or suspended in the liquid carrier or dispersed or suspended in the melted carrier.

Examples of liquid carriers that may be used in preparing the oral dosage forms of the present invention include but are not limited to fatty acids, medium chain triglycerides, fatty acid esters, fatty acid alcohols, vegetable oils such as corn oil, soy bean oil, olive oil, sun flower oil, peanut oil or mixtures thereof. In certain embodiments the liquid carrier should comprise about 10%, 15%, 20%, 25%, 30%, 40%, 45%, 50%, 55%, 60%, 65%, 70%, 75%, 80%, 85%, 90% 95% (w/w) of the composition or any range encompassed by the foregoing values, preferably about 15% (w/w) to about 90% (w/w) and most preferably about 20% (w/w) to about 85% (w/w) of the composition filled into the capsule.

Examples of solid carriers with a melting point between 25° C. and less than 120° C. include aliphatic alcohols, polyethylene glycol, such as polyethylene glycol 1000 with a melting point of 37-40° C., polyethylene glycol 1500 with a melting point of 44-48° C., hard fat (aka hydrogenated vegetable glycerides), hydrogenate vegetable oil, vitamin E polyethylene glycol succinate (aka TPGS), poloxamers (nonionic polyoxyethylene-polyoxypropylene copolymers such as poloxamer 188, poloxamer 237, poloxamer 338 and poloxamer 407), polyoxylglycerides, polyoxyethylene stearates and waxes, such as carnauba wax, cetyl ester wax, microcrystalline wax, white wax, and yellow wax and combinations of the foregoing solid carriers. In certain embodiments, the solid carrier should comprise about 2.5%, 5%, 7.5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 92.5%, 95% (w/w) or any range encompassed by the foregoing values, preferably about 5% (w/w) to about 90% (w/w) and most preferably about 7.5% (w/w) to about 85% (w/w) of the composition filled into the capsule or formed into a tablet.

Additional examples of the solid, semi-sold and liquid carriers that may be used in preparing the solid, semi-solid or liquid dosage forms of the present invention including but not limited to hard gelatin capsules, soft gelatin capsules and tablets of the present invention include wetting agents, emulsifying agents, solubilizing agents, surfactants or combinations thereof that exhibit an HLB value of about 10 or greater, preferably an HLB value of about 11 or greater, more preferably an HLB value of about 12 or greater and most preferably an HLB value of about 14 or greater are described in detail below.

In another embodiment of the present invention, the compositions or dosage forms may comprise the KI $C_8$-$C_{16}$ aliphatic sulfate salt and one or more wetting agent, emulsifying agent, solubilizing agent, surfactant or combinations thereof that exhibits an HLB value of about 10 or greater, preferably an HLB value of about 11 or greater, more preferably about 12 or greater and most preferably about 14 or greater and at least one additional pharmaceutically acceptable excipient. The KI $C_8$-$C_{16}$ aliphatic sulfate salt may be present in the composition in an amount of about 1 wt % to about 80 wt % based on the total weight of the composition or dosage form, preferably about 2 wt % to about 70 wt %, more preferably about 2.5 wt % to about 60 wt % and most preferably about 3 wt % to about 50 wt %. In certain embodiments, the KI $C_8$-$C_{16}$ aliphatic sulfate salt may be present in the composition in an amount of about 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt % 49 wt % 50 wt % or any range encompassed by the foregoing values. The one or more wetting agent, emulsifying agent, solubilizing agent, surfactant or combinations thereof that exhibits an HLB value of about 10 or greater, preferably about 11 or greater, more preferably 12 or greater and most preferably about 14 or greater should be present in the composition or dosage form in an amount of 1 wt % or greater based on the total weight of the composition or dosage form, preferably in an amount of about 2 wt % or greater and most preferably in an amount of about 5 wt % or greater based on the total weight of the composition or dosage form. In certain embodiments, the one or more wetting agent, emulsifying agent, solubilizing agent, surfactant or combinations thereof that exhibits an HLB value of about 10 or greater, preferably about 11 or greater, more preferably about 12 or greater and most preferably about 14 or greater should be present in the composition or dosage form in an amount of about 1 wt % to about 90 wt %, preferably about 2 wt % to about 80 wt % and most preferably about 3 wt % to about 70 wt %. In certain embodiments, the one or more wetting agent, emulsifying agent, solubilizing agent, surfactant or combinations thereof that exhibits an HLB value of about 10 or greater may be present in the composition in an amount of about 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt % 49 wt % 50 wt %, 51 wt %, 52 wt %, 53 wt %, 54 wt %, 55 wt %, 56 wt %, 57 wt %, 58 wt %, 59 wt %, 60 wt % or any range encompassed by the foregoing values.

The one or more wetting agent, emulsifying agent, solubilizing agent, surfactant or combinations thereof that exhibits with an HLB value of about 10 or greater may be a non-ionic surfactant, an ionic surfactant or a combination thereof and is preferably a non-ionic surfactant. Examples of non-ionic surfactants that may be used include polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, polyoxylglycerides, polyoxyethylene stearates or a mixture of the foregoing. A further listing of possible non-ionic surfactants can be found on pages 1243-1249 of Martindale, The Extra Pharmacopoeia, $29^{th}$ ed. which is incorporated herein by reference.

The one or more wetting agent, emulsifying agent, solubilizing agent, surfactant or combinations thereof that exhibits an HLB value of about 10 or greater may be a non-ionic surfactant such as fatty alcohol acid or amide ethoxylates, monoglyceride ethoxylates, sorbitan ester ethoxylates alkyl polyglycosides, and mixtures thereof. Examples of these non-ionic surfactants include but are not limited to polyoxyethylene derivatives of polyol esters, such as Polysorbate 20 (commercially available under the tradename TWEEN® 20), Polysorbate 40 (commercially available under the tradename TWEEN® 40) Polysorbate 60 (commercially available under the tradename TWEEN® 60), and Polysorbate 80 (commercially available under the tradename TWEEN® 80).

The one or more wetting agent, emulsifying agent, solubilizing agent, surfactant or combinations thereof that exhibits an HLB value of about 10 or greater may be a polyoxyethylene castor oil such as polyoxyl castor oil or polyoxyl hydrogenated castor oil or mixtures thereof. Examples of these surfactants include but are not limited to polyoxyl 35 castor oil (commercially available under the tradename CREMAPHOR EL or KOLLIPHOR EL), polyoxyl 40 hydrogenated castor oil (commercially available under the tradename CREMOPHOR RH 40) and polyoxyl 60 hydrogenated castor oil.

The one or more wetting agent, emulsifying agent, solubilizing agent, surfactant or combinations thereof that exhibits an HLB value of about 10 or greater may be a polyoxyethylene alkyl ether such as a polyoxyl cetostearyl ether, polyoxyl cetyl ether, polyoxyl lauryl ether, polyoxyl oleyl ether, polyoxyl stearyl ether or mixtures thereof.

The one or more wetting agent, emulsifying agent, solubilizing agent, surfactant or combinations thereof that exhibits an HLB value of about 10 or greater may be a tyloxapol, a poloxamer, i.e., a nonionic polyoxyethylene-polyoxypropylene copolymers such as poloxamer 188, poloxamer 237, poloxamer 338, poloxamer 407 or a combination thereof.

The one or more wetting agent, emulsifying agent, solubilizing agent, surfactant or combinations thereof that exhibits an HLB value of about 10 or greater may be a fatty acid ester or fatty acid alcohol of a polyglyceride such as a caprylic/capric triglyceride (commercially available under the tradename MYIGLYOL).

In certain embodiments of the present invention, the composition comprises the KI $C_8$-$C_{16}$ aliphatic sulfate and one or more wetting agent, emulsifying agent, solubilizing agent, surfactant or combinations thereof that exhibits an HLB value of about 10 or greater, preferably in an intimate mixture, and may also further comprise at least one additional secondary carrier with a low or no HLB value. The secondary carrier may be one or more wetting agent, emulsifying agent, solubilizing agent, surfactant or combinations thereof that exhibits an HLB value of about less than 10, more preferably an HLB value of about 9 or less, about 8 or less, and most preferably an HLB value of about 7 or less. Examples of the at least one additional secondary carriers with a low HLB value include non-ionic surfactants which include but are not limited to polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, or a mixture of the foregoing. A further listing of possible non-ionic surfactants with low HLB values can be found on pages 1243-1249 of Martindale, The Extra Pharmacopoeia, 29$^{th}$ ed. which is incorporated herein by reference.

In certain embodiments, the secondary carrier with an HLB value of about less than 10 is a medium chain (i.e., about 4 to about 20 carbon atoms, preferably about 6 to about 18 carbon atoms and most preferably about 6 to and 14 carbon atoms) monoglyceride or diglyceride such as a glyceryl caprylate/caprate (commercially available under the tradename CAPMUL MCM), a glyceryl caprylate (commercially available under the tradename CAPMUL MCM $C_8$), glyceryl caprate (commercially available under the tradename CAPMUL MCM $C_{10}$), glyceryl monocaprylo-caprate (commercially available under the tradename CAPMUL 471) or mixtures thereof.

In certain embodiments, the secondary carrier with an HLB value of about less than 10 is a polyoxylglyceride such as caprylocaproyl polyoxylglycerides, lauroyl polyoxylglycerides, linoleoyl polyoxylglycerides, oleoyl polyoxylglycerides, stearoyl polyoxylglycerides, and mixtures of the foregoing.

In certain embodiments, the secondary carrier with an HLB value of about less than 10 is a sorbitan ester or sorbitan fatty acid ester such as sorbitan monolaurate, sorbitan monooleate, sorbitan monopalmitate, sorbitan monostearate, sorbitan sesquioleate, sorbitan trioleate, tyloxapol, and mixtures of the foregoing.

In certain embodiments, the secondary carrier with an HLB value of about less than 10 is a phospholipid or lecithin.

In certain embodiments, the secondary carrier is an oil, a medium chain triglyceride, hydrogenated vegetable oil, suppository bases or combinations thereof.

In certain embodiments, the secondary carrier with an HLB of about less than 10 is liquid at ambient temperature or exhibits a melting point of about 75° C. or less, about 70° C. or less, about 65° C. or less, about 60° C. or less, about 55° C. or less, about 50° C. or less, about 45° C. or less or about 40° C. or less.

In the embodiments employing the secondary carrier with an HLB value of about less than 10, the amount of the secondary carrier with an HLB value about less than 10 may be about 1 wt % to about 90 wt % based on the total weight of the composition, preferably about 5 wt % to about 85 wt % and most preferably about 10 wt % to about 80 wt %. The forgoing weight percentages may be based on a single secondary carrier or a combination of secondary carriers. In certain embodiments, the one or more wetting agent, emulsifying agent, solubilizing agent, surfactant or combinations thereof that exhibits an HLB value of about less than 10 may be present in the composition in an amount of about 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt % 49 wt % 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt % 80 wt % or any range encompassed by the foregoing values.

The compositions and dosage forms of the present invention may also optionally comprise additional pharmaceutically acceptable excipients such as stabilizers, fillers, viscosity enhancing agents, binders, disintegrants, lubricants, glidants, flavoring agents, and combinations thereof.

In certain embodiments the dosage form of the present invention is a solid or semi-solid oral dosage form, preferably a capsule or tablet that comprises:

(i) about 1 wt % to about 60 wt % based on the total weight of the solid composition or dosage form, preferably about 2 wt % to about 55 wt % and most preferably about 5 wt % to about 50 wt % of a KI $C_8$-$C_{16}$ aliphatic sulfate salt;

(ii) about 1 wt % to about 60 wt %, preferably about 2 wt % to about 50 wt % and most preferably about 3 wt % to about 40 wt % of one or more wetting agents, solubilizing agents, emulsifying agents, surfactants or combinations thereof that exhibits an HLB value of about 10 or greater, preferably an HLB value of about 11 or greater, more preferably an HLB value of about 12 or greater and most preferably an HLB value of about 14 or greater; and (iii) at least one additional pharmaceutically acceptable excipient selected from the group consisting of stabilizers, fillers, viscosity enhancing agents, binders, disintegrants, lubricants, glidants, flavoring agents, and combinations thereof.

In further embodiments, such as a semi-solid embodiment, the oral dosage form may further comprise (iv) a viscosity enhancing agent that is a solid at ambient temperatures but that exhibits a melting point below 120° C., preferably below 100° C., more preferably below 80° C. and most preferably below 60° C. If the dosage form comprises item (iv) a viscosity enhancing agent that is a solid at ambient temperatures but that exhibits a melting point below 120° C., item (iv) should comprise about 0.5 wt % to about 60 wt %, preferably about 1 wt % to about 55 wt % and most preferably about 5 wt % to about 50 wt % of the total weight of the composition.

Examples of stabilizers that may be used in the present invention include, but are not limited to, antioxidants, drying agents, buffers, pH adjusting agents, or combination thereof. The stabilizer(s) if present in the dosage form should be less than about 20% of the total weight of the composition, preferably less than about 15% of the total weight of the composition, and most preferably less than about 10% of the total weight of the composition. In certain embodiments, the stabilizer may be present in the composition in an amount of about 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.2 wt %, 1.3 wt %, 1.4 wt %, 1.5 wt %, 1.6 wt %, 1.7 wt %, 1.8 wt %, 1.9 wt %, 2.0 wt %, 2.1 wt %, 2.2 wt %, 2.3 wt %, 2.4 wt %, 2.5 wt %, 2.6 wt %, 2.7 wt %, 2.8 wt %, 2.9 wt %, 3.0 wt %, 3.1 wt %, 3.2 wt %, 3.3 wt %, 3.4 wt %, 3.5 wt %, 3.6 wt %, 3.7 wt %, 3.8 wt %, 3.9 wt % 4.0 wt % 4.1 wt %, 4.2 wt %, 4.3 wt %, 4.4 wt %, 4.5 wt %, 4.6 wt %, 4.7 wt %, 4.8 wt %, 4.9 wt %, 5.0 wt % or any range encompassed by the foregoing values.

Examples of antioxidants that may be used in the present invention include, but are not limited to, ascorbic acid, ascorbyl palmitate (AP), butylated hydroxyanisole (BHA), butylated hydroxytoluene (BHT), citric acid, ethyl oleate, fumaric acid, hypophosphorous acid, malic acid, monothioglycerol, potassium metabisulfite, propyl gallate, sodium bisulfite, sodium formaldehyde sulfoxylate, sodium metabisulfite, sodium sulfite, sodium thiosulfate, sulfur dioxide, tocopherols, methylparaben, ethylparaben, propylparaben, butylparaben, benzyl benzoate, pyridoxine, ethyl vanillin and mixtures thereof. Preferred antioxidants for use according to the invention include BHT, BHA, AP, propyl gallate, alpha tocopherol, or any mixtures thereof. Generally, the amount antioxidant present in the composition of the present invention will comprise about 0.0001 wt % to about 5 wt %, preferably about 0.01 wt % to about 2 wt %, and most preferably about 0.05 wt % to about 1 wt % based on the total weight of the composition.

As used herein, and unless otherwise defined, the term "drying agent" refers to pharmaceutically acceptable excipients that have the ability to bind or absorb water present in the composition. Examples of a drying agent useful in the present invention may include, for example, magnesium oxide (MgO), aluminum oxide, attapulgite, bentonite, kaolin, pectin, saponite, colloidal silicon dioxide, and mixtures thereof. Depending upon the specific dosage form, the viscosity enhancing agents discussed below may also be used as a drying agent. The amount of drying agent, if present, in the composition of the present invention can range from about 0.05 wt % to about 10 wt % of the total weight of the composition, preferably about 0.1 wt % to about 5 wt % of the total weight of the composition, and most preferably about 0.5 wt % to about 2.5 wt % of the total weight of the composition.

Examples of buffers that may be used in the present invention include, but are not limited to, acetic acid, adipic acid, ammonium carbonate, ammonium phosphate, boric acid, citric acid, lactic acid, phosphoric acid, potassium citrate, potassium phosphate, sodium acetate, sodium citrate, sodium carbonate, potassium carbonate, sodium bicarbonate, potassium bicarbonate, sodium lactate, sodium phosphate, succinic acid, and combinations thereof. Typically the buffer will comprise a combination of the foregoing as to create a buffer system such as citric acid and sodium citrate or acetic acid and sodium acetate.

Examples of pH adjusting agents that may be used in the present invention include, but are not limited to, any of the pharmaceutically acceptable acids or bases used to adjust the pH of pharmaceutical compositions. Examples of compounds typically used to adjust the pH of pharmaceutical compositions include hydrochloric acid, citric acid, lactic acid, tartaric acid, glacial acetic acid, sodium hydroxide, potassium hydroxide, arginine, lysine, meglumine, triethanol amine, or combinations thereof.

If employed, the buffer and/or pH adjusting agent may comprise about 0.01 wt % to about 20 wt % of the composition, preferably about 0.1 wt % to about 10 wt % of the composition, and most preferably about 0.5 wt % to about 5 wt % of the composition.

Fillers, sometimes referred to as diluents, may also be used in the present invention and include water; sugars such as lactose, dextrose, sucrose, maltose, or microcrystalline cellulose; clays, and mixtures thereof. Generally, the amount filler present in the compositions of the present invention will comprise about 0 wt % to about 90 wt %, preferably about 0.01 wt % to about 80 wt %, and most preferably about 1 wt % to about 70 wt % based on the total weight of the composition.

Viscosity enhancing agents that may be used in the present invention include organic materials such as natural or synthetic waxes, $C_{12}$-$C_{60}$ alcohols, $C_{12}$-$C_{60}$ acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays. Additional viscosity enhancing agents include polyol polyesters, glyceryl esters, polyglyceryl esters, and polysiloxanes.

Waxes are also suitable for use as viscosity enhancing agents in compositions of the present invention. Natural waxes may include, but are not limited to, carnauba, ozokerite, beeswax, candelilla, paraffin, ceresin, esparto, ouricuri, rezowax and other known mined and mineral waxes. Synthetic waxes may include, but are not limited to, paraffin waxes and microcrystalline waxes.

Still further viscosity enhancing agents that may be included in the compositions of the present invention are gelling agents. Gelling agents are materials that can swell or expand when in contact with water. Examples of gelling agents that may be used in the present invention include swellable polymers, also known as osmopolymers or hydrogels. The swellable polymer can be non-cross-linked or lightly cross-linked. The cross-links can be covalent or ionic bonds with the polymer possessing the ability to swell in the presence of fluid, and when cross-linked, it will not be dissolved in the fluid. The polymer can be of plant, animal, or synthetic origin. Polymeric gelling agents useful for the present purpose include polyhydroxyalkylcellulose having a molecular weight greater than 50,000, such as hydroxyl propylmethylcellulose (METHOCEL K 100M available from Dow Chemical); poly(hydroxyalkylmethacrylate) having a molecular weight of from 5,000 to 5,000,000; poly (vinylpyrrolidone) having a molecular weight of from 100,000 to 3,000,000; anionic and cationic hydrogels; poly (electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams, and the like.

Other gelling agents useful in the present invention include pectin having a molecular weight ranging from 30,000 to 300,000; polysaccharides such as agar, acacia, karaya, tragacanth, algins and guar; CARBOPOL® an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOL® 934, 940 and 941, and its salt derivatives; polyacrylamides; water-swellable indene maleic anhydride polymers; GOOD-RITE® polyacrylic acid having a molecular weight of 80,000 to 200,000; POLYOX™ polyethylene oxide polymers having a molecular weight of 100,000 to 7,000,000; starch graft copolymers; AQUA-KEEP™ acrylate polymers with water absorbability of about 400 times its original weight; diesters of polyglucan; a mixture of cross-linked polyvinyl alcohol and poly(N-vinyl-2-pyrrolidone); poly(ethylene glycol) having a molecular weight of 4,000 to 100,000. Representative polymers possessing gelling properties are described in U.S. Pat. Nos. 6,419,954, 4,915,949, 4,327,725, 4,207,893 and in Handbook of Common Polymers, by Scott and Roff, published by Cleveland Rubber Company, Cleveland, Ohio.

Generally, the amount of viscosity enhancing agent present in the compositions of the present invention will comprise about 0 wt % to about 30 wt %, preferably about 0.01 wt % to about 25 wt %, and most preferably about 1 wt % to about 15 wt % based on the total weight of the composition. In the semi-solid embodiments of the present invention, the viscosity enhancing agent that is a solid at ambient temperatures but that exhibits a melting point below 120° C., preferably below 100° C., more preferably below 80° C. and most preferably below 60° C. as discussed above and may comprise about 7.5 wt % to about 75 wt %, preferably about 10 wt % to about 60 wt % and most preferably about 12 wt % to about 50 wt % of the total weight of the composition. Examples of these viscosity enhancing agents include but are not limited to the natural or synthetic waxes such as carnauba wax, cetyl ester wax, microcrystalline wax, white wax, yellow wax, bees wax, ozokerite, paraffin, ceresin, esparto, ouricuri, and rezowax, hard fats (aka hydrogenated vegetable glycerides), hydrogenated vegetable oils, $C_{12}$-$C_{60}$ alcohols, $C_{12}$-$C_{60}$ acids, alpha-hydroxy fatty acids, polyhydroxy fatty acid esters, polyhydroxy fatty acid amides and combinations thereof described above.

Examples of binders that may be employed in the solid dosage form of the present invention include acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose, or mixtures thereof. Especially preferred binders include water soluble binders such as povidone, hypromellose, hydroxypropyl cellulose, gelatin and mixtures thereof. If the binder is a polymeric binder, it is preferred that the binder have a low molecular weight and/or exhibit a viscosity of less than 200 mPa·s, preferably less than 100 mPa·s, and most preferably less than 50 mPa·s when tested at a concentration of 2% (w/v) aqueous preparation at 20° C.

Generally, the amount binder present in the compositions of the present invention will comprise about 0 wt % to about 30 wt %, preferably about 0.01 wt % to about 25 wt %, and most preferably about 1 wt % to about 15 wt % based on the total weight of the composition.

Examples of disintegrants that may be employed in the solid dosage form of the present invention include croscarmellose sodium, starch, crospovidone, sodium starch glycolate, alginic acid, calcium carboxymethylcellulose, sodium carboxymethylcellulose, potassium carboxymethylcellulose, powdered cellulose, chitosan, guar gum, magnesium aluminum silicate, methylcellulose, sodium alginate, and mixtures thereof. Generally, the amount of disintegrant present in the compositions of the present invention will comprise about 0 wt % to about 40 wt %, preferably about 1 wt % to about 25 wt %, and most preferably about 2 wt % to about 20 wt % based on the total weight of the composition.

Examples of lubricants that may be employed in the solid dosage form of the present invention include magnesium stearate, sodium stearyl fumarate, stearic acid, glyceryl behenate, polyethylene glycols (preferably wherein the polyethylene glycol has a molecular weight of 6000 or more), polyoxyethylene stearate, magnesium lauryl sulfate, sodium oleate, and mixtures thereof. The lubricants may be present in an amount ranging from about 0.1 wt % to about 10 wt % based on the total weight of the dosage form, preferably about 0.2 wt % to about 7 wt %, and most preferably about 0.5 wt % to about 5 wt %.

Examples of glidants that may be employed in the solid dosage form of the present invention include colloidal silicon dioxide, corn starch, talc and mixtures thereof. The glidants may be present in an amount ranging from about 0.1 wt % to about 10 wt % based on the total weight of the dosage form, preferably about 0.2 wt % to about 7 wt %, and most preferably about 0.5 wt % to about 5 wt %.

Examples of flavoring agents that may be employed in the solid dosage form of the present invention include artificial sweeteners such as aspartame, saccharin, dipotassium glycyrrhizinate, stevia, thaumatin, and flavorants such as citric acid, peppermint oil, wintergreen oil, menthol, lemon, lime, orange, grape, cherry, and vanilla extract. Additional taste enhancing agents are described in U.S. Pat. No. 6,027,746 which is incorporated herein by reference.

Embodiment A of the present invention is an oral liquid dosage form, preferably in a hard or soft capsule comprising:

(i) about 1 wt % to about 80 wt %, preferably about 2 wt % to about 70 wt %, more preferably about 3 wt % to about 60 wt % and most preferably about 5 wt % to about 50 wt % of a KI $C_8$-$C_{16}$ aliphatic sulfate salt, preferably wherein the KI is selected from the group consisting of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, and vemurafenib and most preferably from the group consisting of afatinib, dasatinib, erlotinib, imatinib, nilotinib, nintedanib, osimertinib, pazopanib and ponatinib and preferably wherein the KI $C_8$-$C_{16}$ aliphatic sulfate salt is a KI lauryl sulfate salt and most preferably a KI mono- or di-lauryl sulfate salt;

(ii) about 1 wt % to about 95 wt %, preferably about 5 wt % to about 90 wt % and most preferably about 10 wt % to about 80 wt % of a liquid carrier selected from the group consisting of fatty acids, medium chain triglycerides, fatty acid esters, fatty acid alcohols, vegetable oils such as corn oil, soy bean oil, olive oil, sun flower oil, peanut oil or mixtures thereof; and (iii) optionally one or more additional pharmaceutically acceptable excipients selected from the group consisting of a stabilizer, a filler, a viscosity enhancing agent, a binder, a disintegrant, a lubricant, a glidant, a flavoring agent, and combinations thereof.

Embodiment B of the present invention is an oral solid or semi-solid dosage form that may be a tablet, or hard or soft capsule comprising:

(i) about 1 wt % to about 80 wt %, preferably about 2 wt % to about 70 wt %, more preferably about 3 wt % to about 60 wt % and most preferably about 5 wt % to about 50 wt % of a KI $C_8$-$C_{16}$ aliphatic sulfate salt, preferably wherein the KI is selected from the group consisting of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, and vemurafenib and most preferably from the group consisting of afatinib, dasatinib, erlotinib, imatinib, nilotinib, nintedanib, osimertinib, pazopanib and ponatinib and preferably wherein the KI $C_8$-$C_{16}$ aliphatic sulfate salt is a KI lauryl sulfate salt and most preferably a KI mono- or di-lauryl sulfate salt;

(ii) about 1 wt % to about 90 wt %, preferably about 2.5 wt % to about 80 wt %, more preferably about 3 wt % to about 70 wt % and most preferably about 5 wt % to about 60 wt % of a solid carrier with a melting point between 25° C. and less than 120° C., preferably less than 100° C., more preferably less than 80° C. and most preferably less than 60° C., and wherein the solid carrier is preferably selected from the group consisting of polyethylene glycol, hard fat, hydrogenate vegetable oil, vitamin E polyethylene glycol succinate, wax, poloxamer and combinations of the foregoing; and (iii) optionally one or more additional pharmaceutically acceptable excipients selected from the group consisting of a stabilizer, a filler, a viscosity enhancing agent, a binder, a disintegrant, a lubricant, a glidant, a flavoring agent, and combinations thereof.

Embodiment C of the present invention is an oral dosage form, such as a hard or soft capsule comprising:

(i) about 1 wt % to about 80 wt %, preferably about 2 wt % to about 70 wt %, more preferably about 3 wt % to about 60 wt % and most preferably about 5 wt % to about 50 wt % of a KI $C_8$-$C_{16}$ aliphatic sulfate salt, preferably wherein the KI is selected from the group consisting of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, and vemurafenib and most preferably from the group consisting of afatinib, dasatinib, erlotinib, imatinib, nilotinib, nintedanib, osimertinib, pazopanib and ponatinib and preferably wherein the KI $C_8$-$C_{16}$ aliphatic sulfate salt is a KI lauryl sulfate salt and most preferably a KI mono- or di-lauryl sulfate salt;

(ii) about 1 wt % to about 60 wt %, preferably about 2 wt % to about 50 wt % and most preferably about 3 wt % to about 40 wt % of at least one wetting agent, emulsifying agent, solubilizing agent, surfactant or combinations thereof that exhibits an HLB value of about 10 or greater, preferably about 11 or greater, more preferably about 12 or greater and most preferably about 14 or greater and wherein the at least one wetting agent, emulsifying agent, solubilizing agent, surfactant or combinations thereof that exhibits an HLB value of about 10 or greater is preferably selected from the group consisting of fatty alcohol acid or amide ethoxylates, monoglyceride ethoxylates, sorbitan ester ethoxylates alkyl polyglycosides, polyoxyethylene castor oil, polyoxyethylene hydrogenated castor oil, poloxamer, tyloxapol, a fatty acid ester or fatty acid alcohol of a polyglyceride or combinations thereof and most preferably selected form the group consisting of polyoxyethylene castor oil, polyoxyethylene hydrogenated castor oil, poloxamer, a caprylic/capric triglyceride or combinations thereof;

(iii) about 5 wt % to about 90 wt %, preferably about 10 wt % to about 85 wt % and most preferably about 15 wt % to about 80 wt % of a secondary carrier with an HLB value of about less than 10, preferably about 9 or less, about 8 or less and most preferably about 7 or less and wherein the secondary carrier is selected form the group consisting of a wetting agent, an emulsifying agent, a solubilizing agent, a surfactant or combinations thereof with an HLB value of about less than 10 and more preferably is selected from the group consisting of medium chain monoglycerides, medium chain diglycerides, polyoxylglycerides, sorbitan esters, sorbitan fatty acid esters, phospholipids and combinations thereof and most preferably medium chain monoglycerides, medium chain diglycerides, lecithins and combinations; and (iv) optionally one or more additional pharmaceutically acceptable excipients selected from the group consisting of a stabilizer, a filler, a viscosity enhancing agent, a binder, a disintegrant, a lubricant, a glidant, a flavoring agent, and combinations thereof.

In certain embodiments of the capsule dosage form, the at least one wetting agent, emulsifying agent, solubilizing agent, surfactant or combinations thereof that exhibits an HLB value of about 10 or greater and the secondary carrier with an HLB value of about less than 10 are liquids at 25° C. and the KI salt, at least one wetting agent, emulsifying agent, solubilizing agent, surfactant or combinations thereof that exhibits an HLB value of about 10 or greater and the secondary carrier with an HLB value of about less than 10 are an intimate mixture.

Embodiment D of the present invention is an oral solid dosage form such as a tablet or capsule wherein the tablet or contents of the capsule comprises:

(i) about 1 wt % to about 80 wt %, preferably about 2 wt % to about 70 wt %, more preferably about 3 wt % to about 60 wt % and most preferably about 5 wt % to about 50 wt % of a KI $C_8$-$C_{16}$ aliphatic sulfate salt, preferably wherein the KI is selected from the group consisting of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, and vemurafenib and most preferably from the group consisting of afatinib, dasatinib, erlotinib, imatinib, nilotinib, nintedanib, osimertinib, pazopanib and ponatinib and preferably wherein the KI $C_8$-$C_{16}$ aliphatic sulfate salt is a KI lauryl sulfate salt and most preferably a KI mono- or di-lauryl sulfate salt;

(ii) about 1 wt % to about 60 wt %, preferably about 2 wt % to about 50 wt % and most preferably about 3 wt % to about 40 wt % of one or more wetting agents, solubilizing agents, emulsifying agents, surfactants or combination thereof that exhibits an HLB value of about 10 or greater, preferably an HLB value of about 11 or greater, more preferably about 12 or greater, and most preferably about 14 or greater wherein the one or more wetting agents, emulsifying agents, solubilizing agents, surfactants or combinations thereof with an HLB value of about 10 or greater is selected from the group consisting of fatty alcohol acid or amide ethoxylates, monoglyceride ethoxylates, sorbitan ester ethoxylates alkyl polyglycosides, polyoxyethylene castor oil, polyoxyethylene hydrogenated castor oil, poloxamer, tyloxapol, a fatty acid ester or fatty acid alcohol of a polyglyceride or combinations thereof and most preferably selected form the group consisting of polyoxyethylene castor oil, polyoxyethylene hydrogenated castor oil, poloxamer, a caprylic/capric triglyceride or combinations thereof;

(iii) about 0 wt % to about 40 wt %, preferably about 1 wt % to about 25 wt % and most preferably about 2.5 wt % to about 20 wt % of a disintegrant;

(iv) about 5 wt % to about 90 wt %, preferably about 15 wt % to about 85 wt % and most preferably about 20 wt % to about 80 wt % of a filler; and (v) optionally one or more additional pharmaceutically acceptable excipients selected from the group consisting of a stabilizer, a viscosity enhancing agent, a binder, a lubricant, a glidant, a flavoring agent, and combinations thereof.

In certain embodiments of Embodiment D, the KI $C_8$-$C_{16}$ aliphatic sulfate salt and at least 25%, 30%, 35%, 40%, 45%, 50%, 55%, 60%, 65%, 70%, 75%, 80%, 85%, 90%, 95% or 100% of the total amount of the one or more wetting agents, emulsifying agents, solubilizing agents, surfactants or combinations thereof with an HLB value of about 10 or greater are present in the solid tablet or solid capsule in an intimate mixture, preferably formed before being combined with the elements (iii), (iv) and/or (v).

Embodiment E of the present invention is an oral semi-solid composition comprising:
(i) about 1 wt % to about 80 wt %, preferably about 2 wt % to about 70 wt %, more preferably about 3 wt % to about 60 wt % and most preferably about 5 wt % to about 50 wt % of a KI $C_8$-$C_{16}$ aliphatic sulfate salt, preferably wherein the KI is selected from the group consisting of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, and vemurafenib and most preferably from the group consisting of afatinib, dasatinib, erlotinib, imatinib, nilotinib, nintedanib, osimertinib, pazopanib and ponatinib and preferably wherein the KI $C_8$-$C_{16}$ aliphatic sulfate salt is a KI lauryl sulfate salt and most preferably a KI mono- or di-lauryl sulfate salt;
(ii) about 1 wt % to about 70 wt %, preferably about 2 wt % to about 60 wt % and most preferably about 5 wt % to about 50 wt % of one or more wetting agents, solubilizing agents, emulsifying agents, surfactants or combination thereof that exhibits an HLB value of about 10 or greater, preferably an HLB value of about 11 or greater, more preferably about 12 or greater, and most preferably about 14 or greater wherein the one or more wetting agents, emulsifying agents, solubilizing agents, surfactants or combinations thereof with an HLB value of about 10 or greater is selected from the group consisting of fatty alcohol acid or amide ethoxylates, monoglyceride ethoxylates, sorbitan ester ethoxylates alkyl polyglycosides, polyoxyethylene castor oil, polyoxyethylene hydrogenated castor oil, poloxamer, tyloxapol, a fatty acid ester or fatty acid alcohol of a polyglyceride or combinations thereof and most preferably selected form the group consisting of polyoxyethylene castor oil, polyoxyethylene hydrogenated castor oil, poloxamer, a caprylic/capric triglyceride or combinations thereof;
(iii) about 1 wt % to about 70 wt %, preferably about 2 wt % to about 60 wt % and most preferably about 5 wt % to about 50 wt % of a secondary carrier with an HLB value of about less than 10, preferably about 9 or less, about 8 or less and most preferably about 7 or less and wherein the secondary carrier is selected form the group consisting of a wetting agent, an emulsifying agent, a solubilizing agent, a surfactant or combinations thereof with an HLB value of about less than 10 and more preferably is selected from the group consisting of medium chain monoglycerides, medium chain diglycerides, polyoxylglycerides, sorbitan esters, sorbitan fatty acid esters, phospholipids and combinations thereof and most preferably medium chain monoglycerides, medium chain diglycerides, lecithin and combinations;
(iv) about 0.5 wt % to about 70 wt %, preferably about 1 wt % to about 60 wt % and most preferably about 2.5 wt % to about 50 wt % of a viscosity enhancing agent that is a solid at ambient temperature but exhibits a melting point below 120° C., preferably below 100° C., more preferably below 80° C. and most preferably below 60° C. where in the viscosity enhancing agent is selected from the group consisting of natural or synthetic waxes such as carnauba wax, cetyl ester wax, microcrystalline wax, white wax, yellow wax, bees wax, ozokerite, paraffin, ceresin, esparto, ouricuri, and rezowax, hard fats (aka hydrogenated vegetable glycerides), hydrogenated vegetable oils, $C_{12}$-$C_{60}$ alcohols, $C_{12}$-$C_{60}$ acids, alpha-hydroxy fatty acids, polyhydroxy fatty acid esters, polyhydroxy fatty acid amides and combinations thereof; and
(v) optionally one or more additional pharmaceutically acceptable excipients selected from the group consisting of a stabilizer, a binder, a lubricant, a glidant, a flavoring agent, and combinations thereof;
wherein the KI $C_8$-$C_{16}$ aliphatic sulfate salt and the one or more wetting agents, emulsifying agents, solubilizing agents, surfactants or combinations thereof with an HLB value of about 10 or greater are present in an intimate mixture.

Embodiment F of the present invention is an oral solid dosage form such as a tablet or capsule wherein the tablet or contents of the capsule comprises a solid dispersion comprising:
(i) about 1 wt % to about 80 wt %, preferably about 2 wt % to about 70 wt %, more preferably about 3 wt % to about 60 wt % and most preferably about 5 wt % to about 50 wt % of a KI $C_8$-$C_{16}$ aliphatic sulfate salt, preferably wherein the KI is selected from the group consisting of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, and vemurafenib and most preferably from the group consisting of afatinib, dasatinib, erlotinib, imatinib, nilotinib, nintedanib, osimertinib, pazopanib and ponatinib and preferably wherein the KI $C_8$-$C_{16}$ aliphatic sulfate salt is a KI lauryl sulfate salt and most preferably a KI mono- or di-lauryl sulfate salt;
(ii) about 1 wt % to about 60 wt %, preferably about 2 wt % to about 50 wt % and most preferably about 3 wt % to about 40 wt % of one or more wetting agents, solubilizing agents, emulsifying agents, surfactants or combination thereof that exhibits an HLB value of about 10 or greater, preferably an HLB value of about 11 or greater, more preferably about 12 or greater, and most preferably about 14 or greater wherein the one or more wetting agents, emulsifying agents, solubilizing agents, surfactants or combinations thereof with an HLB value of about 10 or greater is selected from the group consisting of fatty alcohol acid or amide ethoxylates, monoglyceride ethoxylates, sorbitan ester ethoxylates alkyl polyglycosides, polyoxyethylene castor oil, polyoxyethylene hydrogenated castor oil, poloxamer, tyloxapol, a fatty acid ester or fatty acid alcohol of a polyglyceride or combinations thereof and most preferably selected form the group consisting of polyoxyethylene castor oil, polyoxyethylene hydrogenated castor oil, poloxamer, a caprylic/capric triglyceride or combinations thereof; and (iii) about 1 wt % to about 60 wt %, preferably about 2 wt % to about 50 wt % and most preferably about 3 wt % to about 45 wt % of one or more polymeric agents, preferably water soluble polymeric agents that exhibit a viscosity of less than 200 mPa□s, preferably less than 100 mPa□s, and most preferably less than 50 mPa□s when tested at a concentration of 2% (w/v) aqueous preparation at 20° C. and most preferably wherein the polymeric agent is selected from the group consisting of povidone, hypromellose, hydroxypropyl cellulose, gelatin and mixtures thereof.

The solid dispersion dosage form of Embodiment F may further comprise within the solid dispersion or mixed with the solid dispersion, i.e., extra granular, (iv) about 0 wt % to about 40 wt %, preferably about 1 wt % to about 25 wt % and most preferably about 2.5 wt % to about 20 wt % of a disintegrant;

(v) about 0 wt % to about 90 wt %, preferably about 15 wt % to about 85 wt % and most preferably about 20 wt % to about 80 wt % of a filler; and (vi) optionally one or more additional pharmaceutically acceptable excipients selected from the group consisting of a stabilizer, a viscosity enhancing agent, a binder, a lubricant, a glidant, a flavoring agent, and combinations thereof.

Embodiment G of the present invention is a sustained or controlled release oral solid dosage form such as a tablet or capsule wherein the tablet or contents of the capsule comprises:

(i) about 1 wt % to about 80 wt %, preferably about 2 wt % to about 70 wt %, more preferably about 3 wt % to about 60 wt % and most preferably about 5 wt % to about 50 wt % of a KI $C_8$-$C_{16}$ aliphatic sulfate salt, preferably wherein the KI is selected from the group consisting of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, and vemurafenib and most preferably from the group consisting of afatinib, dasatinib, erlotinib, imatinib, nilotinib, nintedanib, osimertinib, pazopanib and ponatinib and preferably wherein the KI $C_8$-$C_{16}$ aliphatic sulfate salt is a KI lauryl sulfate salt and most preferably a KI mono- or di-lauryl sulfate salt;

(ii) about 1 wt % to about 60 wt %, preferably about 2 wt % to about 50 wt % and most preferably about 3 wt % to about 40 wt % of one or more wetting agents, solubilizing agents, emulsifying agents, surfactants or combination thereof that exhibits an HLB value of about 10 or greater, preferably an HLB value of about 11 or greater, more preferably greater than 12 and most preferably about 14 or greater wherein the one or more wetting agents, emulsifying agents, solubilizing agents, surfactants or combinations thereof with an HLB value of about 10 or greater is selected from the group consisting of fatty alcohol acid or amide ethoxylates, monoglyceride ethoxylates, sorbitan ester ethoxylates alkyl polyglycosides, polyoxyethylene castor oil, polyoxyethylene hydrogenated castor oil, poloxamer, tyloxapol, a fatty acid ester or fatty acid alcohol of a polyglyceride or combinations thereof and most preferably selected form the group consisting of polyoxyethylene castor oil, polyoxyethylene hydrogenated castor oil, poloxamer, a caprylic/capric triglyceride or combinations thereof;

(iii) about 0.5 wt % to about 50 wt %, preferably about 1 wt % to about 40 wt % and most preferably about 2 wt % to about 35 wt % of a controlled or sustained agent, wherein the controlled or sustained release agent is an excipient that controls or sustains the release of the KI $C_8$-$C_{16}$ aliphatic sulfate salt from the dosage form for a period of time greater than one hour, greater than two hours, greater than 3 hours, greater than 4 hours, greater than 5 hours, or greater than six hours and preferably is selected from the viscosity enhancing agents described previously and more preferably is gelling agent as previously described and may be selected from the group consisting of a polyhydroxyalkylcellulose having a molecular weight greater than 50,000, such as hydroxyl propylmethylcellulose (METHOCEL K 100M available from Dow Chemical); a poly(hydroxyalkylmethacrylate) having a molecular weight of from 5,000 to 5,000,000; a poly(vinylpyrrolidone) having a molecular weight of from 100,000 to 3,000,000; pectin having a molecular weight ranging from 30,000 to 300,000; a polysaccharide such as agar, acacia, karaya, tragacanth, algins and guar; an acrylic acid polymer (CARBOPOL®); a polyethylene oxide polymer (POLYOX™) having a molecular weight of 100,000 to 7,000,000 and combinations thereof;

(iv) optionally about 5 wt % to about 90 wt %, preferably about 15 wt % to about 85 wt % and most preferably about 20 wt % to about 80 wt % of a filler; and (v) optionally one or more additional pharmaceutically acceptable excipients selected from the group consisting of a stabilizer, a binder, a lubricant, a glidant, a flavoring agent, and combinations thereof.

In certain embodiments of Embodiment G, the KI $C_8$-$C_{16}$ aliphatic sulfate salt and at least 25%, 30%, 35%, 40%, 45%, 50%, 55%, 60%, 65%, 70%, 75%, 80%, 85%, 90%, 95% or 100% of the total amount of the one or more wetting agents, emulsifying agents, solubilizing agents, surfactants or combinations thereof with an HLB value of about 10 or greater are present in the solid tablet or solid capsule in an intimate mixture, preferably formed before being combined with the elements (iii), (iv) and/or (v).

In certain embodiments of Embodiment G, the sustained or controlled release oral solid dosage form will release the KI $C_8$-$C_{16}$ aliphatic sulfate salt when tested using a USP Type II Apparatus (Paddle) with 900 ml of an aqueous media with a pH of 6.8 and 0.1% sodium lauryl sulfite at 75 rpm with or without a sinker as follows:

| Time (hour) | Preferred | More Preferred | Most Preferred |
|---|---|---|---|
| 2 | 0-40% | 0-35% | 0-30% |
| 4 | 5%-70% | 7.5%-60% | 10%-50% |
| 6 | 10%-100% | 15%-100% | 20%-100% |
| 10 | NLT* 45% | NLT 50% | NLT 55% |
| 12 | NLT 50% | NLT 60% | NLT 70% |

*NLT = Not Less Than

In certain embodiments of the present invention and specifically Embodiments A-F, the oral solid dosage form will release the KI $C_8$-$C_{16}$ aliphatic sulfate salt when tested using a USP Type II Apparatus (Paddle) with 500 ml of 0.1 N HCl at 75 rpm, with or without a sinker and 37° C. as follows:

| Time (minutes) | Preferred | More Preferred | Most Preferred |
|---|---|---|---|
| 15 | 0-50% | 5%-50% | 10%-50% |
| 30 | 10%-70% | 25%-70% | 35%-70% |
| 45 | 35%-100% | 45%-100% | 50%-100% |
| 60 | NLT 80% | NLT 85% | NLT 90% |

Certain embodiments of the present invention and specifically the liquid oral dosage forms will release the KI $C_8$-$C_{16}$ aliphatic sulfate salt when tested using a USP Type II Apparatus (Paddle) with 500-900 ml of 0.1 N HCl at 75 rpm, with or without a sinker and 37° C. as follows:

| Time (minutes) | Preferred | More Preferred | Most Preferred |
|---|---|---|---|
| 15 | 0-50% | 5%-50% | 10%-50% |
| 30 | 5%-70% | 10%-60% | 10%-55% |
| 60 | 10%-80% | 15%-80% | 20%-80% |
| 120 | NLT 35% | NLT 40% | NLT 45% |

Alternatively certain embodiments of the present invention and specifically the liquid oral dosage forms will release the KI $C_8$-$C_{16}$ aliphatic sulfate salt when tested using a USP Type II Apparatus (Paddle) with 900 ml of 0.1 N HCl and 0.1% Tween 80 at 75 rpm, with or without a sinker and 37° C. as follows:

| Time (minutes) | Preferred | More Preferred | Most Preferred |
|---|---|---|---|
| 15 | 5%-50% | 10%-50% | 15%-50% |
| 30 | 10%-85% | 15%-80% | 20%-75% |
| 60 | 40%-95% | 45%-95% | 50%-95% |
| 120 | NLT 70% | NLT 80% | NLT 85% |

The compositions and dosage forms of the present invention and specifically the compositions and dosage forms described above in Embodiments A-G will be stable when prepared and stored under normal and accelerated conditions. More specifically, the dosage forms of the present invention will contain about 1.0% or less of any individual degradation product, preferably about 0.75% or less of any individual degradation product, and most preferably about 0.5% or less of any individual degradation product when the dosage form is stored in a sealed bottle, preferably a sealed plastic bottle such as a high density polyethylene bottle (with or without a desiccant), at approximately 25° C. and approximately 60% relative humidity for at least three months, preferably at least six months and most preferably at least one year and/or at approximately 40° C. and approximately 75% relative humidity for one month, two months, or three months.

The compositions and dosage forms of the present invention and specifically the compositions and dosage forms described above in Embodiments A-G should also contain a total amount of degradation products of about 2.0% or less, preferably about 1.5% or less, and most preferably about 1.0% or less when the dosage form is stored in a sealed bottle, preferably a sealed plastic bottle such as a high density polyethylene bottle (with or without a desiccant) at approximately 25° C. and approximately 60% relative humidity for at least three months, preferably at least six months, and most preferably at least one year and/or at approximately 40° C. and approximately 75% relative humidity for one month, two months, or three months.

KI $C_8$-$C_{16}$ aliphatic sulfate salt and specifically the KI lauryl sulfate salt employed in the compositions and dosage forms of the present invention and specifically the compositions and dosage forms described above in Embodiments A-G can be in an amorphous or crystalline form. The KI $C_8$-$C_{16}$ aliphatic sulfate salt and specifically the KI lauryl sulfate salt employed the solid dispersion dosage forms of Embodiment F will preferably be in an amorphous form.

Table 1 shows the amount of some KI lauryl sulfate salts that will be present in the dosage forms of the present invention and specifically the dosage forms described above in Embodiments A-G:

TABLE 1

| | Amount of KI free base per dosage unit | | |
|---|---|---|---|
| KI | Preferred | More Preferred | Most Preferred |
| acalabrutinib lauryl sulfate | 25-400 | 50-350 | 75-300 |
| afatinib lauryl sulfate | 5-200 | 7.5-150 | 10-100 |
| alectinib lauryl sulfate | 25-400 | 50-350 | 75-300 |
| axitinib lauryl sulfate | 0.25-20 | 0.5-15 | 0.75-10 |
| bosutinib lauryl sulfate | 35-500 | 40-500 | 50-500 |
| brigatinib lauryl sulfate | 10-300 | 20-250 | 25-200 |
| cabozantinib lauryl sulfate | 5-200 | 10-150 | 15-100 |
| ceritinib lauryl sulfate | 25-400 | 50-350 | 75-300 |
| cobimetinib lauryl sulfate | 5-50 | 10-40 | 15-30 |
| crizotinib lauryl sulfate | 75-500 | 100-400 | 150-300 |
| dabrafenib lauryl sulfate | 10-200 | 25-150 | 30-100 |
| dasatinib lauryl sulfate | 5-250 | 10-175 | 15-150 |
| enasidenib lauryl sulfate | 10-200 | 25-175 | 30-150 |
| erlotinib lauryl sulfate | 5-250 | 10-200 | 15-175 |
| fostamatinib lauryl sulfate | 50-250 | 75-200 | 80-175 |
| gefitinib lauryl sulfate | 100-400 | 150-350 | 200-300 |
| ibrutinib lauryl sulfate | 25-650 | 50-600 | 60-575 |
| imatinib lauryl sulfate | 50-600 | 70-650 | 80-500 |
| lapatinib lauryl sulfate | 100-400 | 150-350 | 200-300 |
| lenvatinib lauryl sulfate | 0.25-20 | 0.5-15 | 0.75-10 |
| neratinib lauryl sulfate | 10-100 | 15-80 | 25-75 |
| nilotinib lauryl sulfate | 10-400 | 15-350 | 25-300 |
| nintedanib lauryl sulfate | 25-300 | 50-250 | 75-200 |
| osimertinib lauryl sulfate | 10-175 | 25-150 | 30-100 |
| pazopanib lauryl sulfate | 50-600 | 100-500 | 150-450 |
| ponatinib lauryl sulfate | 2.5-100 | 5-75 | 10-50 |
| regorafenib lauryl sulfate | 10-100 | 15-80 | 25-75 |
| ruxolitinib lauryl sulfate | 1-50 | 2-40 | 3-30 |
| sorafenib lauryl sulfate | 50-400 | 100-300 | 150-250 |
| sunitinib lauryl sulfate | 2.5-100 | 5-75 | 10-50 |
| trametinib lauryl sulfate | 0.25-10 | 0.3-7.5 | 0.4-5 |
| vandetanib lauryl sulfate | 50-500 | 75-400 | 80-350 |
| vemurafenib lauryl sulfate | 100-500 | 150-400 | 200-300 |

Table 2 shows the U.S. FDA approved indications for the preferred KI compounds and the conditions which the KI $C_8$-$C_{16}$ aliphatic sulfate salts and specifically the KI lauryl sulfate salts of the present invention may be used to treat:

TABLE 2

| KI | U.S. FDA Approved Treatments |
|---|---|
| acalabrutinib | non-Hodgkin lymphoma (i.e., mantle cell lymphoma) |
| afatinib | non-small cell lung carcinoma (NSCLC) |

TABLE 2-continued

| KI | U.S. FDA Approved Treatments |
|---|---|
| alectinib | non-small cell lung carcinoma (NSCLC) |
| axitinib | renal cell carcinoma |
| bosutinib | chronic myelogenous leukemia. |
| brigatinib | non-small cell lung carcinoma (NSCLC) |
| cabozantinib | thyroid cancer; renal cell carcinoma; and hepatocellar carcinoma |
| ceritinib | non-small cell lung carcinoma (NSCLC) |
| cobimetinib | melanoma |
| crizotinib | non-small cell lung carcinoma (NSCLC) |
| dabrafenib | melanoma |
| dasatinib | chronic myeloid leukemia (CML); acute lymphoblastic leukemia (ALL) |
| enasidenib | acute myeloid leukemia |
| erlotinib | non-small cell lung carcinoma (NSCLC); pancreatic cancer |
| fostamatinib | thrombocytopenia |
| gefitinib | non-small cell lung carcinoma (NSCLC) |
| ibrutinib | mantle cell lymphoma (MCL); chronic lymphocytic leukemia (CLL)/small lymphocytic lymphoma (SLL); Waldenstrom's macroglobulinemia (WM); marginal zone lymphoma (MZL); and chronic graft versus host disease (cGVHD) |
| imatinib | chronic myeloid leukemia; acute lymphoblastic leukemia; myelodysplastic/myeloproliferative diseases; aggressive systemic mastocytosis (ASM); hypereosinophilic syndrome (HES) and/or chronic eosinophilic leukemia (CEL); dermatofibrosarcoma protuberans (DFSP); gastrointestinal stromal tumors (GIST) |
| lapatinib | breast cancer |
| lenvatinib | differentiated thyroid cancer (DTC); renal cell carcinoma (RCC); hepatocellular carcinoma (HCC) |
| neratinib | breast cancer |
| nilotinib | chronic myeloid leukemia (CML) |
| nintedanib | idiopathic pulmonary fibrosis |
| osimertinib | non-small cell lung carcinoma (NSCLC) |
| pazopanib | advanced renal cell carcinoma; advanced soft tissue sarcoma |
| ponatinib | chronic myeloid leukemia (CML); acute lymphoblastic leukemia (ALL) |
| regorafenib | metastatic colorectal cancer (CRC); gastrointestinal stromal tumor (GIST); hepatocellular carcinoma (HCC) |
| ruxolitinib | intermediate or high-risk myelofibrosis; polycythemia vera; steroid-refractory acute graft-versus-host disease |
| sorafenib | hepatocellular carcinoma; advanced renal cell carcinoma; differentiated thyroid carcinoma |
| sunitinib | gastrointestinal stromal tumor; advanced renal cell carcinoma |
| trametinib | melanoma; non-small cell lung cancer (NSCLC); anaplastic thyroid cancer (ATC) |
| vandetanib | medullary thyroid cancer |
| vemurafenib | melanoma; Erdheim Chester Disease |

The present invention includes methods for treating the various conditions identified in Table 2 by orally administering one or more dosage forms comprising a KI $C_8$-$C_{16}$ aliphatic sulfate salts and preferably one or more dosage forms comprising a KI lauryl sulfate salt. In certain embodiments: (i) the oral administration may be with or without food and the oral administration will exhibit substantially constant pharmacokinetic values or will not exhibit a food effect as described in detail below; (ii) the oral administration will allow for a reduction in the total daily dose of KI compared to the currently U.S. FDA approved KI compositions while maintaining similar pharmacokinetics as described in detail below; (iii) the oral administration may be with or without the co-administration of a gastric acid reducing agent and the oral administration will not exhibit a gastric acid reducing agent effect as described in detail below; or (iv) the oral administration will exhibit a combination of (i); (ii) and/or (iii).

In certain embodiments, the present invention includes methods for treating the conditions identified in Table 2 by orally administering one or more dosage forms described in Embodiments A-G and comprising a KI lauryl sulfate salt within the amounts recited in Table 1. In these embodiments: (i) the oral administration may be with or without food and the oral administration will exhibit substantially constant pharmacokinetic values or will not exhibit a food effect as described in detail below; (ii) the oral administration will allow for a reduction in the total daily dose of KI compared to the currently U.S. FDA approved KI compositions while maintaining similar pharmacokinetics as described in detail below; (iii) the oral administration may be with or without the co-administration of a gastric acid reducing agent and the oral administration will not exhibit a gastric acid reducing agent effect as described in detail below; or (iv) the oral administration will exhibit a combination of (i); (ii) and/or (iii).

For example, a dosage form as described in Embodiments A-G and comprising 10-400 mg of nilotinib lauryl sulfate, preferably 15-350 mg and more preferably 25-300 mg can be orally administered to a patient to treat chronic myeloid leukemia wherein (i) the oral administration may be with or without food and the oral administration will not exhibit a food effect; (ii) the oral administration will allow for a reduction in the total daily dose of nilotinib free base compared to the currently approved dosing for nilotinib hydrochloride while maintaining similar pharmacokinetics as the oral administration of nilotinib hydrochloride; and (iii) the oral administration may be with or without the co-administration of a gastric acid reducing agent and the oral administration will not exhibit a gastric acid reducing agent effect.

Similarly, a dosage form as described in Embodiments A-G and comprising 5-250 mg of dasatinib lauryl sulfate, preferably 10-175 mg and more preferably 15-150 mg can be orally administered to a patient to treat chronic myeloid leukemia and/or acute lymphoblastic leukemia wherein (i) the oral administration may be with or without food and the oral administration will not exhibit a food effect; and (ii) the oral administration may be with or without the co-administration of a gastric acid reducing agent and the oral administration will not exhibit a gastric acid reducing agent effect.

The compositions and dosage forms of the present invention, including but not limited to Embodiments A-G, can be administered to a subject, wherein the subject may be either in a fed state or a fasted state and the administration will under either fed or fasted conditions will result in substantially constant pharmacokinetic values or no food effect. In general, a fed state is defined as having consumed food within about 30 minutes prior to administration of the composition or dosage form. The food may be a high fat meal, a low fat meal, a high calorie meal, or a low calorie meal. A fasted state may be defined as not having ingested food for at least 10 hours prior to administration of the composition or dosage form. In some embodiments, the subject may have fasted for at least 10 hours prior to administration and refrains from ingesting food for about 30 minutes to 2 hours, preferably about one hour following administration. In other embodiments, the fasted subject may not have ingested food for at least 1 hour, 2 hours, 3 hours, 4 hours, 5 hours, 6 hours, 7 hours, 8 hours, 9 hours, or 10 hours prior to administration of each dose of the composition or dosage form.

The method of orally administering the composition and/or dosage form of the present invention, including but not limited to Embodiments A-G, to a patient or healthy subject will produce substantially constant pharmacokinetic values such as $T_{max}$, $C_{max}$ and AUC whether the composition is administered with or without food. A substantially constant pharmacokinetic value means the measured pharmacokinetic value obtained after a single or multiple dose administration of the composition or dosage form, including but not limited to Embodiments A-G, to a patient or healthy subject under fasting conditions as described by the U.S. FDA Guidance documents does not change by more than 40%, preferably does not change by more than 30% and most preferably does not change by more than 20% when the same composition is administered to the same patient or healthy subject under fed conditions as described in the U.S. FDA Guidance documents. For example, if a $T_{max}$ of 3 hours was obtained after a single dose administration to a patient under fasting conditions, a $T_{max}$ in the range of 1.8 hours to 4.2 hours would be considered substantially constant, i.e., 3 hours±40%.

In certain preferred embodiments of the present invention, a single oral dose administration of a composition or dosage form prepared in accordance with the present invention, including but not limited to Embodiment A-G will be bioequivalent when administered under fed and fasting conditions or exhibit no food effect. The terms "bioequivalent" and "no food effect" are used in accordance with the U.S. FDA Guidance documents.

In certain embodiments of the present invention, a single oral administration of the composition or dosage form prepared in accordance with the present invention, including but not limited to Embodiments A-G, will produce a ratio of the KI $C_{max}$ administered with food to the KI $C_{max}$ administered without food ($C_{max\ fed}/C_{max\ fast}$) of about 0.60 to about 2.5, preferably about 0.70 to about 2.0, more preferably about 0.75 to about 1.5 and most preferably about 0.8 to about 1.25. Similarly, in certain embodiments of the present invention, a single oral administration of the composition or dosage form prepared in accordance with the present invention, including but not limited to Embodiments A-G will produce a ratio of the KI $AUC_{0-\infty}$ of the pharmaceutical composition administered with food to the KI $AUC_{0-\infty}$ of the pharmaceutical composition administered without food ($AUC_{0-\infty\ fed}/AUC_{0-\infty\ fast}$) of about 0.60 to about 2.5, preferably about 0.70 to about 2.0, more preferably about 0.75 to about 1.5 and most preferably about 0.8 to about 1.25.

Upon oral administration of the compositions or dosage forms of the present invention, including but not limited to Embodiments A-G, a KI plasma profile is obtained wherein at least one pharmacokinetic parameter differs by less than about 40% under fed and fasted conditions. In various embodiments, the pharmacokinetic parameter may vary by less than about 35%, 30%, 25%, 20%, 15%, 10%, or 5% under fed and fasted conditions. The pharmacokinetic parameter that is independent of food may be, but is not limited to, $C_{max}$, AUC, $T_{max}$, or combinations thereof.

Certain embodiments of the present invention include methods for treating cancer in human patients comprising the step of orally administering to the patient one or more dosage forms as described in Embodiments A-G wherein the administration may be with or without food and wherein the dose of the KI $C_8$-$C_{16}$ aliphatic sulfate salts and particularly the KI lauryl sulfate does not require an adjustment in dose or a change in time of administration.

In certain embodiments, the administration of compositions or dosage forms prepared in accordance with the present invention allow for a reduction in the amount of KI base currently approved by the U.S. FDA and still obtain an equivalent therapeutic level. More specifically, the compositions of the present invention will allow at least a 10%, 15%, 20%, 25%, 30%, 35% 40%, 45% or 50% reduction in the daily amount of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, or vemurafenib and still provide equivalent therapeutic levels, i.e., equivalent plasma levels.

Table 3 shows the currently U.S. FDA approved dosing for some of the preferred KIs:

TABLE 3

| KI | U.S. FDA Approved Form (free base amount) | U.S. FDA Recommended Daily Dose |
|---|---|---|
| acalabrutinib hydrochloride | 150 mg capsule | 1200 mg |
| afatinib dimaleate | 20 mg, 30 mg and 40 mg tablets | 40 mg |
| alectinib hydrochloride | 150 mg capsule | 600 mg |

TABLE 3-continued

| KI | U.S. FDA Approved Form (free base amount) | U.S. FDA Recommended Daily Dose |
|---|---|---|
| axitinib free base | 1 mg and 5 mg tablet | 10 mg-20 mg |
| bosutinib free base | 100 mg, 400 mg and 500 mg tablet | 100 mg-600 mg |
| brigatinib free base | 30 mg, 90 mg and 180 mg tablet | 90 mg-180 mg |
| cabozantinib (S) malate | 20 mg and 80 mg capsule and 20 mg, 40 mg and 60 mg tablet | 60 mg-180 mg |
| ceritinib free base | 150 mg capsule | 150 mg-450 mg |
| cobimetinib fumarate | 20 mg tablet | 60 mg |
| crizotinib | 200 mg and 250 mg capsule | 200 mg-500 mg |
| dabrafenib mesylate | 50 mg and 75 mg capsule | 100 mg-300 mg |
| dasatinib free base | 20 mg, 50 mg, 70 mg, 80 mg, 100 mg and 140 mg tablet | 70 mg-140 mg |
| enasidenib mesylate | 50 mg and 100 mg tablet | 50 mg-100 mg |
| erlotinib hydrochloride | 25 mg, 100 mg and 150 mg | 100 mg-150 mg |
| fostamatinib disodium | 100 mg and 150 mg tablet | 100 mg-300 mg |
| gefitinib free base | 250 mg tablet | 250 mg-500 mg |
| ibrutinib free base | 70 mg and 140 mg capsule and 140 mg 280 mg, 420 mg and 560 mg tablet | 70 mg-560 mg |
| imatinib mesylate | 100 mg and 400 mg tablets | 300 mg-800 mg |
| lapatinib ditosylate | 250 mg tablet | 1,250 mg-1,500 mg |
| lenvatinib mesylate | 4 mg and 10 mg capsule | 10 mg-24 mg |
| neratinib maleate | 40 mg tablet | 80 mg-240 mg |
| nilotinib hydrochloride | 50 mg, 150 mg and 200 mg capsule | 600 mg-800 mg |
| nintedanib esylate | 100 mg and 150 mg capsule | 100 mg-300 mg |
| osimertinib mesylate | 40 mg and 80 mg tablet | 80 mg |
| pazopanib hydrochloride | 200 mg and 400 mg tablet | 200 mg-800 mg |
| ponatinib hydrochloride | 15 mg, 30 mg and 45 mg tablet | 30 mg-45mg |
| regorafenib free base | 40 mg tablet | 80 mg-160 mg |
| ruxolitinib phosphate | 5 mg, 10 mg, 15 mg, 20 mg and 25 mg tablet | 10 mg-40 mg |
| sorafenib tosylate | 200 mg tablet | 800 mg |
| sunitinib malate | 12.5 mg, 25 mg, 37.5 mg and 50 mg capsule | 37.5 mg-50 mg |
| trametinib dimethyl sulfoxide | 0.5 mg, 1 mg and 2 mg tablet | 1 mg-2 mg |
| vandetanib free base | 100 mg and 300 mg tablet | 100 mg-300 mg |
| vemurafenib free base | 240 mg tablet | 480 mg-960 mg |

In certain embodiments, the oral administration of the KI $C_8$-$C_{16}$ aliphatic sulfate salt of the present invention and specifically the KI lauryl sulfate salt, will allow at least a 10%, 15%, 20%, 25%, 30%, 35% 40%, 45% or 50% reduction in the total daily recommended dose in of the KI free base reported in Table 3 while maintaining similar pharmacokinetics. For example, the currently approved daily dose for nilotinib hydrochloride is 600-800 mg based on the free base amount of nilotinib. The oral administration of the nilotinib lauryl sulfate salt will allow at least a 25% reduction in the daily dose, i.e. 450-600 mg while maintaining the same or substantially similar pharmacokinetics such as $C_{max}$, $T_{max}$ and/or AUC. Alternatively, a patient receiving 800 mg of nilotinib (as the hydrochloride) will be able to receive 600 mg of nilotinib (as the lauryl sulfate) as maintain similar plasma levels of nilotinib.

The solubility of many of the KI drugs is pH dependent. The solubility of many of the KIs decrease with increasing pH. Patients taking a KI drug may also be receiving or co-administered a gastric acid reducing agent such as an antacid, $H_2$ antagonist or proton pump inhibitor to reduce gastric acid secretion or increase gastric pH. Because the gastric acid reducing agent will increase the pH of a patient's stomach, the solubility of a co-administered KI drug will decrease in the patient's stomach and thereby result in a decreased absorption. In order to avoid this decreased absorption or gastric acid reducing agent effect, patients are warned to take antacids at least two hours before or two hours after taking the KI drug or to discontinue the use of $H_2$ antagonist or proton pump inhibitors during treatment with the KI drug. The present invention avoids the need for staggered administration of antacids or discontinuing the use of $H_2$ antagonist or proton pump inhibitors during treatment with the KI drug. The KI $C_8$-$C_{16}$ aliphatic sulfate salt of the present invention and specifically the KI lauryl sulfate salts can be orally administered to a patient or healthy subject and it will produce similar or substantially constant pharmacokinetic values such as $T_{max}$, $C_{max}$ and AUC whether the administration occurs with or without a gastric reducing agent. A substantially constant pharmacokinetic value means the measured pharmacokinetic value such as $C_{max}$ and/or AUC obtained after a single or multiple dose administration of the composition or dosage form of the present invention, including but not limited to Embodiments A-G, to a patient or healthy subject under fasting conditions with a gastric acid reducing agent does not change by more than 40%, 35%, 30%, 25%, 20%, 15%, 10%, or 5% when the same composition is administered to the same patient or healthy subject under fasting condition without a gastric acid reducing agent.

In certain embodiments of the present invention, a single oral administration of the composition or dosage form prepared in accordance with the present invention, including but not limited to Embodiments A-G, will produce a ratio of the KI $C_{max}$ administered with a gastric acid reducing agent to the KI $C_{max}$ administered without a gastric acid reducing agent ($C_{max\ w/gastric\ acid\ reducing}/C_{max\ w/o\ gastric\ acid\ reducing}$) of about 0.60 to about 2.5, preferably about 0.70 to about 2.0, more preferably about 0.75 to about 1.5 and most preferably about 0.8 to about 1.25. Similarly, in certain embodiments of the present invention, a single oral administration of the composition or dosage form prepared in accordance with the present invention, including but not limited to Embodiments A-E will produce a ratio of the KI $AUG_{0-\infty}$ of the pharmaceutical composition administered with gastric acid reducing agent to the KI $AUG_{0-\infty}$ of the pharmaceutical composition administered without gastric acid reducing agent ($AUC_{0-\infty\ w/gastric\ acid\ reducing}/AUC_{0-\infty\ w/o\ gastric\ acid\ reducing}$) of about 0.60 to about 2.5, preferably about 0.70 to about 2.0, more preferably about 0.75 to about 1.5, and most preferably about 0.80 to about 1.25.

Certain embodiments of the present invention will employ the dosage forms of Embodiments A-G, the amounts of bosutinib, dasatinib, erlotinib, gefitinib, neratinib, nilotinib, and pazopanib recited in Table 1 to treat the conditions recited in Table 2 and the administration will be orally with or without the co-administration of a gastric acid reducing agent and the administration will produce substantially constant pharmacokinetic values such as $T_{max}$, $C_{max}$ and AUC whether the administration occurs with or without a gastric reducing agents.

Certain embodiments of the present invention include methods for treating cancer in human patients comprising the step of orally administering to the patient one or more dosage forms as described in Embodiments A-G and co-administering a gastric acid reducing agent to the patient wherein the dose of the KI $C_8$-$C_{16}$ aliphatic sulfate salts and particularly the KI lauryl sulfate does not require an adjustment in dose or a change in time of administration. Examples of the KI particularly useful in this embodiment are bosutinib, dasatinib, erlotinib, gefitinib, neratinib, nilotinib, and pazopanib and in the amounts recited in Table 1 to treat the specific cancers recited in Table 2.

DESCRIPTION OF EMBODIMENTS

The following are provided by way of example only and are by no means intended to be limiting.

Example 1

A nilotinib lauryl sulfate salt was prepared by dissolving 2.48 g of nilotinib hydrochloride monohydrate in 1900 mL of 0.1N hydrochloric acid solution and dissolving 1.16 g of sodium lauryl sulfate in 100 mL of 0.1N hydrochloric acid solution. Once the nilotinib hydrochloride monohydrate and sodium lauryl sulfate were dissolved, the two solutions were mixed well and allowed to sit for 24 hours. The precipitated nilotinib lauryl sulfate was collected by removing the upper liquid and dried at 40° C. for 18 hours.

Example 2

Lauryl sulfate salts of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nintedanib, osimertinib, pazopanib, ponatinib, regorafenib, ruxolitinib, sorafenib, sunitinib, trametinib, vandetanib, or vemurafenib may be formed in a similar manner as described in Example 1 by dissolving the acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nintedanib, osimertinib, pazopanib, ponatinib, regorafenib, ruxolitinib, sorafenib, sunitinib, trametinib, vandetanib, or vemurafenib in a suitable solvent such as 0.1 N HCl or a combination of 0.1 N HCl and a $C_1$-$C_6$ alcohol such as methanol, ethanol, isopropanol and adding sodium lauryl sulfate or an aqueous solution of sodium lauryl sulfate to the acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nintedanib, osimertinib, pazopanib, ponatinib, regorafenib, ruxolitinib, sorafenib, sunitinib, trametinib, vandetanib, or vemurafenib solution.

Example 3

A nilotinib lauryl sulfate capsule dosage form was prepared by mixing the nilotinib lauryl sulfate (dry precipitate) prepared in Example 1 with CAPMUL® MCM (glyceryl caprylate/caprate) and KOLLIPHOR® EL (polyoxyl 35 castor oil) and filling the liquid mixture into size 00 hard gelatin capsules.

The composition of the capsule content is as follows:

|  | mg | wt % |
|---|---|---|
| Nilotinib lauryl sulfate (Dry precipitate) | 75.0 | 12.5 |
| Glyceryl Caprylate/Caprate | 420.0 | 70.0 |
| Polyoxyl 35 Castor Oil | 105.0 | 17.5 |
| Total | 600.0 | 100.0 |

Example 4

A nilotinib lauryl sulfate capsule was prepared by dissolving 1940 mg of nilotinib lauryl sulfate (dry precipitate) and 1040 mg of poloxamer 188 in 5 mL of ethanol. The solution was manually mixed with 3100 mg of AVICEL PH 101 (microcrystalline cellulose) and 3100 mg of lactose. The resulting granules were dried and milled through a 60 mesh screen and blended with 210 mg of colloidal silicon dioxide, 1040 mg of sodium starch glycolate and 100 mg of magnesium stearate. The dry solid blend was filled into size 00 hard gelatin capsules.

The composition of the capsule content is as follows:

|  | mg | wt % |
|---|---|---|
| Nilotinib lauryl sulfate (Dry precipitate) | 75.0 | 18.5 |
| Microcrystalline cellulose | 119.5 | 29.4 |
| Lactose | 119.5 | 29.4 |
| Sodium starch glycolate | 40.0 | 9.9 |
| Poloxamer 188 | 40.0 | 9.9 |
| Colloidal Silicon Dioxide | 8.0 | 2.0 |
| Magnesium Stearate | 4.0 | 0.9 |
| Total | 600.0 | 100.0 |

Example 5

The capsules similar to those prepared in Examples 3 and 4 but adjusted to contain a weight providing approximately 50 mg nilotinib free base were administered to six (6) healthy adult beagle dogs in a fasted state along with a capsule, obtained by dividing commercially available 200 mg TASIGNA capsule into 4 capsules (each contained equivalent to 50 mg of nilotinib free base) in a single-center, single-dose study. Blood samples were drawn before dosing and at 0.25, 0.5, 1, 2, 3, 4, 5, 6, 8, 10, 12 and 24 hours after dosing. The mean nilotinib plasma values were determined as follows:

|  | Capsule Prepared According to the Procedure of Example 3 | Capsule Prepared According to the Procedure of Example 4 | REFERENCE (TASIGNA) |
|---|---|---|---|
| $AUC_{0-24}$ (ng·hr/mL) | 4903.17 | 1906.55 | 1455.60 |

-continued

|  | Capsule Prepared According to the Procedure of Example 3 | Capsule Prepared According to the Procedure of Example 4 | REFERENCE (TASIGNA) |
|---|---|---|---|
| $C_{max}$ (ng/mL) | 1114.65 | 436.93 | 241.36 |

A graph of the mean plasma profiles is shown in FIG. 1.

The individual data from the study is shown in the following tables:

$C_{max}$

|  | 101 | 102 | 201 | 202 | 301 | 302 | Mean | SD | CV (%) |
|---|---|---|---|---|---|---|---|---|---|
| Ref | 182.49 | 219.79 | 896.70 | 72.73 | 12.88 | 63.59 | 241.36 | 330.35 | 136.9 |
| Ex 3 | 577.78 | 1734.45 | 1006.85 | 1426.88 | 689.57 | 1252.34 | 1114.65 | 442.98 | 39.7 |
| Ex 4 | 60.40 | 170.49 | 153.03 | 1499.36 | 62.88 | 675.44 | 436.93 | 569.02 | 130.2 |

$AUC_{0-24}$

|  | 101 | 102 | 201 | 202 | 301 | 302 | Mean | SD | CV (%) |
|---|---|---|---|---|---|---|---|---|---|
| Ref | 1458.11 | 651.13 | 5732.02 | 567.55 | 41.97 | 282.85 | 1455.60 | 2149.29 | 147.7 |
| Ex 3 | 2522.04 | 5749.49 | 7045.54 | 5218.75 | 2082.07 | 6800.50 | 4903.17 | 2127.45 | 43.4 |
| Ex 4 | 448.88 | 509.93 | 1759.07 | 5221.25 | 156.63 | 3343.55 | 1906.55 | 2010.55 | 105.5 |

Reference (TASIGNA)

| Time (hr) | Blood concentration (ng/mL) | | | | | | | | |
|---|---|---|---|---|---|---|---|---|---|
|  | 101 | 102 | 201 | 202 | 301 | 302 | Mean | SD | CV % |
| 0 | 0.00 | 0.00 | 0.00 | 0.00 | 0.00 | 0.00 | 0.00 | 0.00 | 0.0 |
| 0.25 | 0.00 | 0.00 | 0.00 | 0.00 | 1.01 | 0.00 | 0.17 | 0.41 | 241.2 |
| 0.5 | 34.67 | 0.00 | 0.00 | 6.03 | 5.16 | 4.00 | 8.31 | 13.16 | 158.4 |
| 1 | 103.75 | 84.24 | 6.54 | 17.65 | 12.88 | 58.26 | 47.22 | 40.98 | 86.8 |
| 2 | 78.83 | 219.79 | 269.62 | 22.47 | 10.41 | 63.59 | 110.79 | 107.92 | 97.4 |
| 3 | 40.06 | 133.04 | 673.00 | 15.14 | 6.33 | 50.31 | 152.98 | 258.70 | 169.1 |
| 4 | 30.20 | 88.34 | 896.70 | 11.70 | 4.33 | 38.29 | 178.26 | 353.20 | 198.1 |
| 5 | 14.99 | 46.22 | 620.46 | 6.03 | 2.16 | 22.79 | 118.78 | 246.27 | 207.3 |
| 6 | 8.93 | 31.69 | 436.35 | 4.17 | 1.72 | 17.29 | 83.36 | 173.27 | 207.9 |
| 8 | 87.93 | 15.50 | 295.18 | 2.16 | 1.48 | 9.67 | 68.65 | 115.69 | 168.5 |
| 10 | 182.49 | 8.98 | 221.15 | 72.73 | 1.35 | 6.33 | 82.17 | 97.07 | 118.1 |
| 12 | 90.38 | 4.06 | 150.29 | 34.02 | BLQ | 4.74 | 56.69 | 63.01 | 111.1 |
| 24 | 2.72 | BLQ | 88.02 | 17.09 | BLQ | BLQ | 35.94 | 45.67 | 127.1 |

Capsule Prepared as in Example 3

| Time (hr) | Blood concentration (ng/mL) | | | | | | | | |
|---|---|---|---|---|---|---|---|---|---|
|  | 101 | 102 | 201 | 202 | 301 | 302 | Mean | SD | CV % |
| 0 | 0.00 | 0.00 | 0.00 | 0.00 | 0.00 | 0.00 | 0.00 | 0.00 | 0.0 |
| 0.25 | 28.66 | 0.00 | 0.00 | 0.00 | 0.00 | 0.00 | 4.78 | 11.70 | 244.8 |
| 0.5 | 532.48 | 273.32 | 71.53 | 182.95 | 0.00 | 0.00 | 176.71 | 204.68 | 115.8 |
| 1 | 577.78 | 1734.45 | 494.18 | 1111.85 | 10.24 | 127.50 | 676.00 | 647.62 | 95.8 |
| 2 | 459.11 | 1520.12 | 1006.85 | 1426.88 | 301.22 | 1252.34 | 994.42 | 509.34 | 51.2 |
| 3 | 249.47 | 828.22 | 1002.63 | 883.51 | 689.57 | 1223.97 | 812.89 | 329.50 | 40.5 |
| 4 | 190.52 | 646.31 | 948.47 | 694.87 | 404.08 | 1006.20 | 648.41 | 312.91 | 48.3 |
| 5 | 87.12 | 385.13 | 557.23 | 351.32 | 187.37 | 556.34 | 354.08 | 190.90 | 53.9 |
| 6 | 53.79 | 237.90 | 490.02 | 223.13 | 112.63 | 431.30 | 258.13 | 172.23 | 66.7 |
| 8 | 39.18 | 124.66 | 306.40 | 99.45 | 47.00 | 305.85 | 153.76 | 122.27 | 79.5 |
| 10 | 107.48 | 66.81 | 220.19 | 56.47 | 31.28 | 211.28 | 115.59 | 81.42 | 70.4 |

-continued

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 12 | 72.47 | 30.57 | 132.09 | 25.92 | 21.96 | 131.31 | 69.05 | 51.81 | 75.0 |
| 24 | 2.39 | 2.10 | 70.01 | 21.95 | 2.26 | 10.94 | 18.28 | 26.51 | 145.0 |

Capsule Prepared as in Example 4

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | 0.00 | 0.00 | 0.00 | 0.00 | 0.00 | 0.00 | 0.00 | 0.00 | 0.0 |
| 0.25 | 3.21 | 0.00 | 0.00 | 1.07 | 3.05 | 0.00 | 1.22 | 1.54 | 126.2 |
| 0.5 | 56.72 | 5.90 | 9.64 | 149.41 | 44.04 | 0.00 | 44.28 | 56.29 | 127.1 |
| 1 | 40.54 | 170.49 | 128.86 | 1059.13 | 62.88 | 12.24 | 245.69 | 402.74 | 163.9 |
| 2 | 22.22 | 108.08 | 81.27 | 1499.36 | 35.63 | 649.87 | 399.40 | 588.78 | 147.4 |
| 3 | 15.89 | 76.17 | 70.87 | 865.20 | 19.63 | 675.44 | 287.20 | 379.83 | 132.3 |
| 4 | 10.36 | 55.68 | 54.68 | 653.73 | 12.47 | 500.68 | 214.60 | 285.68 | 133.1 |
| 5 | 9.20 | 35.52 | 30.11 | 324.49 | 8.00 | 291.36 | 116.45 | 149.09 | 128.0 |
| 6 | 26.37 | 30.08 | 23.71 | 224.68 | 4.25 | 254.89 | 94.00 | 113.68 | 120.9 |
| 8 | 60.40 | 17.10 | 16.95 | 111.14 | 2.71 | 144.55 | 58.81 | 57.85 | 98.4 |
| 10 | 31.54 | 9.77 | 12.80 | 65.06 | 1.78 | 90.92 | 35.31 | 35.43 | 100.3 |
| 12 | 14.50 | 5.54 | 153.03 | 39.79 | 1.11 | 48.32 | 43.72 | 56.77 | 129.8 |
| 24 | 2.30 | BLQ | 42.60 | 9.98 | BLQ | 4.25 | 14.78 | 18.83 | 127.4 |

Example 6

Capsule dosage forms may be prepared using the lauryl sulfate salts of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, or vemurafenib as prepared in Examples 1 and 2 using the procedure described in Example 3.

The composition of the capsule content is as follows:

| | Wt % |
|---|---|
| KI lauryl sulfate | 1-50 |
| Carrier (preferably a wetting agent, emulsifying agent, solubilizing agent, surfactant or combination thereof) with HLB value of less than 10 | 30-85 |
| Carrier (preferably a wetting agent, emulsifying agent, solubilizing agent, surfactant or combination thereof) with HLB value of 10 or greater | 10-50 |
| Total | 100.0 |

Example 7

Capsule dosage forms may be prepared using the lauryl sulfate salts of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, or vemurafenib as prepared in Examples 1 and 2 using the procedure described in Example 4.

The composition of the capsule content is as follows:

| | Wt % |
|---|---|
| KI lauryl sulfate | 1-50 |
| Filler | 10-80 |
| disintegrant | 0-25 |
| Carrier (preferably a wetting agent, emulsifying agent, solubilizing agent, surfactant or combination thereof) with HLB value of 10 or greater | 2-40 |
| Glidant/lubricant | 0-10 |
| Total | 100.0 |

Example 8

Capsule dosage forms may be prepared using the lauryl sulfate salts of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, or vemurafenib as prepared in Examples 1 and 2 using the procedure described in Example 3.

The composition of the capsule content is as follows:

| | wt % |
|---|---|
| KI lauryl sulfate | 1-50 |
| Carrier (liquid or solid) | 10-95 |
| Stabilizer | 0-50 |
| Total | 100.0 |

Example 9

A nilotinib lauryl sulfate salt was prepared by dissolving 2.92 g of nilotinib hydrochloride monohydrate in 2900 mL of 0.1N hydrochloric acid solution and dissolving 1.50 g of sodium lauryl sulfate in 100 mL of 0.1N hydrochloric acid solution. Once the nilotinib hydrochloride monohydrate and sodium lauryl sulfate were dissolved, the two solutions were combined, mixed well and allowed to sit for 24 hours. The precipitated nilotinib lauryl sulfate was collected by removing the upper liquid and the collected precipitate was dried at 40° C. for 18 hours.

A nilotinib lauryl sulfate capsule dosage form was prepared by mixing the nilotinib lauryl sulfate (dry precipitate) with CAPMUL® MCM (glyceryl caprylate/caprate) and KOLLIPHOR® EL (polyoxyl 35 castor oil) and filling the liquid mixture into size 00 hard gelatin capsules.

The composition of the capsule content is as follows:

|  | mg | wt % |
|---|---|---|
| Nilotinib lauryl sulfate (Dry precipitate) | 100.0 | 16.0 |
| Glyceryl Caprylate/Caprate | 420.0 | 67.2 |
| Polyoxyl 35 Castor Oil | 105.0 | 16.8 |
| Total | 625.0 | 100.0 |

Example 10

Capsules prepared according to Example 9 were administered to nine (9) healthy subjects under fasted and fed conditions. The administration was a randomized, open-label, single dose, three treatment, three sequences, three periods, and crossover design with at least a 5-day washout period between doses. The Reference drug (Ref) was TASIGNA Capsule, nilotinib HCl, with a strength of 200 mg (free base) while the Test drug (Test) was a capsule prepared according to the procedure of Example 9 but containing approximately 50 mg free base of nilotinib. Based on the results reported in Example 5 herein, the dose of the Test capsules selected was 100 mg (2 capsules, each capsule containing 50 mg nilotinib free base). The nine (9) healthy subjects enrolled in this study were randomized to one of the sequences as shown in the following table.

|  | Period 1 | Period II | Period III |
|---|---|---|---|
| Sequence 1 | Ref (fasted) | Test (fasted) | Test (fed) |
| Sequence 2 | Test (fasted) | Test (fed) | Ref (fasted) |
| Sequence 3 | Test (fed) | Ref (fasted) | Test (fasted) |

During each treatment period, blood samples were taken at 0 (prior to the dosing), 0.5, 1, 2, 3, 4, 5, 6, 7, 8, 10, 12, 14, 24, 36 and 48 hours after dosing. $AUC_{0-48}$, $AUC_{0-\infty}$, $C_{max}$, $T_{max}$, and $T_{1/2}$ were determined for each subject based on non-compartmental analyses. The results of the study were normalized to 200 mg dose and summarized in Table 1. Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in Table 2. The data shows that the compositions of the present invention exhibit an increase of $C_{max}$ by 3.4 fold and an increase of AUC by 2.3 fold compared to the U.S. FDA approved nilotinib HCl. The data also shows that the compositions of the present invention do not exhibit a food effect i.e., the compositions of the present invention exhibit comparable pharmacokinetics under fasted and fed conditions.

TABLE 1

The Pharmacokinetic Parameters for Reference and Test Formulations (Normalized to 200 m g dose)

| Treatment | Parameters | Normalized to 200 mg dose Mean |
|---|---|---|
| $Ref_{Fasted}$ | $C_{max}$ (ng/mL) | 588 |
|  | $AUC_{0-48}$ (ng · h/mL) | 11271 |
|  | $AUC_{0-\infty}$ (ng · h/mL) | 12697 |
| $Test_{Fasted}$ | $C_{max}$ (ng/mL) | 2022 |
|  | $AUC_{0-48}$ (ng · h/mL) | 26766 |
|  | $AUC_{0-\infty}$ (ng · h/mL) | 28390 |
| $Test_{Fed}$ | $C_{max}$ (ng/mL) | 1864 |
|  | $AUC_{0-48}$ (ng · h/mL) | 27980 |
|  | $AUC_{0-\infty}$ (ng · h/mL) | 29378 |

$Ref_{Fasted}$: Tasigna Capsule 200 mg (free base) under fasted condition
$Test_{Fasted}$: Test drug (Test) 100 mg (free base) (2 capsules, 50 mg* 2) under fasted condition
$Test_{Fed}$: Test drug (Test) 100 mg (free base) (2 capsules, 50 mg* 2) under fed condition

TABLE 2

The Comparisons between Test vs. Reference and $Test_{Fed}$ vs. $Test_{Fasted}$ (Normalized to 200 mg dose)

| Comparisons | Parameters | Geometric Mean Ratios | 90% Confidence Intervals |
|---|---|---|---|
| Test~Ref (Fasted) | $C_{max}$ (ng/mL) | 341.53% | 289.35%~403.12% |
|  | $AUC_{0-48}$ (ng-h/mL) | 235.14% | 202.31%~273.29% |
|  | $AUC_{0-\infty}$ (ng-h/mL) | 224.28% | 197.49%~254.69% |
| $Test_{Fed}$~ $Test_{Fasted}$ | $C_{max}$ (ng/mL) | 93.48% | 87.04%~100.41% |
|  | $AUC_{0-48}$ (ng-h/mL) | 107.24% | 94.52%~121.68% |
|  | $AUC_{0-\infty}$ (ng-h/mL) | 105.73% | 93.83%~119.14% |

The individual subject data normalized to 200 mg dose obtained from the study is as follows: Reference Drug (TASIGNA®) under fasted condition (Concentration (ng/mL))

| Time (hr) | Subject | | | | | | | | |
|---|---|---|---|---|---|---|---|---|---|
|  | 1 | 2 | 3 | 4 | 5 | 6 | 7 | 8 | 9 |
| 0 | 0 | 0 | 0 | 0 | 0 | 0 | 0 | 0 | 0 |
| 0.5 | 107 | 30.8 | 51.6 | 87.9 | 88 | 105 | 98.7 | 58.2 | 138 |
| 1 | 385 | 139 | 283 | 296 | 252 | 251 | 351 | 262 | 289 |
| 2 | 562 | 277 | 508 | 541 | 389 | 367 | 536 | 569 | 362 |
| 3 | 460 | 439 | 586 | 711 | 440 | 459 | 643 | 787 | 447 |
| 4 | 497 | 438 | 612 | 824 | 514 | 467 | 631 | 755 | 431 |
| 5 | 383 | 359 | 518 | 756 | 434 | 350 | 463 | 633 | 372 |
| 6 | 347 | 348 | 461 | 708 | 402 | 321 | 437 | 572 | 329 |
| 7 | 349 | 330 | 397 | 597 | 413 | 311 | 444 | 531 | 317 |
| 8 | 300 | 311 | 430 | 594 | 360 | 290 | 393 | 504 | 301 |
| 10 | 266 | 308 | 377 | 547 | 343 | 294 | 501 | 467 | 289 |
| 12 | 269 | 255 | 381 | 480 | 318 | 237 | 334 | 390 | 288 |
| 14 | 254 | 232 | 352 | 473 | 293 | 225 | 347 | 398 | 238 |
| 24 | 169 | 176 | 284 | 386 | 204 | 156 | 335 | 365 | 120 |
| 36 | 60.6 | 74.7 | 157 | 157 | 24.1 | 153 | 225 | 96.1 | 21.3 |
| 48 | 16.5 | 19.2 | 72.6 | 47.6 | N.D. | 121 | 156 | 27 | N.D. |

Test Drug under fasted condition (Concentration (ng/mL))

| Time | Subject | | | | | | | | |
|---|---|---|---|---|---|---|---|---|---|
| (hr) | 1 | 2 | 3 | 4 | 5 | 6 | 7 | 8 | 9 |
| 0 | 0 | 0 | 0 | 0 | 0 | 0 | 0 | 0 | 0 |
| 0.5 | 141.8 | 145.6 | 150 | 1038 | 338 | 620 | 772 | 316 | 390 |
| 1 | 592 | 430 | 444 | 1932 | 1068 | 1110 | 2320 | 616 | 1590 |
| 2 | 2120 | 944 | 720 | 2360 | 1534 | 2080 | 3300 | 1832 | 1856 |
| 3 | 2060 | 1164 | 1452 | 2160 | 1464 | 2180 | 3000 | 1588 | 1624 |
| 4 | 1822 | 1438 | 1582 | 2020 | 1354 | 1998 | 2440 | 1480 | 1462 |
| 5 | 1326 | 842 | 1354 | 1662 | 1112 | 1204 | 1468 | 1150 | 1178 |
| 6 | 1134 | 742 | 1090 | 1526 | 984 | 922 | 1250 | 1016 | 936 |
| 7 | 1054 | 708 | 1046 | 1536 | 916 | 896 | 1164 | 976 | 904 |
| 8 | 954 | 612 | 962 | 1370 | 822 | 782 | 1006 | 890 | 848 |
| 10 | 966 | 556 | 876 | 1302 | 848 | 606 | 1316 | 812 | 808 |
| 12 | 736 | 428 | 762 | 1244 | 772 | 744 | 918 | 750 | 722 |
| 14 | 688 | 370 | 692 | 1046 | 730 | 636 | 824 | 712 | 726 |
| 24 | 576 | 161.8 | 494 | 960 | 274 | 480 | 686 | 538 | 408 |
| 36 | 230 | 21.6 | 230 | 400 | N.D. | 184.8 | 288 | 135.2 | 72.8 |
| 48 | 80.8 | N.D. | 107.6 | 185.6 | N.D. | 108.4 | 166 | 34 | N.D. |

Test Drug under fed condition (Concentration (ng/mL))

| Time | Subject | | | | | | | | |
|---|---|---|---|---|---|---|---|---|---|
| (hr) | 1 | 2 | 3 | 4 | 5 | 6 | 7 | 8 | 9 |
| 0 | 0 | 0 | 0 | 0 | 0 | 0 | 0 | 0 | 0 |
| 0.5 | 127.4 | 24.6 | 0 | 0 | 146 | 0 | 0 | 0 | 0 |
| 1 | 932 | 220 | 131.4 | 68 | 766 | 47.6 | 159 | 408 | 0 |
| 2 | 1742 | 832 | 394 | 962 | 1332 | 374 | 1018 | 1312 | 438 |
| 3 | 1836 | 1620 | 1302 | 1938 | 1710 | 1020 | 2060 | 1734 | 1646 |
| 4 | 1796 | 1472 | 1470 | 2440 | 1694 | 1654 | 2580 | 1720 | 1726 |
| 5 | 1418 | 1102 | 1318 | 2120 | 1642 | 1528 | 1534 | 1602 | 1290 |
| 6 | 1212 | 1032 | 1202 | 1808 | 1376 | 1210 | 1382 | 1408 | 1198 |
| 7 | 974 | 894 | 1002 | 1602 | 1308 | 1014 | 1218 | 1242 | 1068 |
| 8 | 928 | 802 | 972 | 1356 | 1118 | 854 | 1084 | 1124 | 1006 |
| 10 | 926 | 748 | 876 | 1222 | 1034 | 742 | 1136 | 1086 | 876 |
| 12 | 778 | 672 | 812 | 1200 | 910 | 694 | 1002 | 904 | 766 |
| 14 | 752 | 506 | 700 | 1056 | 812 | 628 | 890 | 866 | 776 |
| 24 | 636 | 260 | 526 | 802 | 750 | 462 | 788 | 704 | 436 |
| 36 | 177.8 | 47 | 208 | 382 | 78.4 | 204 | 416 | 290 | 119.8 |
| 48 | 46.8 | N.D. | 77.6 | 133.4 | N.D. | 92 | 262 | 69.2 | 21.8 |

Figure 2:
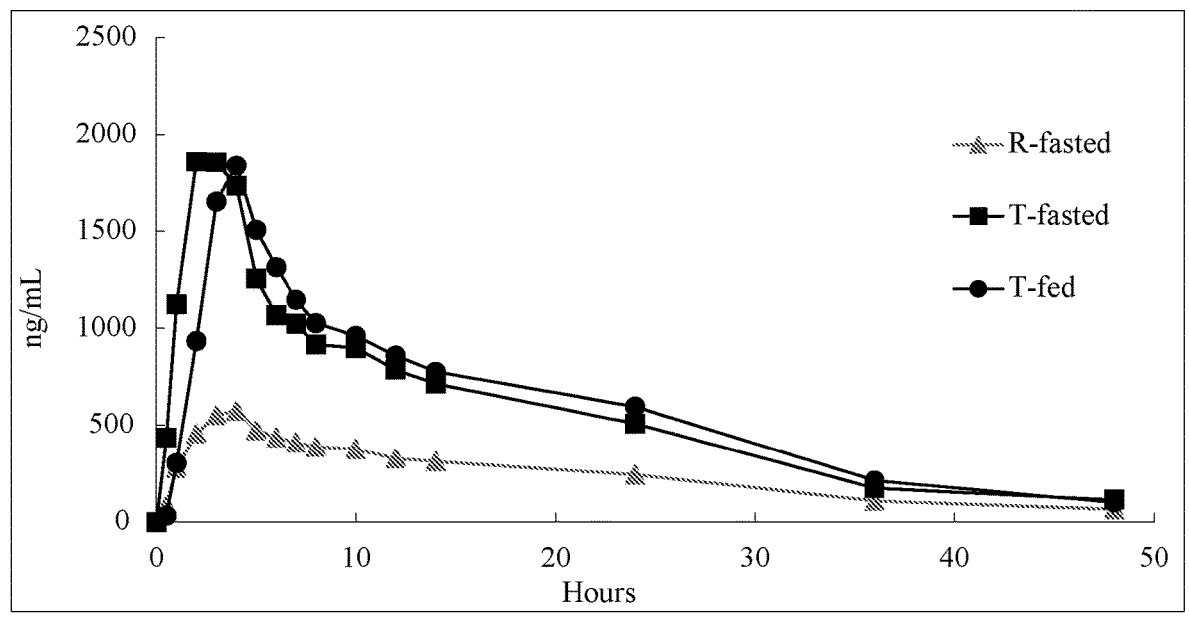
FIG. 2 is a graph of the mean in vivo plasma data provided in Example 10.

A graph of the normalized mean plasma profiles is shown in FIG. 2.

Example 11

A dasatinib lauryl sulfate salt was prepared by dissolving 253.0 mg of dasatinib monohydrate in 1000 mL of 0.1N hydrochloric acid solution and dissolving 432.0 mg of sodium lauryl sulfate in 100 mL of 0.1N hydrochloric acid solution. Once the dasatinib monohydrate and sodium lauryl sulfate were dissolved, the two solutions were combined, mixed well and allowed to sit for 20 hours. The precipitated dasatinib lauryl sulfate was collected by removing the upper liquid and the collected precipitate was dried at 50° C. for 20 hours.

The precipitate was analyzed by dissolving approximately 10.44 mg of the precipitate in 50 mL of methanol followed by 5 minutes of sonication and 5 minutes of stirring and subjecting the solution to high pressure liquid chromatography (HPLC). The results of the analysis indicated that the precipitate contained dasatinib dilauryl sulfate.

Example 12

A dasatinib monolauryl sulfate salt was prepared by the following general procedure:

a. 13 g of dasatinib monohydrate (dasatinib·H₂O) and 650 mL of methanol (50V) were combined and stirred at 50-55° C.;
b. 7.4 g of sodium lauryl sulfate (SLS) (1 molar equivalent to the dasatinib·H₂O) was combined with 39 mL of methanol (3V) and 25.7 mL of 1 N HCl (1 molar equivalent to the SLS);
c. The composition of step (b) was added to the composition of step (a) and stirred for 30 minutes while maintaining the temperature at 50-55° C., then cooled to room temperature for about an hour;
d. 650 mL of purified water (50V) was added to the reaction mass of step (c) and stirred at room temperature for 30 minutes.
e. The solvent was removed from the reaction mass of step (d) and the residue collected;
f. 260 mL of ethyl acetate (20V) was added to the residue of step (e) and the resulting reaction mass was washed with 130 mL of purified water for three times (10V×3);
g. The organic extracts were combined and 130 mL of methanol (10V) was added;
h. The reaction mass of step (g) was dried in a vacuum at 40° C. for 6 hours to obtain crude dasatinib monolauryl sulfate (dasatinib-1LS);
i. The crude dasatinib-1LS was combined with 130 mL of hexane (10 V) and stirred for 30 minutes, the solids were isolated by filtration, washed with hexane and dried in a vacuum at 40° C. for 16 hours to obtain dasatinib-1LS as a white powder which was exhibited a chromatographic purity greater than 99%.

Figure 3:
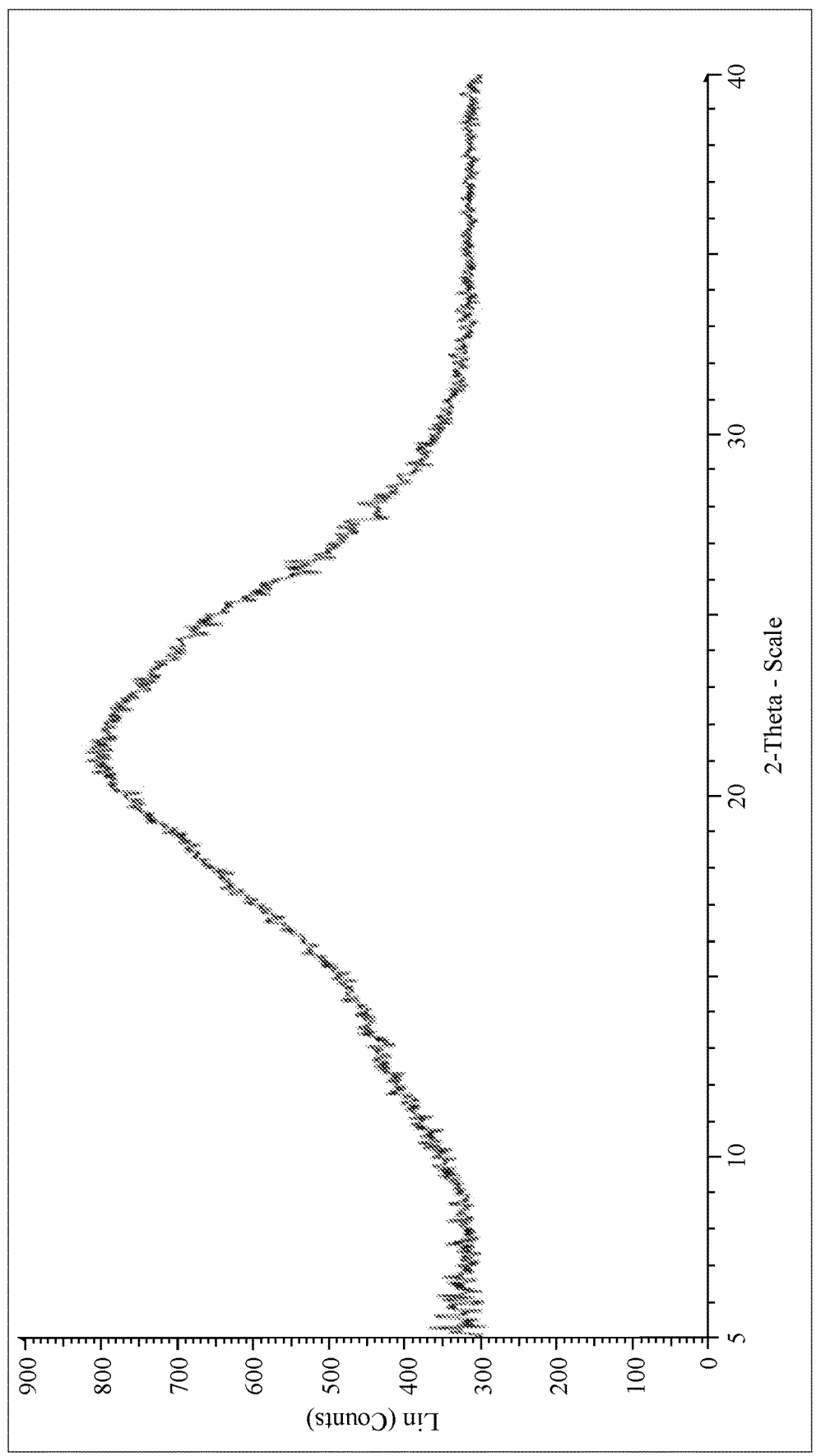
FIG. 3 is an XRPD pattern of the dasatinib monolauryl sulfate salt of Example 12.

The X-ray Powder Diffraction Pattern ("XRPD") for the white powder dasatinib monolauryl sulfate salt is shown in FIG. 3. The XRPD was obtained using D8 Discover with GADDS (Bruker AXS Gmbh, Karlsruhe, Germany) (GADDS: General Area Diffraction Detection System) and employing the following testing condition:

Cuk$\alpha_{1+2}$=1.54184 Å,
40 kV 40 mA
Beam size: 1.0 mm (the collimator system allows the analysis of 1000 μm$^2$ surface areas)
Detector type: Vantec-2000 (14×14 cm$^2$ area and 2048× 2048 pixel density)
Sample to detector distance: 15.05 cm
300 sec/frame (The exposure time was 300 s per frame).

The above synthesis was conducted multiple times and the results are summarized in the following table:

| dasatinib-H2O | SLS (eq) | dasatinib-1LS | Yield | Purity |
| --- | --- | --- | --- | --- |
| 13 g | 1 | 16.17 g | 83.00% | 99.96% |
| 30 g | 1 | 42.0 g | 93.90% | 99.91% |
| 75 g | 1 | 104.78 g | 93.70% | 100% |
| 75 g | 1 | 106.68 g | 95.40% | 100% |

Example 13

A dasatinib dilauryl sulfate salt was prepared by the following general procedure:
a. 10 g of dasatinib·H$_2$O and 500 mL of methanol (50V) were combined and stirred at 50-55° C.;
b. 11.4 g of SLS (2 molar equivalent to the dasatinib H$_2$O) was combined with 30 mL of methanol (3V) and 79 mL of 1 N HCl (2 molar equivalent to the SLS);
c. The composition of step (b) was added to the composition of step (a) and stirred for 30 minutes while maintaining the temperature at 50-55° C., then cooled to room temperature for about an hour;
d. 500 mL of Purified water (50V) was added to the reaction mass of step (c) and stirred at room temperature for 30 minutes.
e. The solvent was removed from the reaction mass of step (d) and the residue collected;
f. 200 mL of ethyl acetate (20V) was added to the residue of step (e) and the resulting reaction mass was washed with 100 mL of purified water for three times (10V×3);
g. The organic extracts were combined and 100 mL of methanol (10V) was added;
h. The reaction mass of step (g) was dried in a vacuum at 40° C. for 6 hours to obtain crude dasatinib dilauryl sulfate (dasatinib-2LS);
i. The crude dasatinib-2LS was combined with 100 mL of hexane (10 V) and stirred for 30 minutes, the solids were isolated by filtration, washed with hexane and dried in a vacuum at 40° C. for 16 hours to obtain dasatinib dilauryl sulfate as a white powder which was exhibited a chromatographic purity greater than 99%.

Figure 4:
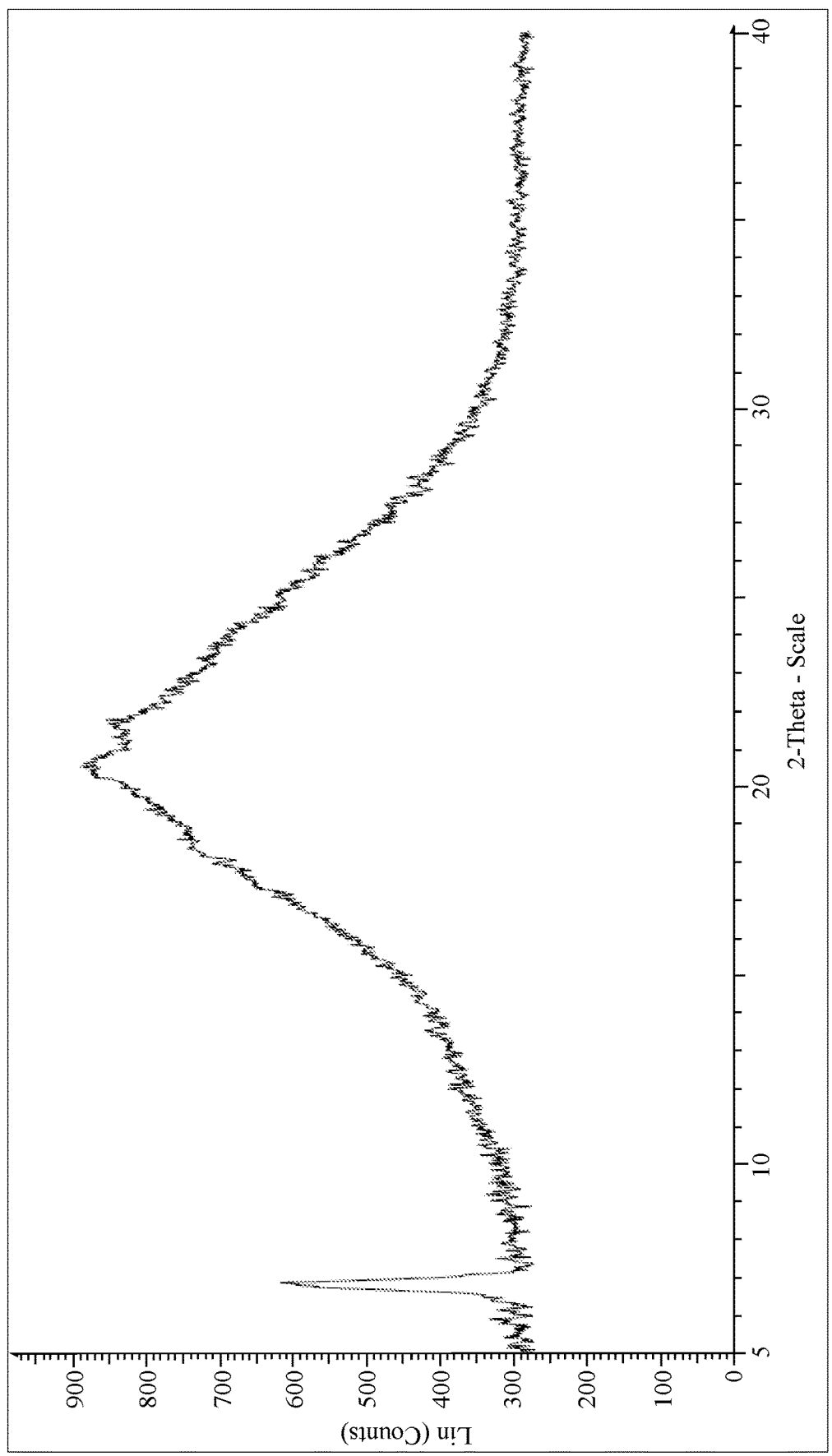
FIG. 4 is an XRPD pattern of the dasatinib dilauryl sulfate salt of Example 13.

The XRPD for the white powder dasatinib dilauryl sulfate salt is shown in FIG. 4. The XRPD was obtained using D8 Discover with GADDS (Bruker AXS Gmbh, Karlsruhe, Germany) (GADDS: General Area Diffraction Detection System) and employing the following testing condition:

Cuk$\alpha_{1+2}$=1.54184 Å,
40 kV 40 mA
Beam size: 1.0 mm (the collimator system allows the analysis of 1000 μm$^2$ surface areas)
Detector type: Vantec-2000 (14×14 cm$^2$ area and 2048× 2048 pixel density)
Sample to detector distance: 15.05 cm
300 sec/frame (The exposure time was 300 s per frame).

The above synthesis was conducted multiple times and the results are summarized in the following table:

| dasatinib · H$_2$O | SLS (eq) | dasatinib-2LS | Yield | Purity |
| --- | --- | --- | --- | --- |
| 10 g | 2 | 18.38 g | 91.10% | 99.97% |
| 53 g | 2 | 90.3 g | 84.50% | 100% |
| 33 g | 2 | 56.6 g | 85.00% | 99.97% |
| 38 g | 2 | 65.2 g | 85.00% | 99.98% |

Example 14

A dasatinib lauryl sulfate salt was prepared by dissolving 1.012 g of dasatinib monohydrate in 1800 mL of 0.1N hydrochloric acid (HCl) solution and dissolving 1.728 g of sodium lauryl sulfate in 200 mL of 0.1N hydrochloric acid (HCl) solution. Once the dasatinib monohydrate and sodium lauryl sulfate were dissolved, the two solutions were mixed well, dilute with 0.1N HCl to total volume of 5330 mL and stir for 2 hours. The precipitated dasatinib lauryl sulfate was collected by removing the upper liquid and dried at 50° C. for 20 hours.

Example 15

A dasatinib lauryl sulfate capsule dosage form was prepared by mixing 522.0 mg of the dasatinib lauryl sulfate (dry precipitate) prepared in Example 14 with 2100.0 mg of CAPMUL® MCM (glyceryl caprylate/caprate) and 525.0 mg of KOLLIPHOR® EL (polyoxyl 35 castor oil) and filling the suspension mixture into size 00 hard gelatin capsules.

The composition of the capsule content is as follows:

| | mg/cap | wt % |
| --- | --- | --- |
| Dasatinib lauryl sulfate (Dry precipitate) | 104.4 | 16.6 |
| Glyceryl Caprylate/Caprate | 420.0 | 66.7 |
| Polyoxyl 35 Castor Oil | 105.0 | 16.7 |
| Total | 629.4 | 100.0 |

Example 16

A pazopanib monolauryl sulfate salt was prepared by the following general procedure:
a. 20 g of pazopanib hydrochloride (PZB·HCl), 200 mL methanol (10V) and 400 mL purified water (20V) were combined and stirred at 50-55° C.;
b. 12.17 g sodium lauryl sulfate (SLS) (1 molar equivalent to the PZB·HCl) was combined with 60 mL of methanol (3V) and 60 mL of purified water (3V);
c. The composition of step (b) was added to the composition of step (a) and stirred for 30 minutes while maintaining the temperature at 50-55° C., then cooled to room temperature for about an hour;

d. 400 mL of purified water (20V) was added to the cooled reaction mass of step (c) and stirred at room temperature for 1 hour;

e. The precipitate (white crystals) of step (d) was collected by filtration, washed with 100 mL of purified water (5V) to obtain crude pazopanib monolauryl sulfate (PZB-1LS);

f. The crude PZB-1LS was combined with 200 mL of purified water (10 V) stirred for 30 minutes, the solids were collected by filtration, washed with 100 mL of purified water (5 V) and vacuum dried to obtain 28 g of PZB-1LS as a white powder which was exhibited a chromatographic purity 100% and a yield of 94%.

The solubility of the pazopanib monolauryl sulfate prepared above and a commercially available sample of pazopanib hydrochloride was measured by adding the sample to 300 mL of the designated medium at 37° C. and shaking or stirring for at least 18 hours to obtain a saturated condition. The reaction mass was filtered and the filtrate solution was measured by HPLC.

| pH condition | Pazopanib Hydrochloride (μg/mL) | Pazopanib Monolauryl Sulfate (μg/mL) |
|---|---|---|
| 0.1 NHCl, pH = 1.0 | 3361.05 | 118.68 |
| 0.05 M acetate buffer, pH = 4.5 | 1.1924 | 0.3212 |
| 0.05 M phosphate buffer, pH = 6.8 | 0.0 | 1.242 |

Example 17

A PZB-1LS salt was prepared by the procedure of Example 16 wherein 17.4 g of PZB·HCl and 10.58 g of SLS were used as the starting materials. The process resulted in 20.5 g of PZB-1LS (80% yield) with a chromatographic purity of 99.99%.

Example 18

A pazopanib lauryl sulfate capsule dosage form was prepared by mixing 1009.7 mg of the PZB-1LS prepared according to the procedure of Examples 16 & 17, 4981.0 mg of CAPMUL® 808G (glyceryl monocaprylate), 1.25 mg of butylated hydroxytoluene, 281.8 mg of PURAC® FCC 88 (lactic acid), and 960.1 mg of KOLLIPHOR® ELP (polyoxyl 35 castor oil) and filling the liquid mixture into size 0 hard gelatin capsules.

The composition of the capsule content is as follows:

| | mg | wt % |
|---|---|---|
| Pazopanib mono lauryl sulfate (EQ to 50 mg base) | 80.5 | 13.94 |
| Glyceryl monocaprylate | 400.0 | 69.25 |
| Polyoxyl 35 Castor Oil | 75.0 | 12.98 |
| Lactic acid | 22 | 3.81 |
| Butylated hydroxytoluene | 0.1 | 0.02 |
| Total | 577.6 | 100.00 |

The above pazopanib monolauryl sulfate capsule was tested using the following High Performance Liquid Chromatography (HPLC) method:

| Parameter | Setting/Description |
|---|---|
| System | HPLC Equipped with a UV/Vis Detector |
| Column | Develosil RP Aqueous-3, C-30 (3 μm, 150*4.6 mm) |
| Detection | UV at 268 nm |
| Flow rate | 1 mL/min |
| Injection volume | 10 μL |
| Column temperature | 35° C. |
| Sample temperature | Ambient |
| Run time | 40 minutes |

| Mode of Analysis | Gradient as shown below: | | |
|---|---|---|---|
| | Time (min) | Mobile phase A | Mobile phase B |
| | 0 | 90 | 10 |
| | 1 | 90 | 10 |
| | 31 | 46 | 54 |
| | 33 | 90 | 10 |
| | 40 | 90 | 10 |

The mobile phase A was water/trifluoracetic acid in a volume ratio of 100/0.1.

The mobile phase B was acetonitrile/trifluoracetic acid in a volume ratio of 100/0.1.

The test sample was prepared by weighing approximately 8.0 mg of pazopanib monolauryl sulfate into a 25 mL amber volumetric flask, adding about 20 mL of a diluent comprising acetonitrile/water/trifluoracetic acid in a volume ratio of 50/50/0.1, sonicating for about 5 minutes and stirring at about 800 rpms for about 5 minutes until the pazopanib monolauryl sulfate is dissolved. Additional diluent is added so the test sample is approximately 0.20 mg of pazopanib per mL.

The results of the HPLC testing was as follows:

| | RRT | | | | | | |
|---|---|---|---|---|---|---|---|
| | 0.31 | 0.60 | 0.85 | 0.95 | 0.98 | 1.17 | 1.30 |
| Room Temp. | | 0.01 | | | | | |
| 60° C./75% R.H. (1 week) | 0.01 | 0.09 | 0.02 | 0.06 | 0.01 | 0.01 | |

RRT = relative retention time.

The capsules were stored in a high-density polyethylene (HDPE) bottle with child resistant closure and foil induction seal (126 c.c, with 2~3 g of silica gel).

The above table demonstrates the capsules have not more than ("NMT") 0.5% of any individual impurity, preferably NMT 0.35% of any individual impurity and most preferably NMT 0.25% of any individual impurity and the total impurity should be NMT 1.0%, preferably NMT 0.75% and most preferably NMT 0.60%.

The pazopanib monolauryl sulfate capsule release not less than 90%, preferably not less than 85% and most preferably not less than 80% of the pazopanib within 45 minutes of in vitro testing using a USP Type II Apparatus (Paddle) with 500 ml of 0.1 N HCl at 75 rpm, with or without a sinker and 37° C.

Example 19

A pazopanib lauryl sulfate capsule was prepared by dissolving 226 mg of poloxamer 188 in 1.2 g of ethanol. The solution was manually mixed with 2421 mg of PZB-1LS prepared according to the procedure of Examples 16 and 17, 1398.3 mg of lactose monohydrate and 238.9 mg of polyvinyl pyrrolidone. The resulting granules were dried and milled through a 60 mesh screen and blended with 28.1 mg of colloidal silicon dioxide, 216.2 mg of sodium starch glycolate, 1259.1 mg of lactose monohydrate and 29.2 mg of magnesium stearate. The dry solid blend was filled into size 0 hard gelatin capsules.

The composition of the capsule content is as follows:

|  | mg | wt % |
|---|---|---|
| Granule | | |
| Pazopanib mono lauryl sulfate (EQ to 50 mg base) | 80.5 | 40.25 |
| Lactose monohydrate | 46.7 | 23.35 |
| Polyvinyl pyrrolidone | 8.0 | 4.00 |
| Poloxamer 188 | 8.2 | 4.10 |
| Ethanol | 40.0 | — |
| External phase | | |
| Lactose monohydrate | 46.6 | 23.30 |
| Sodium starch glycolate | 8.0 | 4.00 |
| Colloidal Silicon Dioxide | 1.0 | 0.50 |
| Magnesium Stearate | 1.0 | 0.50 |
| Total | 200.0 | 100.00 |

The above pazopanib monolauryl sulfate capsule was tested using the HPLC method described in Example 18 and the following results were obtained:

| | RRT | | | | | | |
|---|---|---|---|---|---|---|---|
| | 0.31 | 0.60 | 0.85 | 0.95 | 0.98 | 1.17 | 1.30 |
| Room Temp. | 0.01 | | | 0.02 | 0.02 | | |
| 60° C./75% R.H. (1 week) | 0.01 | | | 0.04 | 0.02 | | |

The capsules were stored in a high-density polyethylene (HDPE) bottle with child resistant closure and foil induction seal (126 c.c, with 2~3 g of silica gel).

The above table demonstrates the capsules have NMT 0.5% of any individual impurity, preferably NMT 0.35% of any individual impurity and most preferably NMT 0.25% of any individual impurity and the total impurity should be NMT 1.0%, preferably NMT 0.75% and most preferably NMT 0.60%.

The pazopanib monolauryl sulfate capsule should release not less than 90%, preferably not less than 85% and most preferably not less than 80% of the pazopanib within 45 minutes of in vitro testing using a USP Type II Apparatus (Paddle) with 500 ml of 0.1 N HCl at 75 rpm, with or without a sinker and 37° C.

Example 20

The capsules prepared in Examples 18 and 19 containing PZB-1LS equivalent to 50 mg of pazopanib free base were administered to six (6) healthy adult beagle dogs in a fasted state along with a capsule, obtained by dividing the content from a commercially available 200 mg VOTRIENT FILM COATED tablet (containing 216.7 mg of pazopanib HCl) into 4 capsules (each capsule containing pazopanib hydrochloride equivalent to 50 mg of pazopanib free base) in a single-center, single-dose study. Blood samples were drawn before dosing and at 0.5, 1, 1.5, 2, 2.5, 3, 4, 6, 8, 12 and 24 hours after dosing. The mean pazopanib plasma values were determined as follows:

| | Capsule Prepared According to the Procedure of Example 18 (T1) | Capsule Prepared According to the Procedure of Example 19 (T2) | REFERENCE (VOTRIENT) (R) |
|---|---|---|---|
| $AUC_{0-24}$ (ng · hr/mL) | 7885.29 | 2394.47 | 1279.27 |
| $C_{max}$ (ng/mL) | 2608.42 | 847.44 | 313.00 |

Figure 5:
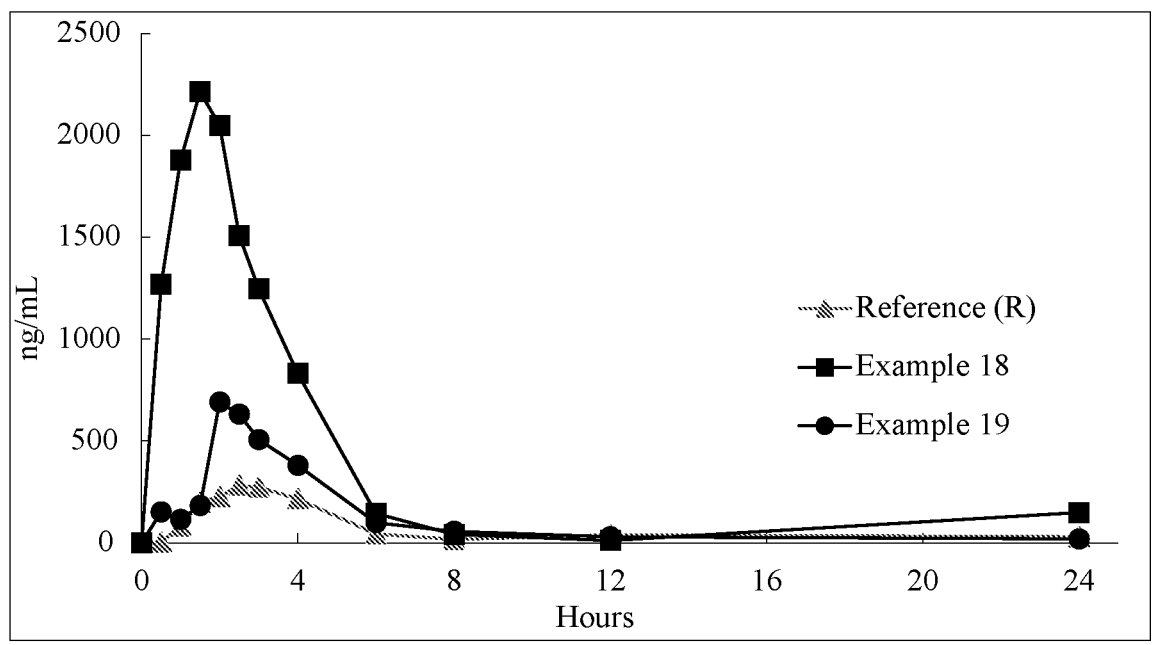
FIG. 5 is a graph of the mean in vivo plasma data provided in Example 20.

A graph of the mean plasma profiles is shown in FIG. 5.

The individual data from the study is shown in the following tables:

$C_{max}$ (ng/mL)

| | 101 | 102 | 201 | 202 | 301 | 302 | Mean | SD | CV (%) |
|---|---|---|---|---|---|---|---|---|---|
| Ref | 138.77 | 112.04 | 71.65 | 215.42 | 989.72 | 350.40 | 313.00 | 345.79 | 110.5 |
| Ex 18 | 1264.89 | 1475.94 | 6776.81 | 1599.92 | 679.50 | 3853.45 | 2608.42 | 2313.05 | 88.7 |
| Ex 19 | 229.52 | 288.57 | 780.60 | 3396.11 | 82.23 | 307.60 | 847.44 | 1270.54 | 149.9 |

$AUC_{0-24}$ (ng·hr/mL)

|     | 101 | 102 | 201 | 202 | 301 | 302 | Mean | SD | CV (%) |
|---|---|---|---|---|---|---|---|---|---|
| Ref | 368.96 | 268.45 | 816.48 | 693.44 | 3834.53 | 1693.74 | 1279.27 | 1349.74 | 105.5 |
| Ex 18 | 6429.59 | 5400.80 | 16849.29 | 6819.58 | 1525.84 | 10286.63 | 7885.29 | 5215.17 | 66.1 |
| Ex 19 | 539.82 | 663.49 | 3989.39 | 7765.88 | 356.31 | 1051.93 | 2394.47 | 2959.33 | 123.6 |

Reference (VOTRIENT)

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | BLQ | BLQ | BLQ | BLQ | BLQ | BLQ | NA | NA | NA |
| 0.5 | BLQ | 2.14 | BLQ | BLQ | 4.75 | 4.82 | 3.90 | 1.53 | 39.2 |
| 1 | 13.47 | 5.83 | 52.69 | 204.08 | 188.16 | 25.87 | 81.68 | 90.20 | 110.4 |
| 1.5 | 11.99 | 9.72 | 49.62 | 215.42 | 586.82 | 314.89 | 198.08 | 226.81 | 114.5 |
| 2 | 16.44 | 11.59 | 71.65 | 180.47 | 795.17 | 287.95 | 227.21 | 297.85 | 131.1 |
| 2.5 | 42.82 | 112.04 | 57.08 | 170.43 | 955.39 | 350.40 | 281.36 | 348.50 | 123.9 |
| 3 | 123.99 | 105.75 | 37.42 | 115.31 | 989.72 | 270.95 | 273.86 | 358.95 | 131.1 |
| 4 | 138.77 | 68.96 | 18.93 | 97.81 | 797.13 | 170.26 | 215.31 | 289.89 | 134.6 |
| 6 | 10.90 | 6.69 | 2.53 | 33.64 | 195.30 | 14.14 | 43.87 | 74.97 | 170.9 |
| 8 | 3.65 | 1.66 | BLQ | 7.76 | 57.16 | 15.41 | 17.13 | 22.99 | 134.2 |
| 12 | BLQ | BLQ | BLQ | BLQ | 7.24 | 70.36 | 38.80 | 44.64 | 115.1 |
| 24 | BLQ | BLQ | 68.80 | BLQ | 1.90 | 17.63 | 29.44 | 34.98 | 118.8 |

Capsule Prepared as in Example 18

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | BLQ | BLQ | BLQ | BLQ | BLQ | BLQ | NA | NA | NA |
| 0.5 | 762.79 | 1360.21 | 3739.87 | 1599.92 | 25.98 | 133.55 | 1270.39 | 1364.82 | 107.4 |
| 1 | 1083.37 | 1475.94 | 6776.81 | 1027.53 | 179.49 | 737.07 | 1880.04 | 2437.27 | 129.6 |
| 1.5 | 1208.80 | 1396.37 | 5642.07 | 830.73 | 679.50 | 3528.04 | 2214.25 | 1971.06 | 89.0 |
| 2 | 1091.19 | 1261.88 | 5102.56 | 556.34 | 424.78 | 3853.45 | 2048.37 | 1948.50 | 95.1 |
| 2.5 | 1241.99 | 1013.86 | 3091.67 | 459.99 | 333.63 | 2913.10 | 1509.04 | 1206.21 | 79.9 |
| 3 | 1146.82 | 928.57 | 2717.07 | 410.02 | 214.64 | 2067.39 | 1247.42 | 970.76 | 77.8 |
| 4 | 1264.89 | 539.23 | 1482.79 | 281.44 | 126.69 | 1290.15 | 830.86 | 584.31 | 70.3 |
| 6 | 280.32 | 191.84 | 139.86 | 95.50 | 32.12 | 125.05 | 144.11 | 84.99 | 59.0 |
| 8 | 96.69 | 56.50 | 39.63 | 16.01 | 10.29 | 29.62 | 41.46 | 31.74 | 76.6 |
| 12 | 13.19 | 9.82 | 6.10 | 1.71 | 31.30 | 6.15 | 11.38 | 10.50 | 92.3 |
| 24 | 3.64 | 1.61 | BLQ | 599.99 | 1.27 | 138.35 | 148.97 | 258.93 | 173.8 |

Capsule Prepared as in Example 19

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | BLQ | BLQ | BLQ | BLQ | BLQ | BLQ | NA | NA | NA |
| 0.5 | 229.52 | 288.57 | 2.09 | 2.23 | 82.23 | 307.60 | 152.04 | 140.46 | 92.4 |
| 1 | 209.08 | 191.32 | 39.73 | 14.02 | 61.28 | 176.33 | 115.29 | 86.24 | 74.8 |
| 1.5 | 159.86 | 170.91 | 162.41 | 414.05 | 47.57 | 144.37 | 183.19 | 121.92 | 66.6 |
| 2 | 123.06 | 97.88 | 356.84 | 3396.11 | 43.84 | 130.32 | 691.34 | 1329.42 | 192.3 |
| 2.5 | 99.25 | 83.80 | 419.43 | 3062.05 | 32.74 | 93.08 | 631.73 | 1198.68 | 189.7 |
| 3 | 76.97 | 56.02 | 727.55 | 2078.21 | 26.51 | 77.51 | 507.13 | 814.98 | 160.7 |
| 4 | 42.10 | 39.99 | 780.60 | 1350.90 | 16.30 | 54.69 | 380.76 | 560.54 | 147.2 |
| 6 | 3.70 | 5.36 | 385.73 | 192.92 | 2.47 | 5.34 | 99.25 | 159.36 | 160.6 |
| 8 | 1.16 | 1.49 | 174.68 | 49.60 | BLQ | BLQ | 56.73 | 81.86 | 144.3 |
| 12 | BLQ | BLQ | 39.21 | 5.75 | BLQ | 44.87 | 29.94 | 21.14 | 70.6 |
| 24 | BLQ | 15.14 | 28.90 | 26.00 | 17.05 | 10.12 | 19.44 | 7.80 | 40.1 |

Example 21

A nintedanib dilauryl sulfate salt was prepared by the following general procedure:
a. 15 g of nintedanib esylate was added to a co-solvent of ethyl acetate/10% aqueous NaHCO$_3$ (450 ml/150 ml) (30V/10V) and stirred at 40° C. for 1 hour;
b. The organic layer of the reaction mixture of step (a) was separated and washed twice with 150 mL of purified water (10V×2);
c. The organic extracts of step (b) were combined and concentrated to obtain nintedanib free base as a yellow powder (12.3 g, 98.7% yield);
d. 738 mL of methanol (60V) was added to the 12.3 g of nintedanib free base and the mixture was stirred at 50-55° C.;
e. An SLS solution was prepared by dissolving 13.1 g of SLS (2 molar equivalents to the nintedanib) in a co-solvent of 36.9 mL methanol/90 mL 1 N HCl (3V);
f. The SLS solution of step (e) is added to the mixture of step (d) and stirred at 50-55° C. for 30 minutes;
g. 246 mL of purified water (20V) was added to the reaction mixture of step (f) and stirred at room temperature for 1 hour;
h. The precipitate (crystals) of step (g) were collected by filtration, washed with 61.5 mL of purified water (5V) to obtain crude nintedanib dilauryl sulfate;
i. The crude nintedanib dilauryl sulfate was combined with 123 mL of purified water (10 V), stirred for 30 minutes, the solids were collected by filtration, washed with 61.5 mL of purified water (5 V) and vacuum dried to obtain 21.83 g of nintedanib dilauryl sulfate as a golden yellow powder which was exhibited a chromatographic purity 100% and a yield of 89.3%.

Example 21A

A nintedanib dilauryl sulfate tablet dosage form was prepared by the following wet granulating process:
(i) 9.940 g of nintedanib dilauryl sulfate prepared according to the procedure of Example 21 was mixed with 1.800 g of poloxamer 407 and 1.575 g of poloxamer 188;
(ii) the mixture of step (i) is granulated with a solution comprising 1.500 g of alcohol (95%) and 1.500 g of purified water;
(iii) 6.000 g of anhydrous lactose and 8.278 g of microcrystalline cellulose are passed through a 40 mesh sieve, added to the granules of step (ii) and the resulting composition is blended;
(iv) the blend of step (iii) is dried in an oven at 50° C. to evaporate the alcohol and water and after drying is passed through a 40 mesh sieve;
(v) the dried and sieved material from step (iv) is mixed with 0.600 g of colloidal silicon dioxide and 1.500 g of polyethylene oxide with an average molecular weight of 7,000,000 (Polyox WSR303) which have been passed through a 40 mesh sieve;
(vi) 0.007 g of butylated hydroxytoluene (BHT) is passed through a 40 mesh sieve, added to the composition of step (v) and mixed;
(vii) 0.300 g of magnesium stearate is passed through a 40 mesh sieve, added to the composition of step (vi) and blended to obtain a final blend; and
(viii) the final blend is compressed into tablets using a capsule-shaped punch (17.5 mm length and 7.1 mm width) and with a target hardness of about 10 kp.

The composition of the tablet is as follows:

|  | mg | wt % |
| --- | --- | --- |
| Nintedanib dilauryl sulfate, NTB-2LS (EQ to 100 mg strength) | 198.80 | 33.13 |
| Poloxamer 407 | 36.00 | 6.00 |
| Poloxamer 188 | 31.50 | 5.25 |
| Anhydrous lactose | 120.00 | 20.00 |
| Microcrystalline cellulose | 165.56 | 27.59 |
| Colloidal silicon dioxide | 12.00 | 2.00 |
| Polyethylene oxide 7000000 (Polyox WSR303) | 30.00 | 5.00 |
| Butylated Hydroxytoluene | 0.14 | 0.02 |
| Magnesium stearate | 6.00 | 1.00 |
| Total | 600.00 | 100.00 |
| 95% alcohol | 30.0 | N/A |
| Purified water | 30.0 | N/A |

Example 21B

A nintedanib dilauryl sulfate tablet dosage form was prepared by the procedure described in Example 21A and the composition of the tablet is as follows:

|  | mg | wt % |
| --- | --- | --- |
| Nintedanib dilauryl sulfate, NTB-2LS (EQ to 100 mg strength) | 198.80 | 33.13 |
| Poloxamer 407 | 36.00 | 6.00 |
| Poloxamer 188 | 31.50 | 5.25 |
| Anhydrous lactose | 120.00 | 20.00 |
| Microcrystalline cellulose | 123.56 | 20.59 |
| Colloidal silicon dioxide | 12.00 | 2.00 |
| Polyethylene oxide 7000000 (Polyox WSR303) | 72.00 | 12.00 |
| Butylated Hydroxytoluene | 0.14 | 0.02 |
| Magnesium stearate | 6.00 | 1.00 |
| Total | 600.00 | 100.00 |
| 95% alcohol | 30.0 | N/A |
| Purified water | 30.0 | N/A |

Example 21C

The dosage forms prepared in Examples 21A and 21B (n=2) were tested using a USP Type II Apparatus (Paddle) with 675 ml of 0.1 N HCl for 2 hours followed by a pH change to 6.8 (final volume: 900 ml) with 0.1% sodium lauryl sulfite at 100 rpm, with a sinker and 37° C. The results of this dissolution testing are as follows:

| | Time (Hour) | | | | | | | | | | | |
| --- | --- | --- | --- | --- | --- | --- | --- | --- | --- | --- | --- | --- |
| | 0.5 | 1 | 1.5 | 2 | 4 | 6 | 8 | 10 | 12 | 14 | 16 | 18 |
| Ex 21A | 1.8 | 3.5 | 4.6 | 5.3 | 63.4 | 96.5 | 101 | 100.8 | 101.0 | 100.9 | 100.9 | 101.0 |
| Ex 21B | 0.4 | 0.8 | 1.3 | 1.8 | 24.1 | 46 | 66.1 | 84.8 | 102.3 | 103.7 | 103.8 | 104.0 |

The dosage forms prepared in Examples 21A and 21B (n=2) were also tested using a USP Type II Apparatus (Paddle) with 900 ml of an aqueous media with a pH of 6.8 and 0.1% sodium lauryl sulfite at 100 rpm, with a sinker and 37° C. The results of this dissolution testing are as follows:

|  | Time (Hour) | | | | | | | | | | |
| --- | --- | --- | --- | --- | --- | --- | --- | --- | --- | --- | --- |
|  | 0.5 | 1 | 1.5 | 2 | 4 | 6 | 8 | 10 | 12 | 14 | 16 |
| Ex 21A | 6.8 | 12.9 | 19.9 | 27.6 | 63.6 | 98.4 | 98.7 | 98.8 | 98.9 | 98.8 | 98.9 |
| Ex 21B | 1.0 | 1.9 | 3.2 | 4.9 | 15.7 | 29.5 | 45.2 | 62.3 | 78.4 | 90.7 | 99.0 |

The above in vitro dissolution data demonstrates that dosage forms prepared in accordance with the present invention can exhibit sustained release properties allowing for once or twice daily dosing. For example, a sustained release dosage form will release nintedanib lauryl sulfate salts when tested using a USP Type II Apparatus (Paddle) with 900 ml of an aqueous media with a pH of 6.8 and 0.1% sodium lauryl sulfite at 75 rpm as follows:

| Time (hour) | Preferred | More Preferred | Most Preferred |
| --- | --- | --- | --- |
| 2 | 0-40% | 0-35% | 0-30 |
| 4 | 5-70% | 7.5%-60% | 10-50% |
| 6 | 10-100% | 15-100% | 20-100% |
| 10 | NLT 45% | NLT 50% | NLT55% |
| 12 | NLT 50% | NLT 60% | NLT 70% |

NLT: not less than

The dosage forms prepared in Examples 21A and 21B were also tested for impurities using the following HPLC methods:

| Parameter | Setting/Description |
| --- | --- |
| System | HPLC Equipped with a UV/Vis Detector |
| Column | Nucleodur C18 Gravity, 50 mm* 4 mm, 5 μm |
| Detection | 0~7 min: UV at 235 nm; 7~19 min: UV at 357 nm |
| Flow rate | 1.0 mL/min |
| Injection volume | 5 μL |
| Column temperature | 40° C. |
| Sample temperature | Ambient |
| Run time | 19 minutes |

| Mode of Analysis | Gradient as shown below: | | |
| --- | --- | --- | --- |
|  | Time (min) | Mobile phase A | Mobile phase B |
|  | 0 | 5 | 95 |
|  | 13 | 70 | 30 |
|  | 14 | 70 | 30 |
|  | 15 | 5 | 95 |
|  | 19 | 5 | 95 |

Mobile phase A was 100% acetonitrile.
Mobile phase B was 0.0075M diammonium hydrogen phosphate (pH 6.4±0.2).

The test samples were prepared in triplicate by crushing the tablet and transferring the crushed material into a 100 mL amber volumetric flask, adding about 80 mL of methanol, stirring for about 120 minutes or longer until the material disintegrates, sonicating for an additional 15 minutes and stirring at about 800 rpms for about 10 minutes. The resulting composition is filtered through a 0.45 μm nylon filter with the first 3 mL of filtrate discarded.

The nintedanib dilauryl sulfate tablets prepared in Examples 21A and 21B were determined to have the following impurity profile:

| RRT | | 0.23 | 0.59 | 0.92 | 1.10 | 1.34 | 1.38 | 1.41 | 1.44 |
|---|---|---|---|---|---|---|---|---|---|
| | | | | | % Impurity | | | | |
| Ex 21A | Initial | | 0.01 | 0.01 | 0.04 | 0.03 | | | |
| | 60° C./75% R.H. 2 weeks | | 0.01 | 0.01 | 0.08 | 0.03 | | | |
| Ex21B | Initial | | | 0.01 | 0.05 | 0.03 | | | |
| | 60° C./75% R.H. 2 weeks | | | 0.01 | 0.06 | 0.03 | | | |

The above data demonstrate the nintedanib lauryl sulfate dosage forms of the present invention have NMT 0.5% of any individual impurity, preferably NMT 0.35% of any individual impurity and most preferably NMT 0.25% of any individual impurity and the total impurity should be NMT 1.0%, preferably NMT 0.75% and most preferably NMT 0.60%.

Example 21D

The tablets prepared in Example 21A (Test Formulation 1 or T1) and Example 21B (Test Formulation 2 or T2) containing nintedanib dilauryl sulfate (equivalent to 100 mg of nintedanib free base) were administered to six (6) healthy subjects in a fasted state along with the commercially available OFEV® capsules (Reference) containing 120.4 mg of nintedanib esylate (equivalent to 100 mg of nintedanib free base) in a single-center, single-dose study. This administration was an open-label, randomized, 3-treatment, 3-sequence, 3-period crossover bioavailability study in healthy subjects under fasted conditions. All subjects were randomized to the sequences as shown in the following table with a washout period of 7 days between the periods.

| Sequence | Period I | Period II | Period III |
|---|---|---|---|
| 1 | Rfast | T1fast | T2fast |
| 2 | T2fast | Rfast | T1fast |
| 3 | T1fast | T2fast | Rfast |

* Rfast: Reference under fasted condition; T1fast: Test 1 under fasted condition; T2fast: Test 2 under fasted condition During each treatment period, blood samples were taken at 0 (prior to the dosing), 0.5, 1, 1.5, 2, 3, 4, 6, 8, 10, 12, 24 and 48 hours after dosing. $AUC_{0-24}$, $AUC_{0-\infty}$, $C_{max}$, $T_{max}$, and $T_{1/2}$ were determined for each subject based on non-compartmental analyses. The results of the study were summarized in the following tables. Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following tables:

The Pharmacokinetic Parameters for Reference and Test Formulations (100 mg Dose)

| Treatment | Parameters | Mean |
|---|---|---|
| Ref | $C_{max}$ (ng/mL) | 17.5 |
| | $AUC_{0-t}$ (ng · h/mL) | 143 |
| | $AUC_{0-\infty}$ (ng · h/mL) | 155 |
| Ex 21A (T1) | $C_{max}$ (ng/mL) | 15.5 |
| | $AUC_{0-t}$ (ng · h/mL) | 133 |
| | $AUC_{0-\infty}$ (ng · h/mL) | 144 |
| Ex 21B (T2) | $C_{max}$ (ng/mL) | 13.3 |
| | $AUC_{0-t}$ (ng · h/mL) | 114 |
| | $AUC_{0-\infty}$ (ng · h/mL) | 123 |

The Comparisons Between Ex 21A (T1) Vs. Reference and Ex 21B (T2) Vs. Reference

| Comparisons | Parameters | Geometric Mean Ratios |
|---|---|---|
| T1~Ref | $C_{max}$ (ng/mL) | 92.29% |
| | $AUC_{0-t}$ (ng · h/mL) | 91.97% |
| | $AUC_{0-\infty}$ (ng · h/mL) | 91.52% |
| T2~Ref | $C_{max}$ (ng/mL) | 77.82% |
| | $AUC_{0-t}$ (ng · h/mL) | 79.45% |
| | $AUC_{0-\infty}$ (ng · h/mL) | 79.29% |

The individual subject data obtained from the study is as follows:

Reference Drug (OFEV®) Under Fasted Condition (Concentration (Ng/mL))

| Time (hr) | Subject | | | | | | Mean | SD | CV % |
|---|---|---|---|---|---|---|---|---|---|
| | 1 | 2 | 3 | 4 | 5 | 6 | | | |
| 0 | 0 | 0.133 | 0.115 | 0.147 | 0 | 0.112 | 0.0845 | 0.0667 | 78.90 |
| 0.5 | 1.72 | 0.196 | 0.00 | 5.91 | 6.50 | 7.54 | 3.64 | 3.39 | 92.9 |
| 1 | 4.04 | 4.93 | 5.04 | 15.40 | 3.23 | 13.70 | 7.72 | 5.36 | 69.3 |
| 1.5 | 6.54 | 6.96 | 3.62 | 13.30 | 2.34 | 23.80 | 9.43 | 8.00 | 84.9 |
| 2 | 8.44 | 3.95 | 2.54 | 10.90 | 2.16 | 19.70 | 7.95 | 6.72 | 84.5 |
| 3 | 8.41 | 6.50 | 1.45 | 18.10 | 22.90 | 13.30 | 11.8 | 7.90 | 67.1 |
| 4 | 9.01 | 9.54 | 1.52 | 25.40 | 14.60 | 13.80 | 12.3 | 7.90 | 64.3 |
| 6 | 7.69 | 8.30 | 14.40 | 13.60 | 11.70 | 10.70 | 11.1 | 2.7 | 24.6 |
| 8 | 4.60 | 4.83 | 7.89 | 7.73 | 6.49 | 6.45 | 6.33 | 1.39 | 22 |
| 10 | 3.10 | 2.84 | 3.65 | 5.28 | 4.74 | 4.58 | 4.03 | 0.97 | 24.3 |
| 12 | 2.26 | 2.51 | 2.64 | 3.85 | 3.38 | 3.35 | 3.00 | 0.61 | 20.60 |

-continued

| Time (hr) | Subject 1 | 2 | 3 | 4 | 5 | 6 | Mean | SD | CV % |
|---|---|---|---|---|---|---|---|---|---|
| 24 | 1.33 | 1.15 | 1.08 | 1.75 | 1.56 | 1.85 | 1.45 | 0.31 | 21.8 |
| 48 | 0.477 | 0.483 | 0.454 | 0.758 | 0.572 | 0.556 | 0.55 | 0.112 | 20.4 |

Example 21A (T1) Drug Under Fasted Condition (Concentration (ng/mL))

| Time (hr) | Subject 1 | 2 | 3 | 4 | 5 | 6 | Mean | SD | CV % |
|---|---|---|---|---|---|---|---|---|---|
| 0 | 0.11 | 0 | 0 | 0 | 0.18 | 0.199 | 0.0815 | 0.0941 | 115.43 |
| 0.5 | 1.41 | 1.34 | 0.00 | 0 | 0.279 | 0.444 | 0.579 | 0.64 | 110.6 |
| 1 | 0.97 | 2.35 | 0.119 | 0.245 | 3.61 | 3.31 | 1.77 | 1.54 | 86.9 |
| 1.5 | 0.891 | 2.05 | 0.245 | 3.74 | 5.10 | 3.39 | 2.57 | 1.84 | 71.6 |
| 2 | 1.16 | 3.51 | 1.11 | 4.21 | 4.37 | 4.80 | 3.19 | 1.65 | 51.60 |
| 3 | 7.80 | 10.20 | 0.843 | 9.30 | 8.07 | 15.30 | 8.59 | 4.67 | 54.4 |
| 4 | 17.70 | 13.80 | 5.44 | 19.60 | 16.00 | 18.40 | 15.2 | 5.2 | 34.1 |
| 6 | 9.59 | 8.20 | 7.51 | 16.40 | 13.50 | 13.40 | 11.4 | 3.5 | 30.8 |
| 8 | 5.79 | 4.99 | 3.09 | 9.15 | 6.93 | 6.89 | 6.14 | 2.05 | 33.4 |
| 10 | 4.12 | 3.54 | 2.20 | 5.25 | 4.70 | 4.35 | 4.03 | 1.06 | 26.4 |
| 12 | 3.09 | 2.46 | 1.92 | 3.78 | 4.02 | 3.29 | 3.09 | 0.79 | 25.6 |
| 24 | 1.83 | 1.08 | 0.716 | 1.84 | 1.69 | 1.56 | 1.45 | 0.45 | 31.4 |
| 48 | 0.652 | 0.45 | 0.269 | 0.548 | 0.462 | 0.641 | 0.504 | 0.143 | 28.4 |

Example 21B (T2) Drug Under Fasted Condition (Concentration (ng/mL))

| Time (hr) | Subject 1 | 2 | 3 | 4 | 5 | 6 | Mean | SD | CV % |
|---|---|---|---|---|---|---|---|---|---|
| 0 | 0.143 | 0 | 0 | 0.173 | 0.13 | 0 | 0.0743 | 0.0826 | 111.1 |
| 0.5 | 0.149 | 0 | 0.00 | 0.192 | 0.369 | 0.00 | 0.118 | 0.149 | 126. |
| 1 | 0.165 | 0.00 | 0.177 | 0.215 | 1.37 | 0.319 | 0.374 | 0.499 | 133.2 |
| 1.5 | 0.196 | 0.00 | 0.368 | 0.409 | 0.79 | 0.967 | 0.455 | 0.363 | 79.7 |
| 2 | 0.527 | 1.72 | 1.16 | 1.74 | 0.816 | 2.63 | 1.43 | 0.76 | 53.0 |
| 3 | 4.80 | 3.85 | 1.93 | 5.07 | 4.07 | 1.87 | 3.60 | 1.39 | 38.6 |
| 4 | 6.46 | 12.10 | 9.91 | 9.95 | 9.14 | 15.40 | 10.5 | 3.0 | 28.7 |
| 6 | 5.49 | 18.80 | 11.90 | 10.00 | 17.10 | 8.81 | 12.0 | 5.1 | 42.2 |
| 8 | 3.00 | 10.30 | 4.35 | 5.17 | 8.53 | 4.39 | 5.96 | 2.82 | 47.4 |
| 10 | 2.34 | 6.41 | 2.87 | 3.24 | 5.90 | 2.62 | 3.90 | 1.78 | 45.7 |
| 12 | 1.98 | 4.85 | 2.14 | 2.52 | 4.23 | 2.33 | 3.01 | 1.22 | 40.4 |
| 24 | 0.998 | 1.66 | 1.04 | 1.20 | 1.56 | 1.16 | 1.27 | 0.28 | 21.7 |
| 48 | 0.365 | 0.54 | 0.35 | 0.518 | 0.656 | 0.347 | 0.463 | 0.128 | 27.7 |

Figure 6:
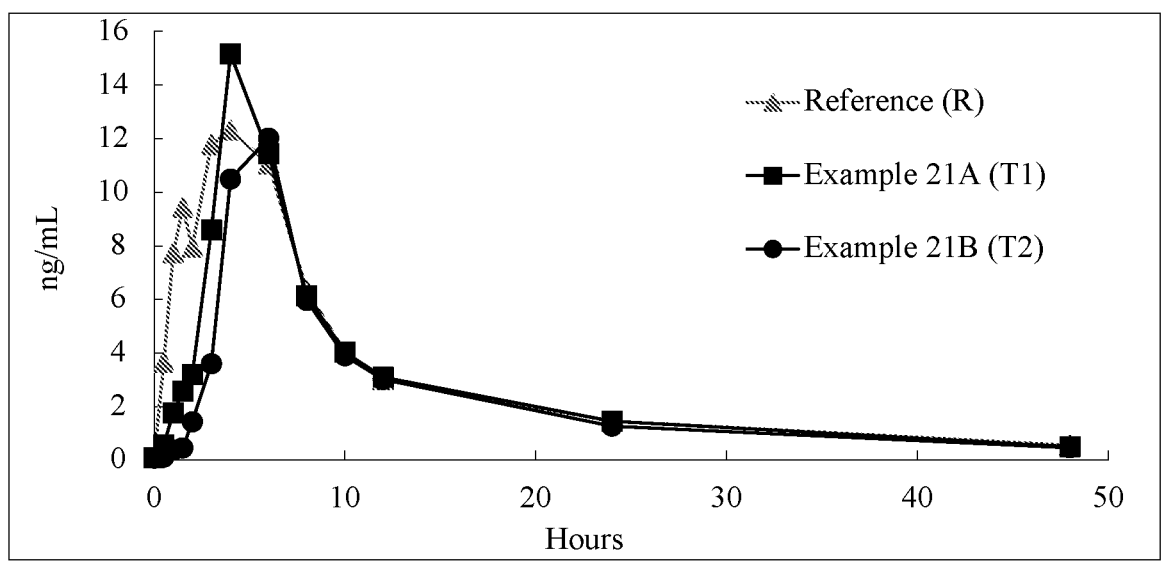
FIG. 6 is a graph of the mean in vivo plasma data provided in Example 21D.

A graph of the mean plasma profiles provided in this Example is shown in FIG. 6.

Example 22

Nintedanib dilauryl sulfate capsules were prepared by manually blending 2386 mg of nintedanib dilauryl sulfate (powder) prepared according to the procedure of Example 21 with 468 mg of croscarmellose sodium and 2122 mg of lactose anhydrous. The blend was passed through a 40 mesh screen. 2122 mg of microcrystalline cellulose (PH102), 390 mg of poloxamer 188 and 234 mg of hydroxypropyl cellulose (HPC-H) were passed through a 40 mesh screen and mixed with the blend. 78 mg of magnesium stearate was passed through a 40 mesh screen and added to the blend. The dried solid blend was filled into size 1 hard gelatin capsule.

The composition of the capsule content is as follows:

| | mg | wt % |
|---|---|---|
| Nintedanib dilauryl sulfate, (EQ to 30 mg base) | 59.64 | 30.58 |
| Croscarmellose sodium | 11.70 | 6.00 |
| Lactose anhydrous | 53.05 | 27.21 |
| Microcrystalline cellulose PH 102 | 53.06 | 27.21 |
| Poloxamer 188 | 9.75 | 5.00 |
| Hydroxypropyl cellulose (HPC-H) | 5.85 | 3.00 |
| Magnesium stearate | 1.95 | 1.00 |
| Total | 195.00 | 100.00 |

Example 23

A nintedanib dilauryl sulfate capsule dosage form was prepared by mixing 2386 mg of the nintedanib dilauryl sulfate prepared according to the procedure of Example 21 (powder, passed through 80 mesh screen) with a mixture of 4649 mg of medium chain triglycerides (Miglyol 812N), 1920 mg of diethylene glycol monoethyl ether (Transcutol HP), 10 mg of butylated hydroxytoluene (BHT), and 1200 mg of lecithin to obtain uniform dispersion. 1836 mg of hard fat (Gelucire 43/01) was melted in water bath (50° C.) and added into the dispersion to obtain a uniform suspension (semi-solid). The semi-solid suspension was filled into size 1 hard gelatin capsule.

The composition of the capsule content is as follows:

|  | mg | wt % |
|---|---|---|
| Nintedanib dilauryl sulfate, (EQ to 30 mg base) | 59.64 | 19.88 |
| Medium Chain Triglycerides, NF | 116.22 | 38.74 |
| Hard Fat | 45.90 | 15.30 |
| Diethylene glycol monoethyl ether | 48.00 | 16.00 |
| Butylated hydroxytoluene | 0.24 | 0.08 |
| Lecithin | 30.00 | 10.00 |
| Total | 300.00 | 100.00 |

Example 24

The capsules prepared in Examples 22 and 23 containing nintedanib dilauryl sulfate (equivalent to 30 mg of nintedanib free base) were administered to six (6) healthy adult beagle dogs in a fasted state along with an equivalent 30 mg capsule prepared from OFEV® capsule, 100 mg. (obtained by collecting the content from commercially available 100 mg OFEV® capsules containing 120.40 mg of nintedanib esylate and refilling into new capsules in which each content is equivalent to 30 mg of nintedanib free base) in a single-center, single-dose study. Blood samples were drawn before dosing and at 0.5, 1, 1.5, 2, 2.5, 3, 4, 5, 6, 8, 12, 24 and 36 hours after dosing. The mean nintedanib plasma values were determined as follows:

|  | Capsule Prepared According to the Procedure of Example 22 (T1) | Capsule Prepared According to the Procedure of Example 23 (T2) | REFERENCE (OFEV®) (R) |
|---|---|---|---|
| $AUC_{0-t}$ (ng · hr/mL) | 549.12 | 619.63 | 349.47 |
| $C_{max}$ (ng/mL) | 64.00 | 66.75 | 31.98 |

Figure 7:
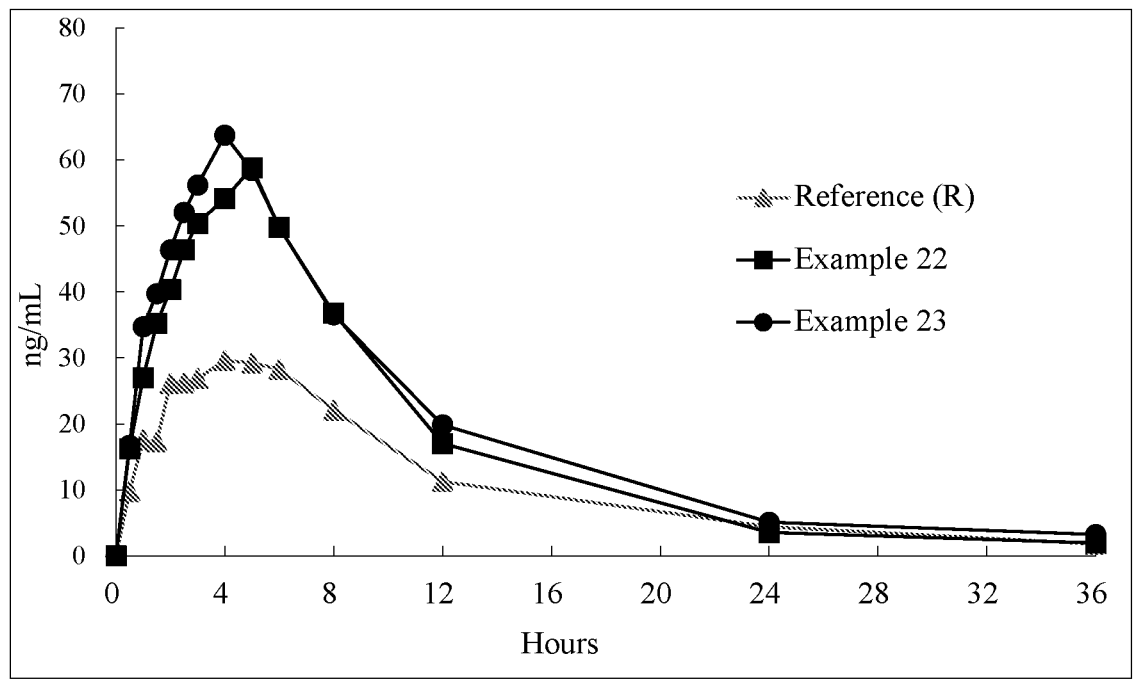
FIG. 7 is a graph of the mean in vivo plasma data provided in Example 24.

A graph of the mean plasma profiles is shown in FIG. 7. The individual data from the study is shown in the following tables:

$C_{max}$ (ng/mL)

|  | 101 | 102 | 201 | 202 | 301 | 302 | Mean | SD | CV (%) |
|---|---|---|---|---|---|---|---|---|---|
| Ref | 38.16 | 10.18 | 28.59 | 31.85 | 23.30 | 59.78 | 31.98 | 16.57 | 51.82 |
| Ex 22 | 59.43 | 66.08 | 52.50 | 73.18 | 66.63 | 66.19 | 64.00 | 7.12 | 11.12 |
| Ex 23 | 49.48 | 86.93 | 50.35 | 94.11 | 63.12 | 56.53 | 66.75 | 19.19 | 28.74 |

$AUC_{0-t}$ (ng·hr/mL)

|  | 101 | 102 | 201 | 202 | 301 | 302 | Mean | SD | CV (%) |
|---|---|---|---|---|---|---|---|---|---|
| Ref | 391.06 | 142.18 | 228.30 | 402.56 | 323.60 | 609.13 | 349.47 | 161.42 | 46.2 |
| Ex 22 | 464.36 | 598.41 | 372.25 | 840.45 | 446.46 | 572.80 | 549.12 | 165.45 | 30.1 |
| Ex 23 | 629.37 | 696.53 | 499.95 | 1070.95 | 412.54 | 408.45 | 619.63 | 249.60 | 40.3 |

Reference (OFEV®)

| Time (hr) | Blood concentration (ng/mL) | | | | | | | | |
|---|---|---|---|---|---|---|---|---|---|
|  | 101 | 102 | 201 | 202 | 301 | 302 | Mean | SD | CV % |
| 0 | BLQ | BLQ | BLQ | BLQ | BLQ | BLQ | NA | NA | NA |
| 0.5 | 10.24 | 4.35 | 14.66 | BLQ | BLQ | BLQ | 9.75 | 5.17 | 53.0 |
| 1 | 21.61 | 5.77 | 25.40 | BLQ | BLQ | BLQ | 17.59 | 10.42 | 59.2 |
| 1.5 | 30.18 | 5.60 | 25.39 | 14.24 | 13.90 | 14.19 | 17.25 | 8.93 | 51.8 |
| 2 | 34.02 | 6.23 | 27.86 | 23.24 | 23.30 | 42.37 | 26.17 | 12.18 | 46.5 |
| 2.5 | 38.16 | 5.61 | 24.94 | 25.15 | 21.38 | 42.02 | 26.21 | 12.98 | 49.5 |
| 3 | 32.18 | 5.75 | 24.01 | 27.36 | 21.74 | 50.26 | 26.88 | 14.53 | 54.1 |
| 4 | 37.11 | 6.34 | 28.59 | 31.85 | 23.23 | 50.48 | 29.60 | 14.70 | 49.7 |
| 5 | 34.78 | 8.38 | 26.33 | 31.19 | 18.76 | 55.87 | 29.22 | 16.11 | 55.1 |
| 6 | 29.99 | 10.18 | 22.36 | 30.65 | 16.84 | 59.78 | 28.30 | 17.29 | 61.1 |
| 8 | 23.00 | 8.34 | 15.85 | 27.99 | 17.79 | 39.58 | 22.09 | 10.85 | 49.1 |
| 12 | 12.90 | 3.94 | 7.58 | 18.21 | 10.77 | 14.17 | 11.26 | 5.04 | 44.7 |
| 24 | 1.79 | 6.26 | BLQ | 2.01 | 4.95 | 7.02 | 4.41 | 2.40 | 54.6 |
| 36 | BLQ | BLQ | BLQ | BLQ | 1.97 | 1.63 | 1.80 | 0.24 | 13.4 |

Capsule Prepared as in Example 22

| Time (hr) | Blood concentration (ng/mL) | | | | | | | | |
|---|---|---|---|---|---|---|---|---|---|
| | 101 | 102 | 201 | 202 | 301 | 302 | Mean | SD | CV % |
| 0 | BLQ | BLQ | BLQ | BLQ | BLQ | BLQ | NA | NA | NA |
| 0.5 | BLQ | 2.26 | 18.72 | 11.48 | 32.50 | BLQ | 16.24 | 12.76 | 78.6 |
| 1 | BLQ | 8.09 | 29.45 | 40.31 | 55.41 | 1.88 | 27.03 | 22.24 | 82.3 |
| 1.5 | 2.30 | 32.72 | 39.48 | 64.58 | 63.59 | 8.59 | 35.21 | 26.40 | 75.0 |
| 2 | 13.96 | 45.57 | 43.15 | 60.71 | 66.63 | 12.02 | 40.34 | 22.97 | 56.9 |
| 2.5 | 26.62 | 51.25 | 40.76 | 65.23 | 63.18 | 31.10 | 46.35 | 16.23 | 35.0 |
| 3 | 32.71 | 56.74 | 46.59 | 69.56 | 58.40 | 38.55 | 50.43 | 13.71 | 27.2 |
| 4 | 30.21 | 58.52 | 52.50 | 73.18 | 54.11 | 56.49 | 54.17 | 13.88 | 25.6 |
| 5 | 59.43 | 66.08 | 43.45 | 68.21 | 49.68 | 66.19 | 58.84 | 10.15 | 17.3 |
| 6 | 40.91 | 51.72 | 38.58 | 64.09 | 38.22 | 65.08 | 49.77 | 12.49 | 25.1 |
| 8 | 29.66 | 35.51 | 26.23 | 57.74 | 25.74 | 45.81 | 36.78 | 12.70 | 34.5 |
| 12 | 13.93 | 18.46 | 9.51 | 30.27 | 11.83 | 18.18 | 17.03 | 7.38 | 43.3 |
| 24 | 4.60 | 4.92 | BLQ | 2.37 | BLQ | 2.32 | 3.55 | 1.40 | 39.5 |
| 36 | 1.96 | BLQ | BLQ | BLQ | BLQ | BLQ | 1.96 | NA | NA |

Capsule Prepared as in Example 23

| Time (hr) | Blood concentration (ng/mL) | | | | | | | | |
|---|---|---|---|---|---|---|---|---|---|
| | 101 | 102 | 201 | 202 | 301 | 302 | Mean | SD | CV % |
| 0 | BLQ | BLQ | BLQ | BLQ | BLQ | BLQ | NA | NA | NA |
| 0.5 | BLQ | 29.69 | 1.94 | 8.79 | 41.33 | 2.03 | 16.76 | 17.83 | 106.4 |
| 1 | BLQ | 55.37 | 8.42 | 44.56 | 50.28 | 15.00 | 34.72 | 21.48 | 61.9 |
| 1.5 | 25.94 | 58.79 | 11.04 | 62.32 | 55.66 | 24.78 | 39.75 | 21.74 | 54.7 |
| 2 | 41.69 | 60.44 | 21.67 | 65.33 | 51.42 | 37.65 | 46.37 | 16.07 | 34.7 |
| 2.5 | 44.60 | 69.23 | 32.96 | 73.12 | 52.64 | 39.85 | 52.07 | 16.17 | 31.1 |
| 3 | 49.33 | 67.20 | 35.12 | 74.95 | 63.12 | 47.50 | 56.20 | 14.75 | 26.2 |
| 4 | 46.16 | 86.93 | 50.35 | 86.92 | 55.67 | 56.53 | 63.76 | 18.33 | 28.8 |
| 5 | 49.48 | 64.56 | 47.24 | 94.11 | 38.86 | 56.09 | 58.39 | 19.52 | 33.4 |
| 6 | 46.08 | 55.12 | 41.31 | 75.23 | 35.02 | 46.04 | 49.80 | 14.10 | 28.3 |
| 8 | 35.68 | 37.34 | 26.44 | 62.18 | 24.61 | 32.95 | 36.53 | 13.54 | 37.1 |
| 12 | 23.96 | 18.11 | 14.63 | 36.74 | 9.32 | 16.32 | 19.85 | 9.55 | 48.1 |
| 24 | 4.83 | 3.05 | 5.19 | 7.30 | BLQ | BLQ | 5.09 | 1.74 | 34.3 |
| 36 | 2.47 | BLQ | 2.90 | 4.29 | BLQ | BLQ | 3.22 | 0.95 | 29.6 |

Example 25

A nintedanib monolauryl sulfate salt was prepared by the following general procedure:
a. 17 g of nintedanib esylate was added to a co-solvent of ethyl acetate/10% aqueous NaHCO₃ (510 mL/170 mL) (30V/10V) and stirred at 40° C. for 1 hour;
b. The organic layer of the reaction mass of step (a) was separated and washed twice with 170 mL of purified water (10V×2);
c. The organic extracts of step (b) were combined and concentrated to obtain nintedanib free base as a yellow powder (13.4 g, 95% yield);
d. 1340 mL of anhydrous ethanol (100V) was added to the 13.4 g of nintedanib free base and the mixture was stirred at 60° C.;
e. An SLS solution was prepared by adding 7.16 g of SLS (1 molar equivalent to the nintedanib) to 40.2 mL of methanol (3V) and 2.3 mL of 12 N HCl (1.1 molar equivalent) and stirred at room temperature for 10 minutes and adding 10 mL of a 10% aqueous NaHCO₃ solution and stirring at room temperature for 5 minutes;
f. The SLS solution of step (e) was added to the mixture of step (d) and stirred at 60° C. for 1 hour;
g. The reaction mass of step (f) was concentrated and 268 mL of ethyl acetate (20V) is added and the resulting reaction mixture was washed with 134 mL of purified water (10V×3);
h. The organic extracts of step (g) were combined, concentrated and the solids collected and vacuum dried at 40° C. for 16 hours to obtain 16.3 g of nintedanib monolauryl sulfate as a yellow powder which was exhibited a chromatographic purity 100% and a yield of 81.5%.

The nintedanib monolauryl sulfate may be used to prepared oral dosages such as those described in Examples 22 and 23.

Example 25A

The solubility of the nintedanib lauryl sulfate salts prepared in Example 21 and 25 and a commercially available sample of nintedanib esylate was measured by adding the sample to 5-20 mL of the designated medium at room temperature and shaking or stirring for at least 18 hours to obtain a saturated condition. The reaction mass was filtered and the filtrate solution was measured by HPLC. The results of the solubility measurements are as follows:

| pH condition | Nintedanib Esylate (µg/mL) | Nintedanib Dilauryl Sulfate (µg/mL) | Nintedanib Monolauryl Sulfate (µg/mL) |
|---|---|---|---|
| 0.1N HCl, pH = 1.0 | 106,600 | 27 | 1081.8 |
| 0.05M acetate buffer, pH = 4.5 | 6260 | 4.3 | 0 |
| 0.05M phosphate buffer, pH = 6.8 | 2.2 | 660 | 0 |

Example 25B

The impurity and stability of the nintedanib lauryl sulfate salts prepared in Example 21 and 25 was measured using the HPLC methods outlined in Example 21C.

The test sample were prepared by respectively weighing about 29.88 mg of nintedanib monolauryl sulfate or 39.76 mg of nintedanib dilauryl sulfate (equivalent to 20 mg of Nintedanib) and transfer into a 20-mL amber volumetric flask, adding 16 mL of diluent (methanol), sonicating for about 5 minutes and stirring at 800 rpms for about 5 minutes until fully dissolved. Additional diluent is added so the test sample is approximately 1.0 mg of nintedanib per mL.

The following results were obtained:

| RRT | 0.23 | 0.59 | 0.92 | 1.10 | 1.34 | 1.36 | 1.38 | 1.14 | 1.44 |
|---|---|---|---|---|---|---|---|---|---|
| | | | | % Impurity | | | | | |
| Ex 21 Initial | | 0.02 | | 0.02 | | 0.03 | | | |
| 40° C./75% R.H. 1 month | | 0.02 | | 0.02 | | 0.03 | | | |
| Ex 25 Initial | | | 0.26 | | 0.09 | | 0.09 | | 0.04 |
| 40° C./75% R.H. 1 month | | | 0.25 | | 0.18 | | 0.11 | 0.01 | 0.04 |

The above data demonstrates the nintedanib dilauryl sulfate is more stable than the monolauryl sulfate and both the dilauryl and monolauryl sulfate salts of the present invention have NMT 0.5% of any individual impurity, preferably NMT 0.35% of any individual impurity and most preferably NMT 0.30% of any individual impurity and the total impurity should be NMT 1.0%, preferably NMT 0.75% and most preferably NMT 0.60%.

Example 26

A nilotinib dilauryl sulfate salt was prepared by the following general procedure:
a. 100 mL of methanol (10V) was added to 10 g of nilotinib HCl and stirred at room temperature;
b. 1.57 mL of 12N HCl (1.1 molar equivalent) was added to the mixture of step (a) and stirred at 50-55° C. for 2 hours;
c. The mixture of step (b) was distilled under vacuum and the residue was stirred with 100 mL of hexane (10V) for 30 minutes;
d. The solids of step (c) were isolated by filtration, washed with hexane and dried in a vacuum at 40° C. for 3 hours to obtain 10.8 g of nilotinib dihydrochloride salt as a golden yellow powder (yield 98%);
e. 216 mL of methanol (20V) was added to the 10.8 g of nilotinib dihydrochloride from step (d) and the mixture was stirred at 50-55° C.;
f. 9.76 g of SLS (2 molar equivalents) was added to 54 mL of methanol (5V) and the resulting mixture was added to the mixture of step (e) and stirred at 50-55° C. for 3 hours;
g. The reaction mixture of step (f) was concentrated, 324 mL of ethyl acetate (30V) was added and the resulting reaction mixture was washed with 216 mL of purified water for three times (20V×3);
h. The organic extracts of step (g) were combined, concentrated and dried in a vacuum at 40° C. for 6 hours to obtain crude nilotinib dilauryl sulfate;
i. The crude nilotinib dilauryl sulfate was combined with 108 mL of hexane (10V) and stirred for 30 minutes;
j. The solids from the reaction mixture of step (i) were isolated by filtration, washed with hexane and dried in a vacuum at 40° C. for 16 hours to obtain 10.6 g of nilotinib dilauryl sulfate as a yellow powder which was exhibited a chromatographic purity 99.98% and a yield of 91%.

Example 27

A nilotinib dilauryl sulfate salt was prepared by the procedure of Example 26 wherein 30 g of nilotinib HCl and 4.71 mL of 12 N HCl were used to obtain 32.4 g of nilotinib dihydrochloride (yield 98%) and the 32.4 g of nilotinib dihydrochloride was combined with 29.3 g of SLS to obtain 48.5 g of nilotinib dilauryl sulfate (90% yield) with a chromatographic purity of 99.97%.

Example 28

A nilotinib dilauryl sulfate salt was prepared by the following general procedure:
a. 768 mL of methanol (30V) was added to 25.6 g of nilotinib HCl and stirred at room temperature;
b. 4.02 mL of 12N HCl (1.1 molar equivalent) was added to the mixture of step (a) and stirred at 50-55° C. for 2 hours;
c. The mixture of step (b) was distilled under vacuum and the residue was stirred with 256 mL of hexane (10V) for 30 minutes;
d. The solids of step (c) were isolated by filtration, washed with hexane and dried in a vacuum at 40° C. for 3 hours to obtain 25.7 g of nilotinib dihydrochloride salt as a golden yellow powder (yield 92%);
e. 514 mL of methanol (20V) was added to the 25.7 g of nilotinib dihydrochloride from step (d) and the mixture was stirred at 50-55° C.;
f. 23.2 g of SLS (2 molar equivalents) was added to 128.5 mL of methanol (5V) and the resulting mixture was added to the mixture of step (e) and stirred at 50-55° C. for 3 hours;
g. The reaction mixture of step (f) was concentrated, 771 mL of ethyl acetate (30V) was added and the resulting reaction mixture was washed with 514 mL of purified water for three times (20V×3);
h. The organic extracts are combined, concentrated and dried in a vacuum at 40° C. for 6 hours to obtain crude nilotinib dilauryl sulfate;
i. The crude nilotinib dilauryl sulfate was combined with 257 mL of hexane (10V) and stirred for 30 minutes;
j. The solids from the reaction mixture of step (i) were isolated by filtration, washed with hexane and dried in a vacuum at 40° C. for 16 hours to obtain 36.5 g of nilotinib dilauryl sulfate as a golden yellow powder which was exhibited a chromatographic purity 99.93% and a yield of 85%.

Example 29

The nilotinib dilauryl sulfate prepared in Examples 26, 27 and 28 may be used to prepare oral dosages such as those described in Examples 3, 4, 9, 15, 18, 19, 22, 23, 30, 31, 33, 34, 37 or 39.

Example 30

Nintedanib monolauryl sulfate capsule dosage form was prepared by wet granulating 1,793 mg of nintedanib monolauryl sulfate prepared according to the procedure of Example 25 with 600 mg of poloxamer 407, 480 mg of poloxamer 188 and 1,600 mg of alcohol dehydrated in a container, heated at 70° C. and mixed for 10 min. A powder mixture of 600 mg of lactose anhydrous, 1,747 mg of microcrystalline cellulose PH102 (part I) and 300 mg of sodium starch glycolate (part I) has been passed through a 40 mesh sieve were added into the nintedanib monolauryl sulfate granules and mixed. The resulting mixture was dried in the oven at 70° C. to evaporate the alcohol. The dried mixture was combined with 300 mg of sodium starch glycolate (part II), 120 mg of colloidal silicon dioxide and 800 mg of microcrystalline cellulose PH102 (part II) that has been passed through a 40 mesh sieve and dry mixed. The resulting dry mixture was passed through 40 mesh sieve and collected in a suitable container. 60 mg of magnesium stearate was passed through a 40 mesh sieve and added to the container and mixed to obtain a final blend. The dry solid final blend was filled into size 1 hard gelatin capsules.

The composition of the capsule content was as follows:

| | mg | wt % |
|---|---|---|
| Nintedanib monolauryl sulfate, NTB-1LS (EQ to 30 mg base) | 44.82 | 26.36 |

-continued

| | mg | wt % |
|---|---|---|
| Lactose anhydrous | 15.00 | 8.82 |
| Microcrystalline cellulose (part I) | 43.68 | 25.69 |
| Sodium starch glycolate (part I) | 7.50 | 4.41 |
| Poloxamer 407 | 15.00 | 8.82 |
| Poloxamer 188 | 12.00 | 7.06 |
| Sodium starch glycolate (part II) | 7.50 | 4.41 |
| Colloidal silicon dioxide | 3.00 | 1.76 |
| Microcrystalline cellulose (part II) | 20.00 | 11.76 |
| Magnesium stearate | 1.50 | 0.88 |
| Total | 170.00 | 100.00 |
| Alcohol dehydrated | 40.00 | N/A |

Example 31

A nintedanib monolauryl sulfate capsule dosage form was prepared by mixing 2,441 mg of medium chain triglycerides (Miglyol 812N), 680 mg of diethylene glycol monoethyl ether (Transcutol HP), 6 mg of butylated hydroxytoluene (BHT), and 680 mg of lecithin to obtain uniform dispersion. 1200 mg of hard fat (Gelucire 43/01) was melted in water bath (50° C.) and added into the uniform dispersion to obtain uniform suspension (semi-solid). 1,793 mg of nintedanib monolauryl sulfate prepared according to the procedure of Example 25 was passed through 80 mesh sieve and added into the suspension to obtain uniform suspension and/or coagulate into semi-solid. The semi-solid suspension was filled into size 1 hard gelatin capsule.

The composition of the capsule content was as follows:

| | mg | wt % |
|---|---|---|
| Nintedanib monolauryl sulfate, NTB-1LS (EQ to 30 mg base) | 44.82 | 26.36 |
| Medium Chain Triglycerides, NF | 61.02 | 35.89 |
| Hard Fat | 30.00 | 17.65 |
| Diethylene glycol monoethyl ether | 17.00 | 10.00 |
| Butylated hydroxytoluene | 0.16 | 0.09 |
| Lecithin | 17.00 | 10.00 |
| Total | 170.00 | 100.00 |

Example 32

The capsules prepared in Examples 30 and 31 containing nintedanib monolauryl sulfate (equivalent to 30 mg of nintedanib free base) were administered to six (6) healthy adult beagle dogs in a fasted state along with an equivalent 30 mg capsule prepared from OFEV® capsule, 100 mg. (obtained by collecting the content from commercially available 100 mg OFEV® capsules containing 120.40 mg of nintedanib esylate and refilling into new capsules in which each content is equivalent to 30 mg of nintedanib free base) in a single-center, single-dose study. Blood samples were drawn before dosing and at 0.5, 1, 1.5, 2, 2.5, 3, 4, 5, 6, 8, 12, 24 and 36 hours after dosing. The mean nintedanib plasma values were determined as follows:

| | Capsule Prepared According to the Procedure of Example 30 (T1) | Capsule Prepared According to the Procedure of Example 31 (T2) | REFERENCE (OFEV ®) (R) |
|---|---|---|---|
| AUC$_{0-t}$ (ng · hr/mL) | 470.92 | 522.07 | 313.92 |
| C$_{max}$ (ng/mL) | 40.81 | 46.10 | 26.09 |

Figure 8:
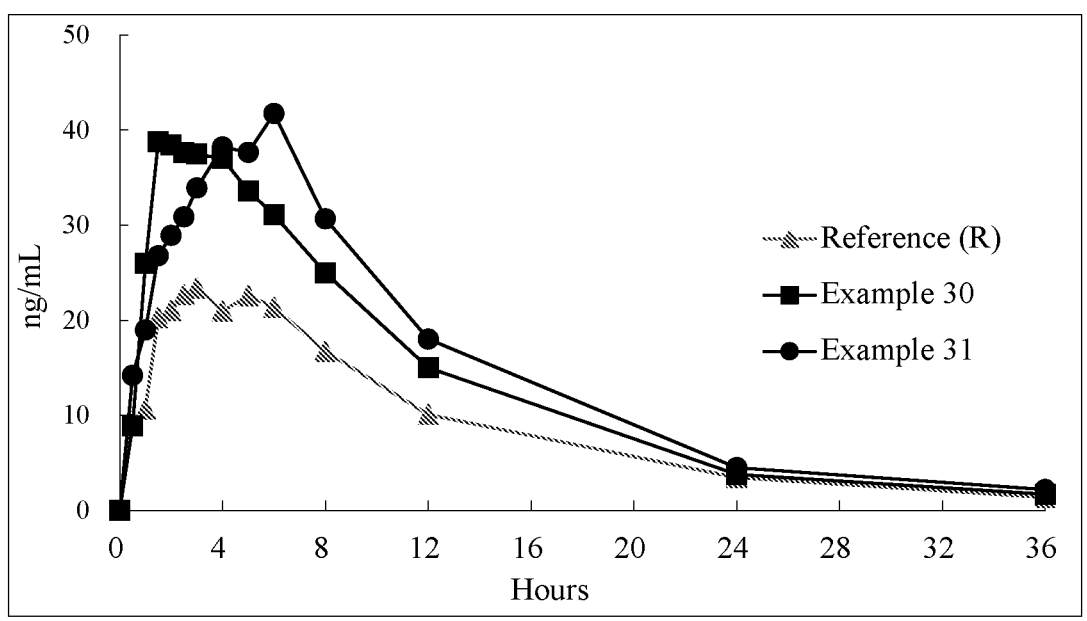
FIG. 8 is a graph of the mean in vivo plasma data provided in Example 32.

A graph of the mean plasma profiles is shown in FIG. 8.

The individual data from the study is shown in the following tables:

C$_{max}$ (ng/mL)

| | 101 | 102 | 201 | 202 | 301 | 302 | Mean | SD | CV (%) |
|---|---|---|---|---|---|---|---|---|---|
| Ref | 36.23 | 20.20 | 22.57 | 49.15 | 12.45 | 15.93 | 26.09 | 13.94 | 53.42 |
| Ex 30 | 17.63 | 51.91 | 42.34 | 30.02 | 18.32 | 84.62 | 40.81 | 25.32 | 62.04 |
| Ex 31 | 33.41 | 52.08 | 40.03 | 56.21 | 36.26 | 58.60 | 46.10 | 10.85 | 23.54 |

AUC$_{0-t}$ (ng·hr/mL)

| | 101 | 102 | 201 | 202 | 301 | 302 | Mean | SD | CV (%) |
|---|---|---|---|---|---|---|---|---|---|
| Ref | 420.87 | 326.13 | 311.61 | 499.02 | 143.17 | 182.71 | 313.92 | 135.81 | 43.26 |
| Ex 30 | 268.40 | 571.31 | 487.05 | 417.71 | 262.23 | 818.83 | 470.92 | 209.18 | 44.42 |
| Ex 31 | 512.55 | 666.21 | 522.56 | 508.13 | 408.65 | 514.33 | 522.07 | 82.44 | 15.79 |

Reference (OFEV®)

| Time (hr) | Blood concentration (ng/mL) | | | | | | | | |
|---|---|---|---|---|---|---|---|---|---|
| | 101 | 102 | 201 | 202 | 301 | 302 | Mean | SD | CV % |
| 0 | BLQ | BLQ | BLQ | BLQ | BLQ | BLQ | NA | NA | NA |
| 0.5 | 23.00 | 1.30 | 9.60 | BLQ | 3.64 | BLQ | 9.38 | 9.73 | 103.66 |
| 1 | 29.25 | 4.93 | 17.88 | 5.14 | 5.92 | 0.55 | 10.61 | 10.82 | 101.98 |
| 1.5 | 31.34 | 16.93 | 19.54 | 36.44 | 7.66 | 9.66 | 20.26 | 11.55 | 57.02 |
| 2 | 30.59 | 15.57 | 19.23 | 42.73 | 6.15 | 11.90 | 21.03 | 13.42 | 63.80 |
| 2.5 | 30.50 | 16.04 | 16.78 | 49.15 | 7.61 | 15.93 | 22.67 | 14.92 | 65.83 |
| 3 | 36.23 | 17.60 | 22.57 | 41.95 | 8.01 | 13.91 | 23.38 | 13.19 | 56.42 |
| 4 | 35.73 | 18.04 | 18.88 | 31.04 | 7.97 | 14.11 | 20.96 | 10.47 | 49.96 |
| 5 | 34.32 | 20.20 | 17.58 | 39.52 | 8.31 | 15.52 | 22.57 | 11.91 | 52.75 |
| 6 | 32.43 | 19.21 | 18.06 | 36.02 | 7.22 | 15.19 | 21.35 | 10.87 | 50.91 |
| 8 | 19.39 | 16.69 | 14.75 | 28.42 | 12.45 | 8.68 | 16.73 | 6.79 | 40.61 |
| 12 | 11.82 | 10.60 | 12.10 | 14.00 | 4.92 | 7.01 | 10.08 | 3.43 | 34.03 |
| 24 | 3.37 | 6.01 | 3.39 | 5.53 | 1.11 | 1.27 | 3.45 | 2.05 | 59.58 |
| 36 | 1.59 | 1.91 | 1.30 | 2.10 | 0.75 | 0.58 | 1.37 | 0.62 | 44.91 |

Capsule Prepared as in Example 30

| Time (hr) | Blood concentration (ng/mL) | | | | | | | | |
|---|---|---|---|---|---|---|---|---|---|
| | 101 | 102 | 201 | 202 | 301 | 302 | Mean | SD | CV % |
| 0 | BLQ | BLQ | BLQ | BLQ | BLQ | BLQ | NA | NA | NA |
| 0.5 | 9.97 | 18.56 | 5.45 | 3.83 | 6.69 | 8.82 | 8.89 | 5.23 | 58.88 |

-continued

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 1 | 16.49 | 17.04 | 34.32 | 22.62 | 17.48 | 47.91 | 25.98 | 12.68 | 48.81 |
| 1.5 | 15.63 | 51.91 | 36.40 | 27.94 | 16.01 | 84.62 | 38.75 | 26.27 | 67.79 |
| 2 | 14.11 | 51.85 | 38.96 | 27.33 | 17.81 | 80.78 | 38.47 | 24.96 | 64.87 |
| 2.5 | 16.07 | 51.73 | 40.72 | 27.49 | 16.47 | 73.48 | 37.66 | 22.40 | 59.48 |
| 3 | 17.31 | 50.30 | 32.93 | 26.79 | 18.32 | 79.26 | 37.49 | 23.74 | 63.34 |
| 4 | 17.63 | 42.78 | 42.34 | 30.02 | 16.66 | 72.54 | 37.00 | 20.80 | 56.22 |
| 5 | 16.26 | 39.46 | 33.71 | 25.30 | 17.96 | 68.97 | 33.61 | 19.49 | 57.99 |
| 6 | 16.56 | 37.72 | 33.15 | 26.43 | 16.67 | 56.02 | 31.09 | 14.90 | 47.94 |
| 8 | 15.90 | 28.45 | 26.50 | 21.37 | 14.09 | 43.57 | 24.98 | 10.72 | 42.90 |
| 12 | 11.05 | 16.19 | 16.92 | 12.99 | 8.63 | 24.26 | 15.01 | 5.50 | 36.63 |
| 24 | 1.66 | 5.56 | 3.04 | 5.70 | 2.73 | 4.08 | 3.79 | 1.62 | 42.66 |
| 36 | 0.77 | 2.94 | 1.23 | 1.94 | 1.26 | 2.05 | 1.70 | 0.78 | 45.69 |

Capsule Prepared as in Example 31

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | BLQ | BLQ | BLQ | BLQ | BLQ | BLQ | NA | NA | NA |
| 0.5 | 27.55 | BLQ | 4.52 | BLQ | BLQ | 10.52 | 14.20 | 11.95 | 84.17 |
| 1 | 32.95 | 4.94 | 6.45 | BLQ | 6.37 | 44.18 | 18.98 | 18.32 | 96.57 |
| 1.5 | 33.39 | 23.15 | 26.87 | 0.61 | 18.07 | 58.60 | 26.78 | 19.13 | 71.44 |
| 2 | 32.05 | 35.21 | 32.89 | 1.63 | 24.00 | 47.80 | 28.93 | 15.43 | 53.33 |
| 2.5 | 32.30 | 39.22 | 37.73 | 6.08 | 25.88 | 44.05 | 30.88 | 13.65 | 44.22 |
| 3 | 33.41 | 46.17 | 37.30 | 14.05 | 27.52 | 45.06 | 33.92 | 12.01 | 35.42 |
| 4 | 30.71 | 52.08 | 36.37 | 29.29 | 31.50 | 49.41 | 38.23 | 10.02 | 26.22 |
| 5 | 30.07 | 47.64 | 37.49 | 39.78 | 30.99 | 40.03 | 37.67 | 6.51 | 17.28 |
| 6 | 30.31 | 50.20 | 40.03 | 56.21 | 36.26 | 37.47 | 41.75 | 9.62 | 23.05 |
| 8 | 26.87 | 36.41 | 31.90 | 33.46 | 26.62 | 28.77 | 30.67 | 3.92 | 12.77 |
| 12 | 20.45 | 20.94 | 19.28 | 18.73 | 14.05 | 14.69 | 18.02 | 2.95 | 16.35 |
| 24 | 3.61 | 8.92 | 3.77 | 5.74 | 2.94 | 2.01 | 4.50 | 2.49 | 55.46 |
| 36 | 2.44 | 3.57 | 1.88 | 3.48 | 1.08 | 0.73 | 2.20 | 1.19 | 54.16 |

Example 33

Dasatinib monolauryl sulfate capsule dosage form was prepared by wet granulating 1,865 mg of dasatinib monolauryl sulfate prepared according to the procedure of Example 12 with 750 mg of poloxamer 407, 600 mg of poloxamer 188 and 2,000 mg of alcohol dehydrated in a suitable container, heated to 70° C. and mixed for 10 min. 600 mg of lactose anhydrous, 1,405 mg of microcrystalline cellulose PH102 and 300 mg of sodium starch glycolate (part I) were passed through a 40 mesh sieve and added the dasatinib monolauryl sulfate granules and mixed. The resulting mixture was dried in an oven at 50° C. to evaporate the alcohol. The dried mixture was combined with 300 mg of sodium starch glycolate (part II) and 120 mg of colloidal silicon dioxide that has been passed through a 40 mesh sieve and mixed. The resulting mixture was passed through 40 mesh sieve and collected in suitable container. 60 mg of magnesium stearate was passed through a 40 mesh sieve and added to the container and mixed to obtain a final blend. The dry solid final blend was filled into size 1 hard gelatin capsule.

The composition of the capsule content was as follows:

| | mg | wt % |
|---|---|---|
| Dasatinib monolauryl sulfate, dasatinib-1LS | 37.3 | 31.1 |
| Lactose anhydrous | 12.0 | 10.0 |
| Microcrystalline cellulose | 28.1 | 23.4 |
| Sodium starch glycolate (part I) | 6.0 | 5.0 |
| Poloxamer 407 | 15.0 | 12.5 |
| Poloxamer 188 | 12.0 | 10.0 |
| Sodium starch glycolate (part II) | 6.0 | 5.0 |
| Colloidal silicon dioxide | 2.4 | 2.0 |
| Magnesium stearate | 1.2 | 1.0 |
| Total | 120.0 | 100.0 |
| Alcohol dehydrated | 40.0 | N/A |

Example 34

Dasatinib dilauryl sulfate capsule dosage form was prepared by wet granulating the 2,520 mg of dasatinib dilauryl sulfate prepared according to the procedure of Example 13 with 750 mg of poloxamer 407, 600 mg of poloxamer 188 and 1000 mg of alcohol dehydrated in a suitable container. 300 mg of lactose anhydrous, 1,050 mg of microcrystalline cellulose PH102 and 300 mg of sodium starch glycolate (I) were passed through a 40 mesh sieve and added to the dasatinib dilauryl sulfate granules and mixed. The resulting mixture was dried in the oven at 50° C. to evaporate the alcohol. The dried mixture was combined with 300 mg of sodium starch glycolate (II) and 120 mg of colloidal silicon dioxide that has been passed through a 40 mesh sieve and mixed. The resulting mixture was passed through 40 mesh sieve and collected in a suitable container. 60 mg of magnesium stearate was passed through a 40 mesh sieve and added to the container and mixed to obtain a final blend. The dry solid final blend was filled into size 1 hard gelatin capsule.

The composition of the capsule content was as follows:

| | mg | wt % |
|---|---|---|
| Dasatinib dilauryl sulfate, dasatinib-2LS | 50.4 | 42.0 |
| Lactose anhydrous | 6.0 | 5.0 |
| Microcrystalline cellulose | 21.0 | 17.5 |
| Sodium starch glycolate (part I) | 6.0 | 5.0 |
| Poloxamer 407 | 15.0 | 12.5 |
| Poloxamer 188 | 12.0 | 10.0 |
| Sodium starch glycolate (part II) | 6.0 | 5.0 |
| Colloidal silicon dioxide | 2.4 | 2.0 |
| Magnesium stearate | 1.2 | 1.0 |
| Total | 120.0 | 100.0 |
| Alcohol dehydrated | 20.0 | N/A |

Example 35

The capsules prepared in Examples 33 and 34 containing dasatinib monolauryl sulfate or dasatinib dilauryl sulfate were administered to six (6) healthy adult beagle dogs in a fasted state along with an equivalent 25 mg capsule obtained by dividing the content from a commercially available 50 mg Sprycel® film coated tablet (containing 50 mg of dasatinib) into 2 capsules in a single-center, single-dose study. Blood samples were drawn before dosing and at 0.33, 0.67, 1, 1.5, 2, 3, 4, 6, 8, 12 and 24 hours after dosing. The dose which in analyses was normalized to 25 mg dasatinib monohydrate for test drug and 25 mg dasatinib for Sprycel® in this example. The 25 mg normalized mean dasatinib plasma values were determined as follows:

|  | Capsule Prepared According to the Procedure of Example 33 (T1) | Capsule Prepared According to the Procedure of Example 34 (T2) | REFERENCE (Sprycel ®) (R) |
|---|---|---|---|
| AUC$_{0-t}$ (ng · hr/mL) | 161.81 | 209.06 | 22.41 |
| C$_{max}$ (ng/mL) | 52.12 | 76.28 | 3.91 |

Figure 9:
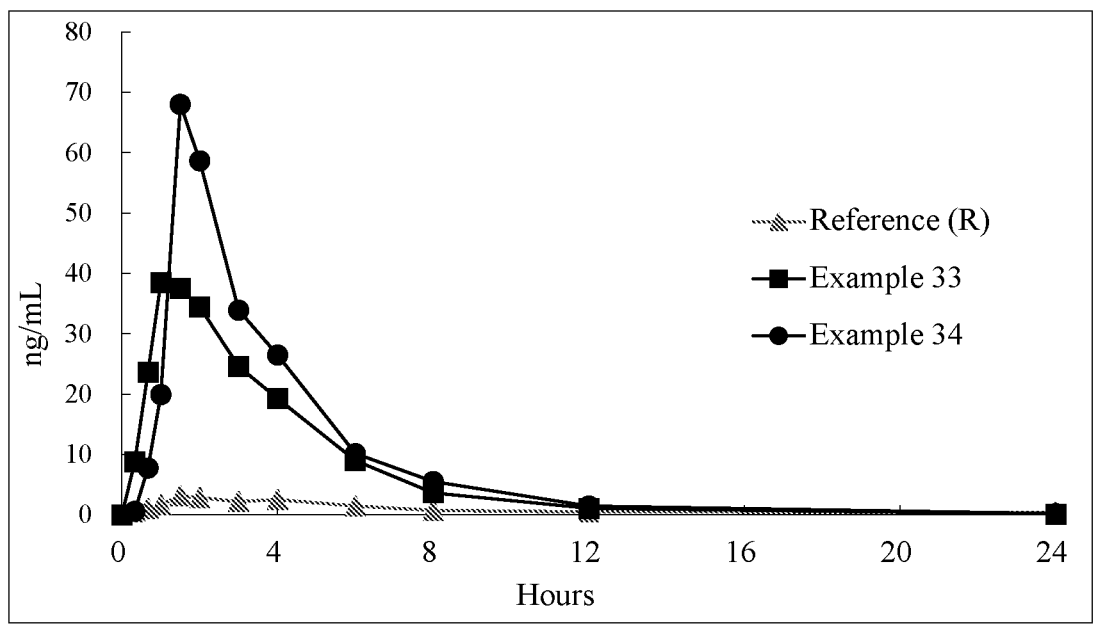
FIG. 9 is a graph of the mean in vivo plasma data provided in Example 35.

A graph of the normalized mean plasma profiles is shown in FIG. 9.

The normalized individual data from the study is shown in the following tables:

C$_{max}$ (ng/mL)

|  | 101 | 102 | 201 | 202 | 301 | 302 | Mean | SD | CV (%) |
|---|---|---|---|---|---|---|---|---|---|
| Ref | 1.61 | 1.62 | 1.63 | 2.03 | 0.65 | 15.92 | 3.91 | 5.90 | 150.89 |
| Ex 33 | 39.77 | 94.41 | 22.26 | 53.70 | 63.64 | 38.97 | 52.12 | 25.06 | 48.08 |
| Ex 34 | 86.69 | 77.07 | 26.64 | 77.95 | 169.56 | 19.75 | 76.28 | 53.80 | 70.53 |

AUC$_{0-t}$ (ng·hr/mL)

|  | 101 | 102 | 201 | 202 | 301 | 302 | Mean | SD | CV (%) |
|---|---|---|---|---|---|---|---|---|---|
| Ref | 10.49 | 19.81 | 9.03 | 11.61 | 8.11 | 75.42 | 22.41 | 26.30 | 117.37 |
| Ex 33 | 131.33 | 221.27 | 89.60 | 181.24 | 167.82 | 179.59 | 161.81 | 45.62 | 28.20 |
| Ex 34 | 182.01 | 188.79 | 126.64 | 197.76 | 441.39 | 117.78 | 209.06 | 118.64 | 56.75 |

Reference (Sprycel®)

| Time (hr) | Blood concentration (ng/mL) | | | | | | | | |
|---|---|---|---|---|---|---|---|---|---|
|  | 101 | 102 | 201 | 202 | 301 | 302 | Mean | SD | CV % |
| 0 | BLQ | BLQ | BLQ | BLQ | BLQ | BLQ | NA | NA | NA |
| 0.33 | 0.12 | 0.27 | 1.03 | BLQ | 0.20 | 1.06 | 0.54 | 0.47 | 87.54 |
| 0.67 | 0.60 | 0.74 | 0.86 | 0.02 | 0.39 | 3.58 | 1.03 | 1.28 | 124.47 |
| 1 | 0.45 | 0.57 | 0.86 | 0.03 | 0.57 | 7.36 | 1.64 | 2.81 | 171.81 |
| 1.5 | 0.62 | 0.73 | 0.92 | 0.05 | 0.65 | 15.92 | 3.15 | 6.26 | 198.86 |
| 2 | 1.61 | 0.57 | 1.07 | 0.12 | 0.55 | 13.12 | 2.84 | 5.06 | 178.31 |
| 3 | 0.55 | 0.24 | 1.38 | 0.65 | 0.23 | 10.15 | 2.20 | 3.92 | 178.07 |
| 4 | 0.54 | 0.22 | 1.63 | 2.03 | 0.15 | 10.58 | 2.53 | 4.02 | 159.23 |
| 6 | 0.43 | 0.12 | 0.52 | 0.56 | 0.09 | 6.93 | 1.44 | 2.70 | 186.96 |
| 8 | 0.50 | 0.24 | 0.24 | 0.47 | 0.27 | 2.78 | 0.75 | 1.00 | 132.96 |
| 12 | 0.56 | 0.90 | 0.11 | 0.52 | 0.22 | 0.57 | 0.48 | 0.28 | 58.70 |
| 24 | 0.06 | 1.62 | 0.05 | 0.12 | 0.62 | 0.04 | 0.42 | 0.63 | 151.06 |

Capsule Prepared as in Example 33

| Time (hr) | Blood concentration (ng/mL) | | | | | | | | |
|---|---|---|---|---|---|---|---|---|---|
|  | 101 | 102 | 201 | 202 | 301 | 302 | Mean | SD | CV % |
| 0 | BLQ | BLQ | BLQ | BLQ | BLQ | BLQ | NA | NA | NA |
| 0.33 | 13.05 | 0.32 | 21.62 | 0.03 | BLQ | BLQ | 8.75 | 10.51 | 120.03 |
| 0.67 | 21.78 | 59.48 | 19.71 | 38.42 | 1.68 | 0.73 | 23.63 | 22.49 | 95.18 |
| 1 | 33.92 | 94.41 | 22.26 | 53.70 | 22.45 | 4.29 | 38.51 | 31.84 | 82.69 |
| 1.5 | 39.77 | 61.61 | 18.95 | 31.21 | 63.64 | 9.68 | 37.48 | 22.03 | 58.79 |
| 2 | 34.84 | 49.50 | 14.89 | 27.13 | 61.38 | 18.81 | 34.42 | 18.07 | 52.49 |
| 3 | 22.77 | 27.22 | 12.75 | 20.81 | 24.81 | 38.97 | 24.56 | 8.62 | 35.10 |
| 4 | 14.22 | 21.06 | 10.70 | 17.03 | 13.94 | 38.61 | 19.26 | 10.10 | 52.42 |
| 6 | 4.48 | 7.40 | 4.64 | 16.61 | 6.49 | 14.25 | 8.98 | 5.17 | 57.59 |
| 8 | 1.66 | 3.21 | 1.32 | 6.65 | 2.90 | 6.08 | 3.63 | 2.24 | 61.57 |
| 12 | 0.77 | 1.20 | 0.45 | 1.28 | 1.05 | 1.76 | 1.08 | 0.45 | 41.54 |
| 24 | BLQ | 0.22 | 0.04 | 0.06 | BLQ | 0.16 | 0.12 | 0.08 | 71.06 |

Capsule Prepared as in Example 34

| Time (hr) | Blood concentration (ng/mL) | | | | | | | | |
|---|---|---|---|---|---|---|---|---|---|
|  | 101 | 102 | 201 | 202 | 301 | 302 | Mean | SD | CV % |
| 0 | BLQ | BLQ | BLQ | BLQ | BLQ | BLQ | NA | NA | N/A |
| 0.33 | 0.12 | 1.83 | 0.18 | BLQ | BLQ | 0.12 | 0.56 | 0.85 | 150.72 |
| 0.67 | 1.75 | 12.82 | 18.92 | BLQ | 0.06 | 5.24 | 7.76 | 7.93 | 102.26 |
| 1 | 8.78 | 76.71 | 23.08 | 0.33 | 1.67 | 8.88 | 19.91 | 28.97 | 145.55 |
| 1.5 | 86.69 | 77.07 | 23.90 | 34.10 | 169.56 | 16.75 | 68.01 | 57.39 | 84.38 |
| 2 | 61.68 | 44.63 | 22.48 | 77.95 | 125.34 | 19.75 | 58.64 | 39.62 | 67.56 |
| 3 | 26.30 | 25.23 | 26.64 | 47.11 | 64.27 | 13.79 | 33.89 | 18.37 | 54.20 |
| 4 | 21.49 | 18.34 | 22.11 | 28.68 | 51.42 | 16.82 | 26.47 | 12.89 | 48.68 |
| 6 | 5.43 | 5.35 | 6.08 | 8.59 | 24.54 | 10.85 | 10.14 | 7.37 | 72.71 |
| 8 | 3.00 | 3.07 | 2.76 | 3.96 | 15.23 | 5.10 | 5.52 | 4.84 | 87.64 |
| 12 | 1.04 | 0.67 | 0.81 | 1.47 | 3.11 | 1.56 | 1.44 | 0.89 | 61.54 |
| 24 | 0.23 | 0.34 | BLQ | BLQ | 0.14 | 0.11 | 0.21 | 0.10 | 49.39 |

Example 36

A nilotinib lauryl sulfate salt was prepared by mixing 43 gm of nilotinib hydrochloride monohydrate, 1,935 mL of anhydrous alcohol mix at 50-55° C. To the solution, 21.23 gm of sodium lauryl sulfate [in 63.7 mL of alcohol (95%) and 42.5 mL of purified water] was added. The mixture was stirred at 50-55° C. for 30 min, room temperature for 1 h and in 0~10° C. for 30 min. To the mixture, 1,505 mL of purified water was added and stirred at 0~10° C. for 30 min. The resulting white crystals were collected by filtration, washed with 215 mL of 85.5% ethanol aqueous solution, to obtain nilotinib monolauryl sulfate crude-1. The nilotinib monolauryl sulfate crude-1 was added 430 mL of purified water stirred 30 min, and collected by filtration, washed with 430 mL of purified water, to obtain nilotinib monolauryl sulfate crude-2. Nilotinib monolauryl sulfate crude-2 was added 430 mL of hexane stirred 30 min, and collected by filtration, washed with 215 mL of hexane, to obtain 48 g of nilotinib monolauryl sulfate salt (82% yield) as an off-white powder with a chromatographic purity of 99.92%.

Example 37

A nilotinib monolauryl sulfate capsule dosage form was prepared by mixing 3.754 gm of nilotinib monolauryl sulfate prepared according to the procedure of Example 36, with 12.528 gm of CAPMUL® MCM (Glyceryl Caprylate/Caprate), and 3.133 gm of KOLLIPHOR® EL (polyoxyl 35 castor oil) and filling the mixture into soft gelatin capsules.

The composition of the capsule content was as follows:

|  | mg | wt % |
|---|---|---|
| Nilotinib mono lauryl sulfate | 75.06 | 19.35 |
| Glyceryl Caprylate/Caprate | 250.31 | 64.52 |
| Polyoxyl 35 Castor Oil | 62.58 | 16.13 |
| Total | 387.95 | 100.00 |

Example 38

A nilotinib dilauryl sulfate salt was prepared by mixing 25.6 gm of nilotinib hydrochloride monohydrate, 768 mL of methanol at room temperature. To the solution, 4.02 mL of hydrochloric acid solution (12N) was added. The mixture was distilled out completely under vacuum. To the residue, 256 mL of hexane was added and stirred at room temperature for 30 min. The solid was isolated by filtration, washed with hexane and dried in a vacuum at 40° C. for 3 hours to obtain nilotinib dihydrochloride salt as a golden yellow powder. 25.7 gm of nilotinib dihydrochloride salt and 514 mL of methanol were mix at 50-55° C. To the solution, 23.2 gm of sodium lauryl sulfate (in 116 mL of methanol) was added. The mixture was stirred at 50-55° C. for 3 hours. The mixture was concentrated, then 771 mL of ethyl acetate was added and the resulting reaction mass was washed with 514 mL of purified water. The organic extracts were concentrated, and dried in a vacuum at 40° C. for 6 hours to obtain crude nilotinib dilauryl sulfate salt. The crude nilotinib dilauryl sulfate salt was added to 257 mL of hexane stirred 30 min. The solid was isolated by filtration, washed with hexane and dried in a vacuum at 40° C. for 16 hours to obtain 36.5 g of nilotinib dilauryl sulfate salt (85% yield) as a golden yellow powder with a chromatographic purity of 99.93%.

Figure 10:
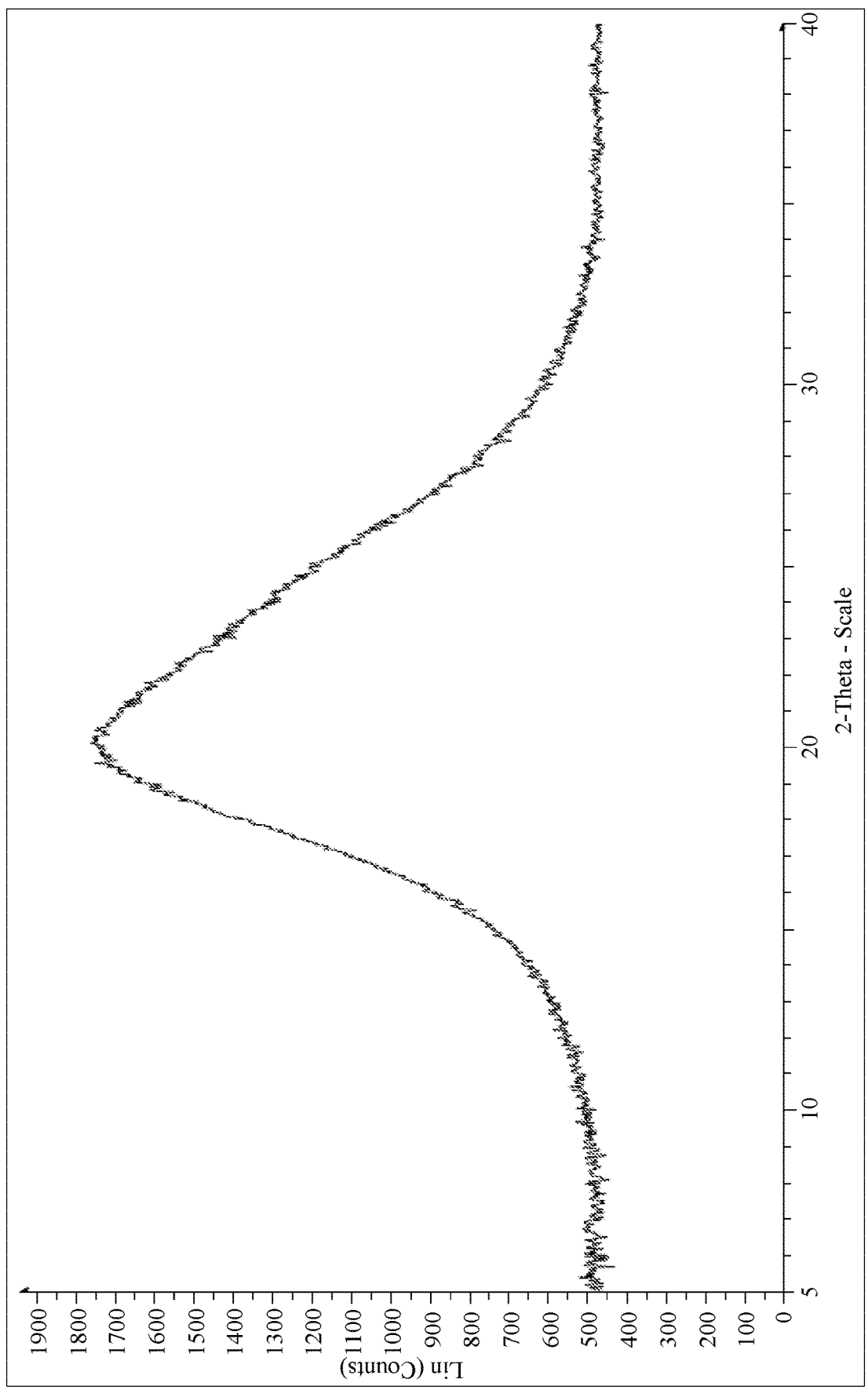
FIG. 10 is an XRPD pattern of the nilotinib dilauryl sulfate salt of Example 38.

The XRPD for the golden yellow powder nilotinib dilauryl sulfate salt is shown in FIG. 10. The XRPD was obtained using D8 Discover with GADDS (Bruker AXS Gmbh, Karlsruhe, Germany) (GADDS: General Area Diffraction Detection System) and employing the following testing condition:

Cukα$_{1+2}$=1.54184 Å, 40 kV 40 mA

Beam size: 1.0 mm (the collimator system allows the analysis of 1000 μm$^2$ surface areas)

Detector type: Vantec-2000 (14×14 cm$^2$ area and 2048× 2048 pixel density)

Sample to detector distance: 15.05 cm 300 sec/frame (The exposure time was 300 s per frame).

Example 38A

The solubility of the nilotinib monolauryl sulfate salts prepared in Examples 36 and a commercially available sample of nilotinib hydrochloride monohydrate was measured by adding the sample to 300 mL of the designated medium at 37° C. and shaking or stirring for at least 18 hours to obtain a saturated condition. The solubility of the nilotinib dilauryl sulfate salts prepared in Examples 38 was measured by adding the sample to 5-20 mL of the designated medium at room temperature and shaking or stirring for at least 18 hours to obtain a saturated condition. The reaction mass was filtered and the filtrate solution was measured by HPLC. The results of the solubility measurements are as follows:

| pH condition | Nilotinib HCl (μg/mL) | Niliotinib Dilauryl Sulfate (μg/mL) | Nilotinib Monolauryl Sulfate (μg/mL) |
|---|---|---|---|
| 0.1N HCl, pH = 1.0 | 3797.17 | 197.81 | 247.86 |
| 0.05M acetate buffer, pH = 4.5 | — | — | 0 |
| 0.05M phosphate buffer, pH = 6.8 | 0 | 0.50 | 0 |

Example 39

A nilotinib dilauryl sulfate capsule dosage form was prepared by mixing 8.022 gm of nilotinib dilauryl sulfate salt prepared according to the procedure of Example 38 with 20.042 gm of CAPMUL® MCM (Glyceryl Caprylate/Caprate), 5.010 gm of KOLLIPHOR® EL (polyoxyl 35 castor oil) and 0.667 gm of sodium hydrogen carbonate and filling the mixture into soft gelatin capsules.

The composition of the capsule content was as follows:

|  | mg | wt % |
|---|---|---|
| nilotinib dilauryl sulfate | 100.25 | 23.79 |
| Glyceryl Caprylate/Caprate | 250.31 | 59.39 |
| Polyoxyl 35 Castor Oil | 62.58 | 14.85 |
| Sodium hydrogen carbonate | 8.33 | 1.97 |
| Total | 421.47 | 100.00 |

Example 40

The capsules similar to those prepared in Examples 37 and 39 but adjusted to contain a weight providing approximately equivalent to 50 mg nilotinib free base were administered to six (6) healthy adult beagle dogs in a fasted state along with a capsule, obtained by dividing commercially available 200 mg TASIGNA capsule into 4 capsules (each contained equivalent to 50 mg of nilotinib free base) in a single-center, single-dose study. Blood samples were drawn before dosing and at 0.25, 0.5, 1, 2, 3, 4, 5, 6, 8, 10, 12 and 24 hours after dosing. The mean nilotinib plasma values were determined as follows:

|  | Capsule Prepared According to the Procedure of Example 37 | Capsule Prepared According to the Procedure of Example 39 | REFERENCE (TASIGNA) |
|---|---|---|---|
| $AUC_{0-24}$ (ng·hr/mL) | 2827.37 | 1053.39 | 754.74 |
| $C_{max}$ (ng/mL) | 675.73 | 396.67 | 171.96 |

Figure 11:
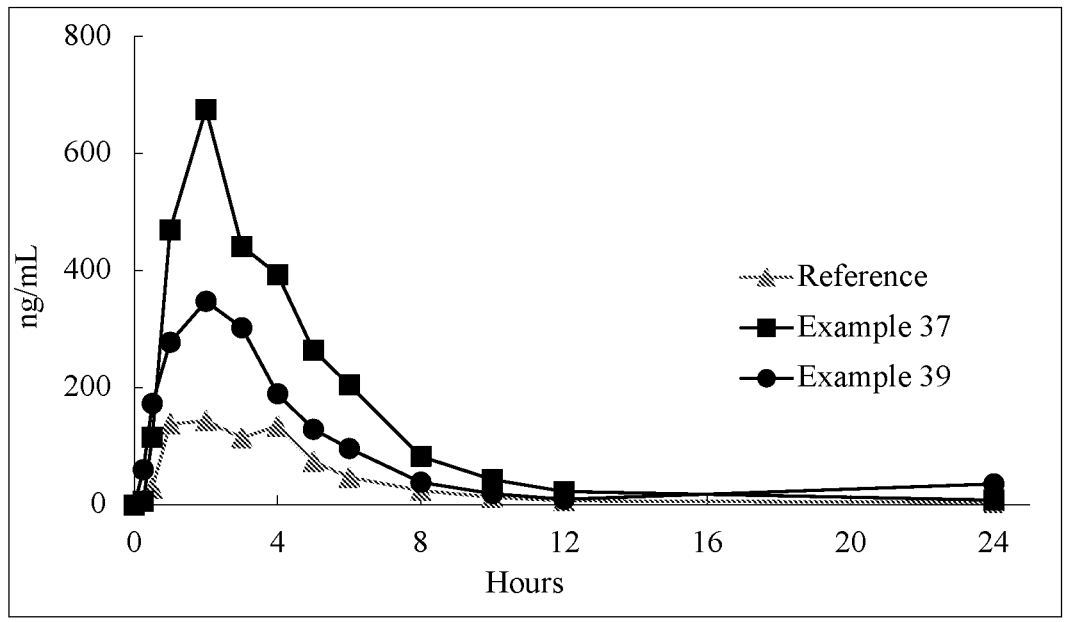
FIG. 11 is a graph of the mean in vivo plasma data provided in Example 40.

A graph of the mean plasma profiles is shown in FIG. 11.

The individual data from the study is shown in the following tables:

$C_{max}$

|  | 101 | 102 | 201 | 202 | 301 | 302 | Mean | SD | CV (%) |
|---|---|---|---|---|---|---|---|---|---|
| Ref | 38.32 | 108.73 | 514.07 | 21.22 | 281.97 | 67.46 | 171.96 | 192.17 | 111.8 |
| Ex 37 | 241.14 | 331.19 | 764.01 | 1051.15 | 543.62 | 1123.29 | 675.73 | 367.17 | 54.3 |
| Ex 39 | 505.19 | 273.09 | 344.76 | 163.62 | 285.11 | 808.25 | 396.67 | 230.61 | 58.1 |

$AUC_{0-24}$

|  | 101 | 102 | 201 | 202 | 301 | 302 | Mean | SD | CV (%) |
|---|---|---|---|---|---|---|---|---|---|
| Ref | 187.46 | 322.80 | 2804.66 | 97.84 | 841.82 | 273.84 | 754.74 | 1037.39 | 137.4 |
| Ex 37 | 902.38 | 1056.24 | 3979.91 | 4335.56 | 2327.08 | 4363.05 | 2827.37 | 1615.80 | 57.1 |
| Ex 39 | 1588.08 | 741.95 | 1796.96 | 685.43 | 1392.16 | 2815.74 | 1503.39 | 784.45 | 52.2 |

Reference (TASIGNA)

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | BLQ | BLQ | BLQ | BLQ | BLQ | BLQ | 0 | 0 | 0 |
| 0.25 | 1.59 | 12.20 | BLQ | BLQ | BLQ | BLQ | 2.30 | 4.89 | 212.8 |
| 0.5 | 11.38 | 64.43 | 31.75 | BLQ | 3.68 | BLQ | 18.54 | 25.45 | 137.3 |
| 1 | 38.32 | 108.73 | 396.29 | BLQ | 123.78 | 22.58 | 114.95 | 146.21 | 127.2 |
| 2 | 35.86 | 75.49 | 514.07 | 15.97 | 158.93 | 60.47 | 143.47 | 188.11 | 131.1 |
| 3 | 25.10 | 47.58 | 395.32 | 21.22 | 128.74 | 67.46 | 114.23 | 143.14 | 125.3 |
| 4 | 17.42 | 37.15 | 399.26 | 15.96 | 281.97 | 55.32 | 134.51 | 164.53 | 122.3 |
| 5 | 8.76 | 19.04 | 303.51 | 12.98 | 76.08 | 25.32 | 74.28 | 114.93 | 154.7 |
| 6 | 6.15 | 12.67 | 200.15 | 10.35 | 35.42 | 17.45 | 47.03 | 75.70 | 161.0 |
| 8 | 3.51 | 4.83 | 109.42 | 4.56 | 15.95 | 6.99 | 24.21 | 41.99 | 173.5 |
| 10 | 2.08 | 2.12 | 60.41 | 2.83 | 7.29 | 3.24 | 13.00 | 23.31 | 179.4 |
| 12 | 1.24 | 1.88 | 33.61 | 1.42 | 2.29 | 1.69 | 7.02 | 13.03 | 185.6 |
| 24 | 6.31 | BLQ | 1.37 | BLQ | BLQ | BLQ | 1.28 | 2.52 | 197.2 |

Below the Limit of Quantitation (BLQ) as 0

Capsule Prepared as in Example 37

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | BLQ | BLQ | BLQ | BLQ | BLQ | BLQ | 0 | 0 | 0 |
| 0.25 | BLQ | BLQ | BLQ | 8.34 | 3.94 | BLQ | 2.05 | 3.46 | 169.2 |
| 0.5 | 13.34 | BLQ | 9.16 | 234.32 | 264.04 | 54.38 | 95.87 | 120.58 | 125.8 |
| 1 | 184.76 | 176.94 | 242.25 | 862.60 | 451.72 | 901.90 | 470.03 | 334.70 | 71.2 |
| 2 | 241.14 | 331.19 | 764.01 | 1051.15 | 543.62 | 1123.29 | 675.73 | 367.17 | 54.3 |
| 3 | 156.47 | 250.93 | 640.73 | 709.42 | 216.03 | 676.71 | 441.71 | 258.92 | 58.6 |
| 4 | 103.70 | 135.21 | 507.50 | 575.99 | 427.10 | 611.90 | 393.56 | 221.73 | 56.3 |
| 5 | 52.93 | 80.89 | 384.47 | 401.68 | 248.45 | 414.15 | 263.76 | 163.91 | 62.1 |
| 6 | 35.13 | 45.15 | 336.42 | 319.93 | 187.23 | 305.82 | 204.95 | 138.11 | 67.4 |

-continued

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 8 | 15.29 | 18.84 | 166.46 | 115.35 | 65.92 | 114.54 | 82.73 | 60.00 | 72.5 |
| 10 | 6.91 | 8.18 | 105.63 | 58.27 | 18.12 | 61.43 | 43.09 | 39.06 | 90.6 |
| 12 | 3.62 | 3.55 | 62.16 | 33.29 | 4.18 | 29.53 | 22.72 | 23.62 | 104.0 |
| 24 | 13.69 | BLQ | 2.36 | BLQ | BLQ | BLQ | 2.67 | 5.48 | 204.8 |

Below the Limit of Quantitation (BLQ) as 0

Capsule Prepared as in Example 39

| Time | Blood concentration (ng/mL) | | | | | | | | |
|---|---|---|---|---|---|---|---|---|---|
| (hr) | 101 | 102 | 201 | 202 | 301 | 302 | Mean | SD | CV % |
| 0 | BLQ | BLQ | BLQ | BLQ | BLQ | BLQ | 0 | 0 | 0 |
| 0.25 | BLQ | BLQ | 104.70 | BLQ | 66.07 | 8.75 | 29.92 | 44.79 | 149.7 |
| 0.5 | BLQ | BLQ | 344.76 | 2.65 | 242.80 | 102.05 | 115.38 | 147.21 | 127.6 |
| 1 | 160.09 | BLQ | 344.08 | 163.62 | 285.11 | 435.30 | 231.37 | 155.17 | 67.1 |
| 2 | 310.06 | 273.09 | 304.78 | 139.21 | 249.98 | 808.25 | 347.56 | 234.07 | 67.3 |
| 3 | 505.19 | 178.17 | 272.17 | 115.24 | 194.45 | 550.26 | 302.58 | 181.98 | 60.1 |
| 4 | 157.39 | 108.20 | 227.98 | 78.63 | 186.13 | 379.33 | 189.61 | 107.20 | 56.5 |
| 5 | 90.20 | 63.00 | 175.81 | 75.09 | 135.70 | 234.05 | 128.97 | 66.39 | 51.5 |
| 6 | 54.45 | 43.26 | 114.93 | 50.43 | 116.42 | 198.08 | 96.26 | 59.63 | 61.9 |
| 8 | 21.93 | 17.23 | 68.58 | 24.15 | 43.93 | 55.03 | 38.48 | 20.69 | 53.8 |
| 10 | 11.75 | 8.26 | 37.27 | 10.51 | 17.98 | 27.95 | 18.95 | 11.45 | 60.4 |
| 12 | 6.06 | 3.64 | 18.61 | 8.57 | 6.03 | 13.84 | 9.46 | 5.67 | 60.0 |
| 24 | 35.62 | BLQ | 434.62* | BLQ | BLQ | BLQ | 7.12 | 15.93 | 223.6 |

*The outlier, not for calculation.
Below the Limit of Quantitation (BLQ) as 0

Example 41

A cabozantinib monolauryl sulfate salt was prepared by the following general procedure:
  a. 37 g of cabozantinib S-malate was added to a co-solvent of (1850 mL/740 mL) of ethyl acetate/10% aqueous $NaHCO_3$ (50V/20V) and stirred at 45° C. for 2 hour;
  b. The organic layer of the reaction mixture of step (a) was separated and washed twice with 740 mL of purified water (20V×2);
  c. The organic extracts of step (b) were combined and concentrated to obtain cabozantinib free base as a white powder (29.2 g, 100% yield);
  d. 1022 mL of methanol (35V) was added to the 29.2 g of cabozantinib free base and the mixture was stirred at 50-55° C.;
  e. An SLS solution was prepared by dissolving 16.8 g of SLS (1 molar equivalent to the cabozantinib) in a co-solvent of 87.6 mL of methanol (3V)/58.26 mL of 1 N HCl (1 molar equivalent);
  f. The SLS solution of step (e) is added to the mixture of step (d) and stirred at 50-55° C. for 30 minutes then adjusted to room temperature for 1 hour;
  g. 1460 mL of purified water (50V) was added to the reaction mixture of step (f) and stirred at room temperature for 30 minutes;
  h. The precipitate (crystals) of step (g) were collected by filtration, washed with 292 mL of purified water (10V) to obtain crude cabozantinib monolauryl sulfate;
  i. The crude cabozantinib monolauryl sulfate was combined with 584 mL of purified water (20 V), stirred for 30 minutes, the solids were collected by filtration, washed with 146 mL of purified water (5 V) to obtain 41 g of cabozantinib monolauryl sulfate as a white powder which was exhibited a UPLC chromatographic purity 100% and a yield of 91.7%.

The solubility of the cabozantinib monolauryl sulfate prepared above was measured by adding the sample to 50 mL of the designated medium at 37° C. and shaking or stirring for at least 1 hour to obtain a saturated condition. The reaction mass was filtered and the filtrate solution was measured by HPLC. The results of the solubility measurements are as follows:

| pH condition | Cabozantinib Monolauryl Sulfate (μg/mL) |
|---|---|
| 0.1N HCl, pH = 1.0 | 9.87 |
| 0.05M acetate buffer, pH = 4.5 | 0.9 |
| 0.05M phosphate buffer, pH = 6.8 | 0.0 |
| water | 0.0 |

Example 42

The cabozantinib monolauryl sulfate prepared in Example 41 may be used to prepared oral dosages such as those described in Examples 3, 4, 9, 15, 18, 19, 22, 23, 30, 31, 33, 34, 37 or 39.

Example 42A

A cabozantinib monolauryl sulfate capsule dosage form was prepared by a wet granulating process as follows:
  (i) a granulating solution was prepared by dissolving 3.0595 g of cabozantinib monolauryl sulfate prepared according to the procedure of Example 41, 6.10 g of poloxamer 407 and 3.05 g of poloxamer 188 in 300 mL of 95% alcohol;

(ii) 1.75 g of anhydrous lactose, 3.6405 g of microcrystalline cellulose PH112, 1.00 g of croscarmellose sodium (Part I) and 0.20 g of colloidal silicon dioxide (Part I) were passed through a 40 mesh sieve, blended and granulated with the granulating solution of step (i);
(iii) the wet granules were passed through a 20 mesh sieve, dried in an oven at 55° C. to evaporate the alcohol and the dry granules were passed through a 24 mesh sieve;
(iv) the dried granules of step (iii) were mixed with 1.00 g of croscarmellose sodium (Part II) and 0.10 g of colloidal silicon dioxide (Part II);
(v) 0.10 g of magnesium stearate was added to the mixture of step (iv) and blended well to obtain final blend; and
(vi) the dry solid final blend was filled into size 1 hard gelatin capsule.

The composition of the capsule content is as follows:

|  | mg | wt % |
| --- | --- | --- |
| Cabozantinib monolauryl sulfate, CT-1LS (EQ to 20 mg free base) | 30.595 | 15.30 |
| Poloxamer 407 | 61.00 | 30.50 |
| Poloxamer 188 | 30.50 | 15.25 |
| Anhydrous lactose | 17.50 | 8.75 |
| Microcrystalline cellulose PH112 | 36.405 | 18.20 |
| Croscarmellose Sodium (Part I) | 10.00 | 5.00 |
| Colloidal Silicon Dioxide (Part I) | 2.00 | 1.00 |
| Croscarmellose Sodium (Part II) | 10.00 | 5.00 |
| Colloidal Silicon Dioxide (Part II) | 1.00 | 0.50 |
| Magnesium stearate | 1.00 | 0.50 |
| Total | 200.00 | 100.00 |
| Alcohol 95% | 3.00 mL | N/A |

Example 42B

A cabozantinib monolauryl sulfate capsule dosage form was prepared by the following processes:
(i) 8 mg of butylated hydroxytoluene (BHT) was dissolved a mixture of 14.6856 g of CAPMUL® MCM (Glyceryl Caprylate/Caprate) and 5.2112 g of KOLLIPHOR® EL (polyoxyl 35 castor oil);
(ii) 4.8952 g of cabozantinib monolauryl sulfate prepared according to the procedure of Example 41 was passed through 60 mesh sieve and added into the solution of step (i) to obtain uniform dispersion;
(iii) 2.40 g of hard fat (Gelucire 43/01) was melted using a water bath at 55° C. and the melted hard fat was added to the dispersion of step (ii) while maintaining the temperature at 55° C. and homogenized to obtain uniform suspension; and
(iv) the suspension of step (iii) was filled into size 3 hard gelatin capsule.

The composition of the capsule content is as follows:

|  | mg | wt % |
| --- | --- | --- |
| Cabozantinib monolauryl sulfate, CT-1LS (EQ to 20 mg free base) | 30.595 | 18.00 |
| CAPMUL® MCM (Glyceryl Caprylate/Caprate) | 91.785 | 53.99 |
| KOLLIPHOR® EL (polyoxyl 35 castor oil) | 32.57 | 19.16 |
| Butylated hydroxytoluene (BHT) | 0.05 | 0.03 |
| Hard Fat (Gelucire 43/01) | 15.00 | 8.82 |
| Total | 170.00 | 100.00 |

Example 42C

A cabozantinib malate tablet dosage form was prepared by the following processes:
(i) 2.0276 g of cabozantinib malate was passed through 60 mesh sieve and blended with 2.4864 g of microcrystalline cellulose PH102, 1.2428 g of anhydrous lactose and 0.192 g of croscarmellose sodium (Part I) that had been previously passed through a 40 mesh sieve;
(ii) the mixture of step (i) was wet granulated with a granulating solution prepared by dissolving 0.192 g of hydroxypropyl cellulose EXF in 1.28 g of purified water;
(iii) the wet granules were passed through a 20 mesh sieve, dried in the oven at 60° C. to evaporate the purified water and the dry granules were passed through a 24 mesh sieve;
(iv) the dried and sieved granules were mixed with 0.192 g of croscarmellose sodium (Part II) and 0.0192 g of colloidal silicon dioxide;
(v) 0.048 g of magnesium stearate was added to the mixture of step (iv) and blended well to obtain final blend; and
(vi) the final blend was compressed into tablets using a 6 mm round-shaped punch and a target hardness of about 4 kp.

The composition of the tablet content is as follows:

|  | mg | wt % |
| --- | --- | --- |
| Cabozantinib malate, (EQ to 20 mg free base) | 25.345 | 31.68 |
| Microcrystalline cellulose PH 102 | 31.08 | 38.85 |
| Lactose Anhydrous | 15.535 | 19.42 |
| Hydroxypropyl cellulose EXF | 2.40 | 3.00 |
| Croscarmellose Sodium (Part I) | 2.40 | 3.00 |
| Croscarmellose Sodium (Part II) | 2.40 | 3.00 |
| Colloidal Silicon Dioxide | 0.24 | 0.30 |
| Magnesium stearate | 0.60 | 0.75 |
| Total | 80.00 | 100.00 |
| Purified water | 16.00 | N/A |

Example 42D

The following capsule formulations were prepared according to the procedure of Example 42B. The composition of the capsules is as follows:

|  | CT1902211 (mg) | CT1902212 (mg) |
| --- | --- | --- |
| Cabozantinib monolauryl sulfate, CT-1LS (EQ to 40 mg free base) | 61.19 | 61.19 |
| CAPMUL® MCM (Glyceryl Caprylate/Caprate) | 183.57 | 61.71 |
| KOLLIPHOR® EL (polyoxyl 35 castor oil) | 65.14 | 61.00 |
| Butylated hydroxytoluene (BHT) | 0.10 | 0.10 |
| Hard Fat (Gelucire 43/01) | 30.00 | — |
| Total | 340.00 | 184.00 |

Example 42E

The dosage forms prepared in Examples 42A-42D (n=3) were tested using a USP Type II Apparatus (Paddle) with 900 ml of 0.1 N HCl (with 0.5% TRITON™ X-100 (t-octyl phenoxy polyethoxy ethanol, a nonionic surfactant)) at 75 rpm, with a sinker and 37° C. The results of this dissolution testing are as follows:

|  |  | Time (min) | | | | | | | | |
|---|---|---|---|---|---|---|---|---|---|---|
|  |  | 5 | 10 | 15 | 20 | 30 | 45 | 60 | 90 | 120 |
| Ex 42A | Avg % | 16.5 | 43.7 | 58.0 | 66.4 | 76.8 | 83.5 | 86.3 | 89.1 | 90.8 |
|  | RSD % | 18.2 | 0.8 | 4.1 | 7.7 | 9.4 | 8.0 | 7.4 | 7.0 | 5.9 |
| Ex 42B | Avg % | 0.1 | 3.8 | 14.9 | 30.0 | 56.3 | 80.5 | 91.6 | 99.3 | 102.2 |
|  | RSD % | 42.2 | 28.6 | 44.6 | 48.8 | 33.4 | 12.2 | 5.1 | 1.4 | 0.5 |
| Ex 42C* | Avg % | 69.7 | 98.0 | 100.6 | 101.8 | 101.7 | 102.2 | 102.2 | 102.1 | 102.0 |
|  | RSD % | 1.3 | 1.7 | 1.7 | 1.8 | 1.5 | 2.1 | 1.9 | 2.3 | 2.1 |
| Ex 42D** | Avg % | 0.1 | 4.1 | 19.8 | 34.7 | 53.0 | 67.8 | 75.1 | 81.9 | 85.2 |
|  | RSD % | 31.5 | 44.0 | 45.5 | 44.0 | 34.9 | 36.5 | 22.8 | 19.0 | 17.6 |

*without a sinker
**capsule without Gelucire 43/01

The above in vitro dissolution data demonstrates that dosage forms prepared in accordance with the present invention will release: (i) at least 40%, preferably at least 45% and most preferably at least 50% of the cabozantinib after 30 minutes of testing; (ii) at least 55%, preferably at least 60% and most preferably at least 65% of the cabozantinib after 45 minutes of testing; and (iii) at least 70%, preferably at least 75% and most preferably at least 80% of the cabozantinib after 60 minutes of testing.

Example 42F

The dosage forms prepared in Examples 42A-42D were tested for impurities and stability using the following HPLC method:

| Parameter | Setting/Description |
|---|---|
| System | HPLC Equipped with a UV/Vis Detector |
| Column | YMC Pack ODS AQ, 4.6 × 150 mm, 3 μm, or Equivalent |
| Detection | UV at 245 nm |
| Flow rate | 0.8 mL/min |
| Injection volume | 5 μL |
| Column temperature | 20° C. |
| Sample temperature | Ambient |
| Run time | 60 minutes |
| Mode of Analysis | Gradient as shown below: |

| Time (min) | Mobile phase A | Mobile phase B |
|---|---|---|
| 0 | 70 | 30 |
| 15 | 45 | 55 |
| 36 | 25 | 75 |
| 44 | 20 | 80 |
| 53 | 20 | 80 |
| 53.5 | 70 | 30 |
| 60 | 70 | 30 |

Mobile phase A was a buffer prepared by dissolving 2.72 g of Potassium dihydrogen phosphate and 1 mL of Triethylamine in 1000 mL of water, and adjust the pH to 3.20±0.05 with phosphoric acid.

Mobile phase B was acetonitrile/methanol/water in a volume ratio of 60/30/10.

The results of the testing were as follows:

|  |  | RRT | | | | | | | |
|---|---|---|---|---|---|---|---|---|---|
|  |  | 0.27 | 0.70 | 0.75 | 0.83 | 0.95 | 1.09 | 1.42 | 1.62 |
| Ex 42A | Initial |  |  | 0.07 |  |  |  |  |  |
|  | 60° C./75% R.H. 1 week |  |  | 0.07 |  |  |  | 0.03 |  |
|  | 60° C./75% R.H. 2 week |  |  | 0.08 |  |  |  | 0.06 |  |
| Ex 42C | Initial |  |  |  | 0.04 | 0.02 |  |  |  |
|  | 60° C./75% R.H. 1 week |  |  |  | 0.04 | 0.02 |  |  |  |
|  | 60° C./75% R.H. 2 week |  |  |  | 0.04 | 0.02 |  |  |  |

-continued

|  | | \multicolumn{8}{c}{RRT} |
|---|---|---|---|---|---|---|---|---|---|
|  | | 0.27 | 0.70 | 0.75 | 0.83 | 0.95 | 1.09 | 1.42 | 1.62 |
| Ex 42D (CT1902211) | Initial | 0.02 |  | 0.03 |  |  |  |  | 0.03 |
|  | 60° C./75% R.H. 1 week | 0.02 |  | 0.06 |  |  |  |  | 0.07 |
|  | 60° C./75% R.H. 2 week |  | 0.03 | 0.03 |  |  |  |  | 0.07 |
| Ex 42D (CT1902212) | Initial |  |  | 0.03 |  |  |  |  | 0.03 |
|  | 60° C./1 week |  |  | 0.03 |  |  | 0.03 |  | 0.06 |
|  | 60° C./2 week |  | 0.01 | 0.02 |  |  |  |  | 0.05 |

The capsules were stored in a high-density polyethylene (HDPE) bottle with child resistant closure and foil induction seal (126 c.c, with 2~3 g of silica gel).

Employing the above HPLC method the cabozantinib monolauryl sulfate dosage forms were determined to have NMT 0.5% of any individual impurity, preferably more than 0.35% of any individual impurity and most preferably not more than 0.25% of any individual impurity and the total impurity should not be more than 1.0%, preferably not more than 0.75% and most preferably not more than 0.60%.

Example 42G

The capsules prepared in Examples 42A (Test Formulation 1 or T1) and 42B (Test Formulation 2 or T2) containing cabozantinib monolauryl sulfate (equivalent to 20 mg of cabozantinib free base) were administered to six (6) healthy adult beagle dogs in a fasted state along with an equivalent 20 mg cabozantinib malate tablet prepared in Example 42C (equivalent to 20 mg of cabozantinib free base) in a single-center, single-dose study. Blood samples were drawn before dosing and at 0.25, 1, 1.5, 2, 3, 4, 6, 8, 12, 16 and 24 hours after dosing. The mean cabozantinib plasma values were determined as follows:

|  | Capsule Prepared According Example 42A (T1) | Capsule Prepared According Example 42B (T2) | Tablet Prepared According Example 42C (R) |
|---|---|---|---|
| $AUC_{0-t}$ (ng · hr/mL) | 4022.38 | 3827.32 | 4601.27 |
| $C_{max}$ (ng/mL) | 746.83 | 670.10 | 729.52 |

Figure 12:
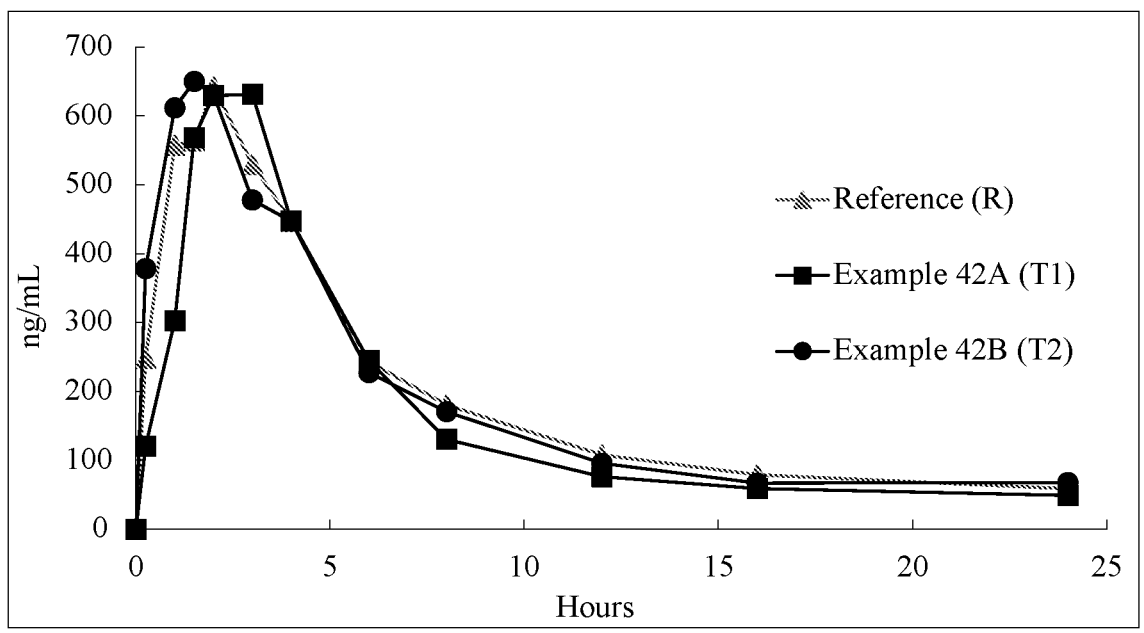
FIG. 12 is a graph of the mean in vivo plasma data provided in Example 42G.

A graph of the mean plasma profiles is shown in FIG. 12. The individual data from the study is shown in the following tables:

$C_{max}$ (ng/mL)

|  | 101 | 102 | 201 | 202 | 301 | 302 | Mean | SD | CV (%) |
|---|---|---|---|---|---|---|---|---|---|
| Ex 42C (R) | 615.78 | 747.13 | 486.31 | 601.65 | 1181.30 | 744.96 | 729.52 | 242.11 | 33.19 |
| Ex 42A (T1) | 1189.18 | 767.83 | 735.43 | 660.40 | 850.18 | 277.93 | 746.83 | 294.71 | 39.46 |
| Ex 42B (T2) | 528.99 | 339.47 | 936.48 | 934.88 | 1211.58 | 69.18 | 670.10 | 430.02 | 64.17 |

$AUC_{0-t}$ (ng·hr/mL)

|  | 101 | 102 | 201 | 202 | 301 | 302 | Mean | SD | CV (%) |
|---|---|---|---|---|---|---|---|---|---|
| Ex 42C (R) | 2596.52 | 3067.45 | 5830.22 | 6636.12 | 6689.28 | 2788.05 | 4601.27 | 1983.44 | 43.11 |
| Ex 42A (T1) | 4849.99 | 3185.92 | 4089.18 | 3816.12 | 6165.36 | 2027.73 | 4022.38 | 1414.40 | 35.16 |
| Ex 42B (T2) | 2096.90 | 2992.37 | 5455.89 | 6128.48 | 5980.58 | 309.72 | 3827.32 | 2393.70 | 62.54 |

Tablet Prepared as in Example 42C (R)

| Time (hr) | \multicolumn{9}{c}{Blood concentration (ng/mL)} | | | | | | | | |
|---|---|---|---|---|---|---|---|---|---|
|  | 101 | 102 | 201 | 202 | 301 | 302 | Mean | SD | CV % |
| 0 | BLQ | BLQ | BLQ | BLQ | BLQ | BLQ | NA | NA | NA |
| 0.25 | 139.31 | 454.41 | 206.06 | 142.05 | 213.12 | 333.71 | 248.11 | 123.26 | 49.68 |

-continued

| Time (hr) | Blood concentration (ng/mL) | | | | | | Mean | SD | CV % |
|---|---|---|---|---|---|---|---|---|---|
| | 101 | 102 | 201 | 202 | 301 | 302 | | | |
| 1 | 615.78 | 747.13 | 300.71 | 410.80 | 524.89 | 744.96 | 557.38 | 180.57 | 32.40 |
| 1.5 | 561.35 | 552.08 | 382.12 | 490.02 | 725.62 | 669.01 | 563.37 | 123.16 | 21.86 |
| 2 | 464.79 | 554.73 | 420.41 | 601.65 | 1181.30 | 628.17 | 641.84 | 275.97 | 43.00 |
| 3 | 416.21 | 414.54 | 356.87 | 508.70 | 1074.27 | 407.07 | 529.61 | 271.31 | 51.23 |
| 4 | 287.92 | 343.52 | 486.31 | 504.90 | 729.04 | 330.56 | 447.04 | 163.72 | 36.62 |
| 6 | 93.77 | 118.56 | 378.94 | 443.94 | 317.94 | 105.42 | 243.09 | 155.67 | 64.04 |
| 8 | 57.12 | 66.09 | 313.78 | 378.56 | 226.31 | 40.24 | 180.35 | 146.34 | 81.14 |
| 12 | 33.38 | 38.31 | 204.16 | 224.43 | 130.69 | 15.11 | 107.68 | 92.05 | 85.49 |
| 16 | 21.67 | 22.13 | 149.77 | 166.24 | 105.63 | 7.47 | 78.82 | 70.66 | 89.65 |
| 24 | 10.56 | 7.49 | 133.02 | 106.83 | 91.68 | 2.55 | 58.69 | 58.35 | 99.42 |

Capsule Prepared as in Example 42A (T1)

| Time (hr) | Blood concentration (ng/mL) | | | | | | Mean | SD | CV % |
|---|---|---|---|---|---|---|---|---|---|
| | 101 | 102 | 201 | 202 | 301 | 302 | | | |
| 0 | BLQ | BLQ | BLQ | BLQ | BLQ | BLQ | NA | NA | NA |
| 0.25 | 125.80 | 3.98 | BLQ | 350.06 | BLQ | 1.48 | 120.33 | 163.77 | 136.11 |
| 1 | 178.09 | 148.77 | 484.49 | 645.16 | 346.82 | 12.74 | 302.68 | 234.76 | 77.56 |
| 1.5 | 786.97 | 767.83 | 531.84 | 477.84 | 816.04 | 32.23 | 568.79 | 298.62 | 52.50 |
| 2 | 919.53 | 750.95 | 735.43 | 430.88 | 850.18 | 90.36 | 629.56 | 312.70 | 49.67 |
| 3 | 1189.18 | 546.82 | 546.32 | 660.40 | 659.94 | 184.67 | 631.22 | 324.57 | 51.42 |
| 4 | 659.08 | 367.36 | 440.11 | 396.28 | 544.10 | 277.93 | 447.47 | 135.61 | 30.31 |
| 6 | 295.87 | 180.11 | 218.28 | 233.47 | 311.46 | 229.06 | 244.71 | 49.63 | 20.28 |
| 8 | 107.14 | 89.34 | 122.41 | 108.73 | 219.27 | 134.75 | 130.27 | 46.21 | 35.47 |
| 12 | 50.18 | 48.68 | 83.48 | 64.52 | 151.47 | 58.62 | 76.16 | 38.98 | 51.19 |
| 16 | 29.58 | 29.05 | 60.85 | 43.59 | 164.85 | 25.86 | 58.96 | 53.49 | 90.72 |
| 24 | 30.87 | 12.17 | 64.91 | 27.06 | 137.78 | 20.39 | 48.86 | 47.16 | 96.51 |

Capsule Prepared as in Example 42B (T2)

| Time (hr) | Blood concentration (ng/mL) | | | | | | Mean | SD | CV % |
|---|---|---|---|---|---|---|---|---|---|
| | 101 | 102 | 201 | 202 | 301 | 302 | | | |
| 0 | BLQ | BLQ | BLQ | BLQ | BLQ | BLQ | NA | NA | NA |
| 0.25 | 528.99 | 25.34 | 826.36 | 390.63 | 293.54 | 2.72 | 378.31 | 341.15 | 90.18 |
| 1 | 407.28 | 176.00 | 936.48 | 917.10 | 584.82 | 8.04 | 611.61 | 433.54 | 70.89 |
| 1.5 | 344.09 | 257.35 | 664.52 | 670.35 | 1211.58 | 53.73 | 650.05 | 473.12 | 72.78 |
| 2 | 239.98 | 292.17 | 632.86 | 934.88 | 887.19 | 69.18 | 631.03 | 397.33 | 62.97 |
| 3 | 207.79 | 339.47 | 517.94 | 700.89 | 633.25 | 59.11 | 477.80 | 289.16 | 60.52 |
| 4 | 192.16 | 314.90 | 607.70 | 475.12 | 663.63 | 42.17 | 447.15 | 281.32 | 62.91 |
| 6 | 103.20 | 265.80 | 298.65 | 295.25 | 291.71 | 23.62 | 227.31 | 135.82 | 59.75 |
| 8 | 71.03 | 168.25 | 167.56 | 312.45 | 190.24 | 11.56 | 170.45 | 123.57 | 72.50 |
| 12 | 33.80 | 85.42 | 103.75 | 146.47 | 128.13 | 4.05 | 95.60 | 63.49 | 66.41 |
| 16 | 21.72 | 48.07 | 70.41 | 97.84 | 96.96 | 2.05 | 66.82 | 45.01 | 67.37 |
| 24 | 11.20 | 10.92 | 70.89 | 52.34 | 79.99 | BLQ | 67.74 | 14.10 | 20.81 |

Example 43

Liquid dosage forms may be prepared using the mono- or di-lauryl sulfate salts of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, or vemurafenib as prepared in Examples 1, 11-14, 16-17, 21, 25-27, 33-34, 36, 38 and 41 using the procedure described in Example 3, 9, 15, 18, 37 and 39.

The composition of the capsule content comprises the following:

| | Wt % | Wt % (preferred) |
|---|---|---|
| KI lauryl sulfate | 1-80 | 2.5-50 |
| Carrier (preferably a wetting agent, an emulsifying agent, a solubilizing agent, a surfactant or combinations thereof) with HLB value of less than 10 | 1-90 | 10-80 |
| Carrier (preferably a wetting agent, an emulsifying agent, a solubilizing agent, a surfactant or | 1-90 | 10-50 |

| | Wt % | Wt % (preferred) |
|---|---|---|
| combinations thereof) with HLB value of 10 or greater | | |
| Stabilizer | 0-15 | 0.01-10 |
| Total | 100.0 | 100 |

Example 44

Solid dosage forms, such as a tablet or capsule may be prepared using the mono- or di-lauryl sulfate salts of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, or vemurafenib as prepared in Examples 1, 11-14, 16-17, 21, 25-27, 33-34, 36, 38 and 41 using the procedure described in Example 4, 19, 22, 30, 33, and 34.

The composition of the solid dosage form will comprise the following:

| | Wt % | Wt % (preferred) |
|---|---|---|
| KI lauryl sulfate | 1-80 | 10-60 |
| Filler | 5-90 | 20-70 |
| Disintegrant | 0-25 | 2-15 |
| Carrier (preferably a wetting agent, an emulsifying agent, a solubilizing agent, a surfactant or combinations thereof) with an HLB value of 10 or greater | 1-60 | 2-40 |
| Glidant/lubricant | 0-15 | 0.5-10 |
| Stabilizer | 0-15 | 0.01-10 |
| Binder | 0-15 | 0.5-10 |
| Total | 100.0 | 100 |

Example 45

Semi-solid dosage forms may be prepared using the mono- or di-lauryl sulfate salts of acalabrutinib, afatinib, alectinib, axitinib, bosutinib, brigatinib, cabozantinib, ceritinib, cobimetinib, crizotinib, dabrafenib, dasatinib, defactinib, enasidenib, erlotinib, fostamatinib, gefitinib, ibrutinib, imatinib, lapatinib, lenvatinib, neratinib, nilotinib, nintedanib, osimertinib, pazopanib, ponatinib, regorafenib, ruxolitinib, sorafenib, sunitinib, trametinib, vandetanib, or vemurafenib as prepared in Examples 1, 11-14, 16-17, 21, 25-27, 33-34, 36, 38 and 41 using the procedure described in Example 23 or 31.

The composition of the semi-solid dosage form will comprise the following:

| | Wt % | Wt % (preferred) |
|---|---|---|
| KI lauryl sulfate | 1-80 | 2.5-50 |
| Viscosity enhancing agent | 0-60 | 0.5-50 |
| Carrier (preferably a wetting agent, an emulsifying agent, a solubilizing agent, a surfactant or combinations thereof) with an HLB value of 10 or greater | 1-90 | 10-50 |
| Carrier (preferably a wetting agent, an emulsifying agent, a solubilizing agent, a surfactant or combinations thereof) with HLB value of less than 10 | 1-90 | 10-80 |
| Stabilizer | 0-15 | 0.01-10 |
| Total | 100.0 | 100 |

Example 46

A Nilotinib monolauryl sulfate salt was prepared by the following general procedure:

a. Nilotinib free base (3 g) was suspended with MeOH (30V), the mixture was stirred at less than 60° C., preferably about 55±5° C. for about 20 minutes.
b. Sodium lauryl sulfate (1 eq) and 1N HBr (1 eq) in 3V MeOH and 3V Purified Water (including the Purified Water in the 1N HBr) were combined and the resulting mixture was stirred at room temperature for 10±5 min.
c. Once all the solids in step (b) were dissolved, the nilotinib suspension of step (a) was added to the sodium lauryl sulfate/HBr solution of step (b) and the resulting mixture was stirred at less than 60° C., preferably at 55±5° C. for 30±10 min.
d. Once all the solids in the reaction mixture prepared in step (c) were dissolved, the temperature was then adjusted to room temperature and stirred for 60±10 min.
e. After stirring, Purified Water (30V) was added to the reaction mixture of step (d) and further stirred at room temperature for about 30 min.
f. The resulting off white crystals formed in step (e) were collected by filtration, washed with Purified Water (5V), to yield nilotinib monolauryl sulfate salt (3.747 g) (yield: 88.81%) (HPLC purity: 99.52%).

Crystallization Method A

Crude nilotinib monolauryl sulfate salt prepared according to steps (a)-(f) was recrystallized according to the following procedure:

1. MeOH (15V) was added to crude nilotinib monolauryl sulfate (2 g), the mixture stirred at a temperature less than 60° C., preferably about 55±5° C. until the nilotinib monolauryl sulfate was dissolved (approximately 10±5 min).
2. Purified Water (15V) was added to the solution of step (1) and the temperature of less than 60° C., preferably about 55±5° C. was maintained for 30±10 min to obtain the precipitate, and then the temperature of the reaction mass was adjusted to room temperature.
3. The precipitate formed in step (2) was collected by filtration and washed with Purified Water (2×2V).
4. The precipitate collected in step (3) was dried in high vacuo to obtain a white crystalline nilotinib monolauryl sulfate salt (1.7846 g) (yield: 89.2%) (HPLC purity 99.89%).

Figure 13:
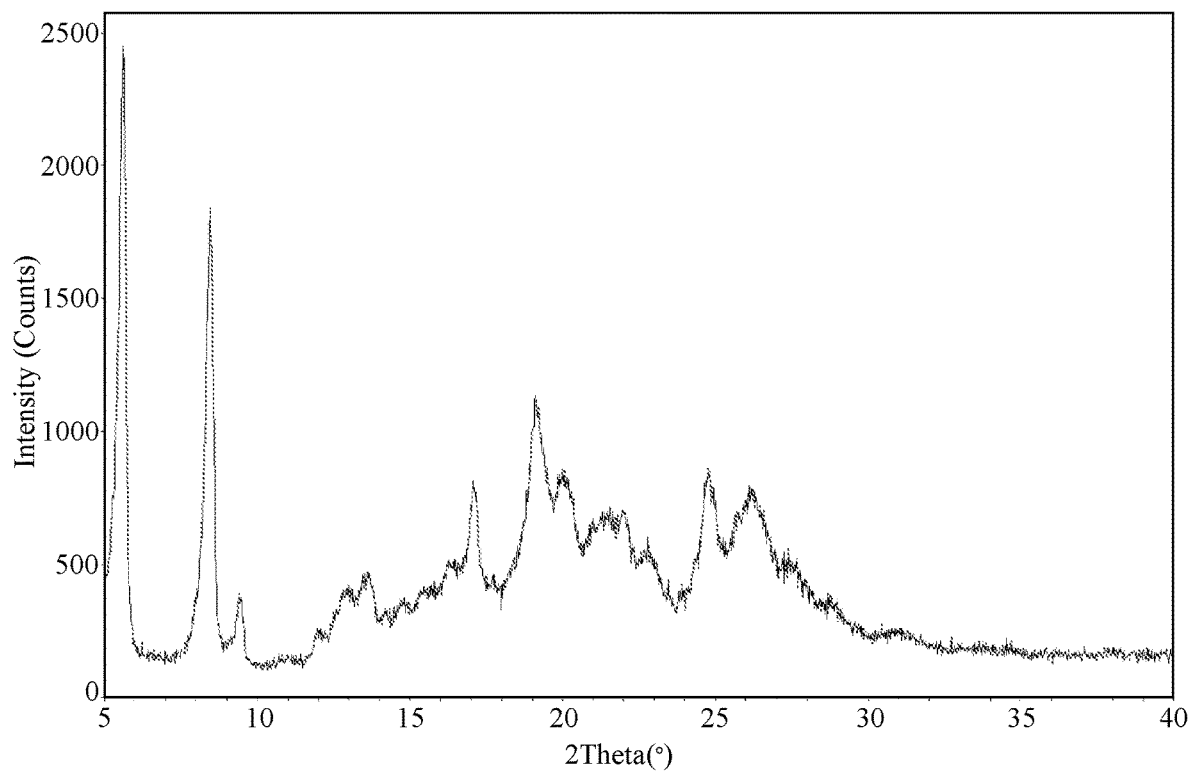
FIG. 13 is an XRPD pattern of the nilotinib monolauryl sulfate salt of Example 46, crystallization method A.

The XRPD for a white crystalline nilotinib monolauryl sulfate salt prepared by a method outlined above is shown in FIG. 13. The XRPD was obtained using Rigaku, D/MAX 2200 and employing the following testing condition:

$Cu k\alpha_{1+2} = 1.54184$ Å,

Power: 40 kV 30 mA

Beam size: 1.0 mm
Scan axis: 2Theta/theta
Angle: 5~40°
DivH.L.Slit: 5 mm
RecSlit: 1.0 mm The crystalline nilotinib monolauryl sulfate prepared by crystallization Method A will exhibit one or more of the following 2θ peaks: 5.6±0.2; 8.5±0.2; 9.4±0.2; 13.0±0.2; 13.6±0.2; 17.1±0.2; 19.1±0.2; 20.2±0.2; 21.5±0.2; 22.0±0.2; 22.8±0.2; 24.8±0.2; 25.8±0.2; 26.1±0.2 and/or 26.6±0.2.

Crystallization Method B

Crude nilotinib monolauryl sulfate salt prepared according to step (a)-(f) was recrystallized according to the following procedure:
1. MeOH (15V) was added to crude nilotinib monolauryl sulfate (3.747 g), the mixture stirred at a temperature less than 60° C., preferably about 55±5° C. until the nilotinib monolauryl sulfate was dissolved (approximately 10±5 min).
2. The solution of step (1) was filtered hot to remove dust or other particulate matter and washed with MeOH (5V).
3. The obtained filtrate was heated to a temperature less than 60° C., preferably about 55±5° C.
4. Purified Water (30V) was added dropwise to the solution of step (3) over a period of about 30±10 minutes while maintaining the temperature at about 55±5° C.
5. Once the Purified Water was added and the precipitate was formed, the reaction mass was cooled to room temperature, then further cooled to 0-5° C. to allow for additional precipitation.
6. The precipitate formed in step (5) was collected by filtration and washed with Purified Water (2×2V).
7. The precipitate collected in step (6) was dried in high vacuo to obtain a white crystalline nilotinib monolauryl sulfate salt (3.4201 g) (yield: 91.3%) (HPLC purity 99.93%).

Crystallization Method C

Crude nilotinib monolauryl sulfate salt prepared according to steps (a)-(f) was recrystallized according to the following procedure:
1. EtOH (35V) was added to crude nilotinib monolauryl sulfate (2 g), the mixture stirred at a temperature less than 60° C., preferably about 55±5° C. until the nilotinib monolauryl sulfate was dissolved (approximately 10±5 min).
2. Purified Water (60V) was added to the solution of step (1) and the temperature of less than 60° C., preferably about 55±5° C. is maintained for 30±10 min to obtain the precipitate, and then the temperature of the reaction mass was adjusted to room temperature.
3. The precipitate formed in step (2) was collected by filtration and washed with Purified Water (2×2V).
4. The precipitate collected in step (3) was dried in high vacuo to obtain a white crystalline nilotinib monolauryl sulfate salt (1.7695 g) (yield: 88.5%) (HPLC purity 99.88%).

Figure 14:
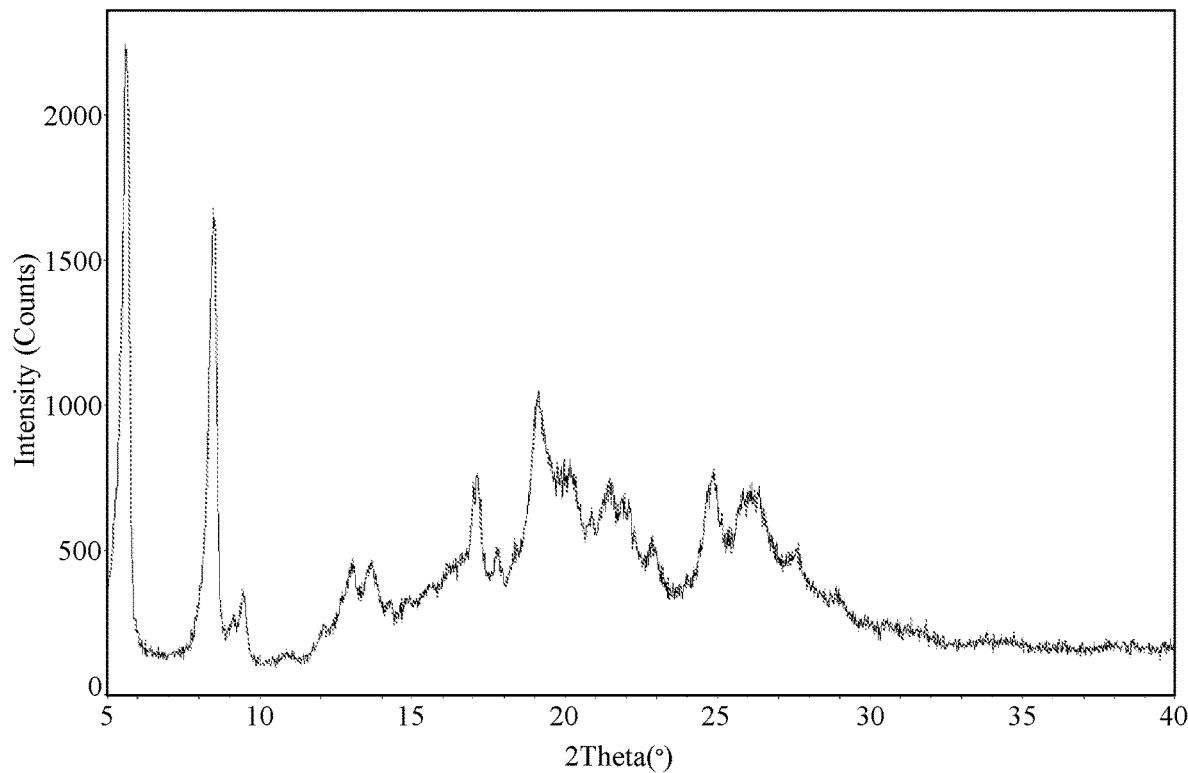
FIG. 14 is an XRPD pattern of the nilotinib monolauryl sulfate salt of Example 46, crystallization method C.

The XRPD pattern for a white crystalline nilotinib monolauryl sulfate salt prepared by crystallization Method C was obtain by the procedure outlined in crystallization Method A and is shown in FIG. 14.

The crystalline nilotinib monolauryl sulfate prepared by crystallization Method C will exhibit one or more of the following 2θ peaks: 5.6±0.2; 8.5±0.2; 9.2±0.2; 9.4±0.2; 13.1±0.2; 13.7±0.2; 17.1±0.2; 17.8±0.2; 19.1±0.2; 20.2±0.2; 21.5±0.2; 22.0±0.2; 24.9±0.2; 25.8±0.2; 26.5±0.2; 27.7±0.2 and/or 29.0±0.2.

Crystallization Method D

Crude nilotinib monolauryl sulfate salt prepared according to steps (a)-(f) was recrystallized according to the following procedure:
1. IPA (100V) was added to crude nilotinib monolauryl sulfate (2 g), the mixture stirred at a temperature less than 60° C., preferably about 55±5° C. until the nilotinib monolauryl sulfate was dissolved (approximately 10±5 min).
2. Purified Water (265V) was added to the solution of step (1) and the temperature of less than 60° C., preferably about 55±5° C. was maintained for 30±10 min to obtain the precipitate, and then the temperature of the reaction mass was adjusted to room temperature.
3. The precipitate formed in step (2) was collected by filtration and washed with Purified Water (2×2V).
4. The precipitate collected in step (3) was dried in high vacuo to obtain a white crystalline nilotinib monolauryl sulfate salt (1.6742 g) (yield: 83.7%) (HPLC purity 99.88%).

Figure 15:
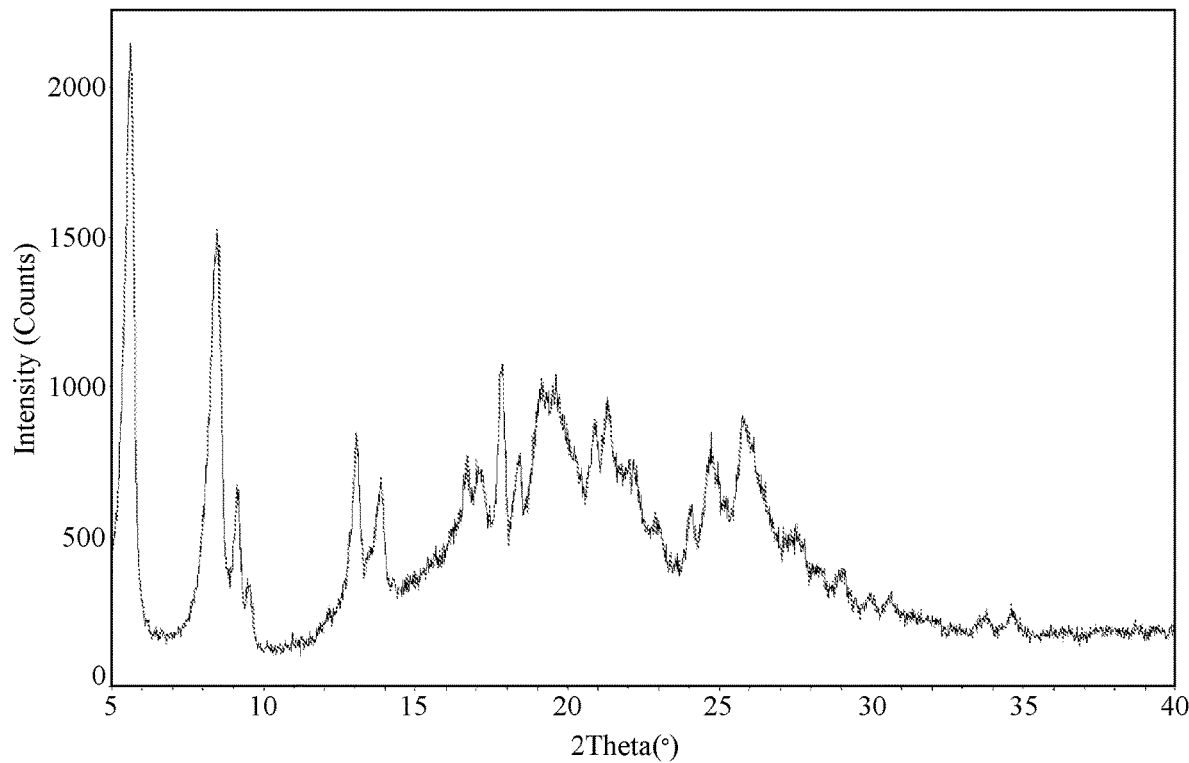
FIG. 15 is an XRPD pattern of the nilotinib monolauryl sulfate salt of Example 46, crystallization method D.

The XRPD pattern for a white crystalline nilotinib monolauryl sulfate salt prepared by crystallization Method D was obtain by the procedure outlined in crystallization Method A and is shown in FIG. 15.

The crystalline nilotinib monolauryl sulfate prepared by crystallization Method D will exhibit one or more of the following 2θ peaks: 5.6±0.2; 8.5±0.2; 9.1±0.2; 9.6±0.2; 13.1±0.2; 13.9±0.2; 16.7±0.2; 17.2±0.2; 17.9±0.2; 18.4±0.2; 19.1±0.2; 19.6±0.2; 20.9±0.2; 21.3±0.2; 23.0±0.2; 24.1±0.2; 24.7±0.2; 25.8±0.2; 27.7±0.2; 29.0±0.2; 30.0±0.2; 30.7±0.2; 33.8±0.2; 34.6±0.2 and/or 38.7±0.2.

Example 47

A dasatinib monolauryl sulfate salt was prepared by the following general procedure:
a. MeOH (25V) was added to dasatinib monohydrate (6 g), the mixture was stirred at refluxing temperature.
b. Sodium lauryl sulfate (1 eq) and 1N HCl (1 eq) in 3V MeOH and 3V Purified Water (including the Purified Water in the 1N HCl) were combined and the resulting mixture was stirred at room temperature for 10±5 min.
c. Once all the solids in step (b) were dissolved, the sodium lauryl sulfate/HCl solution of step (b) was added to the dasatinib mixture of step (a) and the resulting mixture was stirred at refluxing temperature (65-70° C.) for about 30±10 minutes then the temperature was adjusted to room temperature for 60±10 min.
d. The reaction mixture of step (c) was concentrated in vacuo by rotary evaporator (T=45° C.) until dryness.
e. The concentrated reaction mass of step (d) was extracted with ethyl acetate (20V) and water (10V).
f. The organic layer of step (e) was separately washed with water (2×10V).
g. The washed organic layer of step (f) was concentrated in vacuo by rotary evaporator (T=45° C.).
h. The product of step (g) was dried in high vacuo to obtain a white crystalline dasatinib monolauryl sulfate (8.7659 g) (yield: 98.0%) (HPLC purity: 99.61%).
i. IPA (10V) was added to the dasatinib monolauryl sulfate of step (h) and stirred at room temperature for 30±10 minutes.

j. The white solid precipitate in the reaction mass of step (i) was collected by filtration and washed with IPA (2×2V).
k. The washed solid precipitate of step (j) was dried in high vacuo to obtain a white crystalline dasatinib monolauryl sulfate (7.89 g) (yield: 90.0%) (HPLC purity: 99.82%).

Crystallization Method A

Crude dasatinib monolauryl sulfate salt prepared according to steps (a)-(k) was recrystallized according to the following procedure:
1. MeOH (5V) was added to crude dasatinib monolauryl sulfate (3 g), the mixture stirred at about 60° C. for approximately 10±5 min.
2. Isopropyl Alcohol (IPA) (40 V) and Hexane (40V) was added to the solution of step (1) while maintaining the temperature at about 60° C. until the precipitate was formed then the temperature of the reaction mass was adjusted to room temperature.
3. The temperature of the reaction mass of step (2) was adjusted to 0-5° C. for about 30±10 minutes and the precipitate was collected by filtration and washed with hexane (2×2V).
4. The precipitate collected in step (3) was dried in high vacuo to obtain a white crystalline dasatinib monolauryl sulfate salt (2.7186 g) (yield: 88.8%) (HPLC purity 99.94%).

Figure 16:
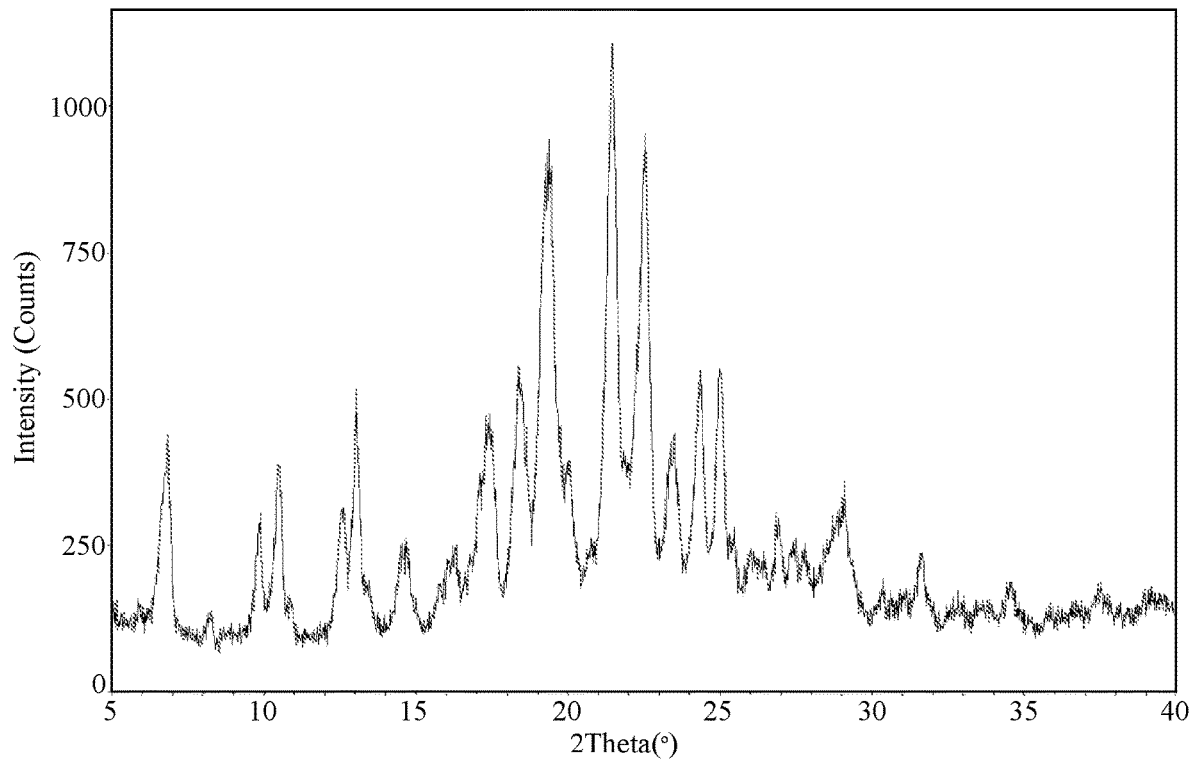
FIG. 16 is an XRPD pattern of the dasatinib monolauryl sulfate salt of Example 47, crystallization method A.

An XRPD pattern was obtained by the procedure outlined in Example 46 on a sample of the dasatinib lauryl sulfate prepared by crystallization Method A and is shown in FIG. 16.

The crystalline dasatinib monolauryl sulfate prepared by crystallization Method A will exhibit one or more of the following 20 peaks: 6.9±0.2; 8.3±0.2; 9.9±0.2; 10.5±0.2; 12.6±0.2; 13.1±0.2; 14.7±0.2; 15.8±0.2; 16.3±0.2; 17.1±0.2; 17.2±0.2; 17.4±0.2; 18.4±0.2; 19.4±0.2; 20.1±0.2; 21.5±0.2; 22.6±0.2; 23.5±0.2; 24.4±0.2; 25.0±0.2; 26.0±0.2; 26.5±0.2; 26.9±0.2; 27.4±0.2; 27.8±0.2; 28.7±0.2; 29.1±0.2; 30.4±0.2; 31.6±0.2; 34.6±0.2; 37.5±0.2; and/or 39.2±0.2.

Crystallization Method B

Crude dasatinib monolauryl sulfate salt prepared according to step (a)-(k) was recrystallized according to the following procedure:
1. MeOH (5V) was added to crude dasatinib monolauryl sulfate (3 g), the mixture stirred at about 60° C. for approximately 10±5 min then the temperature was adjusted to room temperature.
2. Ether (60 V) was added to the solution of step (1) while maintaining the temperature at room temperature.
3. The temperature of the reaction mass of step (2) was adjusted to 0-5° C. for about 30±10 minutes and the precipitate was collected by filtration and washed with ether (2×2V).
4. The precipitate collected in step (3) was dried in high vacuo to obtain a white crystalline dasatinib monolauryl sulfate salt (2.8910 g) (yield: 94.5%) (HPLC purity 99.85%).

Figure 17:
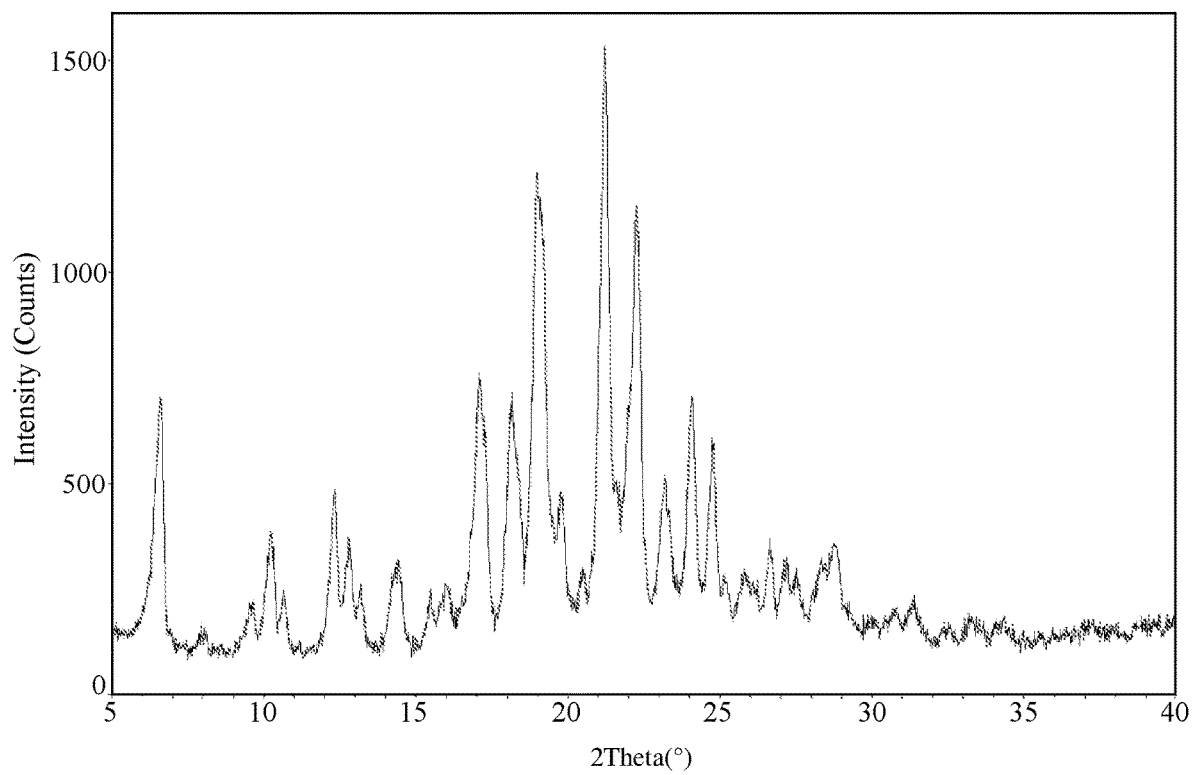
FIG. 17 is an XRPD pattern of the dasatinib monolauryl sulfate salt of Example 47, crystallization method B.

An XRPD pattern was obtained by the procedure outlined in Example 46 on a sample of the dasatinib lauryl sulfate prepared by crystallization Method B and is shown in FIG. 17.

The crystalline dasatinib monolauryl sulfate prepared by crystallization Method B will exhibit one or more of the following 2θ peaks: 6.6±0.2; 8.1±0.2; 9.6±0.2; 10.2±0.2; 10.7±0.2; 12.4±0.2; 12.8±0.2; 14.4±0.2; 15.5±0.2; 16.0±0.2; 17.1±0.2; 18.2±0.2; 19.0±0.2; 19.8±0.2; 20.5±0.2; 21.3±0.2; 22.3±0.2; 23.2±0.2; 24.1±0.2; 24.8±0.2; 25.8±0.2; 26.1±0.2; 26.7±0.2; 27.2±0.2; 27.5±0.2; 28.4±0.2; 28.8±0.2; 30.8±0.2; 31.4±0.2; 32.5±0.2; 33.3±0.2; 34.1±0.2; 34.4±0.2; and/or 39.5±0.2.

Example 47 A

The solubility of the crystalline dasatinib monolauryl sulfate prepared in Example 47, Method A, amorphous dasatinib monolauryl sulfate prepared in Example 12, amorphous dasatinib dilauryl sulfate prepared in Example 13 and a commercially available sample of dasatinib monohydrate free base was measured by adding the sample to 500 mL of the designated medium at 37° C. and shaking or stirring for at least 18 hours to obtain a saturated condition. The reaction mass was filtered and the filtrate solution was measured by HPLC. The results of the solubility measurements are as follows:

| pH condition | Dasatinib Monohydrate (μg/mL) | Dasatinib Dilauryl Sulfate (μg/mL) | Dasatinib Monolauryl Sulfate (crystal) (μg/mL) | Dasatinib Monolauryl Sulfate (amorphous) (μg/mL) |
|---|---|---|---|---|
| 0.1N HCl, pH = 1.0 | 654.4 | 48.9 | 361.9 | 307.9 |
| 0.05M acetate buffer, pH = 4.5 | 86.9 | 16.3 | 39.4 | 22.6 |
| 0.05M phosphate buffer, pH = 6.8 | 0.18 | 11.4 | 4.35 | 4.71 |

The results of the solubility study showed the aqueous solubility of dasatinib varied with pH.

Example 48

A dasatinib monolauryl sulfate salt was prepared by the following general procedure:
a. MeOH (25V) was added to dasatinib monohydrate (3 g), the mixture was stirred at refluxing temperature.
b. Sodium lauryl sulfate (1 eq) and 1N HCl (1 eq) in 3V MeOH and 3V Purified Water (including the Purified Water the 1N HCl) were combined and the resulting mixture was stirred at room temperature for 10±5 min.
c. Once all the solids in step (b) were dissolved, the sodium lauryl sulfate/HCl solution of step (b) was added to the dasatinib mixture of step (a) and the resulting mixture was stirred at refluxing temperature (65-70° C.) for about 30±10 minutes then the temperature was adjusted to room temperature for 60±10 min.
d. The reaction mixture of step (c) was concentrated in vacuo by rotary evaporator (T=45° C.) until dryness.
e. The concentrated reaction mass of step (d) was extracted with ethyl acetate (20V) and water (10V).
f. The organic layer of step (e) was separately washed with water (2×10V).
g. The washed organic layer of step (f) was concentrated in vacuo by rotary evaporator (T=35° C.).
h. MeOH (10V) was added to the product of step (g) and heated at 60° C. until dissolved.
i. The solution of step (h) was filtered under hot conditions to remove any dust or other particulate matter and washed with MeOH (5V).
j. The filtrate of step (i) was concentrated in vacuo by rotary evaporator (T=45° C.) until dryness.
k. The product of step (j) was dried in high vacuo to obtain a white crystalline dasatinib monolauryl sulfate (4.419 g) (yield: 98.8%) (HPLC purity: 99.66%).

Crystallization Method C

Crude dasatinib monolauryl sulfate salt prepared according to steps (a)-(k) was recrystallized according to the following procedure:
1. MeOH (5V) was added to crude dasatinib monolauryl sulfate (3 g) and the mixture stirred at about 60° C. for approximately 10±5 min.
2. IPA (5V) and Hexane (25V) were added to the solution of step (1) while maintaining the temperature at about 60° C. until the precipitate was formed then the temperature of the reaction mass was adjusted to room temperature.
3. The temperature of the reaction mass of step (2) was adjusted to 0-5° C. for about 30±10 minutes and the precipitate was collected by filtration and washed with hexane (2×2V).
4. The precipitate collected in step (3) was dried in high vacuo to obtain a white crystalline dasatinib monolauryl sulfate salt (2.81 g) (yield: 93.7%) (HPLC purity 99.90%).
5. Steps 1-4 were repeated to obtain a white crystalline dasatinib monolauryl sulfate salt (2.68 g) (yield: 95.4%) (HPLC purity 99.96%).

Figure 18:
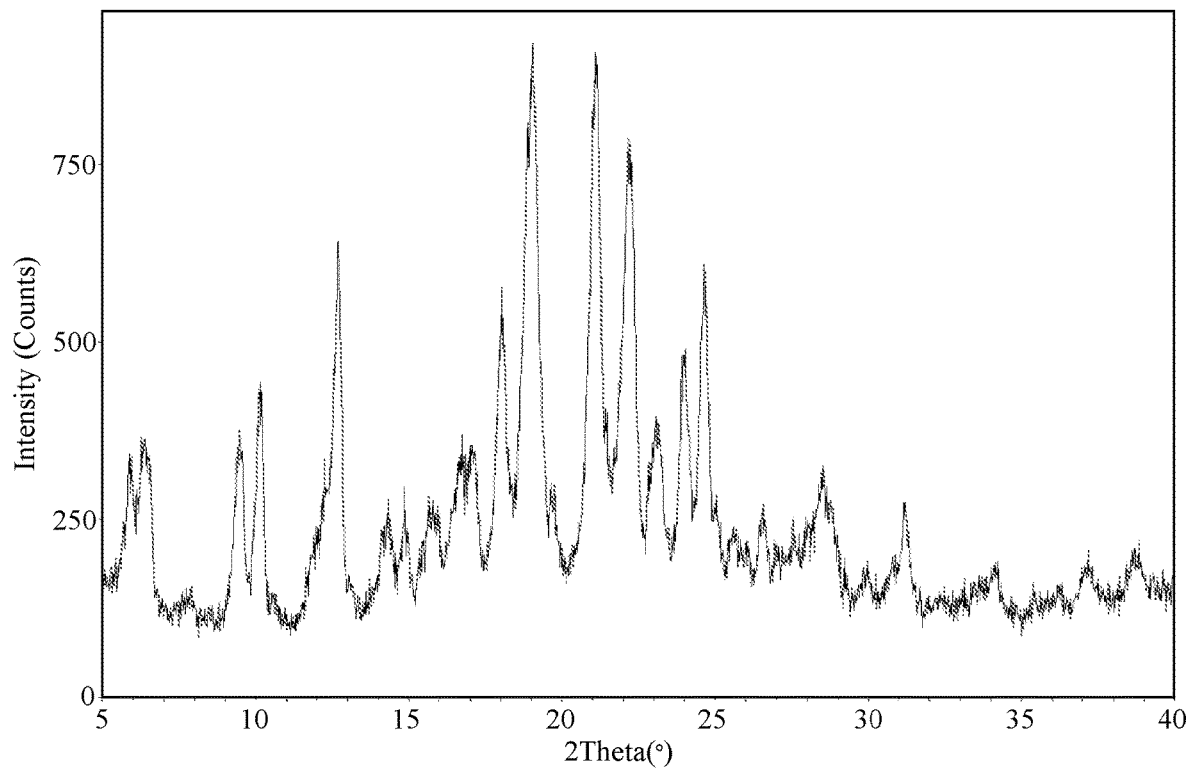
FIG. 18 is an XRPD pattern of the dasatinib monolauryl sulfate salt of Example 48, crystallization method C.

An XRPD pattern was obtained by the procedure outlined in Example 46 on a sample of the dasatinib lauryl sulfate prepared by crystallization Method C and is shown in FIG. 18.

The crystalline dasatinib monolauryl sulfate prepared by crystallization Method C will exhibit one or more of the following 2θ peaks: 5.9±0.2; 6.5±0.2; 7.9±0.2; 9.5±0.2; 10.2±0.2; 12.3±0.2; 12.7±0.2; 14.4±0.2; 14.9±0.2; 16.0±0.2; 16.8±0.2; 17.1±0.2; 18.1±0.2; 19.1±0.2; 19.8±0.2; 21.1±0.2; 22.2±0.2; 23.2±0.2; 24.1±0.2; 24.7±0.2; 25.6±0.2; 26.6±0.2; 27.6±0.2; 28.1±0.2; 28.5±0.2; 28.9±0.2; 30.0±0.2; 30.8±0.2; 31.3±0.2; 34.2±0.2; 35.4±0.2; 37.2±0.2 and/or 38.9±0.2.

Crystallization Method D

A crude dasatinib monolauryl sulfate salt was prepared according to step (a)-(k) wherein the process produced a crude white crystalline dasatinib monolauryl sulfate (4.4373 g) (yield: 99.2%) (HPLC purity: 99.58%) which was recrystallized according to the following procedure:
1. IPA (6V) was added to crude dasatinib monolauryl sulfate (3 g) and the mixture was stirred at room temperature for about 30±10 minutes.
2. The precipitated white solid was filtered and washed with IPA (2V).
3. The precipitate collected in step (2) was dried in high vacuo to obtain a white crystalline dasatinib monolauryl sulfate salt (2.83 g) (yield: 94.3%) (HPLC purity 99.75%).
4. Steps 1-3 were repeated to obtain a white crystalline dasatinib monolauryl sulfate salt (2.70 g) (yield: 95.4%) (HPLC purity 99.81%).

Figure 19:
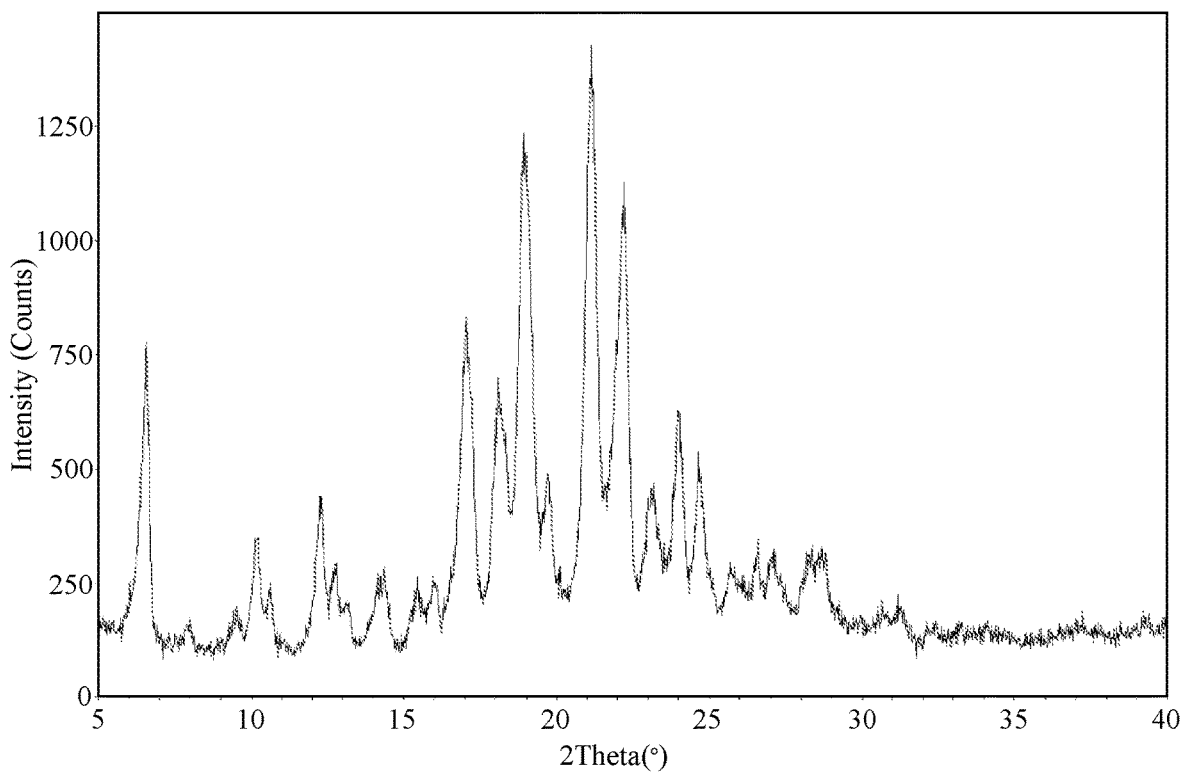
FIG. 19 is an XRPD pattern of the dasatinib monolauryl sulfate salt of Example 48, crystallization method D.

An XRPD pattern was obtained by the procedure outlined in Example 46 on a sample of the dasatinib lauryl sulfate prepared by crystallization Method D and is shown in FIG. 19.

The crystalline dasatinib monolauryl sulfate prepared by crystallization Method D will exhibit one or more of the following 2θ peaks: 6.6±0.2; 8.0±0.2; 9.5±0.2; 10.2±0.2; 10.6±0.2; 12.3±0.2; 12.8±0.2; 13.2±0.2; 14.4±0.2; 15.5±0.2; 16.0±0.2; 17.1±0.2; 18.1±0.2; 18.9±0.2; 19.7±0.2; 21.2±0.2; 22.2±0.2; 23.1±0.2; 24.0±0.2; 24.7±0.2; 25.7±0.2; 26.6±0.2; 27.1±0.2; 28.4±0.2; 28.7±0.2; 30.9±0.2; 31.3±0.2; 32.4±0.2; 37.2±0.2; and/or 39.2±0.2.

Example 48 A

A dasatinib monolauryl sulfate salt was prepared by the following general procedure:
a. MeOH (25V, 1980 g) was added to dasatinib monohydrate (1 eq., 100 g), the mixture was stirred at refluxing temperature (60° C.±5° C.).
b. Sodium lauryl sulfate (1 eq, 57 g) and 1N HCl (1 eq, 197 ml) in MeOH (3V, 237 g) and Purified Water (1.03 V, 103 g) were combined and the resulting mixture was stirred at room temperature for 10±5 min.
c. Once all the solids in step (b) were dissolved, the sodium lauryl sulfate/HCl solution of step (b) was added to the dasatinib mixture of step (a) and the resulting mixture was stirred at refluxing temperature (60° C.±5° C.) for about 30±10 minutes then the temperature was adjusted to room temperature for 60±10 min.
d. The reaction mixture of step (c) was concentrated in vacuo by rotary evaporator (T=40° C.) until dryness.
e. The concentrated reaction mass of step (d) was extracted with ethyl acetate (20V, 1804 g) and stirred at room temperature for 10±5 minutes.
f. The organic layer of step (e) was separately washed with water (3×10V, 3×1000 g).
g. The washed organic layer of step (f) was concentrated in vacuo by rotary evaporator (T=35° C.) until dryness.
h. MeOH (5V, 589 g) was added to the product of step (g) and heated at 60° C. until dissolved.
i. The filtrate of step (h) was concentrated in vacuo by rotary evaporator (T=45° C.) until dryness to obtain crude dasatinib monolauryl sulfate salt.

Crystallization Method E

Crude dasatinib monolauryl sulfate salt prepared according to steps (a)-(i) was recrystallized according to the following procedure:
1. MeOH (3V, 353 g) was added to crude dasatinib monolauryl sulfate salt, and the mixture was stirred at 60° C.±5° C. for 10±5 min.
2. Add IPA (2V, 234 g) slowly to methanol solution of crude product, and the mixture was stirred at 60° C.±5° C. for 10±5 min.
3. Add Hexane (40V, 4000 g) slowly to crude product to obtain the precipitate of pure product at 45° C.±5° C. for 10±5 min (during addition time: 30±10 min), and then adjusted to room temperature for 30±5 min.
4. The temperature of the reaction mass of step (3) was adjusted to 0-5° C. for about 30±10 min and the precipitate was collected by filtration and washed with Hexane (2×2V, 2×200 g).
5. The precipitate collected in step (4) was dried in high vacuo to obtain white crystalline of dasatinib monolauryl sulfate salt (Yield: 79.5%, 118.5 g) (HPLC purity: 100.00%, pH Value: 4.38).

Figure 20:
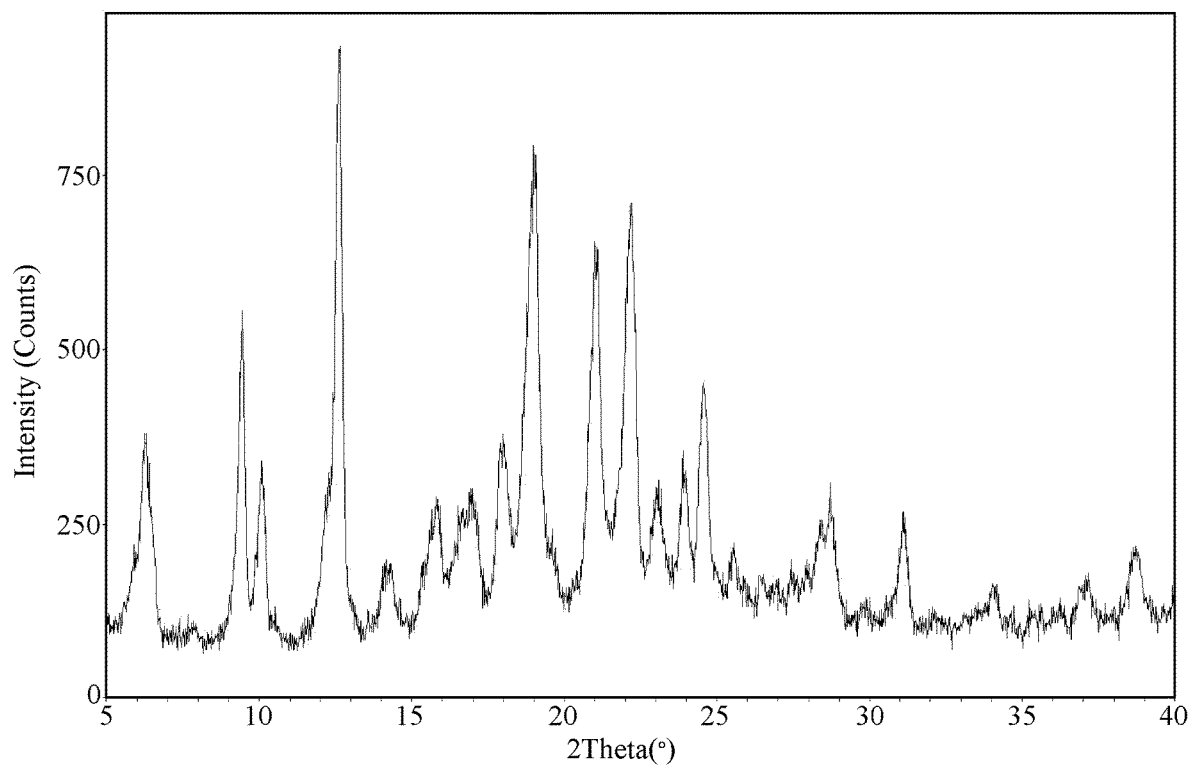
FIG. 20 is an XRPD pattern of the dasatinib monolauryl sulfate salt of Example 48A, crystallization method E.

An XRPD pattern was obtained by the procedure outlined in Example 46 on a sample of the dasatinib lauryl sulfate prepared by crystallization Method E and is shown in FIG. 20.

The crystalline dasatinib monolauryl sulfate prepared by crystallization Method E will exhibit one or more of the following 2θ peaks: 6.3±0.2; 9.5±0.2; 10.1±0.2; 12.2±0.2; 12.7±0.2; 14.4±0.2; 15.9±0.2; 16.7±0.2; 17.0±0.2; 18.0±0.2; 19.0±0.2; 21.0±0.2; 22.2±0.2; 23.1±0.2; 23.9±0.2; 24.6±0.2; 25.6±0.2; 27.5±0.2; 28.5±0.2; 28.7±0.2; 31.2±0.2; 34.2±0.2; 37.2±0.2; and/or 38.7±0.2.

Example 49

A dasatinib monolauryl sulfate capsule dosage form was prepared by wet granulating 2,982 mg of dasatinib monolauryl sulfate prepared according to the procedure of Example 12 with 1,500 mg of poloxamer 407 (Kolliphor® P407) and 1,200 mg of poloxamer 188 (Kolliphor® P188) in 3,200 mg of alcohol (95%) into a suitable container for at least 2 minutes.

1,800 mg of anhydrous lactose (SuperTab® 21AN, anhydrous), 2,958 mg of microcrystalline cellulose (Comprecel® M102D+), 600 mg of sodium starch glycolate (Part I) and 120 mg of colloidal silicon dioxide (AD101) (Part I) were passed through a 40 mesh screen and added to the dasatinib monolauryl sulfate granules and mixed. The resulting blend was dried in an oven at 50° C. to evaporate the alcohol.

600 mg of sodium starch glycolate (Part II) and 120 mg of colloidal silicon dioxide (AD101) (Part II) were passed through a 40 mesh screen, added to the dried blend containing the dasatinib monolauryl sulfate granules and mixed well. After mixing, the resulting mixture was passed through 40 mesh screen and collected in a suitable container. 120 mg of magnesium stearate was passed through a 40 mesh screen and added to the container and blended with dasatinib monolauryl sulfate mixture to obtain a final blend. The final blend was filled into size 2 hard gelatin capsule.

The composition of the capsule was as follows:

|  | mg | wt % |
|---|---|---|
| Dasatinib monolauryl sulfate | 29.82 | 24.85 |
| Poloxamer 407 | 15.00 | 12.50 |
| Poloxamer 188 | 12.00 | 10.00 |
| Anhydrous lactose | 18.00 | 15.00 |
| Microcrystalline cellulose | 29.58 | 24.65 |
| Sodium starch glycolate (part I) | 6.00 | 5.00 |
| Colloidal silicon dioxide (part I) | 1.20 | 1.00 |
| Sodium starch glycolate (part II) | 6.00 | 5.00 |
| Colloidal silicon dioxide (part II) | 1.20 | 1.00 |
| Magnesium stearate | 1.20 | 1.00 |
| Total | 120.00 | 100.00 |
| Alcohol (95%) evaporated | 32.00 | N/A |

Example 50

The capsules prepared in Example 49 containing dasatinib monolauryl sulfate were administered to nine (9) healthy subjects under fasted, fed and fasted with omeprazole pretreatment conditions. Omeprazole is a commercially available proton pump inhibitor (PPI). This was a two-part study. Part 1 is a single dose, open-label, randomized, 3-treatment, 3-sequence, 3-period crossover bioavailability study in healthy subjects under fasted and fed conditions. All subjects were randomized to the sequences as shown in the following table with a 7-day washout period between the periods. Part 2 is a sequential, 2-treatment, drug-drug interaction study in healthy subjects. All subjects were orally administered omeprazole 40 mg QD for 5 days to reach steady state and a 20 mg dasatinib capsule was orally administered approximately 22 hours after the last dose of omeprazole. The Reference drug (Ref) was Sprycel®, dasatinib monohydrate, with a strength of 50 mg while the Test drug (Test) was a capsule prepared according to the procedure of Example 49 but containing approximately a dose of dasatinib monolauryl sulfate equivalent to 20 mg of dasatinib monohydrate. The nine (9) healthy subjects enrolled in this study were randomized to one of the sequences as shown in the following table.

|  | Part 1 | | | Part 2 | |
|---|---|---|---|---|---|
| Sequence | Period I | Period II | Period III | Period IV | Period V |
| 1 | R | $T_{fast}$ | $T_{fed}$ | Omeprazole 40 mg QD for 5 days | $T_{fast}$ |
| 2 | $T_{fed}$ | R | $T_{fast}$ | Omeprazole 40 mg QD for 5 days | $T_{fast}$ |
| 3 | $T_{fast}$ | $T_{fed}$ | R | Omeprazole 40 mg QD for 5 days | $T_{fast}$ |

During each treatment period, blood samples were taken at 0 (prior to the dosing), 0.33, 0.67, 1, 1.5, 2, 2.5, 3, 4, 6, 8, 12 and 24 hours after dosing. $AUC_{0-24}$, $AUC_{0-\infty}$, $C_{max}$, $T_{max}$, and $T_{1/2}$ were determined for each subject based on non-compartmental analyses. The results of the study were normalized to 50 mg dose and summarized in the following Table:

The Pharmacokinetic Parameters for Reference and Test Formulations (Normalized to 50 Mg Dose)

| Treatment | Parameters | Normalized to 50 mg dose Mean |
|---|---|---|
| $Ref_{Fasted}$ | $C_{max}$ (ng/mL) | 75.5 |
|  | $AUC_{0-24}$ (ng · h/mL) | 282 |
|  | $AUC_{0-\infty}$ (ng · h/mL) | 289 |
| $Test_{Fasted}$ | $C_{max}$ (ng/mL) | 47.0 |
|  | $AUC_{0-24}$ (ng · h/mL) | 173.5 |
|  | $AUC_{0-\infty}$ (ng · h/mL) | 178.3 |
| $Test_{Fed}$ | $C_{max}$ (ng/mL) | 28.3 |
|  | $AUC_{0-24}$ (ng · h/mL) | 181.0 |
|  | $AUC_{0-\infty}$ (ng · h/mL) | 190.3 |
| $Test_{Fasted}$ (PPI) with 40 mg omeprazole | $C_{max}$ (ng/mL) | 57.3 |
|  | $AUC_{0-24}$ (ng · h/mL) | 176.0 |
|  | $AUC_{0-\infty}$ (ng · h/mL) | 181.3 |

$Ref_{Fasted}$: Sprycel ® Tab 50 mg under fasted condition
$Test_{Fasted}$: Test drug (Test) 20 mg (dasatinib monohydrate) under fasted condition
$Test_{Fed}$: Test drug (Test) 20 mg (dasatinib monohydrate) under fed condition
$Test_{Fasted}$ (PPI) with 40 mg omeprazole: Test drug (Test) 20 mg (dasatinib monohydrate) with 40 mg omeprazole under fasted condition Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following Table:

The Comparisons Between $Test_{Fasted}$ vs. $Reference_{Fasted}$, $Test_{Fed}$ vs. $Test_{Fasted}$ and $Test_{Fasted}$ (PPI) Vs. $Test_{Fasted}$ (Normalized to 50 mg Dose)

| Comparisons | Parameters | Geometric Mean Ratios |
|---|---|---|
| Test~Ref (Fasted) | $C_{max}$ (ng/mL) | 100.88% |
|  | $AUC_{0-24}$ (ng · h/mL) | 87.63% |
|  | $AUC_{0-\infty}$ (ng · h/mL) | 86.20% |
| $Test_{Fed}$~ $Test_{Fasted}$ | $C_{max}$ (ng/mL) | 59.80% |
|  | $AUC_{0-24}$ (ng · h/mL) | 105.37% |
|  | $AUC_{0-\infty}$ (ng · h/mL) | 107.51% |

-continued

| Comparisons | Parameters | Geometric Mean Ratios |
|---|---|---|
| Test$_{Fasted}$ (PPI)~ | $C_{max}$ (ng/mL) | 104.23% |
| Test$_{Fasted}$ | AUC$_{0-24}$ (ng·h/mL) | 101.14% |
| | AUC$_{0-\infty}$ (ng·h/mL) | 101.46% |

The data shows that the compositions of the present invention exhibit an increase of $C_{max}$ by 1.01 fold and a decrease of AUC by 0.88 fold compared to the U.S. FDA approved dasatinib monohydrate. The data also shows that the compositions of the present invention do not exhibit a gastric acid reducing agent or PPI effect i.e., the compositions of the present invention exhibit comparable pharmacokinetics under fasted and fasted with omeprazole co-administration.

The individual subject data normalized to 50 mg dose obtained from the study is as follows:

Reference Drug (Sprycel®) Under Fasted Condition (Concentration (Ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | BLQ | BLQ | BLQ | BLQ | BLQ | BLQ | BLQ | BLQ | BLQ | N/A | N/A | N/A |
| 0.33 | 3.41 | 9.29 | 9.07 | 0.208 | 6.28 | 1.28 | 8.25 | 0.804 | 1.29 | 4.43 | 3.79 | 85.5 |
| 0.67 | 77.9 | 85 | 35.7 | 4.46 | 63 | 10.5 | 41.4 | 1.44 | 22.3 | 38 | 31.4 | 82.8 |
| 1 | 56.3 | 181 | 28.8 | 18.3 | 57 | 15.6 | 47.3 | 1.56 | 70 | 52.9 | 53.1 | 100.5 |
| 1.5 | 30.6 | 175 | 22.1 | 50.8 | 59.1 | 21.4 | 83.2 | 1.51 | 64.4 | 56.5 | 51.2 | 90.7 |
| 2 | 22 | 116 | 23.7 | 63.5 | 59.1 | 29.5 | 58.1 | 1.41 | 41.3 | 46.1 | 33.3 | 72.3 |
| 2.5 | 19.7 | 78.8 | 23.3 | 53.4 | 41.8 | 23.9 | 44.4 | 1.26 | 27.5 | 34.9 | 22.6 | 64.7 |
| 3 | 16 | 62.4 | 20.7 | 46.5 | 35 | 16 | 34.9 | 1.05 | 21.2 | 28.2 | 18.5 | 65.6 |
| 4 | 12.1 | 43.8 | 29.4 | 34.2 | 24.9 | 11.4 | 30.7 | 1.26 | 15.5 | 22.6 | 13.4 | 59.5 |
| 6 | 7.26 | 27.9 | 13.9 | 22.6 | 13.8 | 12.7 | 21.5 | 0.73 | 6.9 | 14.1 | 8.64 | 61.1 |
| 8 | 4.14 | 17.7 | 10.3 | 12 | 8.51 | 5.86 | 13.4 | 0.56 | 4.49 | 8.55 | 5.35 | 62.6 |
| 12 | 2.25 | 7.49 | 4.29 | 6.74 | 4.51 | 2.3 | 7.31 | 0.364 | 1.7 | 4.11 | 2.63 | 64.1 |
| 24 | 0.774 | 1.3 | 1.21 | 1.11 | 0.833 | 0.491 | 1.54 | 0.185 | 0.44 | 0.876 | 0.449 | 51.3 |

Test Drug Under Fasted Condition (Concentration (Ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | BLQ | BLQ | BLQ | BLQ | BLQ | BLQ | BLQ | BLQ | BLQ | N/A | N/A | N/A |
| 0.33 | 0.43 | 6.85 | BLQ | 7.7 | 0.2875 | BLQ | 0.58 | 16.05 | BLQ | 3.54 | 5.61 | 158.2 |
| 0.67 | 2.85 | 55.5 | 12.475 | 71 | 5.925 | BLQ | 4.875 | 26.75 | 2.575 | 20.22 | 25.95 | 128.4 |
| 1 | 4.875 | 74 | 52.25 | 61.25 | 35.75 | BLQ | 12.45 | 20.95 | 26.25 | 31.98 | 25.84 | 80.8 |
| 1.5 | 8.95 | 57 | 33.75 | 40 | 38.5 | 5.475 | 26.5 | 12.5 | 24.475 | 27.46 | 16.77 | 61.1 |
| 2 | 62.25 | 34.5 | 23.275 | 29.25 | 37.5 | 18.8 | 38 | 9.275 | 17.05 | 29.99 | 15.61 | 52 |
| 2.5 | 48.5 | 28.75 | 18.75 | 22.225 | 32 | 28.5 | 36.25 | 7.3 | 13.25 | 26.17 | 12.45 | 47.6 |
| 3 | 36.5 | 24.65 | 16.05 | 17.85 | 26 | 33.25 | 28.5 | 6.3 | 10.725 | 22.20 | 10.17 | 45.8 |
| 4 | 22.025 | 20.6 | 13.775 | 15.7 | 21.4 | 18.725 | 20.15 | 4.725 | 8.05 | 16.13 | 6.19 | 38.4 |
| 6 | 16.425 | 10.925 | 8.925 | 9.625 | 11.8 | 11.9 | 18.325 | 2.7 | 4.7 | 10.59 | 4.97 | 46.9 |
| 8 | 9.9 | 7.325 | 5.525 | 6.175 | 7.95 | 6.45 | 10.825 | 2.045 | 2.825 | 6.56 | 2.90 | 44.3 |
| 12 | 4.15 | 3.15 | 2.41 | 3.125 | 4.075 | 3.05 | 5.525 | 1.0125 | 1.195 | 3.08 | 1.43 | 46.5 |
| 24 | 1.075 | 0.65 | 0.45 | 0.6825 | 1.065 | 0.445 | 1.0975 | 0.35 | 0.365 | 0.69 | 0.32 | 45.9 |

Test Drug Under Fed Condition (Concentration (Ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | BLQ | BLQ | BLQ | BLQ | BLQ | BLQ | BLQ | BLQ | BLQ | N/A | N/A | N/A |
| 0.33 | BLQ | BLQ | BLQ | BLQ | BLQ | BLQ | BLQ | BLQ | BLQ | N/A | N/A | N/A |
| 0.67 | 0.635 | BLQ | 0.6125 | BLQ | BLQ | BLQ | BLQ | BLQ | BLQ | 0.14 | 0.28 | 198.5 |
| 1 | 2.0625 | BLQ | 0.755 | BLQ | BLQ | 1.2025 | 1.47 | 0.95 | 0.4775 | 0.77 | 0.73 | 94.8 |
| 1.5 | 5.05 | 0.5025 | 1.285 | BLQ | 3.2 | 8.55 | 4.925 | 3.725 | 2.75 | 3.33 | 2.66 | 79.8 |
| 2 | 10.9 | 2.005 | 3.875 | BLQ | 35 | 15.925 | 5.275 | 12.225 | 7.825 | 10.34 | 10.57 | 102.2 |
| 2.5 | 16 | 6.875 | 5.475 | 0.7 | 51 | 20.5 | 9.65 | 14.15 | 15.325 | 15.52 | 14.64 | 94.4 |
| 3 | 21.775 | 27.75 | 7.475 | 2.0925 | 38.25 | 25.5 | 12.175 | 16.175 | 21.7 | 19.21 | 11.05 | 57.5 |
| 4 | 38.25 | 43.5 | 13.35 | 8.9 | 33.25 | 24.125 | 19.625 | 15.375 | 17.8 | 23.80 | 11.95 | 50.2 |
| 6 | 27.75 | 24.45 | 17.85 | 21.225 | 21.625 | 10.9 | 19.85 | 6.3 | 8.65 | 17.62 | 7.39 | 41.9 |
| 8 | 16.075 | 16.7 | 9.25 | 12.55 | 13.25 | 6.25 | 15.625 | 4.45 | 5.825 | 11.11 | 4.77 | 43 |
| 12 | 6.35 | 6.5 | 4.675 | 4.825 | 7.5 | 3.375 | 6.75 | 2.3375 | 2.3925 | 4.97 | 1.94 | 39 |
| 24 | 1.8575 | 2.2725 | 0.9075 | 1.1525 | 1.5725 | 0.94 | 1.59 | 0.55 | 0.475 | 1.26 | 0.61 | 48.3 |

Test Drug Under Fasted Condition with 40 mg Omeprazole
(Concentration (Ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | BLQ | BLQ | BLQ | BLQ | BLQ | BLQ | BLQ | BLQ | BLQ | N/A | N/A | N/A |
| 0.33 | BLQ | BLQ | BLQ | BLQ | BLQ | 1.3325 | BLQ | BLQ | BLQ | 0.15 | 0.45 | 300 |
| 0.67 | 3.975 | 18.525 | 3.525 | BLQ | BLQ | 40.75 | 9.825 | 1.935 | 0.3725 | 8.77 | 13.42 | 153.1 |
| 1 | 109 | 120.75 | 39.75 | 0.3125 | 0.2525 | 44.25 | 16.125 | 2.4725 | 3.7 | 37.40 | 47.02 | 125.7 |
| 1.5 | 63.5 | 75.75 | 101.25 | 2.775 | 3.475 | 38 | 18.425 | 4.75 | 41.25 | 38.80 | 35.36 | 91.1 |
| 2 | 37.5 | 45.75 | 66 | 9.1 | 13.1 | 21.2 | 15.175 | 17.125 | 28.75 | 28.19 | 18.57 | 65.9 |
| 2.5 | 30.25 | 37 | 46.5 | 25.25 | 26.25 | 16.775 | 14.075 | 28 | 18.525 | 26.96 | 10.24 | 38 |
| 3 | 26 | 24.6 | 40.75 | 19.675 | 26.75 | 12.875 | 13.05 | 27.75 | 13.05 | 22.72 | 9.18 | 40.4 |
| 4 | 17.325 | 22.825 | 33 | 17.575 | 15.65 | 10.1 | 10.875 | 20.775 | 11.225 | 17.71 | 7.25 | 40.9 |
| 6 | 7.75 | 14.85 | 19.825 | 11.725 | 11.55 | 5.65 | 12.1 | 9.525 | 4.55 | 10.84 | 4.71 | 43.5 |
| 8 | 5.225 | 8.55 | 12.55 | 6.625 | 7.325 | 2.85 | 7.575 | 6.05 | 2.8 | 6.62 | 2.99 | 45.1 |
| 12 | 2.2725 | 3.625 | 5.15 | 2.49 | 2.9 | 1.465 | 3.6 | 2.4475 | 1.4325 | 2.82 | 1.17 | 41.6 |
| 24 | 0.6775 | 0.785 | 0.925 | 0.7525 | 1.11 | BLQ | 0.86 | 0.46 | 0.2825 | 0.65 | 0.35 | 53.1 |

Figure 21:
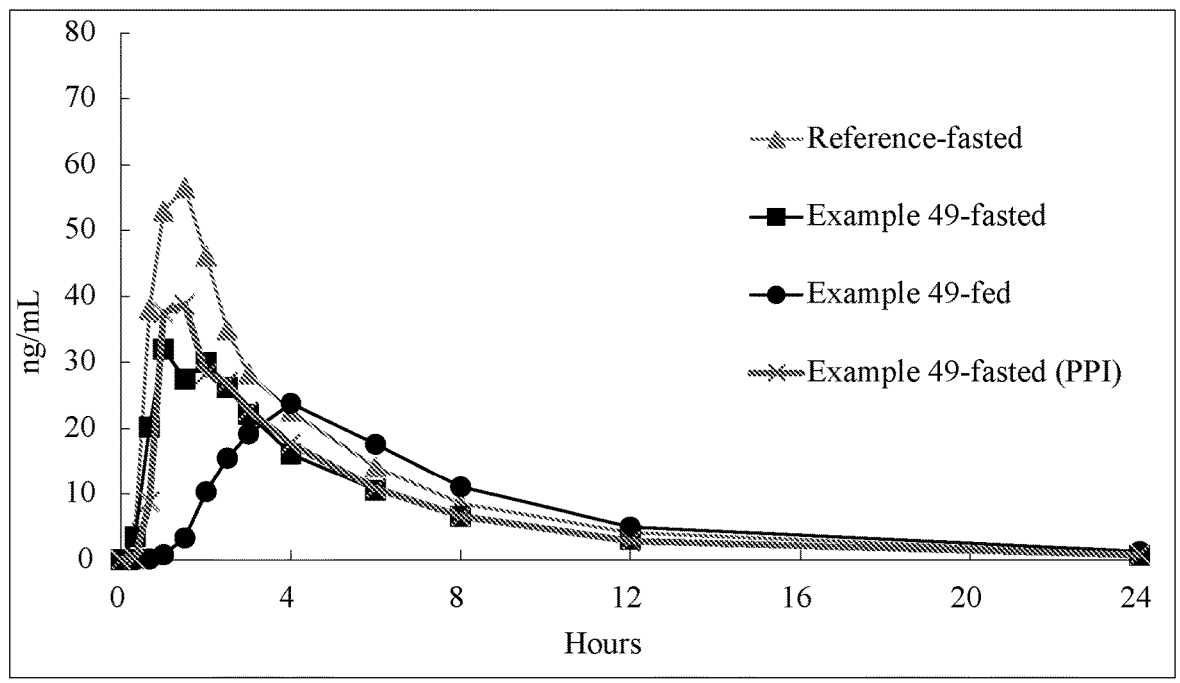
FIG. 21 is a graph of the mean in vivo plasma data provided in Example 50.

A graph of the normalized mean plasma profiles provided in Example 50 is shown in FIG. 21.

Example 51

A dasatinib monolauryl sulfate capsule dosage form was prepared by mixing 7730 mg of dasatinib monolauryl sulfate prepared according to the procedure of Example 48 A, crystallization Method E, which had been passed through a 60 mesh sieve with 2500 mg of anhydrous lactose, 6770 mg of microcrystalline cellulose, 3000 mg of poloxamer 407, 2500 mg of poloxamer 188, 750 mg of hydroxypropyl cellulose (HPC-H), 500 mg of sodium starch glycolate (part I) and 250 mg of colloidal silicon dioxide (part I) which had been passed through a 40 mesh screen for 2 minutes.

The resulting mixture was wet granulated with 2500 mg of an alcohol solution prepared by mixing alcohol (95%) and purified water at a weight ratio of 1:1. The resulting granules were dried in an oven at 50° C. to evaporate the alcohol and water.

The dry granules were passed through a 40 mesh sieve and mixed 500 mg of sodium starch glycolate (part II) and 250 mg of colloidal silicon dioxide (part II) which had been passed through a 40 mesh sieve. 250 mg of magnesium stearate which had been passed through a 40 mesh sieve was added to the resulting mixture and blended to obtain a final blend. The final blend was filled into size 1 hard gelatin capsule.

The composition of the capsule was as follows:

|  | mg | wt % |
|---|---|---|
| Dasatinib monolauryl sulfate (DSB-1LS) | 77.30 | 30.92 |
| Poloxamer 407 | 30.00 | 12.00 |
| Poloxamer 188 | 25.00 | 10.00 |
| Hydroxypropyl cellulose (HPC-H) | 7.50 | 3.00 |
| Anhydrous lactose | 25.00 | 10.00 |
| Microcrystalline cellulose | 67.70 | 27.08 |
| Sodium starch glycolate (part I) | 5.00 | 2.00 |
| Colloidal silicon dioxide (part I) | 2.50 | 1.00 |
| Sodium starch glycolate (part II) | 5.00 | 2.00 |
| Colloidal silicon dioxide (part II) | 2.50 | 1.00 |
| Magnesium stearate | 2.50 | 1.00 |
| Total | 250.00 | 100.00 |
| Alcohol (95%) | 12.50 | N/A |
| Purified water | 12.50 | N/A |

Example 51 A

The capsules prepared in Example 51 containing dasatinib monolauryl sulfate were administered to healthy subjects under fasted, fed and fasted with omeprazole pretreatment conditions. Omeprazole is a commercially available proton pump inhibitor (PPI). This was a two-part study. Part 1 was a single dose, open-label, randomized, 4-treatment, 4-sequence, 4-period crossover bioavailability study in ten (10) healthy subjects under fasted and fed conditions. All subjects were randomized to the sequences as shown in the following table with a 3-day or 4-day washout period between the periods. Part 2 is a sequential, 2-treatment, drug-drug interaction study in nine (9) healthy subjects. All subjects were orally administered omeprazole 40 mg QD for 5 days to reach steady state and a 50 mg dasatinib capsule was orally administered approximately 22 hours after the last dose of omeprazole. The Reference drug (Ref) was Sprycel®, dasatinib monohydrate, with a strength of 50 mg (free base) while the Test drug (Test) was a capsule prepared according to the procedure of Example 51 but containing approximately 50 mg of dasatinib (free base). The ten (10) healthy subjects for part 1 or nine (9) healthy subjects for part 2 enrolled in this study were randomized to one of the sequences as shown in the following table.

| Part 1 | | | | |
|---|---|---|---|---|
| Sequence | Period I | Period II | Period III | Period IV |
| 1 | Rfast | Tfast | Tfed | Rfed |
| 2 | Tfed | Rfast | Rfed | Tfast |
| 3 | Rfed | Tfed | Tfast | Rfast |
| 4 | Tfast | Rfed | Rfast | Tfed |

* Rfast: Reference under fasted condition; Rfed: Reference under fed condition; Tfast Test under fasted condition; Tfed: Test under fed condition.

| Part 2 | | |
|---|---|---|
| Sequence | Period I | Period II | Period III |
| 1 | Tfast | Omeprazole 40 mg QD for 5 days | Tfast |

* Tfast Test under fasted condition

During each treatment period, blood samples were taken at 0 (prior to the dosing), 0.33, 0.67, 1, 1.5, 2, 2.5, 3, 4, 6, 8, 12 and 24 hours after dosing. $AUC_{0-24}$, $AUC_{0-\infty}$, $C_{max}$, $T_{max}$, and $T_{1/2}$ were determined for each subject based on non-compartmental analyses. The results were summarized in the following table:

The Pharmacokinetic Parameters for Reference and Test Formulations

| Treatment | Parameters | 50 mg dose Mean |
|---|---|---|
| Part 1 | | |
| Ref $_{Fasted}$ | $C_{max}$ (ng/mL) | 97.8 |
| | $AUC_{0-24}$ (ng · h/mL) | 302 |
| | $AUC_{0-\infty}$ (ng · h/mL) | 307 |
| Ref $_{Fed}$ | $C_{max}$ (ng/mL) | 47.2 |
| | $AUC_{0-24}$ (ng · h/mL) | 235 |
| | $AUC0-\infty$ (ng · h/mL) | 244 |
| Test $_{Fasted}$ | $C_{max}$ (ng/mL) | 73.6 |
| | $AUC_{0-24}$ (ng · h/mL) | 255 |
| | $AUC_{0-\infty}$ (ng · h/mL) | 261 |
| Test $_{Fed}$ | $C_{max}$ (ng/mL) | 35.9 |
| | $AUC_{0-24}$ (ng · h/mL) | 224 |
| | $AUC_{0-\infty}$ (ng · h/mL) | 235 |
| Part 2 | | |
| Test $_{Fasted}$ | $C_{max}$ (ng/mL) | 82.7 |
| | $AUC_{0-24}$ (ng · h/mL) | 297 |
| | $AUC_{0-\infty}$ (ng · h/mL) | 303 |
| Test $_{Fasted}$ (PPI) with 40 mg omeprazole | $C_{max}$ (ng/mL) | 98.6 |
| | $AUC_{0-24}$ (ng · h/mL) | 349 |
| | $AUC_{0-\infty}$ (ng · h/mL) | 356 |

* Ref $_{Fasted}$: Sprycel ® Tab 50 mg under fasted condition
* Ref $_{Fed}$: Sprycel ® Tab 50 mg under fed condition
* Test $_{Fasted}$: Test drug (Test) 50 mg under fasted condition
* Test $_{Fed}$: Test drug (Test) 50 mg under fed condition
* Test $_{Fasted}$ (PPI) with 40 mg omeprazole: Test drug (Test) 50 mg with 40 mg omeprazole under fasted condition Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following table:

The Comparisons Between Test$_{Fasted}$ vs. Reference Fasted, Test$_{Fed}$ vs. Reference$_{Fed}$, Test$_{Fasted}$ vs. Test$_{Fed}$ and Test$_{Fasted}$ (PPI) Vs. Test$_{Fasted}$

| Comparisons | Parameters | Geometric Mean Ratios |
|---|---|---|
| Test~Ref (Fasted) | $C_{max}$ (ng/mL) | 78.96% |
| | $AUC_{0-24}$ (ng · h/mL) | 84.07% |
| | $AUC_{0-\infty}$ (ng · h/mL) | 84.69% |
| Test~Ref (Fed) | $C_{max}$ (ng/mL) | 75.90% |
| | $AUC_{0-24}$ (ng · h/mL) | 97.71% |
| | $AUC_{0-\infty}$ (ng · h/mL) | 98.24% |
| Test $_{Fast}$~Test $_{Fed}$ | $C_{max}$ (ng/mL) | 191.81% |
| | $AUC_{0-24}$ (ng · h/mL) | 108.97% |
| | $AUC_{0-\infty}$ (ng · h/mL) | 106.71% |
| Test $_{Fasted}$ (PPD)~Test $_{Fasted}$ | $C_{max}$ (ng/mL) | 117.44% |
| | $AUC_{0-24}$ (ng · h/mL) | 113.15% |
| | $AUC_{0-\infty}$ (ng · h/mL) | 113.13% |

The data shows that the compositions of the present invention exhibit a decrease of $C_{max}$ by 0.79 fold and a decrease of AUC by 0.84 fold compared to the U.S. FDA approved dasatinib monohydrate under fasted condition. The data shows that the compositions of the present invention exhibit a decrease of $C_{max}$ by 0.76 fold and a decrease of AUC by 0.98 fold compared to the U.S. FDA approved dasatinib monohydrate under fed condition. The data also shows that the compositions of the present invention exhibit a positive gastric acid reducing agent or PPI effect i.e., the compositions of the present invention during fasted co-administration with omeprazole exhibited an increase of $C_{max}$ by 1.17 fold and an increase of AUC by 1.13 fold compared to the fasted condition.

Figure 22A:
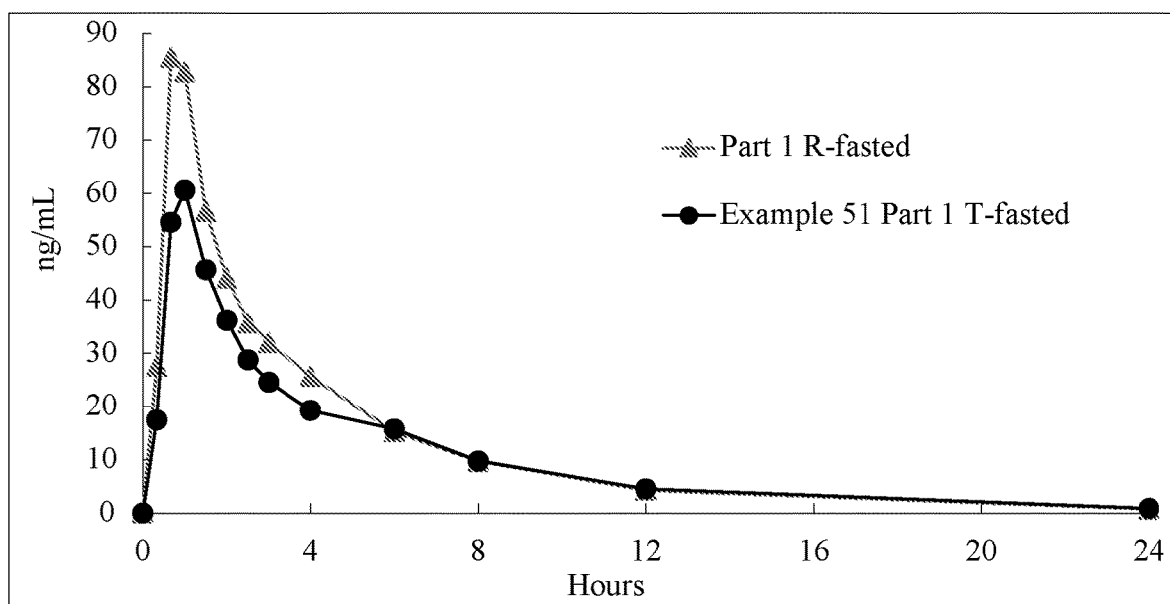
FIG. 22A-22C are graphs of the mean in vivo plasma data provided in Example 51A.

A graph of the mean plasma profiles under fasted condition for this Example is shown in FIG. 22A.

Figure 22B:
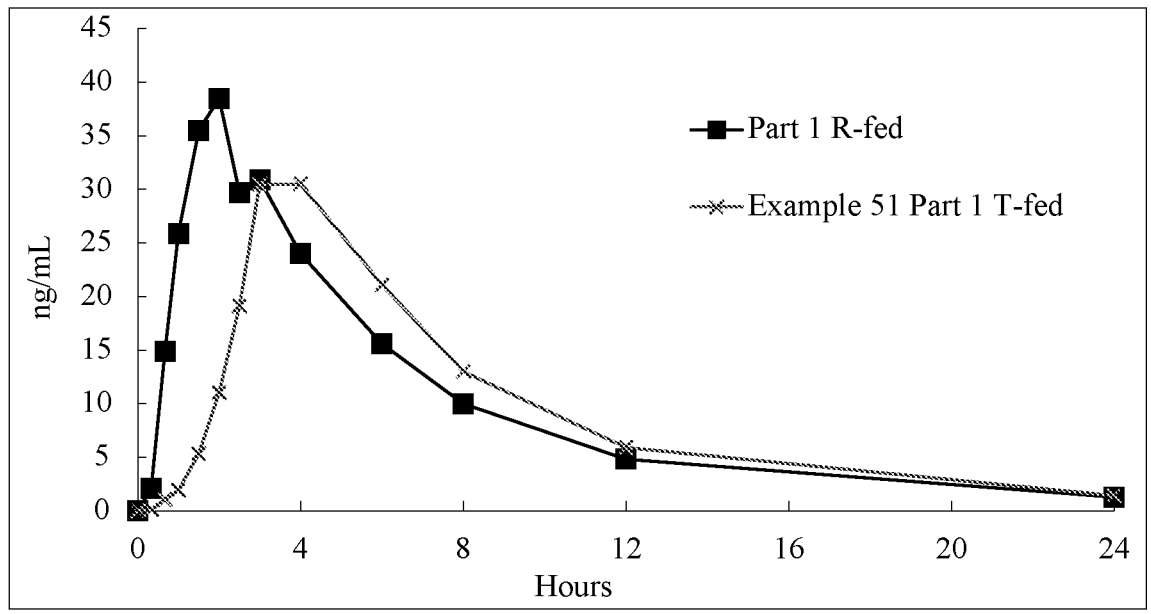

A graph of the mean plasma profiles under fed condition for this Example is shown in FIG. 22 B.

Figure 22C:
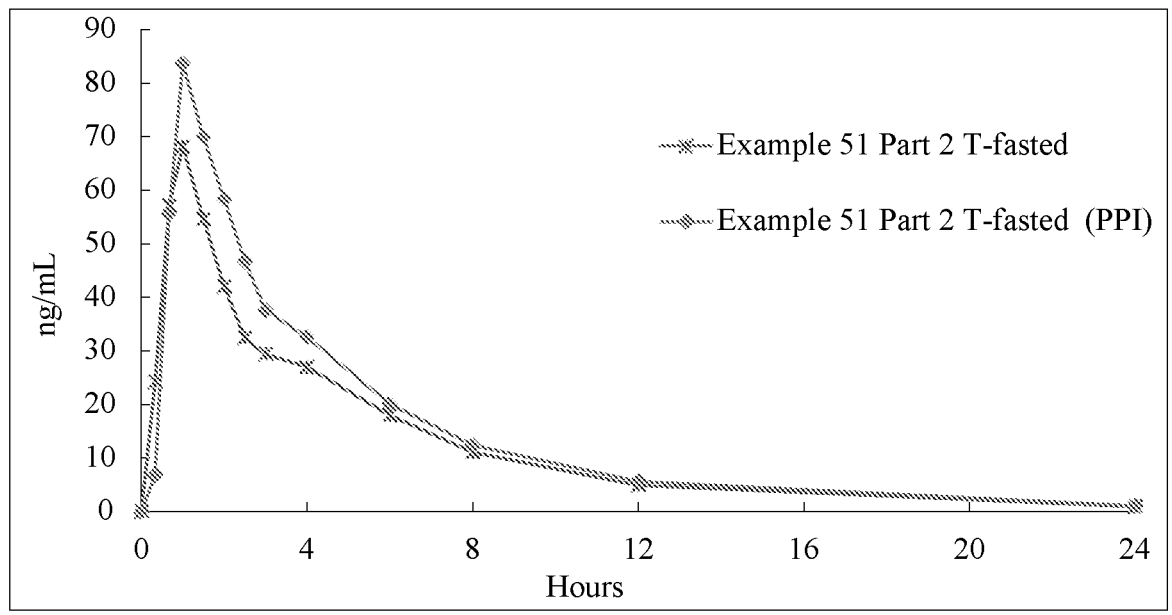

A graph of the mean plasma profiles with 40 mg omeprazole under fasted condition for this Example is shown in FIG. 22C.

The individual subject data of 50 mg dose obtained from the study is as follows:

Part 1: Reference Drug (Sprycel®) Under Fasted Condition (Concentration (ng/mL))

| Time (hr) | Subject | | | | | | | | | | Mean | SD | CV % |
|---|---|---|---|---|---|---|---|---|---|---|---|---|---|
| | 1 | 2 | 3 | 4 | 5 | 6 | 7 | 8 | 9 | 10 | | | |
| 0 | 0 | 0 | 0 | 0 | 0 | 0 | 0 | 0 | 0 | 0 | 0 | 0 | — |
| 0.33 | 26.1 | 8.34 | 43 | 2.9 | 12.4 | 2.79 | 123 | 32.8 | 1.97 | 22.9 | 27.6 | 36.3 | 131.5 |
| 0.67 | 184 | 131 | 55.6 | 23.2 | 71.1 | 51 | 121 | 26.4 | 39.5 | 153 | 85.6 | 57.1 | 66.8 |
| 1 | 194 | 167 | 36.6 | 49 | 60 | 69.3 | 76.7 | 16.1 | 31.3 | 128 | 82.8 | 60.2 | 72.7 |
| 1.5 | 116 | 84.8 | 22.3 | 65.5 | 41.5 | 71 | 49.6 | 13.5 | 21.5 | 80.9 | 56.7 | 32.9 | 58.1 |
| 2 | 81.3 | 52.8 | 16.4 | 60.3 | 31.7 | 76.2 | 37.6 | 9.74 | 15.9 | 59.2 | 44.1 | 25.6 | 58.1 |
| 2.5 | 58.9 | 36.5 | 15 | 47.5 | 24.6 | 60.4 | 29.1 | 12.2 | 18.4 | 55.2 | 35.8 | 18.6 | 52 |
| 3 | 49.4 | 28.5 | 14.2 | 38.8 | 24.4 | 59.3 | 25.2 | 15.4 | 20.2 | 45.7 | 32.1 | 15.4 | 47.9 |
| 4 | 39 | 21.4 | 12.1 | 24.5 | 30.9 | 36.1 | 24 | 9.45 | 20.1 | 39.4 | 25.7 | 10.6 | 41.1 |
| 6 | 19.1 | 12.7 | 9.37 | 11.7 | 16.7 | 16.6 | 21.7 | 7.8 | 16.7 | 20.3 | 15.3 | 4.68 | 30.7 |
| 8 | 13.5 | 8.27 | 6.45 | 7.51 | 11.2 | 11.8 | 11 | 5.48 | 9.4 | 12.9 | 9.75 | 2.75 | 28.3 |

-continued

| Time | Subject | | | | | | | | | | | | |
|---|---|---|---|---|---|---|---|---|---|---|---|---|---|
| (hr) | 1 | 2 | 3 | 4 | 5 | 6 | 7 | 8 | 9 | 10 | Mean | SD | CV % |
| 12 | 5.52 | 4.34 | 2.67 | 3.96 | 4.79 | 5.13 | 4.54 | 2.06 | 4.8 | 5.19 | 4.3 | 1.12 | 26.1 |
| 24 | 1.13 | 0.669 | 0.523 | 0.679 | 0.631 | 1.15 | 0.911 | 0.308 | 0.684 | 1.11 | 0.78 | 0.284 | 36.5 |

Part 1: Test Drug (Example 51) Under Fasted Condition
(Concentration (ng/mL))

| Time | Subject | | | | | | | | | | | | |
|---|---|---|---|---|---|---|---|---|---|---|---|---|---|
| (hr) | 1 | 2 | 3 | 4 | 5 | 6 | 7 | 8 | 9 | 10 | Mean | SD | CV % |
| 0 | 0 | 0 | 0 | 0 | 0 | 0 | 0 | 0 | 0 | 0 | 0 | 0 | — |
| 0.33 | 10.2 | 48.6 | 0.121 | 0 | 4.8 | 2.33 | 47.4 | 37.2 | 3.81 | 20.4 | 17.5 | 19.7 | 112.7 |
| 0.67 | 67.6 | 74.7 | 2.32 | 5.16 | 64.1 | 76.3 | 105 | 31.4 | 42.4 | 77 | 54.6 | 33.4 | 61.2 |
| 1 | 110 | 51.9 | 10.4 | 15.5 | 52.1 | 130 | 74.3 | 21.6 | 42.5 | 97.5 | 60.6 | 41.3 | 68.2 |
| 1.5 | 91.3 | 41.8 | 16.8 | 33.2 | 33.5 | 91.1 | 42.9 | 15.8 | 27 | 63.2 | 45.7 | 27.6 | 60.4 |
| 2 | 61.2 | 39.2 | 10.8 | 45.2 | 27.6 | 67.7 | 32.1 | 12.3 | 22.3 | 43.1 | 36.2 | 19 | 52.6 |
| 2.5 | 51.3 | 36.3 | 9.33 | 26.6 | 21.7 | 51.5 | 26.5 | 10.6 | 18 | 36.6 | 28.8 | 15 | 52 |
| 3 | 43.5 | 30.5 | 7.74 | 17.7 | 18.6 | 41.7 | 21.7 | 8.64 | 18 | 38.2 | 24.6 | 13.1 | 53.2 |
| 4 | 30.3 | 20.3 | 6.53 | 13 | 22.4 | 30.8 | 19.6 | 6.12 | 14.2 | 29.3 | 19.3 | 9.23 | 47.9 |
| 6 | 14.6 | 12.3 | 29.3 | 9.69 | 19.1 | 18.4 | 21.8 | 3.72 | 10.4 | 21.8 | 15.8 | 7.22 | 45.8 |
| 8 | 9.76 | 7.97 | 14.6 | 6.11 | 14.5 | 12.3 | 11.9 | 2.65 | 4.92 | 13.4 | 9.81 | 4.22 | 43.1 |
| 12 | 5.03 | 3.96 | 6.09 | 3.02 | 6.74 | 6.11 | 4.97 | 1.03 | 2.49 | 6.21 | 4.57 | 1.89 | 41.4 |
| 24 | 0.989 | 0.743 | 1.2 | 0.63 | 1.18 | 1.29 | 0.858 | 0.224 | 0.479 | 1.41 | 0.9 | 0.383 | 42.6 |

Part 1: Reference Drug (Sprycel®) Under Fed Condition
(Concentration (ng/mL))

| Time | Subject | | | | | | | | | | | | |
|---|---|---|---|---|---|---|---|---|---|---|---|---|---|
| (hr) | 1 | 2 | 3 | 4 | 5 | 6 | 7 | 8 | 9 | 10 | Mean | SD | CV % |
| 0 | 0 | 0 | 0 | 0 | 0 | 0 | 0 | 0 | 0 | 0 | 0 | 0 | — |
| 0.33 | 7.74 | 0.773 | 5.61 | 1.04 | 1.01 | 1.24 | 3.45 | 0 | 0 | 0 | 2.09 | 2.67 | 127.8 |
| 0.67 | 35.3 | 4.93 | 45.1 | 10.9 | 10.9 | 5.11 | 31.3 | 3.97 | 0.54 | 1.33 | 14.9 | 16.1 | 107.8 |
| 1 | 53.7 | 14.4 | 55.2 | 25.8 | 19.9 | 6.78 | 38.1 | 27.5 | 2.57 | 14.6 | 25.9 | 18.2 | 70.5 |
| 1.5 | 53 | 47.3 | 29.6 | 36.4 | 36.8 | 11.3 | 31.1 | 26.2 | 13.7 | 69.7 | 35.5 | 17.7 | 49.8 |
| 2 | 45 | 60.2 | 21.4 | 34.4 | 47.2 | 24.3 | 31.4 | 17.9 | 27.4 | 76 | 38.5 | 18.6 | 48.2 |
| 2.5 | 41.9 | 15.9 | 17.2 | 37.3 | 37.9 | 37.5 | 23.8 | 16.1 | 25.1 | 44.3 | 29.7 | 11.2 | 37.8 |
| 3 | 34.6 | 39.2 | 15.5 | 38.1 | 39.2 | 49 | 20.5 | 10.1 | 23.5 | 39.1 | 30.9 | 12.6 | 40.8 |
| 4 | 24.5 | 31.4 | 12.2 | 26 | 29 | 46.2 | 17.9 | 7.04 | 13.8 | 32.1 | 24 | 11.6 | 48.3 |
| 6 | 14.7 | 23.1 | 8.43 | 12.8 | 19.7 | 29.1 | 11.7 | 4.48 | 12.9 | 18.8 | 15.6 | 7.24 | 46.5 |
| 8 | 10.6 | 14.7 | 6.29 | 7.01 | 13.9 | 16.1 | 9.07 | 2.72 | 7 | 12.5 | 9.99 | 4.3 | 43.1 |
| 12 | 5.65 | 6.8 | 3.78 | 3.03 | 5.45 | 8.14 | 5.57 | 1.22 | 2.83 | 5.68 | 4.82 | 2.07 | 43 |
| 24 | 2.3 | 1.41 | 1.09 | 0.585 | 1.12 | 1.68 | 1.09 | 0.475 | 0.807 | 2.14 | 1.27 | 0.615 | 48.5 |

Part 1: Test Drug (Example 51) Under Fed Condition
(Concentration (ng/mL))

| Time | Subject | | | | | | | | | | | | |
|---|---|---|---|---|---|---|---|---|---|---|---|---|---|
| (hr) | 1 | 2 | 3 | 4 | 5 | 6 | 7 | 8 | 9 | 10 | Mean | SD | CV % |
| 0 | 0 | 0 | 0 | 0 | 0 | 0 | 0 | 0 | 0 | 0 | 0 | 0 | — |
| 0.33 | 0 | 0 | 0 | 0 | 0.307 | 0.44 | 0 | 0.218 | 0 | 0.105 | 0.107 | 0.161 | 150 |
| 0.67 | 0.572 | 0 | 0 | 0.8 | 4.04 | 3.63 | 0.228 | 1.16 | 0 | 0 | 1.04 | 1.53 | 146.4 |
| 1 | 1.66 | 0 | 0.17 | 1.65 | 6.88 | 5.67 | 0.731 | 1.81 | 0.497 | 0.127 | 1.92 | 2.41 | 125.5 |
| 1.5 | 6.23 | 0 | 0.629 | 9.78 | 9.82 | 7.68 | 2.52 | 12.4 | 3.29 | 1.08 | 5.34 | 4.43 | 83 |
| 2 | 18.4 | 0.336 | 1.68 | 21.7 | 16.8 | 9.79 | 4.89 | 22.1 | 9.64 | 4.42 | 11 | 8.24 | 75 |
| 2.5 | 34.4 | 3.4 | 3.26 | 26.4 | 25.8 | 15.9 | 8.83 | 20.1 | 30 | 22.9 | 19.1 | 11 | 57.3 |
| 3 | 38.8 | 10.2 | 7.19 | 28.6 | 48 | 45 | 16.8 | 18.1 | 58.7 | 33.8 | 30.5 | 17.3 | 56.7 |
| 4 | 39.7 | 25.9 | 24.9 | 24.7 | 31 | 47.4 | 29.8 | 11.7 | 38.6 | 30.9 | 30.5 | 9.87 | 32.4 |
| 6 | 33.8 | 25.2 | 17.4 | 16.8 | 20.1 | 32.3 | 23.4 | 6.82 | 17.4 | 18.2 | 21.1 | 7.94 | 37.6 |
| 8 | 18.1 | 14.2 | 16.1 | 10.3 | 15 | 16.6 | 15.6 | 3.23 | 9.35 | 11.1 | 13 | 4.48 | 34.6 |

-continued

| Time | Subject | | | | | | | | | | Mean | SD | CV % |
|---|---|---|---|---|---|---|---|---|---|---|---|---|---|
| (hr) | 1 | 2 | 3 | 4 | 5 | 6 | 7 | 8 | 9 | 10 | | | |
| 12 | 8.05 | 6.02 | 9.45 | 5.62 | 5.69 | 7.16 | 6.98 | 1.21 | 3.59 | 5.29 | 5.91 | 2.31 | 39 |
| 24 | 2.86 | 1.41 | 1.86 | 1.07 | 0.972 | 1.52 | 1.59 | 0.259 | 0.6 | 1.95 | 1.41 | 0.74 | 52.5 |

Part 2: Test Drug (Example 51) Under Fasted Condition (Concentration (ng/mL))

| Time | Subject | | | | | | | | | Mean | SD | CV % |
|---|---|---|---|---|---|---|---|---|---|---|---|---|
| (hr) | 1 | 2 | 3 | 4 | 5 | 6 | 7 | 8 | 9 | | | |
| 0 | 0 | 0 | 0 | 0 | 0 | 0 | 0 | 0 | 0 | 0 | 0 | — |
| 0.33 | 16.7 | 15.5 | 0 | 52.3 | 28.7 | 2.05 | 31.6 | 0.309 | 70.2 | 24.2 | 24.4 | 101 |
| 0.67 | 82.9 | 89.4 | 0 | 89 | 42.5 | 46.6 | 70.7 | 22.6 | 69.8 | 57.1 | 31.3 | 54.9 |
| 1 | 74.7 | 84.7 | 0.725 | 113 | 39.7 | 145 | 52.6 | 48.7 | 54.3 | 68.2 | 42.4 | 62.3 |
| 1.5 | 52.2 | 46.3 | 6.13 | 84.8 | 30.5 | 103 | 36.1 | 85.4 | 47.1 | 54.6 | 30.8 | 56.5 |
| 2 | 41.7 | 40.4 | 6.31 | 63.6 | 26.2 | 78.4 | 26.9 | 54.5 | 39.8 | 42 | 21.5 | 51.3 |
| 2.5 | 34.8 | 31.9 | 6.85 | 44.1 | 22.3 | 60.1 | 20 | 39 | 32.1 | 32.4 | 15.3 | 47.2 |
| 3 | 32 | 37.4 | 15.4 | 30.6 | 22.7 | 51 | 17.7 | 30.6 | 27.5 | 29.4 | 10.7 | 36.5 |
| 4 | 25.3 | 29.5 | 45.1 | 24.6 | 17.9 | 40.7 | 15.5 | 22.8 | 21.9 | 27 | 9.93 | 36.7 |
| 6 | 24.7 | 13.5 | 35.2 | 13.3 | 11 | 25.2 | 11.5 | 15.4 | 12.1 | 18 | 8.42 | 46.8 |
| 8 | 14.9 | 8.3 | 21.1 | 7.98 | 6.47 | 17.8 | 6.99 | 8.49 | 8.05 | 11.1 | 5.38 | 48.4 |
| 12 | 6.65 | 4.23 | 7.29 | 5.1 | 2.03 | 7.63 | 2.89 | 4.21 | 4.06 | 4.9 | 1.94 | 39.6 |
| 24 | 1.66 | 0.756 | 1.44 | 0.655 | 0.335 | 1.39 | 0.574 | 0.714 | 0.864 | 0.932 | 0.453 | 48.6 |

Part 2: Test Drug (Example 51) Under Fasted Condition with 40 mg Omeprazole (Concentration (ng/mL))

| Time | Sibject | | | | | | | | | Mean | SD | CV % |
|---|---|---|---|---|---|---|---|---|---|---|---|---|
| (hr) | 1 | 2 | 3 | 4 | 5 | 6 | 7 | 8 | 9 | | | |
| 0 | 0 | 0 | 0 | 0 | 0 | 0 | 0 | 0 | 0 | 0 | 0 | — |
| 0.33 | 1.36 | 9.01 | 3.08 | 21.6 | 13.8 | 3.69 | 3.3 | 1.95 | 3.37 | 6.8 | 6.83 | 100.6 |
| 0.67 | 6.29 | 68 | 31.5 | 98.9 | 40.9 | 148 | 37.6 | 51.2 | 17.8 | 55.6 | 44.1 | 79.4 |
| 1 | 6.41 | 125 | 82.7 | 102 | 67.5 | 180 | 31.6 | 72.7 | 84.5 | 83.6 | 50.5 | 60.4 |
| 1.5 | 51.3 | 62 | 70.5 | 75.7 | 56.7 | 124 | 27.4 | 81.1 | 80.5 | 69.9 | 26.4 | 37.8 |
| 2 | 127 | 41.6 | 46.5 | 51.5 | 49.4 | 90.6 | 19.3 | 46.7 | 52.5 | 58.3 | 31.6 | 54.2 |
| 2.5 | 107 | 28.6 | 34.4 | 41.5 | 39.2 | 71.8 | 17.4 | 35.7 | 45 | 46.7 | 27 | 57.7 |
| 3 | 70.2 | 22.6 | 32.2 | 31.7 | 29.4 | 68.6 | 16.9 | 26.5 | 40.2 | 37.6 | 19.2 | 51 |
| 4 | 51.6 | 16.2 | 35.9 | 22.4 | 24.5 | 69.2 | 22.6 | 20.7 | 30 | 32.6 | 17.3 | 53.2 |
| 6 | 33.8 | 9.07 | 25.9 | 10.6 | 14.7 | 39.3 | 14.4 | 17.6 | 15.5 | 20.1 | 10.6 | 52.5 |
| 8 | 19.2 | 5.16 | 14.3 | 6.93 | 9.07 | 28.5 | 8.7 | 9.63 | 9.77 | 12.4 | 7.34 | 59.4 |
| 12 | 9.11 | 2.39 | 6.83 | 3.34 | 3.6 | 12.4 | 3.45 | 4.3 | 5.08 | 5.61 | 3.28 | 58.5 |
| 24 | 1.88 | 0.465 | 1.21 | 0.543 | 0.609 | 2.62 | 0.561 | 0.814 | 0.953 | 1.07 | 0.731 | 68.1 |

Example 52

A dasatinib monolauryl sulfate capsule dosage form was prepared by blending 9276 mg of dasatinib monolauryl sulfate prepared according to the procedure of Example 12 which had been passed through a 325 mesh sieve with 1440 mg of croscarmellose sodium and 6000 mg of anhydrous lactose in a suitable container for about 1 minute. 6324 mg of microcrystalline cellulose and 720 mg of hydroxypropyl cellulose (HPC-H) which had been passed through a 40 mesh sieve were added to blend in the container and further blended for 2 minutes.

240 mg of magnesium stearate which had been passed through a 40 mesh sieve was added to the blend and further blended to obtain a final blend. The final blend was filled into size 1 hard gelatin capsule.

The composition of the capsule was as follows:

|  | Mg | wt % |
|---|---|---|
| Dasatinib monolauryl sulfate (DSB-1LS) | 77.30 | 38.65 |
| Croscarmellose sodium | 12.00 | 6.00 |
| Anhydrous lactose | 50.00 | 25.00 |
| Microcrystalline cellulose | 52.70 | 26.35 |
| Hydroxypropyl cellulose (HPC-H) | 6.00 | 3.00 |
| Magnesium stearate | 2.00 | 1.00 |
| Total | 200.00 | 100.00 |

Example 52 A

The capsules prepared in Example 52 containing dasatinib monolauryl sulfate were administered to six (6) healthy subjects under fasted conditions. This administration was a single dose, open-label, randomized, 2-treatment, 2-sequence, 2-period crossover bioavailability study in healthy subjects under fasted conditions. All subjects were randomized to the sequences as shown in the following table with a 3-day washout period between the periods. The Reference drug (Ref) was Sprycel®, Dasatinib monohydrate, with a strength of 50 mg (free base) while the Test drug (Test) was a capsule prepared according to the procedure of Example 52 but containing approximately 50 mg of dasatinib (free base). The six (6) healthy subjects enrolled in this study were randomized to one of the sequences as shown in the following table.

| Sequence | Period I | Period II |
|---|---|---|
| 1 | Tfast | Rfast |

During each treatment period, blood samples were taken at 0 (prior to the dosing), 0.33, 0.67, 1, 1.5, 2, 2.5, 3, 4, 6, 8, 12 and 24 hours after dosing. $AUC_{0-24}$, $AUC_{0-\infty}$, $C_{max}$, $T_{max}$, and $T_{1/2}$ were determined for each subject based on non-compartmental analyses. The results were summarized in the following table:

The Pharmacokinetic Parameters for Reference and Test Formulations

| Treatment | Parameters | 50 mg dose Mean |
|---|---|---|
| Ref $_{Fasted}$ | $C_{max}$ (ng/mL) | 81.7 |
| | $AUC_{0-24}$ (ng · h/mL) | 235 |
| | $AUC_{0-\infty}$ (ng · h/mL) | 238 |

-continued

| Treatment | Parameters | 50 mg dose Mean |
|---|---|---|
| Test $_{Fasted}$ | $C_{max}$ (ng/mL) | 39.3 |
| | $AUC_{0-24}$ (ng · h/mL) | 194 |
| | $AUC_{0-\infty}$ (ng · h/mL) | 199 |

* Ref $_{Fasted}$: Sprycel ® Tab 50 mg under fasted condition
* Test $_{Fasted}$: Test drug (Test) 50 mg under fasted condition Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following table:

The Comparisons Between Test Fasted Vs. Reference Fasted

| Comparisons | Parameters | Geometric Mean Ratios |
|---|---|---|
| Test~Ref (Fasted) | $C_{max}$ (ng/mL) | 45.58% |
| | $AUC_{0-24}$ (ng · h/mL) | 79.26% |
| | $AUC_{0-\infty}$ (ng · h/mL) | 80.50% |

The data shows that the compositions of the present invention exhibit a decrease of $C_{max}$ by 0.46 fold and a decrease of AUC by 0.79 fold compared to the U.S. FDA approved dasatinib monohydrate.

Figure 23:
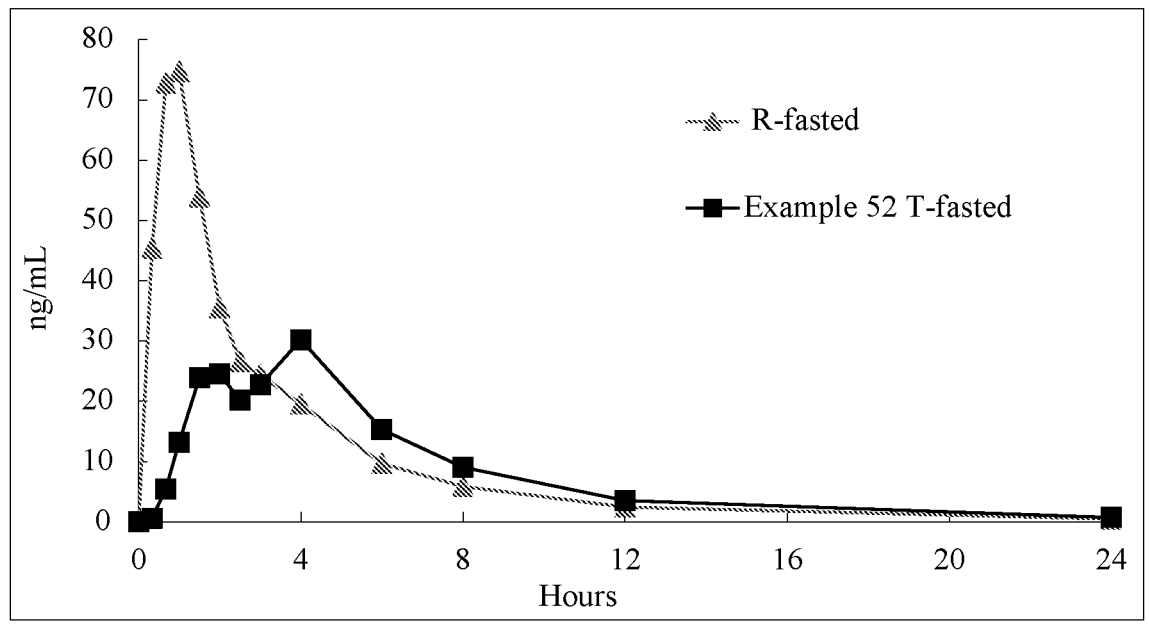
FIG. 23 is a graph of the mean in vivo plasma data provided in Example 52A.

A graph of the mean plasma profiles for this Example is shown in FIG. 23.

The individual subject data of 50 mg dose obtained from the study is as follows:

Reference Drug (Sprycel®) Under Fasted Condition (Concentration (ng/mL))

| Time (hr) | Subject 1 | 2 | 3 | 4 | 5 | 6 | Mean | SD | CV % |
|---|---|---|---|---|---|---|---|---|---|
| 0 | 0 | 0 | 0 | 0 | 0 | 0 | 0 | 0 | — |
| 0.33 | 34.8 | 22.5 | 123 | 44.6 | 40.6 | 6.75 | 45.4 | 40.4 | 89.1 |
| 0.67 | 103 | 28 | 129 | 51.4 | 72.5 | 52.6 | 72.8 | 37.3 | 51.2 |
| 1 | 111 | 23.6 | 100 | 42.9 | 78.9 | 91.7 | 74.7 | 34.3 | 45.9 |
| 1.5 | 76.8 | 17.6 | 76.8 | 27.4 | 64.1 | 60.9 | 53.9 | 25.4 | 47.1 |
| 2 | 40.4 | 13.6 | 56.1 | 22.4 | 46.2 | 34.4 | 35.5 | 15.6 | 43.9 |
| 2.5 | 27.6 | 12.1 | 44.7 | 19 | 33.2 | 23 | 26.6 | 11.4 | 43 |
| 3 | 22 | 13.5 | 33.9 | 30 | 27.9 | 18.8 | 24.4 | 7.61 | 31.3 |
| 4 | 16.2 | 18.1 | 24.1 | 27.1 | 16.9 | 14.6 | 19.5 | 4.95 | 25.4 |
| 6 | 7.46 | 9.11 | 14.7 | 11.3 | 7.7 | 7.57 | 9.64 | 2.88 | 29.9 |
| 8 | 4.4 | 5.49 | 9.08 | 6.93 | 5.2 | 4.01 | 5.85 | 1.88 | 32.1 |
| 12 | 1.46 | 2.12 | 4.36 | 2.52 | 2.01 | 2.09 | 2.43 | 1.01 | 41.5 |
| 24 | 0.199 | 0.42 | 0.871 | 0.556 | 0.396 | 0.386 | 0.471 | 0.227 | 48.1 |

Test Drug Under Fasted Condition (Concentration (ng/mL))

| Time (hr) | Subject 1 | 2 | 3 | 4 | 5 | 6 | Mean | SD | CV % |
|---|---|---|---|---|---|---|---|---|---|
| 0 | 0 | 0 | 0 | 0 | 0 | 0 | 0 | 0 | — |
| 0.33 | 1.53 | 1.27 | 0 | 0 | 0.445 | 0.19 | 0.573 | 0.667 | 116.4 |
| 0.67 | 14.8 | 7.61 | 0.25 | 2.58 | 3.02 | 4.55 | 5.47 | 5.18 | 94.7 |
| 1 | 36.2 | 9.04 | 5.81 | 7.74 | 11.4 | 8.71 | 13.2 | 11.4 | 87 |
| 1.5 | 67 | 9.54 | 25.3 | 11.7 | 19.8 | 10.2 | 23.9 | 22 | 91.9 |
| 2 | 64.2 | 12.2 | 30.9 | 14.1 | 18 | 7.74 | 24.5 | 21 | 85.5 |
| 2.5 | 40.3 | 16 | 27.6 | 15.4 | 15.5 | 6.67 | 20.2 | 11.9 | 58.6 |
| 3 | 29.9 | 22.6 | 37.4 | 11 | 26.6 | 8.61 | 22.7 | 11.1 | 49 |
| 4 | 21 | 37.7 | 71.1 | 9.8 | 26.5 | 15.3 | 30.2 | 22.2 | 73.4 |

-continued

| Time (hr) | Subject 1 | 2 | 3 | 4 | 5 | 6 | Mean | SD | CV % |
|---|---|---|---|---|---|---|---|---|---|
| 6 | 10.6 | 15.7 | 30.2 | 18.3 | 9.44 | 7.32 | 15.3 | 8.38 | 54.9 |
| 8 | 6.68 | 9.49 | 17.1 | 11.9 | 5.54 | 3.6 | 9.05 | 4.91 | 54.3 |
| 12 | 2.55 | 3.62 | 5.93 | 5.48 | 2.24 | 1.28 | 3.52 | 1.86 | 52.8 |
| 24 | 0.477 | 0.593 | 0.924 | 1.07 | 0.527 | 0.653 | 0.707 | 0.237 | 33.5 |

Example 53

A dasatinib monolauryl sulfate capsule dosage form was prepared by:
(i) dissolving 6 mg of butylated hydroxytoluene (BHT) in 9756 mg of medium chain triglycerides;
(ii) melting 3600 mg of Lauroyl polyoxylglycerides (Gelucire 44/14) using a water bath (60° C.);
(iii) adding the melted material of step (ii) to the solution of step (i) to obtain uniform solution;
(iv) adding 4638 mg of dasatinib monolauryl sulfate prepared according to the procedure of Example 48A (crystallization Method E) which had been passed through a 60 mesh sieve to the solution of step (iii) to obtain a uniform semi-solid suspension. The semi-solid suspension was filled into size 1 hard gelatin capsule. The composition of the capsule content is as follows:

| | mg | wt % |
|---|---|---|
| Dasatinib monolauryl sulfate | 30.92 | 25.77 |
| Medium chain triglycerides | 65.04 | 54.20 |
| Lauroyl polyoxylglycerides (Gelucire 44/14) | 24.00 | 20.00 |
| Butylated hydroxytoluene (BHT) | 0.04 | 0.03 |
| Total | 120.00 | 100.00 |

Example 53A

The capsules prepared in Example 53 containing dasatinib monolauryl sulfate were administered to four (4) healthy subjects under fasted conditions. This administration was a single dose, open-label, randomized, 2-treatment, 2-sequence, 2-period crossover bioavailability study in healthy subjects under fasted conditions. All subjects were randomized to the sequences as shown in the following table with a 3-day washout period between the periods. The Reference drug (Ref) was Sprycel®, Dasatinib monohydrate, with a strength of 50 mg (free base) while the Test drug (Test) was a capsule prepared according to the procedure of Example 53 but containing approximately 20 mg of dasatinib (free base). The four (4) healthy subjects enrolled in this study were randomized to one of the sequences as shown in the following table.

| Sequence | Period I | Period II |
|---|---|---|
| 1 | Tfast | Rfast |

During each treatment period, blood samples were taken at 0 (prior to the dosing), 0.33, 0.67, 1, 1.5, 2, 2.5, 3, 4, 6, 8, 12 and 24 hours after dosing. $AUC_{0-24}$, $AUC_{0-\infty}$, $C_{max}$, $T_{max}$, and $T_{1/2}$ were determined for each subject based on non-compartmental analyses. The results were summarized in the following table:

The Pharmacokinetic Parameters for Reference and Test Formulations (Normalized to 50 mg Dose)

| Treatment | Parameters | 50 mg dose Mean |
|---|---|---|
| Ref $_{Fasted}$ | $C_{max}$ (ng/mL) | 84.4 |
| | $AUC_{0-24}$ (ng-h/mL) | 246 |
| | $AUC_{0-\infty}$ (ng·h/mL) | 250 |
| Test $_{Fasted}$ | $C_{max}$ (ng/mL) | 81.5 |
| | $AUC_{0-24}$ (ng-h/mL) | 242 |
| | $AUC_{0-\infty}$ (ng·h/mL) | 246 |

* Ref $_{Fasted}$: Sprycel ® Tab 50 mg under fasted condition
* Test $_{Fasted}$: Test drug (Test) 20 mg under fasted condition Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following table:

The Comparisons Between Test$_{Fasted}$ vs. Reference$_{Fasted}$ (Normalized to 50 mg Dose)

| Comparisons | Parameters | Geometric Mean Ratios |
|---|---|---|
| Test~Ref (Fasted) | $C_{max}$ (ng/mL) | 99.43% |
| | $AUC_{0-24}$ (ng·h/mL) | 97.85% |
| | $AUC_{0-\infty}$ (ng·h/mL) | 97.93% |

The data shows that the compositions of the present invention exhibit a decrease of $C_{max}$ by 0.99 fold and a decrease of AUC by 0.98 fold compared to the U.S. FDA approved dasatinib monohydrate.

Figure 24:
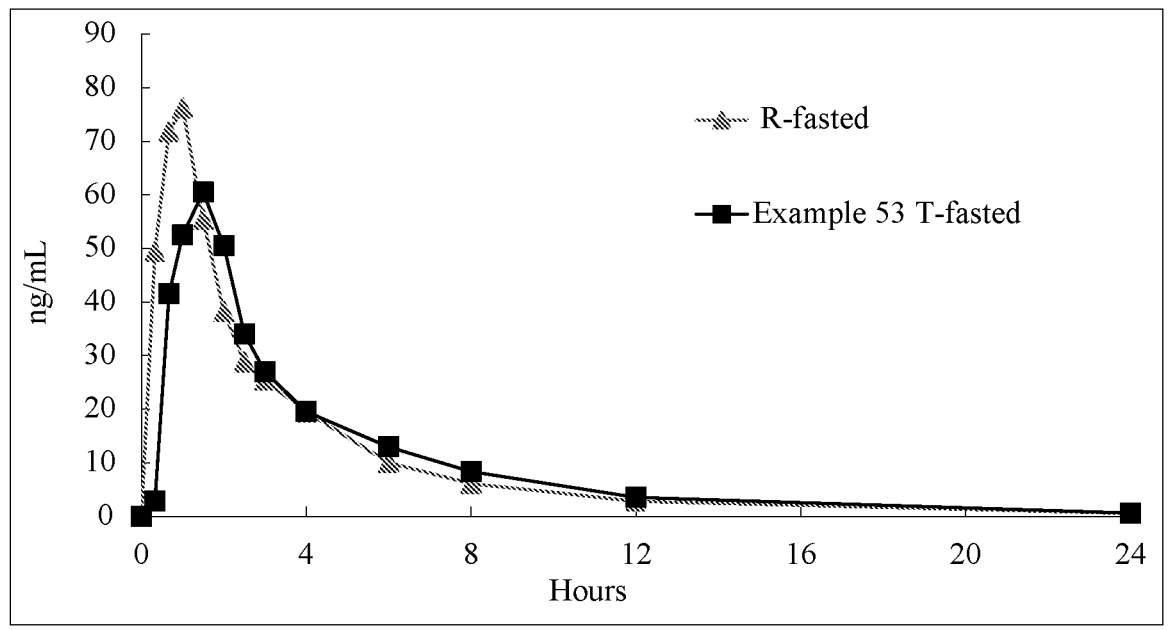
FIG. 24 is a graph of the mean in vivo plasma data provided in Example 53A.

A graph of the mean plasma profiles for this Example is shown in FIG. 24.

The individual subject data of 50 mg dose obtained from the study was as follows:

Reference Drug (Sprycel®) Under Fasted Condition (Concentration (ng/mL))

| Time (hr) | Subject 1 | 2 | 3 | 4 | Mean | SD | CV % |
|---|---|---|---|---|---|---|---|
| 0 | 0 | 0 | 0 | 0 | 0 | 0 | — |
| 0.33 | 22.7 | 126 | 41.3 | 7.42 | 49.4 | 52.9 | 107.3 |
| 0.67 | 30.2 | 131 | 74.1 | 52 | 71.8 | 43.3 | 60.3 |
| 1 | 23.7 | 105 | 80.1 | 96.1 | 76.2 | 36.5 | 47.9 |
| 1.5 | 19.3 | 75.2 | 67.7 | 59.3 | 55.4 | 24.9 | 45 |
| 2 | 13.8 | 57.9 | 46.2 | 35 | 38.2 | 18.8 | 49.1 |
| 2.5 | 13 | 45.6 | 34.1 | 22.6 | 28.8 | 14.1 | 49 |
| 3 | 14.8 | 35.1 | 31.8 | 19.7 | 25.4 | 9.66 | 38.1 |
| 4 | 19.2 | 26 | 17.8 | 15.1 | 19.5 | 4.64 | 23.8 |
| 6 | 9.06 | 15.2 | 8.02 | 7.7 | 10 | 3.52 | 35.2 |
| 8 | 5.52 | 9.51 | 5.39 | 4.01 | 6.11 | 2.37 | 38.8 |

-continued

| Time | Subject | | | | | | |
|---|---|---|---|---|---|---|---|
| (hr) | 1 | 2 | 3 | 4 | Mean | SD | CV % |
| 12 | 2.29 | 4.67 | 2.18 | 2.13 | 2.82 | 1.24 | 43.9 |
| 24 | 0.469 | 0.9 | 0.428 | 0.397 | 0.549 | 0.236 | 43.1 |

Test Drug (Example 53) Under Fasted Condition (Concentration (ng/mL) (Normalized to 50 mg Dose)

| Time | Subject | | | | | | |
|---|---|---|---|---|---|---|---|
| (hr) | 1 | 2 | 3 | 4 | Mean | SD | CV % |
| 0 | 0 | 0 | 0 | 0 | 0 | 0 | — |
| 0.33 | 0.545 | 8.525 | 2.47 | 0 | 2.875 | 3.9 | 135.4 |
| 0.67 | 4.975 | 47.5 | 113.25 | 0.4525 | 41.5 | 52.25 | 125.9 |
| 1 | 14.925 | 96.25 | 69.5 | 29.75 | 52.5 | 37 | 70.6 |
| 1.5 | 32.25 | 117.5 | 42.25 | 50.25 | 60.5 | 38.75 | 63.8 |
| 2 | 44.5 | 83.75 | 33.75 | 40.25 | 50.5 | 22.55 | 44.6 |
| 2.5 | 26.5 | 58.25 | 24.525 | 27 | 34 | 16.15 | 47.4 |
| 3 | 19.15 | 47.5 | 21.95 | 19.45 | 27 | 13.725 | 50.8 |
| 4 | 13.55 | 35.75 | 15.3 | 13.575 | 19.55 | 10.825 | 55.4 |
| 6 | 15.975 | 18.225 | 6.95 | 10.65 | 12.95 | 5.1 | 39.4 |
| 8 | 9.4 | 13.025 | 4.8 | 6.15 | 8.35 | 3.675 | 44.0 |
| 12 | 3.275 | 6.175 | 2.1875 | 2.4575 | 3.525 | 1.8275 | 51.8 |
| 24 | 0.495 | 1.065 | 0.4325 | 0.4875 | 0.62 | 0.2975 | 48.1 |

Example 54

The following impurities were identified as being present in the dasatinib monolauryl sulfate prepared according to Examples 12 and 47.

| Impurity | Chemicals name | Molecular structure | Process/Degradation impurity | Limit |
|---|---|---|---|---|
| Impurity 1 (RRT 0.72) | 2-amino-N(2-chloro-6-methylphenyl)-5-thiazolecarboxamine | 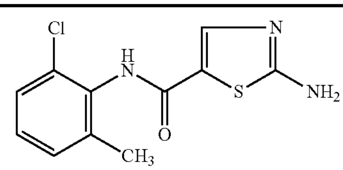 | Process related impurity | NMT 0.20%, preferably NMT 0.15% and most preferably NMT 0.10% |
| Impurity 2 (RRT 0.94) | N-(2-chloro-6-methylphenyl)-2-[[6-[-1-piperazinyl]-2-methyl-4-pyrimidinyl]amino]-5-thiazolecarboxamide | 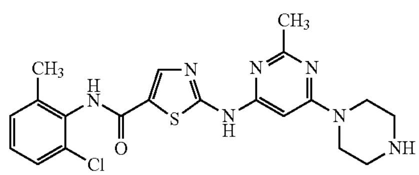 [SMILES: Cc1nc(Nc2ncc(C(=O)Nc3c(C)cccc3Cl)s2)cc(N2CCNCC2)n1] | Process related impurity | NMT 0.20%, preferably NMT 0.15% and most preferably NMT 0.10% |
| Impurity 3 (RRT 0.96) (Dasatinib N-oxide) | N-[2-Chloro-6-methylphenyl]-2-[[6-[4-(2-hydroxyethyl)-1-piperazinyl]-2-methyl-4-pyrimidinyl]amino]-5-thiazolecarboxamide N-Oxide | 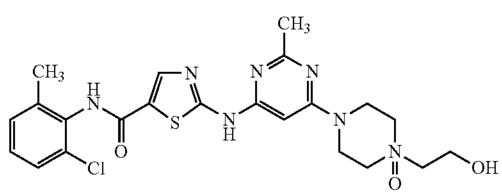 [SMILES: Cc1nc(Nc2ncc(C(=O)Nc3c(C)cccc3Cl)s2)cc(N2CC[N+]([O-])(CCO)CC2)n1] | Degradation (oxidation degradant) | NMT 0.20%, preferably NMT 0.15% and most preferably NMT 0.10% |
| Impurity 4 (RRT 1.10) | 2-chloro-6-methylaniline | 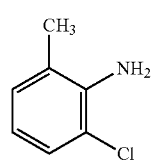 | Process related impurity | NMT 0.20%, preferably NMT 0.15% and most preferably NMT 0.10% |

-continued

| Impurity | Chemicals name | Molecular structure | Process/Degradation impurity | Limit |
|---|---|---|---|---|
| Impurity 5 (RRT 1.28) | 2-(6-chloro-2-methylpyrimidin-4-ylamino}-N-(2-chloro-6-methylphenyl)thiazole-5-carboxamide | 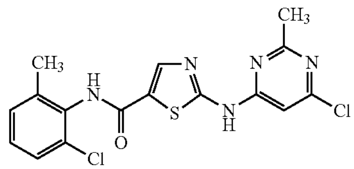 [SMILES: Cc1nc(Cl)cc(Nc2ncc(C(=O)Nc3c(C)cccc3Cl)s2)n1] | Process related impurity | NMT 0.20%, preferably NMT 0.15% and most preferably NMT 0.10% |

NMT = Not More Than

The RRT was determined using HPLC with the following parameters:

| Parameter | Setting/Description |
|---|---|
| System | HPLC Equipped with a UV/Vis Detector |
| Column | YMC Pack Pro ® C18, 3 µm, 4.6 × 150 mm |
| Detection | UV at 320 nm |
| Flow rate | 1.2 mL/min |
| Injection volume | 6 µL |
| Column temperature | 35° C. |
| Sample temperature | Ambient |
| Run time | 55 minutes |

| Mode of Analysis | Gradient as shown below: | | |
|---|---|---|---|
| | Time (min) | Mobile phase A | Mobile phase B |
| | 0 | 100 | 0 |
| | 2 | 100 | 0 |
| | 30 | 63 | 37 |
| | 38 | 40 | 60 |
| | 46 | 0 | 100 |
| | 48 | 0 | 100 |
| | 48.5 | 100 | 0 |
| | 55 | 100 | 0 |

The mobile phase A was 0.05 M aqueous Ammonium Acetate (pH 5.25)/Acetonitrile/Methanol in a volume ratio of 90/5/5.

The mobile phase B was 0.05 M aqueous Ammonium Acetate (pH 5.25)/Acetonitrile/Methanol in a volume ratio of 10/85/5.

The dosage forms prepared in Examples 49, 51-52 and the dasatinib lauryl sulfate salt prepared in Examples 12-13 were tested for impurities and stability using the above HPLC method.

The test samples were prepared by respectively weighing approximately 30.92 mg of dasatinib monolauryl sulfate or 41.84 mg of dasatinib dilauryl sulfate (equivalent to 20 mg of Dasatinib) into a 100 mL amber volumetric flask, adding about 80 mL of methanol, sonicating for about 5 minutes and stirring at about 800 rpms for about 5 minutes until fully dissolved. Additional methanol is added so the test sample is approximately 0.20 mg of dasatinib per mL.

The results of the testing were as follows:

| | | RRT | | | | |
|---|---|---|---|---|---|---|
| | | 0.72 (DAS-5) | 0.87 | 0.94 (DAS PIP) | 0.96 | 1.10 (2-Chloro-6-methylaniline) | 1.31 (DAS-6) |
| Example 12 | Initial | — | 0.02 | 0.02 | 0.09 | 0.02 | 0.02 |
| | 40° C./75% R.H., 1 Month | — | — | — | 0.09 | 0.04 | 0.02 |
| | 40° C./75% R.H., 3 Months | — | 0.02 | 0.03 | 0.10 | 0.03 | 0.03 |
| Example 13 | Initial | — | 0.06 | 0.09 | 0.13 | — | 0.02 |
| | 40° C./75% R.H., 1 Month | — | 0.06 | 0.09 | 0.14 | — | 0.04 |

|  |  | RRT | | | | | |
| --- | --- | --- | --- | --- | --- | --- | --- |
|  |  | 0.72 (DAS-5) | 0.87 | 0.94 (DAS PIP) | 0.96 | 1.10 (2-Chloro-6-methylaniline) | 1.31 (DAS-6) |
| Example 49 | Initial | — | 0.03 | 0.03 | 0.09 | 0.03 | 0.03 |
|  | 40° C./75% R.H., 1 Month | — | 0.02 | — | 0.10 | 0.02 | 0.03 |
|  | 40° C./75% R.H., 3 Months | — | 0.04 | 0.02 | 0.09 | — | 0.03 |
| Example 51 | Room temp. | — | 0.02 | 0.02 | 0.04 | 0.02 | — |
|  | 40° C./75% R.H., 1 Month | — | — | — | 0.02 | 0.03 | — |
| Example 52 | Room temp. | — | 0.03 | 0.02 | 0.10 | 0.02 | 0.02 |
|  | 40° C./75% R.H., 1 Month | — | 0.04 | 0.02 | 0.07 | 0.02 | 0.02 |

The dasatinib monolauryl sulfate capsule was determined to have NMT 0.5% of any individual impurity 1, 2, 3, 4, or 5, preferably not more than 0.35% of any individual impurity and most preferably not more than 0.25% of any individual impurity and the total impurity should not be more than 1.0%, preferably not more than 0.75% and most preferably not more than 0.60%.

The dasatinib monolauryl sulfate capsule should release not less than 90%, preferably not less than 85% and most preferably not less than 80% of the dasatinib within 45 minutes of in vitro testing using a USP Type II Apparatus (Paddle) with 500 ml of 0.1 N HCl at 75 rpm, with or without a sinker and 37° C.

Example 55

A dasatinib monolauryl sulfate capsule dosage form was prepared by blending dasatinib monolauryl sulfate prepared according to the procedure of Example 48 A (crystallization Method E) with the identified excipients and filled into hard gelatin capsules in the amounts indicated:

|  | A (mg/capsule) | B (mg/capsule) | C (mg/capsule) | D (mg/capsule) |
| --- | --- | --- | --- | --- |
| Dasatinib Monolauryl Sulfate | 77.3 | 77.3 | 77.3 | 77.3 |
| Medium Chain Triglyceride (Captex ® 300) | 251.8 | 209.7 | 209.7 |  |
| Caprylocaproyl Polyoxylglycerides (Acconon MC8-2) |  |  |  | 209.7 |
| Butylated Hydroxytoluene | 0.1 | 0.1 | 0.1 | 0.1 |
| Lauroyl Polyoxyl-32 glycerides (Gelucire 44/14) | 28.0 |  |  |  |
| Polysorbate 80 |  | 70.0 |  | 70.0 |
| Polyoxy 1 35 Castor Oil (Kolliphor EL) |  |  | 70.0 |  |
| Total | 357.2 | 357.1 | 357.1 | 357.1 |

Example 55E

A dasatinib monolauryl sulfate capsule dosage form was prepared by adding dasatinib monolauryl sulfate prepared according to the procedure of Example 48 A (crystallization Method E) to melted polyoxyl stearate Type I (Gelucire 48/16). The composition was cooled and mixed with microcrystalline cellulose, hydrogenated vegetable oil (LUBRITAB) and colloidal silicon dioxide and filled in size 2 hard gelatin capsules with the contents of the capsule having the following composition:

|  | mg | wt % |
| --- | --- | --- |
| Dasatinib monolauryl sulfate, DSB-1LSC crystalline API (EQ to 50 mg DSB free base) | 77.30 | 42.94 |
| Polyoxyl stearate Type 1 (Gelucire 48/16) | 62.50 | 34.72 |
| Microcrystalline cellulose | 29.20 | 16.22 |
| Lubritab | 9.00 | 5.00 |
| Colloidal silicon dioxide | 2.00 | 1.11 |
| Total | 180.00 | 100.00 |

Example 55F

A dasatinib monolauryl sulfate capsule dosage form was prepared by the procedure of Example 55, except the Lauroyl polyoxylglycerides was replaced with polyoxyl stearate Type I (Gelucire 48/16). The capsule had the following composition:

|  | mg | wt % |
| --- | --- | --- |
| Dasatinib monolauryl sulfate (DSB-ILS) | 77.30 | 25.77 |
| Medium chain triglycerides (Captex ® 300) | 162.60 | 54.20 |
| Polyoxyl stearate Type I (Gelucire 48/16) | 60.00 | 20.00 |
| Butylated hydroxytoluene (BHT) | 0.10 | 0.03 |
| Total | 300.00 | 100.00 |

Example 56

The dosage forms prepared in Examples 49, 51, 52, 53, and 55 were tested using a USP Type II Apparatus (Paddle) with 500 ml of 0.1 N HCl at 75 rpm, with a sinker and 37° C. The results of this dissolution testing are as follows:

| | Time (minutes) | | | | | | | |
|---|---|---|---|---|---|---|---|---|
| | 5 | 10 | 15 | 30 | 45 | 60 | 120 | (n) |
| Ex 49 | 18.1 | 40.6 | 54.2 | 75.7 | 80.4 | 81.9 | 84.6 | 3 |
| Ex 51 | 20.6 | 47.3 | 61.3 | 75.5 | 78.4 | 79.5 | 82.1 | 5 |
| Ex 52 | 3.9 | 15.1 | 21.3 | 31.7 | 37.6 | 41.7 | 51.8 | 2 |
| Ex 53 | 1.9 | 27.2 | 58.0 | 89.7 | 92.7 | 94.1 | 96.3 | 2 |
| Ex 55 A | | | 36.2 | | | 59.0 | 61.9 | 2 |
| Ex 55 B | | | 91.2 | | | 94.0 | 95.8 | 2 |
| Ex 55 C | | | 83.7 | | | 96.3 | 96.4 | 2 |
| Ex 55 D | | | 93.7 | | | 93.4 | 92.5 | 2 |
| Ex 55 E | | 35.3 | 48.7 | 72.3 | 83.4 | 87.6 | 92.1 | 3 |
| Ex 55 F | 7.2 | 41.5 | 68.9 | 93.8 | 95.4 | 96.1 | 99.5 | 2 |

Example 57

Following table describes the contents of dasatinib monolauryl sulfate capsules prepared by dissolving the dasatinib monolauryl sulfate (according to the procedure of Example 48 A-crystallization Method E) with the indicated excipients and solvents; evaporating the solvent to form granules and blending the granules with the extra granular excipients to form a blend which is filled into hard gelatin capsules:

The dosage prepared in Example 57 were tested using a USP Type II Apparatus (Paddle) with 500 ml of 0.1 N HCl at 75 rpm, with a sinker and 37° C. The results of this dissolution testing are as follows:

| | Time (minutes) | | | | | | | |
|---|---|---|---|---|---|---|---|---|
| | 5 | 10 | 15 | 30 | 45 | 60 | 120 | (n) |
| Ex 57 A | 30.3 | 48.7 | 59.5 | 66.3 | 68.4 | 69.8 | 71.3 | 2 |
| Ex 57 B | 0.3 | 13.0 | 32.3 | 52.4 | 58.8 | 61.9 | 65.3 | 3 |
| Ex 57 C | 16.2 | 41.8 | 58.6 | 74.4 | 82.1 | 85.4 | 89.1 | 2 |
| Ex 57 D | 6.2 | 19.3 | 33.9 | 58.8 | 74.5 | 84.0 | 93.3 | 2 |
| Ex 57 E | 4.0 | 14.67 | 31.17 | 62.35 | 78.03 | 85.74 | 97.76 | 2 |

Example 58

Following table describes the contents of dasatinib monolauryl sulfate capsules prepared by wet granulation similar to the procedures described in Examples 33, 49 and 55 dissolving the dasatinib monolauryl sulfate (according to the procedure of Example 48 A-crystallization Method E) with the indicated excipients and solvents; evaporating the solvent to form granules and blending the granules with the extra granular excipients to form a blend which is filled into hard gelatin capsules:

| | A (mg/capsule) | B (mg/capsule) | C (mg/capsule) | D (mg/capsule) | E (mg/capsule) |
|---|---|---|---|---|---|
| Granules | | | | | |
| Dasatinib monolauryl sulfate (DSB-1LS) | 77.30 | 77.30 | 77.30 | 77.3 | 77.3 |
| Poloxamer 407 | 30.00 | | | | |
| Poloxamer 188 | 25.00 | | | | |
| Povidone K 30 | | 77.30 | 77.3 | | |
| Hypromellose (603) | | | | 77.3 | |
| Anhydrous lactose | | | | | 95.2 |
| Polyoxyl stearate Type I (Gelucire 48/16) | | | 62.5 | 62.5 | 62.5 |
| Solvent | | | | | |
| | Methanol | Alcohol (95%) | Alcohol (95%) | Alcohol (95%)/Purified water (ratio 11.1:1) | Alcohol (95%)/Purified water (ratio 0.92:1) |
| Extra granular | | | | | |
| Anhydrous lactose | 25.0 | 35.4 | 17.9 | 17.9 | |
| Microcrystalline cellulose | 75.2 | | | | |
| Sodium starch glycolate | 10.0 | | | | |
| Colloidal silicon dioxide | 5.0 | | | | |
| Magnesium stearate | 2.5 | | | | |
| Crospovidone X-10 | | 10.0 | 15.0 | 15.0 | 15.0 |
| Total | 250.0 | 200.0 | 250.0 | 250.0 | 250 |

|  | A | B | C | D | E | F | G |
|---|---|---|---|---|---|---|---|
|  |  |  | (mg/capsule) |  |  |  |  |
|  |  |  | Granules |  |  |  |  |
| DSB-1LS | 77.30 | 77.30 | 77.30 | 77.3 | 30.92 | 30.92 | 77.3 |
| Poloxamer 407 | 30.0 | 30.0 |  |  |  |  |  |
| Poloxamer 188 | 25.0 | 25.0 |  |  |  |  |  |
| Caprolactam-polyvinyl acetate-polyethylene glycol graft copolymer |  |  |  |  |  | 10.0 |  |
| Sodium Lauryl Sulfate | 25.0 |  |  |  | 10.0 |  |  |
| Docusate sodium |  | 11.0 |  |  |  |  |  |
| Hydroxypropyl cellulose (HPC-H) | 7.5 | 7.5 |  |  |  |  |  |
| Microcrystalline cellulose | 67.7 | 81.7 |  |  | 21.48 | 21.48 | 72.70 |
| Mannitol |  |  | 47.7 | 85.2 |  |  |  |
| Anhydrous lactose |  |  |  |  | 12.0 | 12.0 |  |
| Sodium starch glycolate | 5.0 | 5.0 | 5.0 |  | 1.6 | 1.6 | 5.0 |
| Colloidal Silicon Dioxide | 2.5 | 2.5 |  |  | 0.8 | 0.8 |  |
| Lubritab |  |  | 62.5 |  |  |  |  |
| Polyoxyl stearate Type I (Gelucire 48/16) |  |  | 37.5 | 62.5 |  |  | 50.0* |
| Granulating fluid | Alcohol (95%)/water (ratio 1:1) | Alcohol (95%)/water (ratio 1:1) | Alcohol (95%) | Alcohol (95%) | Alcohol (95%)/water (ratio 1:1) | Alcohol (95%)/water (ratio 1:1) | water |
|  |  |  | Extra Granular |  |  |  |  |
| Sodium starch glycolate | 5.0 | 5.0 | 12.5 |  | 1.6 | 1.6 | 12.5 |
| Colloidal Silicon Dioxide | 2.5 | 2.5 | 5.0 |  | 0.8 | 0.8 | 5.0 |
| Magnesium stearate | 2.5 | 2.5 | 2.5 |  | 0.8 | 0.8 |  |
| Sodium stearyl fumarate |  |  |  |  |  |  | 2.5 |
| Carnauba wax |  |  |  | 25.0 |  |  |  |
| Microcrystalline cellulose |  |  |  |  |  |  | 25.0 |
| Total | 250 | 250 | 250 | 250 | 80 | 80 | 250 |

*dissolved in the granulating fluid

The dosage prepared in Example 58 were tested using a USP Type II Apparatus (Paddle) with 500 ml of 0.1 N HCl at 75 rpm, with a sinker and 37° C. The results of this dissolution testing are as follows:

|  | Time (minutes) | | | | | | | |
|---|---|---|---|---|---|---|---|---|
|  | 5 | 10 | 15 | 30 | 45 | 60 | 120 | (n) |
| Ex 58 A | 5.3 | 16.7 | 25.4 | 40.0 | 46.9 | 50.4 | 56.2 | 2 |
| Ex 58 B | 18.4 | 35.3 | 43.0 | 53.3 | 59.8 | 63.7 | 71.7 | 2 |
| Ex 58 C | 34.02 | 71.06 | 77.98 | 85.24 | 86.8 | 88.65 | 90.67 | 3 |
| Ex 58 D | 9.19 | 33.83 | 54.74 | 86.91 | 90.10 | 91.13 | 92.54 | 2 |
| Ex 58 E | 1.3 | 5.9 | 11.3 | 27.2 | 37.9 | 43.8 | 57.2 | 2 |
| Ex 58 F | 7.7 | 26.2 | 32.1 | 41.4 | 47.7 | 52.5 | 70.6 | 1 |
| Ex 58 G | 18.14 | 50.54 | 64.59 | 84.12 | 89.59 | 90.64 | 93.00 | 2 |

Example 59A

A dasatinib monolauryl sulfate capsule dosage form was prepared by grinding and mixing the 2319 mg of dasatinib monolauryl sulfate prepared according to the procedure of Example 48 A-crystallization Method E with 1500 mg of polyoxyl stearate Type I (Gelucire 48/16), 375 mg of poloxamer 407, 1806 mg of microcrystalline cellulose and 150 mg of sodium starch glycolate (I) in a small mixer for 15 second. Added 600 mg of purified water into the mixer and granulated for 15 second. Dried the mixture in the oven at 50° C. to evaporate the water, ground into powder and passed through 40 mesh sieve. Passed 750 mg of microcrystalline cellulose, 375 mg of sodium starch glycolate (II) and 150 mg of colloidal silicon dioxide through 40 mesh sieve, mixed well with the mixture. Passed 75 mg of sodium stearyl fumarate through 40 mesh sieve into the container and blended with powder to obtain final blend. The dry solid blend was filled into size 1 hard gelatin capsule.

The composition of the capsule content is as follows:

|  | mg | wt % |
|---|---|---|
| Dasatinib monolauryl sulfate | 77.30 | 30.92 |
| Polyoxyl stearate Type I (Gelucire 48/16) | 50.00 | 20.00 |
| Poloxamer 407 | 12.50 | 5.00 |
| Microcrystalline cellulose | 60.20 | 24.08 |
| Sodium starch glycolate (I) | 5.00 | 2.00 |
| Microcrystalline cellulose | 25.00 | 10.00 |
| Sodium starch glycolate (II) | 12.50 | 5.00 |

-continued

|  | mg | wt % |
| --- | --- | --- |
| Colloidal silicon dioxide | 5.00 | 2.00 |
| Sodium stearyl fumarate | 2.50 | 1.00 |
| Total | 250.00 | 100.00 |
| Purified water | 20.00 | N/A |

Example 59B

A dasatinib monolauryl sulfate capsule dosage form with the following composition was prepared by a procedure similar to that described in Example 59A:

The composition of the capsule content is as follows:

|  | mg | wt % |
| --- | --- | --- |
| Dasatinib monolauryl sulfate | 77.30 | 38.65 |
| Polyoxyl stearate Type I (Gelucire 48/16) | 48.00 | 24.00 |
| Poloxamer 407 | 10.00 | 5.00 |
| Microcrystalline cellulose | 34.00 | 17.00 |
| Sodium starch glycolate (I) | 4.00 | 2.00 |
| Microcrystalline cellulose | 18.70 | 9.35 |
| Sodium starch glycolate (II) | 5.00 | 2.50 |
| Colloidal silicon dioxide | 2.00 | 1.00 |
| Sodium stearyl fumarate | 1.00 | 0.50 |
| Total | 200.00 | 100.00 |
| Purified water | 15.00 | N/A |

Example 59C

A dasatinib monolauryl sulfate capsule dosage form with the following composition was prepared by a procedure similar to that described in Example 59A:

The composition of the capsule content is as follows:

|  | mg | wt % |
| --- | --- | --- |
| Dasatinib monolauryl sulfate, DSB-1LSC crystalline API (EQ to 50 mg DSB free base) | 77.30 | 38.65 |
| Polyoxyl stearate Type I (Gelucire 48/16) | 48.00 | 24.00 |
| Poloxamer 407 | 12.00 | 6.00 |
| Microcrystalline cellulose | 34.00 | 17.00 |
| Povidone K30 | 2.00 | 1.00 |
| Microcrystalline cellulose | 18.70 | 9.35 |
| Sodium starch glycolate | 5.00 | 2.50 |
| Colloidal silicon dioxide | 2.00 | 1.00 |
| Sodium stearyl fumarate | 1.00 | 0.50 |
| Total | 200.00 | 100.00 |
| Purified water | 15.00 | N/A |

The dosage prepared in Example 59A-59C were tested using a USP Type II Apparatus (Paddle) with 500 ml of 0.1 N HCl at 75 rpm, with a sinker and 37° C. The results of this dissolution testing are as follows:

|  | Time (minutes) | | | | | | | |
| --- | --- | --- | --- | --- | --- | --- | --- | --- |
|  | 5 | 10 | 15 | 30 | 45 | 60 | 120 | (n) |
| Ex 59A | 31.83 | 66.56 | 76.54 | 81.26 | 83.19 | 84.92 | 87.08 | 2 |
| Ex 59 B | 13.29 | 28.85 | 40.43 | 69.57 | 82.66 | 86.96 | 90.32 | 2 |
| Ex 59 C | 6.87 | 28.81 | 46.59 | 76.05 | 84.99 | 87.16 | 90.11 | 2 |

Example 60

Nilotinib monolauryl sulfate capsules were prepared according to the procedure outlined in Example 36 with the following compositions:

|  | A (mg) | B (mg) | C (mg) | D (mg) | E (mg) | F (mg) | G (mg) | H (mg) | I (mg) |
| --- | --- | --- | --- | --- | --- | --- | --- | --- | --- |
| Nilotinib MonoLauryl Sulfate | 120 | 120 | 120 | 120 | 120 | 120 | 120 | 120 | 120 |
| Glyceryl Caprylate/Caprate | 424 | 424 | 424 | 424 | 551.2 | 551.2 | 424 | 551.2 | 551.2 |
| Polyoxyl 35 Castor Oil | 106 |  | 106 | 212 | 137.8 | 137.8 | 212 | 137.8 | 137.8 |
| Hard Fat |  |  |  |  |  |  |  | 18 |  |
| Butylated Hydroxytoluene |  | 0.1 | 0.2 | 0.2 | 0.2 | 0.1 | 0.1 | 0.2 | 0.2 |
| Capsule Type (gelatin-based capsule) | Hard capsule | Hard capsule | Hard capsule | Hard capsule | Hard capsule | Soft capsule | Soft capsule | Hard capsule | Hard capsule |
| Total | 650 | 544.1 | 650.2 | 756.2 | 809.2 | 809.1 | 756.1 | 827.2 | 809.2 |

The dosage forms prepared in Examples 60A-60I were tested using a USP Type II Apparatus (Paddle) with 675 ml of 0.1 N HCl at 75 rpm, with a sinker and 37° C. or using a USP Type II Apparatus (Paddle) with 900 ml of 0.1 N HCl and 0.1% Tween 80 at 75 rpm, with a sinker and 37° C. The results of this dissolution testing are as follows:

Mean Values for Testing in 675 ml of 0.1 N HCl at 75 rpm

| Time (minutes) | A (%) | B (%) | C (%) | D (%) | E (%) | F (%) | G (%) | H (%) | I (%) |
|---|---|---|---|---|---|---|---|---|---|
| 15 |  | 3.5 | 17.3 | 19.5 | 31.5 | 28.6 | 21.4 | 18.4 | 24.9 |
| 30 |  | 12.3 | 27.6 | 36.0 | 47.3 | 42.8 | 36.9 | 30.6 | 35.2 |
| 60 |  | 28.9 | 41.7 | 55.7 | 58.8 | 64.9 | 61.3 | 50.2 | 48.2 |
| 120 |  | 51.4 | 57.0 | 67.4 | 59.9 | 67.9 | 70.2 | 59.0 | 62.7 |
| n |  | (2) | (2) | (2) | (2) | (3) | (3) | (2) | (3) |

Mean Values for Testing in 900 ml of 0.1 N HCl and 0.1% Tween 80

| Time (minutes) | A (%) | B (%) | C (%) | D (%) | E (%) | F (%) | G (%) | H (%) | I (%) |
|---|---|---|---|---|---|---|---|---|---|
| 15 |  |  |  |  |  | 27.0 | 25.5 | 20.4 | 39.1 |
| 30 |  |  |  |  |  | 48.1 | 45.4 | 39.6 | 67.8 |
| 60 |  |  |  |  |  | 80.7 | 73.7 | 66.8 | 89.8 |
| 120 |  |  |  |  |  | 99.4 | 98.7 | 95.5 | 97.5 |
| n |  |  |  |  |  | (3) | (3) | (3) | (3) |

Example 61A

The capsule prepared in Example 60A containing nilotinib monolauryl sulfate were administered to nine (9) healthy subjects under fasted and fed conditions. The study was a randomized, open-label, single dose, three treatment, three sequences, three periods, and crossover design with at least a 5-day washout period between doses. The Reference drug (Ref) was TASIGNA® Capsule, nilotinib HCl, with strength of 200 mg (free base) while the Test drug (Test) was a capsule prepared according to the procedure of Example 60A but containing approximately 80 mg free base of nilotinib. The nine (9) healthy subjects enrolled in this study were randomized to one of the sequences as shown in the following table.

|  | Period I | Period II | Period III |
|---|---|---|---|
| Sequence 1 | Ref (fasted) | Test (fasted) | Test (fed) |
| Sequence 2 | Test (fed) | Ref (fasted) | Test (fasted) |
| Sequence 3 | Test (fasted) | Test (fed) | Ref (fasted) |

During each treatment period, blood samples were taken at 0 (prior to the dosing), 0.5, 1, 2, 3, 4, 5, 6, 8, 10, 12, 14, 24, 36 and 48 hours after dosing. $AUC_{0-48}$, $AUC_{0-\infty}$, $C_{max}$, $T_{max}$, and $T_{1/2}$ were determined for each subject based on non-compartmental analyses. The results were normalized to 200 mg dose and are summarized in the following Table:

The Pharmacokinetic Parameters for Reference and Test Formulations (Normalized to 200 mg Dose)

| Treatment | Parameters | Normalized to 200 mg dose Mean |
|---|---|---|
| $Ref_{Fasted}$ | $C_{max}$ (ng/mL) | 486 |
|  | $AUC_{0-48}$ (ng · h/mL) | 7108 |
|  | $AUC_{0-\infty}$ (ng · h/mL) | 7628 |
| $Test_{Fasted}$ | $C_{max}$ (ng/mL) | 1142 |
|  | $AUC_{0-48}$ (ng · h/mL) | 13990 |
|  | $AUC_{0-\infty}$ (ng · h/mL) | 14719 |
| $Test_{Fed}$ | $C_{max}$ (ng/mL) | 1090 |
|  | $AUC_{0-48}$ (ng · h/mL) | 16448 |
|  | $AUC_{0-\infty}$ (ng · h/mL) | 17815 |

$Ref_{Fasted}$: Tasigna Capsule 200 mg (free base) under fasted condition
$Test_{Fasted}$: Test drug (Test) 80 mg (free base) under fasted condition
$Test_{Fed}$: Test drug (Test) 80 mg (free base) under fed condition Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following Table:

The Comparisons Between Test Vs. Reference and $Test_{Fed}$ vs. $Test_{Fasted}$ (Normalized to 200 mg Dose)

| Comparisons | Parameters | Geometric Mean Ratios | 90% Confidence Intervals |
|---|---|---|---|
| Test~Ref (Fasted) | $C_{max}$ (ng/mL) | 246.73% | 193.71%~314.26% |
|  | $AUC_{0-48}$ (ng · h/mL) | 196.60% | 168.20%~229.80% |
|  | $AUC_{0-\infty}$ (ng · h/mL) | 192.92% | 165.56%~224.81% |
| $Test_{Fed}$~$Test_{Fasted}$ | $C_{max}$ (ng/mL) | 94.70% | 74.35%~120.62% |
|  | $AUC_{0-48}$ (ng · h/mL) | 119.05% | 101.85%~139.15% |
|  | $AUC_{0-\infty}$ (ng · h/mL) | 122.10% | 104.78%~142.28% |

The data shows that the compositions of the present invention exhibit an increase of $C_{max}$ by 2.5 fold and an increase of AUC by 2.0 fold compared to the U.S. FDA approved nilotinib HCl. The data also shows that the compositions of the present invention do not exhibit a food effect i.e., the compositions of the present invention exhibit comparable pharmacokinetics under fasted and fed conditions.

The individual subject data (Normalized to 200 mg dose) obtained from the study is as follows:

Reference Drug (TASIGNA®) Under Fasted Condition (Concentration (ng/mL))

| Time (hr) | Subject | | | | | | | | |
|---|---|---|---|---|---|---|---|---|---|
|  | 1 | 2 | 3 | 4 | 5 | 6 | 7 | 8 | 9 |
| 0 | 0 | 0 | 0 | 0 | 0 | 0 | 0 | 0 | 0 |
| 0.5 | 33.3 | 54.2 | 54.1 | 41.5 | 105 | 72.0 | 43.5 | 67.6 | 41.4 |
| 1 | 132 | 187 | 276 | 148 | 467 | 255 | 198 | 200 | 207 |
| 2 | 281 | 377 | 302 | 272 | 859 | 422 | 467 | 302 | 320 |
| 3 | 310 | 398 | 283 | 307 | 707 | 475 | 688 | 333 | 387 |
| 4 | 352 | 378 | 326 | 314 | 687 | 508 | 821 | 341 | 453 |
| 5 | 284 | 294 | 240 | 244 | 426 | 450 | 605 | 257 | 376 |
| 6 | 269 | 269 | 258 | 225 | 351 | 424 | 529 | 241 | 353 |
| 8 | 256 | 297 | 183 | 192 | 292 | 381 | 456 | 224 | 295 |
| 10 | 230 | 260 | 183 | 182 | 289 | 347 | 527 | 179 | 273 |
| 12 | 198 | 220 | 137 | 164 | 223 | 310 | 379 | 133 | 237 |

-continued

| Time |     |     |     |     | Subject |     |     |     |     |
|------|-----|-----|-----|-----|---------|-----|-----|-----|-----|
| (hr) | 1   | 2   | 3   | 4   | 5       | 6   | 7   | 8   | 9   |
| 14   | 184 | 204 | 120 | 155 | 197     | 289 | 312 | 113 | 216 |
| 24   | 91.7| 134 | 59.6| 77.5| 118     | 214 | 246 | 31.8| 126 |
| 36   | 61.3| 27.5| 21.9| 30.2| 29.3    | 66.1| 133 | 16.5| 79.6|
| 48   | 51.4| BQL | BQL | BQL | BQL     | 22.9| 66.7| 14.9| 24.9|

Test Drug (Example 60 A) Under Fasted Condition (Concentration (ng/mL))

| Time |     |     |     |     | Subject |     |     |     |     |
|------|-----|-----|-----|-----|---------|-----|-----|-----|-----|
| (hr) | 1   | 2   | 3   | 4   | 5       | 6   | 7   | 8   | 9   |
| 0    | 0   | 0   | 0   | 0   | 0       | 0   | 0   | 0   | 0   |
| 0.5  | 111 | 363 | 538 | 188 | 253     | 605 | 91  | 0   | 530 |
| 1    | 483 | 958 | 883 | 863 | 1215    | 1445| 580 | 131 | 888 |
| 2    | 978 | 930 | 1030| 1203| 968     | 1543| 1488| 515 | 998 |
| 3    | 1073| 850 | 998 | 1008| 815     | 1470| 1395| 690 | 935 |
| 4    | 1018| 775 | 1080| 938 | 733     | 1305| 1205| 725 | 888 |
| 5    | 720 | 710 | 963 | 753 | 548     | 1118| 963 | 583 | 710 |
| 6    | 683 | 573 | 783 | 708 | 428     | 985 | 898 | 453 | 628 |
| 8    | 583 | 503 | 623 | 570 | 430     | 870 | 793 | 323 | 598 |
| 10   | 498 | 483 | 645 | 490 | 355     | 815 | 733 | 285 | 525 |
| 12   | 403 | 425 | 463 | 393 | 298     | 705 | 618 | 245 | 415 |
| 14   | 340 | 378 | 420 | 325 | 273     | 685 | 585 | 202 | 348 |
| 24   | 95.3| 207 | 200 | 138 | 152     | 450 | 388 | 45.8| 181 |
| 36   | 36.0| 48.5| 45.8| BQL | 32.8    | 155 | 154 | BQL | 45.5|
| 48   | BQL | BQL | BQL | BQL | BQL     | 78.8| 65.8| BQL | 46.5|

Test Drug (Example 60 A) Under Fed Condition (Concentration (ng/mL))

| Time |     |     |     |     | Subject |     |     |     |     |
|------|-----|-----|-----|-----|---------|-----|-----|-----|-----|
| (hr) | 1   | 2   | 3   | 4   | 5       | 6   | 7   | 8   | 9   |
| 0    | 0   | 0   | 0   | 0   | 0       | 0   | 0   | 0   | 0   |
| 0.5  | 0   | 0   | 0   | 0   | 0       | 50.8| 0   | 0   | 32.5|
| 1    | 103 | 0   | 0   | 64.0| 47.8    | 640 | 0   | 217 | 241 |
| 2    | 330 | 54.5| 200 | 520 | 315     | 1223| 140 | 843 | 748 |
| 3    | 550 | 443 | 838 | 975 | 465     | 1460| 488 | 903 | 935 |
| 4    | 775 | 758 | 1288| 1073| 650     | 1468| 843 | 858 | 1555|
| 5    | 953 | 833 | 1268| 938 | 725     | 1395| 980 | 708 | 1158|
| 6    | 923 | 768 | 980 | 850 | 695     | 1258| 1008| 545 | 1020|
| 8    | 770 | 678 | 818 | 698 | 668     | 1178| 900 | 480 | 763 |
| 10   | 653 | 593 | 778 | 725 | 683     | 993 | 895 | 418 | 753 |
| 12   | 555 | 530 | 650 | 640 | 545     | 890 | 730 | 320 | 645 |
| 14   | 503 | 460 | 548 | 528 | 485     | 808 | 648 | 303 | 545 |
| 24   | 163 | 288 | 315 | 290 | 290     | 585 | 420 | 89.3| 288 |
| 36   | BQL | 60.8| 81.0| 44.5| 82.3    | 320 | 198 | BQL | 66.8|
| 48   | BQL | BQL | BQL | BQL | BQL     | 182 | 109 | BQL | BQL |

Figure 25:
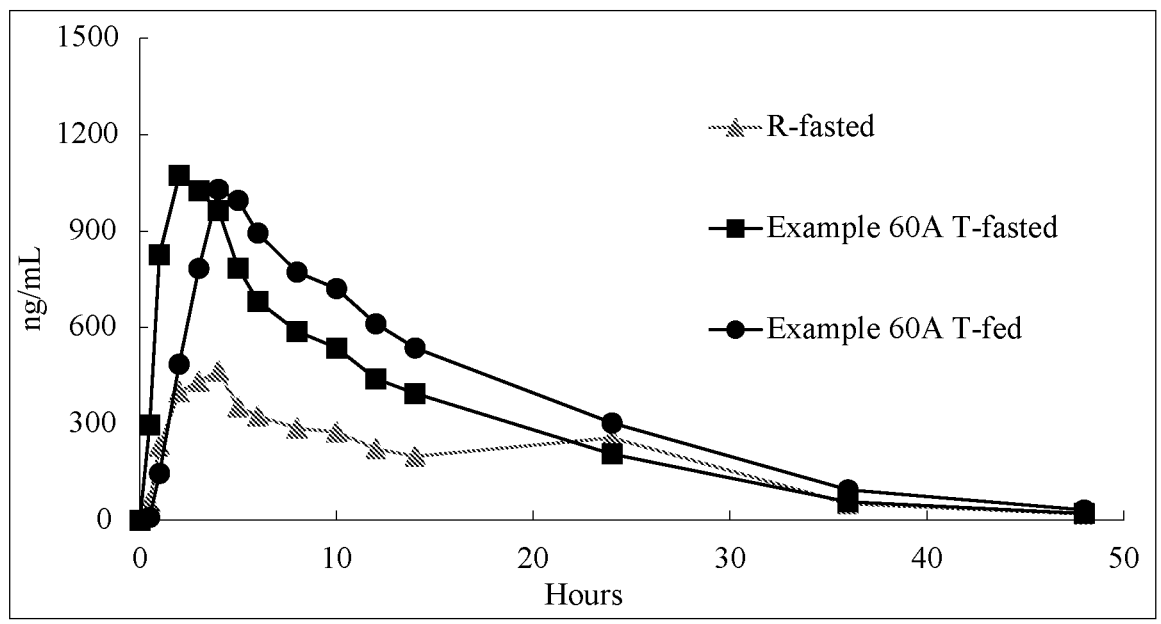
FIG. 25 is a graph of the mean in vivo plasma data provided in Example 61A.

A graph of the normalized mean plasma profiles provided in Example 61A is shown in FIG. 25.

Example 61 B

The capsules prepared in Example 60F containing nilotinib monolauryl sulfate were administered to nine (9) healthy subjects under fasted and fed conditions. This administration was a single dose, open-label, randomized, 3-treatment, 3-sequence, 3-period crossover bioavailability study in healthy subjects under fasted and fed conditions. All subjects were randomized to the sequences as shown in the following table with a washout period of at least 5 days between the periods. The Reference drug (Ref) was TASIGNA® Capsule, nilotinib HCl, with strength of 200 mg (free base) while the Test drug (Test) was a capsule prepared according to the procedure of Example 60F but containing approximately 80 mg free base of nilotinib. The nine (9) healthy subjects enrolled in this study were randomized to one of the sequences as shown in the following table.

| Sequence | Period I | Period II | Period III |
|----------|----------|-----------|------------|
| 1        | Ref      | Tfast     | Tfed       |
| 2        | Tfed     | Ref       | Tfast      |
| 3        | Tfast    | Tfed      | Ref        |

* Ref: Reference under fasted condition; Tfast Test under fasted condition; Tfed: Test under fed condition.

During each treatment period, blood samples were taken at 0 (prior to the dosing), 0.5, 1, 2, 3, 4, 5, 6, 8, 10, 12, 14, 24, 36 and 48 hours after dosing. $AUC_{0-48}$, $AUC_{0-\infty}$, Cmax, $T_{max}$, and $T_{1/2}$ were determined for each subject based on non-compartmental analyses. The results were summarized in the following table:

The Pharmacokinetic Parameters for Reference and Test Formulations (Normalized to 200 mg Dose)

| Treatment | Parameters | Normalized to 200 mg dose (Mean) |
|---|---|---|
| Ref $_{Fasted}$ | $C_{max}$ (ng/mL) | 580 |
| | $AUC_{0-48}$ (ng · h/mL) | 8340 |
| | $AUC_{0-\infty}$ (ng · h/mL) | 9105 |
| Test $_{Fasted}$ | $C_{max}$ (ng/mL) | 1302.5 |
| | $AUC_{0-48}$ (ng · h/mL) | 15392.5 |
| | $AUC_{0-\infty}$ (ng · h/mL) | 16467.5 |
| Test $_{Fed}$ | $C_{max}$ (ng/mL) | 1310 |
| | $AUC_{0-48}$ (ng · h/mL) | 18720 |
| | $AUC_{0-\infty}$ (ng · h/mL) | 20695 |

*Ref $_{Fasted}$: Tasigna Capsule 200 mg (free base) under fasted condition
*Test $_{Fasted}$: Test drug (Test) 80 mg (free base) under fasted condition
*Test $_{Fed}$: Test drug (Test) 80 mg (free base) under fed condition Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following table:

The Comparisons Between Test Vs. Reference and Test $_{Fed}$ vs. Test $_{Fasted}$ (Normalized to 200 mg Dose)

| Comparisons | Parameters | Geometric Mean Ratios |
|---|---|---|
| T1~Ref (Fasted) | $C_{max}$ (ng/mL) | 247.56% |
| | $AUC_{0-48}$ (ng · h/mL) | 193.56% |
| | $AUC_{0-\infty}$ (ng · h/mL) | 192.55% |
| Test $_{Fed}$~Test $_{Fasted}$ | $C_{max}$ (ng/mL) | 101.26% |
| | $AUC_{0-48}$ (ng · h/mL) | 123.73% |
| | $AUC_{0-\infty}$ (ng · h/mL) | 126.12% |

The individual subject data (normalized to 200 mg dose) obtained from the study is as follows:

Reference Drug (TASIGNA®) Under Fasted Condition (Concentration (ng/mL))

| Time (hr) | Subject | | | | | | | | | Mean | SD | CV % |
|---|---|---|---|---|---|---|---|---|---|---|---|---|
| | 1 | 2 | 3 | 4 | 5 | 6 | 7 | 8 | 9 | | | |
| 0 | 0 | 0 | 0 | 0 | 0 | 0 | 0 | 0 | 0 | 0 | 0 | — |
| 0.5 | 63.4 | 176 | 55.1 | 118 | 55.8 | 151 | 11.2 | 77.3 | 0 | 78.6 | 59.5 | 75.6 |
| 1 | 202 | 389 | 171 | 190 | 413 | 385 | 86.7 | 255 | 0 | 232.4 | 142.6 | 61.4 |
| 2 | 321 | 570 | 247 | 261 | 1060 | 762 | 236 | 495 | 14.4 | 440.7 | 319.0 | 72.4 |
| 3 | 339 | 576 | 288 | 267 | 964 | 966 | 428 | 668 | 114 | 512.2 | 305.0 | 59.6 |
| 4 | 394 | 573 | 311 | 265 | 866 | 1040 | 500 | 840 | 202 | 554.6 | 298.1 | 53.7 |
| 5 | 293 | 447 | 244 | 192 | 565 | 769 | 374 | 613 | 228 | 413.9 | 199.5 | 48.2 |
| 6 | 267 | 417 | 218 | 164 | 441 | 671 | 361 | 538 | 226 | 367.0 | 166.9 | 45.5 |
| 8 | 233 | 355 | 189 | 143 | 403 | 634 | 289 | 402 | 226 | 319.3 | 149.7 | 46.9 |
| 10 | 171 | 351 | 161 | 130 | 340 | 572 | 305 | 370 | 212 | 290.2 | 139.1 | 47.9 |
| 12 | 137 | 314 | 127 | 114 | 318 | 447 | 226 | 401 | 201 | 253.9 | 122.3 | 48.2 |
| 14 | 95.5 | 268 | 114 | 99.1 | 299 | 390 | 248 | 344 | 166 | 224.8 | 110.5 | 49.1 |
| 24 | 11.4 | 258 | 60.1 | 57 | 268 | 403 | 24.7 | 136 | 80.8 | 144.3 | 135.1 | 93.6 |
| 36 | BQL | 118 | 10.8 | 25.3 | 122 | 202 | 17.1 | 62.8 | 26.6 | 73.1 | 68.2 | 93.4 |
| 48 | BQL | 55.6 | 5.61 | 15.1 | 62.9 | 147 | 7.09 | 27 | 8.08 | 41.0 | 48.2 | 117.5 |

Test Drug (Example 60 F) Under Fasted Condition (Concentration (ng/mL))

| Time (hr) | Subject | | | | | | | | | Mean | SD | CV % |
|---|---|---|---|---|---|---|---|---|---|---|---|---|
| | 1 | 2 | 3 | 4 | 5 | 6 | 7 | 8 | 9 | | | |
| 0 | 0 | 0 | 0 | 0 | 0 | 0 | 0 | 0 | 0 | 0 | 0 | — |
| 0.5 | 0 | 567.5 | 128.75 | 62.25 | 257.5 | 762.5 | 462.5 | 0 | 14.725 | 250.6 | 282.6 | 112.8 |
| 1 | 275 | 1310 | 657.5 | 692.5 | 755 | 1430 | 907.5 | 537.5 | 193 | 750.9 | 417.4 | 55.6 |
| 2 | 695 | 1407.5 | 1112.5 | 1117.5 | 1382.5 | 1955 | 1147.5 | 1102.5 | 475 | 1155.0 | 423.6 | 36.7 |
| 3 | 1217.5 | 1275 | 1072.5 | 905 | 1617.5 | 1780 | 1142.5 | 1505 | 550 | 1229.4 | 376.0 | 30.6 |
| 4 | 1005 | 1265 | 942.5 | 975 | 1605 | 1560 | 1155 | 1587.5 | 505 | 1177.8 | 368.0 | 31.2 |
| 5 | 667.5 | 895 | 710 | 550 | 1120 | 1167.5 | 680 | 1130 | 562.5 | 831.4 | 251.4 | 30.2 |
| 6 | 567.5 | 952.5 | 625 | 502.5 | 1007.5 | 1000 | 610 | 925 | 450 | 737.8 | 228.8 | 31.0 |
| 8 | 447.5 | 772.5 | 505 | 385 | 790 | 882.5 | 482.5 | 787.5 | 367.5 | 602.2 | 202.2 | 33.6 |
| 10 | 347.5 | 762.5 | 452.5 | 350 | 702.5 | 900 | 412.5 | 635 | 330 | 543.6 | 210.8 | 38.8 |
| 12 | 265 | 665 | 340 | 277.5 | 657.5 | 712.5 | 233.5 | 517.5 | 255 | 435.5 | 200.6 | 46.0 |
| 14 | 193.25 | 630 | 272.5 | 213.25 | 600 | 657.5 | 156 | 450 | 217.25 | 376.6 | 207.2 | 55.0 |
| 24 | 17.825 | 495 | 55.75 | 68.25 | 427.5 | 540 | 23 | 221.75 | 106.25 | 217.3 | 213.2 | 98.1 |
| 36 | BQL | 275 | 15.45 | BQL | 208.25 | 224.75 | 19.475 | 62.75 | 75.5 | 125.9 | 107.1 | 85.1 |
| 48 | BQL | 135.75 | BQL | BQL | 118.75 | 145.25 | BQL | 16.7 | 28.25 | 88.9 | 61.5 | 69.2 |

Test Drug (Example 60 F) Under Fed Condition (Concentration (ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | 0 | 0 | 0 | 0 | 0 | 0 | 0 | 0 | 0 | 0 | 0 | — |
| 0.5 | 20 | 0 | 0 | 0 | 0 | 0 | 0 | 0 | 0 | 2.2 | 6.7 | 300.0 |
| 1 | 96.5 | 0 | 137.75 | 40.75 | 0 | 0 | 0 | 25 | 0 | 33.3 | 50.7 | 152.1 |
| 2 | 700 | 200 | 525 | 427.5 | 487.5 | 545 | 41.25 | 317.5 | 295 | 393.2 | 200.4 | 51.0 |
| 3 | 1172.5 | 957.5 | 772.5 | 720 | 985 | 1040 | 625 | 735 | 562.5 | 841.1 | 205.7 | 24.5 |
| 4 | 1035 | 1275 | 1035 | 907.5 | 1480 | 2060 | 1387.5 | 1307.5 | 695 | 1242.5 | 395.1 | 31.8 |
| 5 | 875 | 1622.5 | 1105 | 825 | 1442.5 | 1657.5 | 1100 | 1347.5 | 715 | 1187.8 | 347.8 | 29.3 |
| 6 | 725 | 1440 | 940 | 722.5 | 1197.5 | 1340 | 962.5 | 1102.5 | 640 | 1007.8 | 284.0 | 28.2 |
| 8 | 615 | 1137.5 | 770 | 555 | 990 | 1170 | 762.5 | 897.5 | 575 | 830.3 | 233.3 | 28.1 |
| 10 | 515 | 1035 | 660 | 492.5 | 900 | 1137.5 | 637.5 | 742.5 | 525 | 738.3 | 236.0 | 32.0 |
| 12 | 437.5 | 975 | 572.5 | 402.5 | 830 | 922.5 | 582.5 | 635 | 450 | 645.3 | 214.8 | 33.3 |
| 14 | 367.5 | 880 | 465 | 350 | 787.5 | 837.5 | 535 | 560 | 430 | 579.2 | 204.8 | 35.4 |
| 24 | 105 | 695 | 193 | 129 | 580 | 725 | 71.5 | 219.5 | 192.75 | 323.4 | 264.3 | 81.7 |
| 36 | BQL | 497.5 | 23.05 | 24.5 | 352.5 | 347.5 | BQL | 66.75 | 36 | 192.5 | 200.0 | 103.8 |
| 48 | BQL | 277.5 | BQL | BQL | 160.75 | 191 | BQL | 19.35 | BQL | 162.2 | 107.3 | 66.2 |

Figure 26:
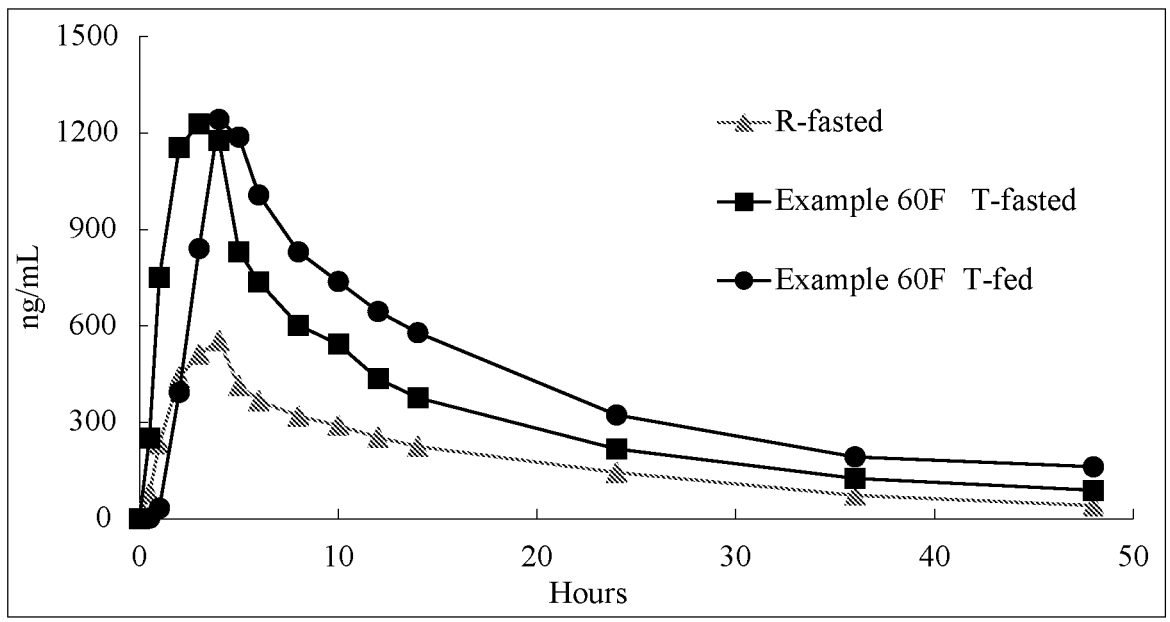
FIG. 26 is a graph of the mean in vivo plasma data provided in Example 61B.

A graph of the mean plasma profiles provided in this Example 61B is shown in FIG. 26.

Example 61 C

The capsules prepared in Example 60G containing nilotinib monolauryl sulfate were administered to nine (9) healthy subjects under fasted and fed conditions. This administration was a single dose, open-label, randomized, 3-treatment, 3-sequence, 3-period crossover bioavailability study in healthy subjects under fasted and fed conditions. All subjects were randomized to the sequences as shown in the following table with a washout period of at least 5 days between the periods. The Reference drug (Ref) was TASIGNA® Capsule, nilotinib HCl, with strength of 200 mg (free base) while the Test drug (Test) was a capsule prepared according to the procedure of Example 60 G but containing approximately 80 mg free base of nilotinib. The nine (9) healthy subjects enrolled in this study were randomized to one of the sequences as shown in the following table.

| Sequence | Period I | Period II | Period III |
|---|---|---|---|
| 1 | Ref | Tfast | Tfed |
| 2 | Tfed | Ref | Tfast |
| 3 | Tfast | Tfed | Ref |

* Ref: Reference under fasted condition; Tfast Test under fasted condition; Tfed: Test under fed condition.

During each treatment period, blood samples were taken at 0 (prior to the dosing), 0.5, 1, 2, 3, 4, 5, 6, 8, 10, 12, 14, 24, 36 and 48 hours after dosing. $AUC_{0-48}$, $AUC_{0-\infty}$, $C_{max}$, $T_{max}$, and $T_{1/2}$ were determined for each subject based on non-compartmental analyses. The results were summarized in the following table:

The Pharmacokinetic Parameters for Reference and Test Formulations (Normalized to 200 mg Dose)

| Treatment | Parameters | Normalized to 200 mg dose (Mean) |
|---|---|---|
| Ref $_{Fasted}$ | $C_{max}$ (ng/mL) | 446 |
| | $AUC_{0-48}$ (ng · h/mL) | 6831 |
| | $AUC_{0-\infty}$ (ng · h/mL) | 7298 |
| Test $_{Fasted}$ | $C_{max}$ (ng/mL) | 1271 |
| | $AUC_{0-48}$ (ng · h/mL) | 14919 |
| | $AUC_{0-\infty}$ (ng · h/mL) | 15721 |
| Test $_{Fed}$ | $C_{max}$ (ng/mL) | 1108 |
| | $AUC_{0-48}$ (ng · h/mL) | 17150 |
| | $AUC_{0-\infty}$ (ng · h/mL) | 17628 |

*Ref $_{Fasted}$: Tasigna Capsule 200 mg (free base) under fasted condition

*Test $_{Fasted}$: Test drug (Test) 80 mg (free base) under fasted condition

*Test $_{Fed}$: Test drug (Test) 80 mg (free base) under fed condition

Ln-transformed $AUC_{0-t}$, $AUC_{0-\infty}$ and $C_{max}$ were analyzed by ANOVA. The sequence, subject (sequence), period and treatment effects were included in the model. A comparison of the data obtained from the Test and Ref dosing is shown in the following table:

The Comparisons Between Test Vs. Reference and Test$_{Fed}$ vs. Test$_{Fasted}$ (Normalized to 200 mg Dose)

| Comparisons | Parameters | Geometric Mean Ratios |
|---|---|---|
| T1~Ref (Fasted) | $C_{max}$ (ng/mL) | 293.64% |
| | $AUC_{0-48}$ (ng · h/mL) | 222.56% |
| | $AUC_{0-\infty}$ (ng · h/mL) | 219.50% |
| Test $_{Fed}$~Test $_{Fasted}$ | $C_{max}$ (ng/mL) | 87.70% |
| | $AUC_{0-48}$ (ng · h/mL) | 114.95% |
| | $AUC_{0-\infty}$ (ng · h/mL) | 112.83% |

The individual subject data (normalized to 200 mg dose) obtained from the study is as follows:

Reference Drug (TASIGNA®) Under Fasted Condition (Concentration (ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | 0 | 0 | 0 | 0 | 0 | 0 | 0 | 0 | 0 | 0.0 | 0.0 | — |
| 0.5 | 42.1 | 29.9 | 59.6 | 126 | 124 | 170 | 47.4 | 120 | 156 | 97.2 | 52.8 | 54.3 |
| 1 | 157 | 151 | 210 | 331 | 350 | 314 | 169 | 407 | 399 | 276.4 | 104.8 | 37.9 |
| 2 | 244 | 191 | 365 | 626 | 487 | 363 | 285 | 515 | 381 | 384.1 | 138.7 | 36.1 |
| 3 | 344 | 211 | 556 | 660 | 493 | 459 | 271 | 462 | 382 | 426.4 | 140.3 | 32.9 |
| 4 | 381 | 200 | 531 | 685 | 505 | 464 | 245 | 441 | 338 | 421.1 | 149.8 | 35.6 |
| 5 | 393 | 163 | 441 | 566 | 402 | 404 | 232 | 316 | 303 | 357.8 | 119.4 | 33.4 |
| 6 | 350 | 145 | 354 | 531 | 392 | 341 | 227 | 268 | 286 | 321.6 | 109.2 | 33.9 |
| 8 | 302 | 126 | 272 | 396 | 382 | 267 | 207 | 249 | 276 | 275.2 | 82.5 | 30.0 |
| 10 | 235 | 103 | 228 | 320 | 320 | 245 | 181 | 244 | 260 | 237.3 | 66.7 | 28.1 |
| 12 | 223 | 85.8 | 200 | 334 | 260 | 220 | 151 | 213 | 208 | 210.5 | 68.2 | 32.4 |
| 14 | 215 | 67.1 | 167 | 261 | 250 | 192 | 131 | 211 | 213 | 189.7 | 60.6 | 31.9 |
| 24 | 109 | 14.1 | 71.4 | 203 | 172 | 131 | 77.9 | 156 | 165 | 122.2 | 59.6 | 48.8 |
| 36 | 18.9 | BQL | 21.8 | 81.7 | 69.4 | 53.6 | 23.4 | 43.9 | 89.3 | 50.3 | 27.9 | 55.5 |
| 48 | BQL | BQL | BQL | 37.5 | 32.4 | 18.3 | 9.28 | BQL | 60.2 | 31.5 | 19.5 | 62.0 |

Test Drug (Example 60 G) Under Fasted Condition (Concentration (ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | 0 | 0 | 0 | 0 | 0 | 0 | 0 | 0 | 0 | 0 | 0 | — |
| 0.5 | 17.65 | 15.6 | 267.5 | 412.5 | 34.75 | 472.5 | 0 | 14.4 | 405 | 182.2 | 203.8 | 111.8 |
| 1 | 154.25 | 342.5 | 725 | 1147.5 | 332.5 | 1620 | 485 | 295 | 1297.5 | 711.0 | 521.3 | 73.3 |
| 2 | 725 | 832.5 | 1087.5 | 1180 | 1397.5 | 1355 | 677.5 | 1045 | 1222.5 | 1058.1 | 262.9 | 24.8 |
| 3 | 1057.5 | 1242.5 | 1072.5 | 1255 | 1557.5 | 1367.5 | 722.5 | 1400 | 1115 | 1198.9 | 243.0 | 20.3 |
| 4 | 1252.5 | 1140 | 862.5 | 1107.5 | 1537.5 | 1262.5 | 655 | 1292.5 | 1057.5 | 1129.7 | 256.9 | 22.7 |
| 5 | 972.5 | 802.5 | 680 | 840 | 1030 | 885 | 510 | 880 | 870 | 830.0 | 155.4 | 18.7 |
| 6 | 865 | 645 | 570 | 792.5 | 950 | 727.5 | 427.5 | 790 | 787.5 | 728.3 | 158.8 | 21.8 |
| 8 | 737.5 | 490 | 492.5 | 695 | 770 | 575 | 365 | 675 | 650 | 605.6 | 134.3 | 22.2 |
| 10 | 672.5 | 397.5 | 427.5 | 655 | 815 | 532.5 | 297.5 | 585 | 610 | 554.7 | 159.4 | 28.7 |
| 12 | 487.5 | 317.5 | 337.5 | 555 | 682.5 | 452.5 | 262.5 | 505 | 532.5 | 459.2 | 132.7 | 28.9 |
| 14 | 485 | 252.5 | 241.75 | 470 | 652.5 | 372.5 | 203 | 482.5 | 492.5 | 405.8 | 148.9 | 36.7 |
| 24 | 131 | 70.75 | 64 | 285 | 497.5 | 225.75 | 96.75 | 325 | 372.5 | 229.8 | 151.8 | 66.1 |
| 36 | 18.05 | BQL | BQL | 103 | 207.75 | 49.75 | 17.275 | 44.25 | 154 | 84.9 | 73.2 | 86.2 |
| 48 | BQL | BQL | BQL | 45 | 124.25 | BQL | BQL | BQL | 82.75 | 84.0 | 39.6 | 47.2 |

Test Drug (Example 60 G) Under Fed Condition (Concentration (ng/mL))

| Time (hr) | Subject 1 | 2 | 3 | 4 | 5 | 6 | 7 | 8 | 9 | Mean | SD | CV % |
|---|---|---|---|---|---|---|---|---|---|---|---|---|
| 0 | 0 | 0 | 0 | 0 | 0 | 0 | 0 | 0 | 0 | 0 | 0 | — |
| 0.5 | 0 | 0 | 0 | 0 | 0 | 0 | 0 | 0 | 0 | 0 | 0 | — |
| 1 | 30.5 | 55.5 | 0 | 59.5 | 0 | 0 | 262.5 | 20.05 | 71.75 | 55.5 | 82.3 | 148.3 |
| 2 | 582.5 | 575 | 345 | 226.25 | 61.75 | 700 | 715 | 397.5 | 712.5 | 479.5 | 234.9 | 49.0 |
| 3 | 1032.5 | 752.5 | 625 | 657.5 | 435 | 1150 | 815 | 735 | 997.5 | 800.0 | 225.4 | 28.2 |
| 4 | 1337.5 | 857.5 | 1005 | 1012.5 | 1247.5 | 1382.5 | 697.5 | 992.5 | 1167.5 | 1077.8 | 225.6 | 20.9 |
| 5 | 870 | 790 | 837.5 | 1000 | 1352.5 | 1082.5 | 565 | 947.5 | 1207.5 | 961.4 | 234.5 | 24.4 |
| 6 | 850 | 655 | 722.5 | 885 | 1165 | 950 | 455 | 880 | 1150 | 856.9 | 226.7 | 26.5 |
| 8 | 660 | 580 | 552.5 | 797.5 | 970 | 710 | 392.5 | 827.5 | 945 | 715.0 | 190.1 | 26.6 |
| 10 | 742.5 | 522.5 | 467.5 | 705 | 910 | 652.5 | 327.5 | 1005 | 790 | 680.3 | 215.1 | 31.6 |
| 12 | 635 | 475 | 442.5 | 660 | 805 | 560 | 295 | 937.5 | 735 | 616.1 | 197.4 | 32.0 |
| 14 | 605 | 412.5 | 367.5 | 610 | 690 | 557.5 | 252.5 | 795 | 657.5 | 549.7 | 172.7 | 31.4 |
| 24 | 223.25 | 124.25 | 153 | 402.5 | 525 | 370 | 97.25 | 637.5 | 492.5 | 336.1 | 195.2 | 58.1 |
| 36 | 29.75 | 25.5 | 31 | 130.5 | 183 | 140.75 | 32.75 | 250 | 211.25 | 114.9 | 88.1 | 76.7 |
| 48 | BQL | BQL | BQL | 42.5 | 61.25 | 55.75 | BQL | 43 | 75.5 | 55.6 | 13.8 | 24.8 |

Figure 27:
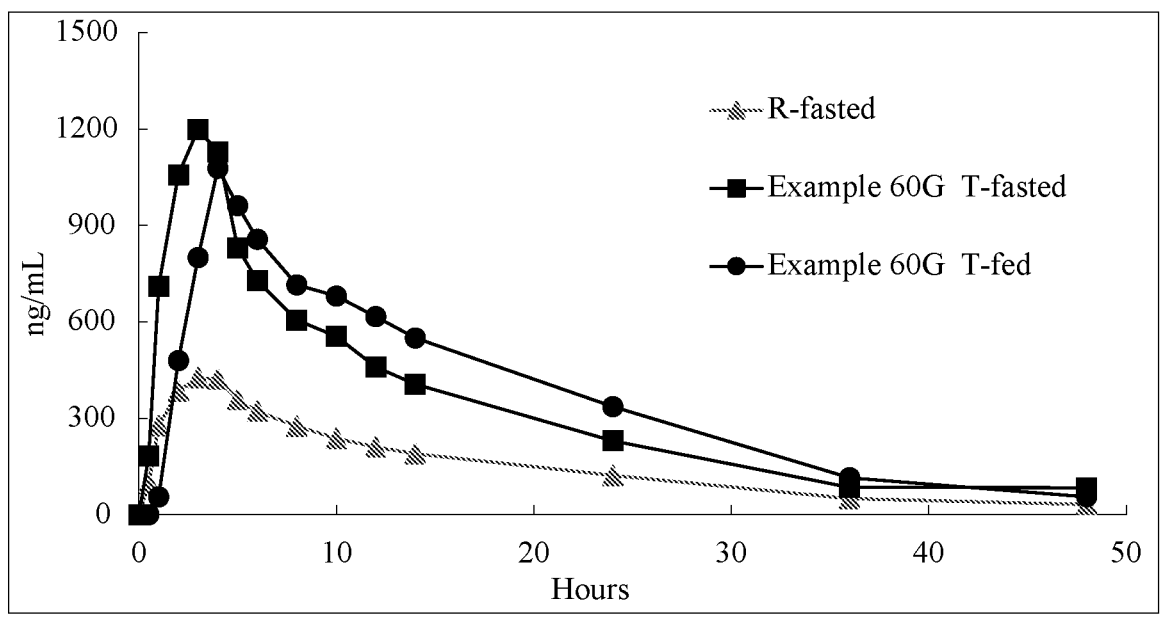
FIG. 27 is a graph of the mean in vivo plasma data provided in Example 61C.

A graph of the mean plasma profiles provided in this Example 61C is shown in FIG. 27.

Example 62

The following impurities were identified as being present in the nilotinib lauryl sulfate salts and nilotinib lauryl sulfate dosage forms prepared in accordance with the present invention:

| Impurity | Chemicals name | Molecular structure |
|---|---|---|
| Impurity 1 (RRT 0.38) | 4-methyl-3-[[4-(pyridin-3-yl)pyrimidin-2-yl]amino]benzoic acid | 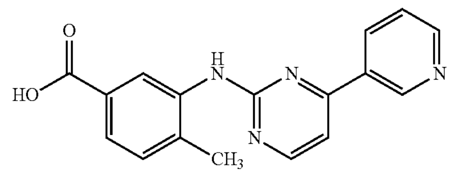 [SMILES: Cc1ccc(C(=O)O)cc1Nc1nccc(-c2cccnc2)n1] |
| Impurity 2 (RRT 0.87) | methyl 4-methyl-3-[[4-(pyridin-3-yl)pyrimidin-2-yl]amino]benzoate, | 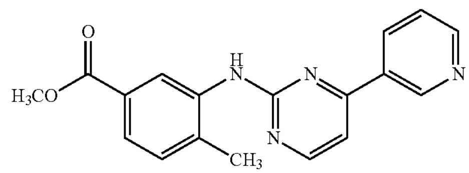 [SMILES: COC(=O)c1ccc(C)c(Nc2nccc(-c3cccnc3)n2)c1] |
| Impurity 3 (RRT 1.16) | N-[3-(4-ethyl-1H-imidazol-1-yl)-5-(trifluoromethyl)phenyl]-4-methyl-3-[[4-(pyridin-3-yl)pyrimidin-2-yl]amino]benzamide | 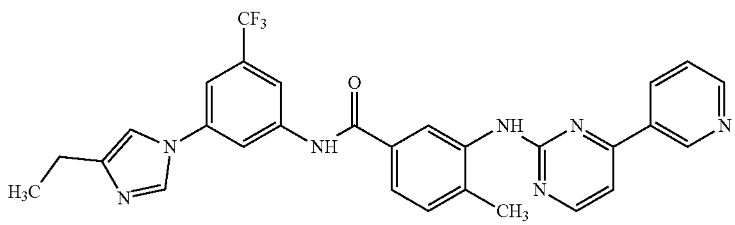 [SMILES: CCc1cn(-c2cc(NC(=O)c3ccc(C)c(Nc4nccc(-c5cccnc5)n4)c3)cc(C(F)(F)F)c2)cn1] |

The above RRT, nilotinib monolauryl sulfate salt and the dosage forms prepared in Examples 60 F and 60 G were determined or tested for impurities and stability using HPLC with the following parameters:

| Parameter | Setting/Description |
|---|---|
| System | HPLC Equipped with a UV/Vis Detector |
| Column | Water Xterra@RP18 150 × 3.0 mm 3.5 μm (for NLB-1LS) |
| Detection | UV at 250 nm |
| Flow rate | 0.8 mL/min |
| Injection volume | 10 μL |
| Column temperature | 40° C. |
| Sample temperature | Ambient |
| Run time | 30 minutes |

| | Gradient as shown below: | | |
|---|---|---|---|
| Mode of Analysis | Time (min) | Mobile phase A | Mobile phase B |
| | 0 | 90 | 10 |
| | 6 | 90 | 10 |
| | 16 | 72 | 28 |
| | 25 | 40 | 60 |
| | 26 | 90 | 10 |
| | 30 | 90 | 10 |

Mobile phase A was 0.25% Formic Acid/acetonitrile in a volume ratio of 90/10.

Mobile phase B was 0.1% Formic Acid/acetonitrile in a volume ratio of 10/90.

The test sample of the nilotinib monolauryl sulfate salt prepared in Example 46 (crystallization Method B) were prepared by weighing about 7.5 mg of nilotinib monolauryl sulfate (equivalent to 5 mg of nilotinib) and transfer into a 50-mL amber volumetric flask, adding 40 mL of diluent (ethanol), sonicating for about 5 minutes and stirring at 800 rpms for about 5 minutes until the nilotinib monolauryl sulfate is dissolved. Additional diluent is added so the test sample is approximately 0.10 mg of nilotinib per mL.

The test sample of the dosage forms prepared in Examples 60 F and 60 G were prepared by the following procedure:

1. Cut the tip of the capsule with scissors and squeeze the contents from the hole into the 100-mL volumetric flask. Cut the capsule into two parts and add the parts to the flask. Add 80% full of ethanol, sonicate for 10 minutes and stir at 800 rpm for 30 minutes to dissolve the contents completely.

2. Dilute to volume with ethanol, mix well by inverting the flask NLT 10 times

3. Pipette 3 ml into 25-mL amber volumetric flask and add ethanol to volume, mix well by inverting the flask NLT 10 times. The test sample is approximately 0.096 mg of nilotinib per mL.

The nilotinib dilauryl sulfate salt prepared in Example 26 were tested for impurities and stability using HPLC with the following parameters:

| Parameter | Setting/Description |
| --- | --- |
| System | HPLC Equipped with a UV/Vis Detector |
| Column | Inertsil ODS-3 150*4.6 mm 5 μm (for NLB-2LS) |
| Detection | UV at 250 nm |
| Flow rate | 0.8 mL/min |
| Injection volume | 10 μL |
| Column temperature | 40° C. |
| Sample temperature | Ambient |
| Run time | 30 minutes |

| | Gradient as shown below: | | |
| --- | --- | --- | --- |
| Mode of Analysis | Time (min) | Mobile phase A | Mobile phase B |
| | 0 | 90 | 10 |
| | 6 | 90 | 10 |
| | 16 | 72 | 28 |
| | 25 | 40 | 60 |
| | 26 | 90 | 10 |
| | 30 | 90 | 10 |

The test sample of the nilotinib dilauryl sulfate salt prepared in Example 26 were prepared by weighing about 10 mg of nilotinib dilauryl sulfate (equivalent to 5 mg of nilotinib) and transfer into a 25-mL amber volumetric flask, adding 20 mL of diluent (ethanol), sonicating for about 5 minutes and stirring at 800 rpms for about 5 minutes until the nilotinib dilauryl sulfate is dissolved. Additional diluent is added so the test sample is approximately 0.20 mg of nilotinib per mL.

The test samples tested using the above procedure and the following results were obtained:

| | | RRT | | | | | |
| --- | --- | --- | --- | --- | --- | --- | --- |
| | Condition | 0.19 | 1.16 | 1.38 | 1.40 | 1.49 | 1.68 |
| Example 46 | Room temp. | | 0.07 | | | | |
| | 60° C./75% R.H. 2 weeks | | 0.07 | | | | |

| | | RRT | | | | | | | |
| --- | --- | --- | --- | --- | --- | --- | --- | --- | --- |
| | Condition | 0.81 | 1.09 | 1.16 | 1.17 | 1.18 | 1.21 | 1.28 | 1.37 |
| Example 26 | Room temp. | | 0.07 | 0.10 | | | | 0.02 | |
| | 60° C./75% R.H. 1 week | 0.05 | 0.07 | 0.11 | | | | 0.08 | |

The samples were stored in a high-density polyethylene (HDPE) bottle with child resistant closure and foil induction seal (126 c.c, with 2~3 g of silica gel).

The above data demonstrates the nilotinib monolauryl sulfate is more stable than the dilauryl sulfate and both the monolauryl and dilauryl sulfate salts of the present invention have NMT 0.5% of any individual impurity, preferably NMT 0.35% of any individual impurity and most preferably NMT 0.30% of any individual impurity and the total impurity should be NMT 1.0%, preferably NMT 0.75% and most preferably NMT 0.60%.

| | | RRT | | | | | |
| --- | --- | --- | --- | --- | --- | --- | --- |
| | Condition | 0.19 | 1.16 | 1.38 | 1.40 | 1.49 | 1.68 |
| Example 60 F | Room temp. | 0.02 | 0.03 | 0.02 | 0.02 | 0.04 | 0.01 |
| | 60° C./75% R.H. 2 weeks | 0.02 | 0.03 | 0.03 | 0.02 | 0.03 | 0.12 |
| Example 60 G | Room temp. | 0.01 | 0.03 | 0.02 | 0.02 | 0.02 | 0.01 |
| | 60° C./75% R.H. 2 weeks | 0.01 | 0.03 | 0.02 | 0.03 | 0.03 | 0.14 |

The capsules were stored in a high-density polyethylene (HDPE) bottle with child resistant closure and foil induction seal (126 c.c, with 2-3 g of silica gel).

Employing the above HPLC method the nilotinib lauryl sulfate dosage forms were determined to have NMT 0.5% of any individual impurity, preferably more than 0.35% of any individual impurity and most preferably not more than 0.25% of any individual impurity and the total impurity should not be more than 1.0%, preferably not more than 0.75% and most preferably not more than 0.60%.

Example 63 A

A dasatinib monolauryl sulfate tablet was prepared by grinding and mixing 7730 mg of dasatinib monolauryl sulfate prepared according to the procedure of Example 48A, crystallization Method E with 4800 mg of polyoxyl stearate Type I in a small mixer for about 15 seconds. 1000 mg of purified water was added to the mixer and granulated for 15 seconds. The granules were dried in an oven at 50° C. to evaporate the water. The dried granules were ground into a powder and passed through a 30 mesh sieve. 16695 mg of microcrystalline cellulose, 1400 mg of sodium starch glycolate, 3500 mg of croscarmellose sodium and 700 mg of colloidal silicon dioxide which had previously been passed through a 40 mesh sieve were mixed with the dried, ground and sieved granules to obtain a pre-blend. 175 mg of sodium stearyl fumarate which had been previously passed through a 40 mesh sieve was added to the pre-blend and blended to obtain final blend. The final blend was compressed into tablets using a 9.5 mm round-shaped punch and a target hardness about 5 kp.

The composition of the tablet content is as follows:

|  | mg | wt % |
| --- | --- | --- |
| Dasatinib monolauryl sulfate, DSB-1LSC crystalline API (EQ to 50 mg free base) | 77.30 | 22.09 |
| Polyoxyl stearate Type I | 48.00 | 13.71 |
| Microcrystalline cellulose | 166.95 | 47.70 |
| Sodium starch glycolate | 14.00 | 4.00 |
| Croscarmellose sodium | 35.00 | 10.00 |
| Colloidal silicon dioxide | 7.00 | 2.00 |
| Sodium stearyl fumarate | 1.75 | 0.50 |
| Total | 350.00 | 100.00 |
| Purified water | 10.00 | N/A |

Example 63 B

A dasatinib monolauryl sulfate tablet was prepared by grinding and mixing 2319 mg of dasatinib monolauryl sulfate prepared according to the procedure of Example 48A, crystallization Method E with 1800 mg of polyoxyl stearate Type I and 1800 mg of microcrystalline cellulose (Part I) in a small mixer for about 15 seconds. 450 mg of purified water was added to the mixer and granulated for 15 seconds. The granules were dried in an oven at 50° C. to evaporate the water. The dried granules were ground into a powder and passed through a 40 mesh sieve. 2638.5 mg of microcrystalline cellulose (Part II), 420 mg of sodium starch glycolate, 1260 mg of croscarmellose sodium and 210 mg of colloidal silicon dioxide which had previously been passed through a 40 mesh sieve were mixed with the dried, ground and sieved granules to obtain a pre-blend. 52.5 mg of sodium stearyl fumarate which had been previously passed through a 40 mesh sieve was added to the pre-blend and blended to obtain final blend. The final blend was compressed into tablets using a 9.5 mm round-shaped punch and a target hardness about 5 kp.

The composition of the tablet content is as follows:

|  | mg | wt % |
| --- | --- | --- |
| Dasatinib monolauryl sulfate, DSB-1LSC crystalline API (EQ to 50 mg DSB free base) | 77.30 | 22.09 |
| Polyoxyl stearate Type I | 60.00 | 17.14 |
| Microcrystalline cellulose (I) | 60.00 | 17.14 |
| Microcrystalline cellulose (II) | 87.95 | 25.13 |
| Sodium starch glycolate | 14.00 | 4.00 |
| Croscarmellose sodium | 42.00 | 12.00 |
| Colloidal silicon dioxide | 7.00 | 2.00 |
| Sodium stearyl fumarate | 1.75 | 0.50 |
| Total | 350.00 | 100.00 |
| Purified water | 15.00 | N/A |

Example 63 C

The dasatinib monolauryl sulfate tablets prepared in Examples 63 A and 63 B were tested using a USP Type II Apparatus (Paddle) with 500 ml of 0.1 N HCl at 75 rpm, with a sinker and 37° C. The results of this dissolution testing are as follows:

| Time (minutes) | 63 A (%) | 63 B (%) |
| --- | --- | --- |
| 5 | 65.3 | 66.8 |
| 10 | 79.4 | 81.1 |
| 15 | 83.5 | 84.3 |
| 30 | 86.1 | 87.2 |
| 45 | 86.8 | 88.7 |
| 60 | 87.4 | 89.7 |
| 120 | 88.0 | 91.1 |
| n | 2 | 3 |

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for treating thyroid cancer, renal cell carcinoma or hepatocellar carcinoma comprising orally administering to a patient in need of such therapy one or more capsules comprising a therapeutically effective amount of cabozantinib lauryl sulfate salt wherein each capsule comprises 5 mg to 200 mg of cabozantinib free base in the form of cabozantinib lauryl sulfate and wherein each capsule further comprises: (i) about 15 wt % to about 33 wt % of cabozantinib lauryl sulfate salt; (ii) about 19 wt % to about 80 wt % of at least one pharmaceutically acceptable non-ionic surfactant with a hydrophilic-lipophilic balance (HLB) value of 10 or greater selected from a group consisting of vitamin E polyethylene glycol succinate, a poloxamer, a polyethoxylated castor oil, a polyoxyethylene hydrogenated castor oil, a polyoxylglycerides, a polyoxyethylene stearate and combinations of the foregoing and (iii) optionally one or more additional pharmaceutically acceptable excipients selected from the group consisting of a stabilizer, a filler, a viscosity enhancing agent, a binder, a disintegrant, a lubricant, a glidant, a flavoring agent, and combinations thereof; the capsule exhibits a dissolution rate of at least 70% after 60 minutes of testing using a USP Type II Apparatus (Paddle) with a 0.1 N HCl at 75 rpm, with or without a sinker at 37° C. and wherein the patient's cabozantinib $AUC_{0-\infty}$ or cabozantinib $AUC_{0-24}$ does not change by more than 30% when the capsule is administered to the patient in a fed state compared to when the capsule is administered to the patient in a fasted state.

2. The method of claim 1 wherein the capsule further comprises at least one pharmaceutically acceptable excipient with a hydrophilic-lipophilic balance (HLB) value of less than 10.

3. The method of claim 2 wherein the at least one pharmaceutically acceptable excipient with an HLB value of less than 10 is selected from a group consisting of a wetting agent, an emulsifying agent, a solubilizing agent, a surfactant or a combination thereof.

4. The method of claim 2 wherein the at least one pharmaceutically acceptable excipient with an HLB value of less than 10 is selected from the group consisting of medium chain monoglycerides, medium chain diglycerides, polyoxylglycerides, sorbitan esters, sorbitan fatty acid esters, phospholipids and combinations thereof.

5. The method of claim 1 wherein the contents of the capsule further comprises at least one pharmaceutically acceptable excipient selected from the group consisting of a stabilizer, a filler, a viscosity enhancing agent, a binder, a disintegrant, a lubricant, a glidant, a flavoring agent, and combinations thereof.

6. The method of claim 1 wherein the dissolution medium includes 0.5% t-octyl phenoxy polyethoxy ethanol.

7. The method of claim 1 wherein the dissolution medium includes 0.5% t-octyl phenoxy polyethoxy ethanol and the capsule exhibits a dissolution rate of at least 75% after 60 minutes of testing using a USP Type II Apparatus (Paddle) with a 0.1 N HCl media at 75 rpm, with or without a sinker at 37° C.

8. The method of claim 1 wherein the capsule is administered to the patient in a fed state or a fasted state and the administration does not exhibit a food effect.

9. The method of claim 1 wherein the patient's cabozantinib $C_{max}$ does not change by more than 40% when the capsule is administered to the patient in a fed state compared to when the capsule is administered to the patient in a fasted state.

10. The method of claim 1 wherein the patient's cabozantinib $AUC_{0-\infty}$ or cabozantinib $AUC_{0-24}$ does not change by more than 20% when the capsule is administered to the patient in a fed state compared to when the capsule is administered to the patient in a fasted state.

11. The method of claim 1 wherein the capsule exhibits a $C_{max\ fed}/C_{max\ fast}$ ratio of about 0.6 to about 2.5 wherein the $C_{max\ fed}$ is a maximum cabozantinib plasma concentration obtained by administering a single dose of the capsule to one or more human patients or healthy human subjects under a fed state and the $C_{max\ fast}$ is a maximum cabozantinib plasma concentration obtained by administering a single dose of the capsule to the one or more patients or subjects under a fasted state.

12. The method of claim 1 wherein the capsule exhibits an $AUC_{0-\infty\ fed}/AUC_{0-\infty\ fast}$ ratio of about 0.8 to about 1.25 wherein the $AUC_{0-\infty\ fed}$ is an AUC obtained from the time of administration of a single dose of the capsule to one or more human patients or healthy human subjects under a fed state to infinity and the $AUC_{0-\infty\ fast}$ is an AUC obtained from the time of administration of a single dose of the capsule to the one or more patients or subjects under a fasted state to infinity.

13. The method of claim 11 wherein the $C_{max\ fed}/C_{max\ fast}$ ratio is a geometric mean ratio.

14. The method of claim 12 wherein the $AUC_{0-\infty\ fed}/AUC_{0-\infty\ fast}$ ratio is a geometric mean ratio.

15. The method of claim 1 wherein the dissolution medium includes 0.5% t-octyl phenoxy polyethoxy ethanol the capsule exhibits a dissolution rate of at least 80% after 60 minutes of testing using a USP Type II Apparatus (Paddle) with a 0.1 N HCl at 75 rpm, with or without a sinker at 37° C.

16. The method of claim 1 wherein the at least one pharmaceutically acceptable non-ionic surfactant excipient with an HLB value of 10 or greater is a solid with a melting point between 25° C. and 120° C.

17. The method of claim 1 wherein the capsules comprises about 33 wt % to about 80 wt % of the non-ionic surfactant with an HLB value of 10 or greater.

18. The method of claim 1 wherein the capsules comprises about 45 wt % to about 80 wt % of the non-ionic surfactant with an HLB value of 10 or greater.

19. The method of claim 1 wherein the non-ionic surfactant with an HLB value of 10 or greater is a poloxamer, a polyethoxylated castor oil, a polyoxyethylene hydrogenated castor oil, a polyoxyethylene stearate and combinations of the foregoing.

* * * * *